US012678510B2

(12) United States Patent
Gianneschi et al.

(10) Patent No.: US 12,678,510 B2
(45) Date of Patent: Jul. 14, 2026

(54) DRUG LOADED PEPTIDE BRUSH POLYMERS

(71) Applicant: NORTHWESTERN UNIVERSITY, Evanston, IL (US)

(72) Inventors: Nathan C. Gianneschi, Evanston, IL (US); Matthew P. Thompson, Evanston, IL (US); Cassandra E. Callmann, Evanston, IL (US)

(73) Assignee: Northwestern University, Evanston, IL (US)

( * ) Notice: Subject to any disclaimer, the term of this patent is extended or adjusted under 35 U.S.C. 154(b) by 769 days.

(21) Appl. No.: 17/921,546

(22) PCT Filed: Apr. 29, 2021

(86) PCT No.: PCT/US2021/029829
§ 371 (c)(1),
(2) Date: Oct. 26, 2022

(87) PCT Pub. No.: WO2021/222523
PCT Pub. Date: Nov. 4, 2021

(65) Prior Publication Data

US 2023/0181747 A1 Jun. 15, 2023

Related U.S. Application Data

(60) Provisional application No. 63/018,991, filed on May 1, 2020.

(51) Int. Cl.
*C08G 61/06* (2006.01)
*A61K 47/59* (2017.01)
(Continued)

(52) U.S. Cl.
CPC ............ *A61K 47/595* (2017.08); *A61K 47/59* (2017.08); *A61K 47/641* (2017.08); *A61P 35/00* (2018.01);
(Continued)

(58) Field of Classification Search
CPC ......... C08G 61/06; A61K 47/34; A61K 47/50
See application file for complete search history.

(56) References Cited

U.S. PATENT DOCUMENTS 4,861,760 A 8/1989 Mazuel et al.
4,911,920 A 3/1990 Jani et al.
(Continued)

FOREIGN PATENT DOCUMENTS

GB 1586614 3/1981
WO WO 2016/018917 2/2016
(Continued)

OTHER PUBLICATIONS

Abderrazak et al. (2015) "NLRP3 inflammasome: from a danger signal sensor to a regulatory node of oxidative stress and inflammatory diseases," Redox Biol, 4, 296-307.
(Continued)

*Primary Examiner* — Rip A Lee
(74) *Attorney, Agent, or Firm* — Leydig, Voit & Mayer, Ltd.

(57) ABSTRACT

Aspects of the invention include a polymer comprising: a plurality of repeating units, each repeating unit comprising a polymer backbone group directly or indirectly covalently linked to one or two side chain moieties; wherein: each polymer backbone group is independently a ROMP-polymerized monomer; each one of the one or two side chain moieties independently comprises a peptide moiety or a non-peptide therapeutic moiety; wherein the polymer comprises a plurality of peptide moieties; each polymer back-
(Continued)

Poly(amino acid sequence)-Dye-PTX bone group is covalently attached to at least one other polymer backbone group; 100% of the ROMP-polymerized monomers are each individually attached to the one or two side chain moieties; and at least one side chain moiety of the polymer comprises a non-peptide therapeutic moiety, one polymer-terminating group comprises a non-peptide therapeutic moiety, and/or each of both polymer-terminating groups comprises a non-peptide therapeutic moiety.

30 Claims, 35 Drawing Sheets

Specification includes a Sequence Listing.

(51) Int. Cl.

| | |
|---|---|
| ***A61K 47/64*** | (2017.01) |
| ***A61P 35/00*** | (2006.01) |
| ***C08G 61/08*** | (2006.01) |
| ***C08G 69/08*** | (2006.01) |
| ***C08G 69/48*** | (2006.01) |
| *A61K 47/34* | (2017.01) |
| *A61K 47/50* | (2017.01) |

(52) U.S. Cl.

CPC ............. *C08G 61/08* (2013.01); *C08G 69/08* (2013.01); *C08G 69/48* (2013.01); *A61K 47/34* (2013.01); *A61K 47/50* (2017.08); *C08G 2261/1412* (2013.01); *C08G 2261/1414* (2013.01); *C08G 2261/1426* (2013.01); *C08G 2261/1432* (2013.01); *C08G 2261/3324* (2013.01); *C08G 2261/418* (2013.01)

(56) References Cited

U.S. PATENT DOCUMENTS

| | | | | |
|---|---|---|---|---|
| 5,034,506 | A | 7/1991 | Summerton et al. | |
| 5,212,162 | A | 5/1993 | Missel et al. | |
| 5,235,033 | A | 8/1993 | Summerton et al. | |
| 5,403,841 | A | 4/1995 | Lang et al. | |
| 5,441,542 | A | 8/1995 | Prota et al. | |
| 5,830,658 | A | 11/1998 | Gryaznov | |
| 6,306,993 | B1 | 10/2001 | Rothbard et al. | |
| 8,232,360 | B2 | 7/2012 | Sampson et al. | |
| 9,040,626 | B2 | 5/2015 | Chien et al. | |
| 9,045,579 | B2 * | 6/2015 | Xia | C08G 81/00 |
| 9,206,271 | B2 | 12/2015 | Kiessling et al. | |
| 9,381,253 | B2 * | 7/2016 | Johnson | A61K 47/58 |
| 9,737,525 | B2 | 8/2017 | Kazantsev et al. | |
| 10,046,057 | B2 | 8/2018 | Tatro et al. | |
| 10,105,449 | B2 * | 10/2018 | Johnson | A61K 33/243 |
| 10,153,513 | B2 * | 12/2018 | Grubbs | C08G 81/00 |
| 10,159,749 | B2 * | 12/2018 | Johnson | A61K 31/704 |
| 10,266,631 | B2 | 4/2019 | Lim et al. | |
| 10,590,414 | B2 * | 3/2020 | Zhang | C12N 15/1135 |
| 10,683,387 | B2 * | 6/2020 | Johnson | A61K 9/146 |
| 10,792,373 | B2 * | 10/2020 | Johnson | C08G 69/48 |
| 10,894,854 | B2 * | 1/2021 | Chung | C08F 291/06 |
| 10,980,744 | B2 * | 4/2021 | Blum | C07K 14/001 |
| 11,072,681 | B2 | 7/2021 | Rush et al. | |
| 11,938,218 | B2 * | 3/2024 | Blum | A61K 9/1075 |
| 2003/0113740 | A1 | 6/2003 | Mirkin et al. | |
| 2008/0052841 | A1 | 3/2008 | Cohen et al. | |
| 2011/0166063 | A1 | 7/2011 | Bossard et al. | |
| 2011/0251363 | A1 | 10/2011 | Sampson et al. | |
| 2012/0149843 | A1 | 6/2012 | Chien et al. | |
| 2014/0105896 | A1 | 4/2014 | Cload et al. | |
| 2014/0256767 | A1 | 9/2014 | Hu et al. | |
| 2017/0072062 | A1 | 3/2017 | Benoit et al. | |
| 2017/0327633 | A1 | 11/2017 | Rush et al. | |
| 2018/0042843 | A1 | 2/2018 | Blum et al. | |
| 2018/0092845 | A1 * | 4/2018 | Gianneschi | A61P 9/04 |
| 2018/0303945 | A1 | 10/2018 | Adams et al. | |
| 2019/0070251 | A1 | 3/2019 | Bossard et al. | |
| 2019/0292310 | A1 * | 9/2019 | Zhang | C12Q 1/6886 |
| 2020/0017563 | A1 | 1/2020 | Eisenberg et al. | |
| 2020/0113934 | A1 | 4/2020 | Gianneschi et al. | |
| 2020/0123297 | A1 * | 4/2020 | Johnson | C08G 61/08 |
| 2021/0283054 | A1 | 9/2021 | Blum et al. | |
| 2021/0301078 | A1 | 9/2021 | Rush et al. | |
| 2021/0386861 | A1 * | 12/2021 | Johnson | C08L 65/00 |
| 2022/0280625 | A1 * | 9/2022 | Gianneschi | A61K 38/095 |
| 2022/0372200 | A1 | 11/2022 | Gianneschi et al. | |

FOREIGN PATENT DOCUMENTS

| | | |
|---|---|---|
| WO | WO 2016/023036 | 2/2016 |
| WO | WO 2018/156617 | 8/2018 |
| WO | WO 2019/198075 | 10/2019 |
| WO | WO 2021/030326 | 2/2021 |
| WO | WO 2021/067293 | 4/2021 |
| WO | WO 2021/096692 | 5/2021 |
| WO | WO 2021/222523 | 11/2021 |
| WO | WO 2022/006387 | 1/2022 |
| WO | WO 2022/216588 | 10/2022 |
| WO | WO 2023/086949 | 5/2023 |
| WO | WO 2023/178074 | 9/2023 |
| WO | WO 2023/196769 | 10/2023 |

OTHER PUBLICATIONS

Abed et al. (2015) "Discovery of direct inhibitors of Keap1-Nrf2 protein-protein interaction as potential therapeutic and preventive agents," Acta Pharmaceutica Sinica B; 5(4): 285-299.

Abskharon et al. (2020) "Crystal structure of a conformational antibody that binds tau oligomers and inhibits pathological seeding by extracts from donors with Alzheimer's disease," J Biol Chem 295:10662-76. https://doi.org/10.1074/jbc.ra120.013638.

Adamiak et al. (2017) "Peptide Brush Polymers and Nanoparticles with Enzyme-Regulated Structure and Charge for Inducing or Evading Macrophage Cell Uptake," ACS Nano, 11(10): 9877-9888. https://doi.org/10.1021/acsnano.7b03686.

Agarwal (2010) "Chemistry, chances and limitations of the radical ring-opening polymerization of cyclic ketene acetals for the synthesis of degradable polyesters," Polym. Chem. 1, 953-964.

Agemy et al. (2011) "Targeted nanoparticle enhanced proapoptotic peptide as potential therapy for glioblastoma," Proc. Natl. Acad. Sci. USA, 108, 17450-17455.

Aharony et al. (2015) "A Huntingtin-Based Peptide Inhibitor of Caspase-6 Provides Protection from Mutant Huntingtin-Induced Motor and Behavioral Deficits," Hum. Mol. Genet. 24 (9), 2604-2614.

Aigner et al. (2018) "Biomedical Applications of Recombinant Silk-Based Materials," Adv. Mater. 30 (19), 1704636. https://doi.org/10.1002/ADMA.201704636.

Aldaye et al. (2008) "Assembling Materials with DNA as the Guide," Science 321(5897): 1795-1799.

Alemdaroglu et al. (2007) "DNA meets synthetic polymers-highly versatile hybrid materials," Org. Biomol. Chem. 5(9): 1311-1320.

Allegrezza et al. (2016) "Trametinib drives T cell-dependent control of k-Ras-mutated tumors by inhibiting pathological myelopoiesis," Cancer Res. 76: 6253-6265. PMC5094194.

Al-Muhammed et al. (1996) "In-vivo studies on dexamethasone sodium phosphate liposomes," J. Microencapsul. 13(3): 293-306.

Alvarez-Lorenzo et al. (2014) "Smart drug delivery systems: from fundamentals to the clinic," Chem. Commun., 50, 7743-7765.

Alzheimer's Association (2021) "Alzheimer's Disease Facts and Figures," Alzheimers Dementia;17(3). 327-406.

Alzheimer's Association (2021) "Special Report: Race, Ethnicity and Alzheimer's in America," Alzheimers Dementia, 17(3), 71-104.

Ambadipudi et al. (2017) "Liquid-liquid phase separation of the microtubule-binding repeats of the Alzheimer-related protein Tau," Nat Commun 8:1-13. https://doi.org/10.1038/s41467-017-00480-0.

Arcidiacono et al. (1998) "Purification and Characterization of Recombinant Spider Silk Expressed in *Escherichia coli*," Appl. Microbiol. Biotechnol. 49 (1), 31-38. https://doi.org/10.1007/s002530051133.

(56) References Cited

OTHER PUBLICATIONS

Armstrong (2019) "Risk factors for alzheimer disease," Folia Neuropathol 57:87-105.
Artigas et al. (1981) "Serum trypsin levels in acute pancreatic and non-pancreatic abdominal conditions," Postgrad. Med. J. 57, 219-222.
Arunachalam et al. (2000) "Enzymatic reduction of disulfide bonds in lysosomes: characterization of a gamma-interferon-inducible lysosomal thiol reductase (GILT)," Proc Natl AcadSci U S A, 97 (2), 745-50.
Averick et al. (publicly available Apr. 2013) "Protein-polymer hybrids: Conducting ARGET ATRP from a genetically encoded cleavable ATRP initiator," Eur. Polym. J. (Oct. 2013) 49(10): 2919-2924.
Averick et al. (publicly available Jan. 2014) "Solid-Phase Incorporation of an ATRP Initiator for Polymer-DNA Biohybrids," Angew. Chem. Int. Ed. (Mar. 2014), 126(10): 2777-2782.
Ayres et al. (2003) "Elastin-Based Side-Chain Polymers Synthesized by ATRP," Macromolecules, 36, 5967-5973.
Ayyoub et al. (1998) "Analysis of the degradation mechanisms of MHC class I-presented tumor antigenic peptides by high performance liquid chromatography/electrospray ionization mass spectrometry: application to the design of peptidase-resistant analogs," Rapid Commun Mass Spectrom, 12 (9), 557-64.
Bae et al. (2011) "Dendron-mediated self-assembly of highly PEGylated block copolymers: a modular nanocarrier platform," Chem. Commun. 47(37): 10302-10304.
Bano et al. (2011) "Neurodegenerative processes in Huntington's disease," Cell Death Dis 2:1-7. https://doi.org/10.1038/cddis.2011.112.
Bao et al. (2018) "Self-stabilized, hydrophobic or PEGylated paclitaxel polymer prodrug nanoparticles for cancer therapy," Polym. Chem., 9, 687-698.
Barbieri et al. (2013) "Peptide Receptor Targeting in Cancer: The Somatostatin Paradigm," Int. J. Pept. 2013, 926295: 20 pp.
Barish et al. (2009) "An information-bearing seed for nucleating algorithmic self-assembly," Proc. Natl. Acad. Sci. U.S.A. 106(15): 6054-6059.
Barnard et al. (2008) "Development and implementation of split-GFP-based bimolecular fluorescence complementation (BiFC) assays in yeast," Biochem Soc Trans 36, 479-482, doi: 10.1042/bst0360479.
Barthélemy et al. (2020) "A soluble phosphorylated tau signature links tau, amyloid and the evolution of stages of dominantly inherited Alzheimer's disease," Nat Med 26:398-407. https://doi.org/10.1038/s41591-020-0781-z.
Bates (2005) "The molecular genetics of Huntington disease—a history," Nat Rev Genet 6, 766-773.
Battistella et al. (Dec. 2019) "Delivery of Immunotherapeutic Nanoparticles to Tumors via Enzyme-Directed Assembly," Adv Healthc Mater, 8 (23), e1901105.
Beaulieu et al. (2020) "Structural and Biophysical Insights into the Function of the Intrinsically Disordered Myc Oncoprotein," Cells 2020;9:1-27. https://doi.org/10.3390/cells9041038.
Becker et al. (2003) "Peptide-polymer bioconjugates: hybrid block copolymers generated via living radical polymerizations from resin-supported peptides," Chem. Commun. 2: 180-181.
Becker et al. (2005) "Functionalized Micellar Assemblies Prepared via Block Copolymers Synthesized by Living Free Radical Polymerization upon Peptide-Loaded Resins," Biomacromolecules 6(1): 220-228.
Becker et al. (2018) "Functional biodegradable polymers via ring-opening polymerization of monomers without protective groups," Chem. Soc. Rev. 47, 7739-7782.
Behzadi et al. (2017) "Cellular uptake of nanoparticles: journey inside the cell," Chem. Soc. Rev., 46, 4218-4244.
Békés et al. (Jan. 2022) "PROTAC targeted protein degraders: the past is prologue," Nature Reviews Drug Discovery 21, 181-200, doi:10.1038/s41573-021-00371-6.
Belitsky et al. (2002) "Cellular uptake of N-methylpyrrole/N-methylimidazole polyamide-dye conjugates," Bioorg. Med. Chem. 10(10): 3313-3318.
Berg et al. (2002) "Small-molecule antagonists of Myc/Max dimerization inhibit Myc-induced transformation of chicken embryo fibroblasts," Proc Natl Acad Sci U S A 99, 3830-3835.
Berge et al. (1977) "Pharmaceutical Salts," Journal of Pharmaceutical Science 66(1): 1-19.
Berger et al. (Mar. 2022) "Mussel Adhesive-Inspired Proteomimetic Polymer," J. Am. Chem. Soc. 144, 10, 4383-4392.
Bertin et al. (2005) "High-density doxorubicin-conjugated polymeric nanoparticles via ring-opening metathesis polymerization," Chem. Commun., issue 30: 3793-3795.
Bhaumik et al. (Jul. 2019) "Controlled Living Cascade Polymerization to Make Fully Degradable Sugar-Based Polymers from D-Glucose and D-Galactose," J. Am. Chem. Soc. 141, 12207-12211.
Biagini et al. (2007) "Investigation into the ROMP copolymerization of peptide- and PEG-functionalized norbornene derivatives," J. Polym. Sci., Part A: Polym. Chem. 45(15): 3178-3190.
Bibb et al. (2000) "Severe Deficiencies in Dopamine Signaling in Presymptomatic Huntington's Disease Mice," Proc. Natl. Acad. Sci. U. S. A. 97 (12), 6809-6814. https://doi.org/10.1073/pnas.120166397.
Bidwell et al. (2005) "Application of thermally responsive polypeptides directed against c-Myc transcriptional function for cancer therapy," Mol Cancer Ther 4, 1076-1085.
Bielawski et al. (2007) "Living ring-opening metathesis polymerization," Prog. Polym. Sci. 32, 1-29.
Billiet et al. (2014) "Triazolinediones enable ultrafast and reversible click chemistry for the design of dynamic polymer systems," Nat. Chem., 6, 815-821.
Biron et al. (2008) "Improving Oral Bioavailability of Peptides by Multiple N-Methylation: Somatostatin Analogues," Angew. Chem., Int. Ed. 47(14): 2595-2599.
Bitler et al. (2015) "Targeting EZH2 methyltransferase activity in ARID1A mutated cells as a synthetic lethal therapeutic strategy," Nature Med.; 21: 231-238. PMC4352133.
Blackman et al. (Jun. 2018) "Confinement of Therapeutic Enzymes in Selectively Permeable Polymer Vesicles by Polymerization-Induced Self-Assembly (PISA) Reduces Antibody Binding and Proteolytic Susceptibility," ACS Cent. Sci. 4 (6), 718-723.
Blackwell et al. (1998) "Highly Efficient Synthesis of Covalently Cross-Linked Peptide Helices by Ring-Closing Metathesis," Angew. Chem., Int. Ed. 37(23): 3281-3284.
Blanchet et al. (2001) "A new generation of Melan-A/MART-1 peptides that fulfill both increased immunogenicity and high resistance to biodegradation: implication for molecular anti-melanoma immunotherapy," J Immunol, 167 (10), 5852-61.
Blum et al. (2014) "Peptides Displayed as High Density Brush Polymers Resist Proteolysis and Retain Bioactivity," J. Am. Chem. Soc. 136 (43), 15422-15437. https://doi.org/10.1021/ja5088216.
Blum et al. (2015) "Stimuli-Responsive Nanomaterials for Biomedical Applications," J. Am. Chem. Soc. 137 (6), 2140-2154. https://doi.org/10.1021/ja510147n.
Blum et al. (2016) "Activating Peptides for Cellular Uptake via Polymerization into High Density Brushes," Chem. Sci. 7 (2), 989-994. https://doi.org/10.1039/c5sc03417e.
Blum et al. (Jan. 2022) "Stimuli Induced Uptake of Protein-Like Peptide Brush Polymers," Chem. Eur. J. 28, e202103438.
Blum et al. (Oct. 2019) "Peptide Brush Polymers for Efficient Delivery of a Gene Editing Protein to Stem Cells," Angew. Chem. Int. Ed. 58: 15646-15649.
Boeynaems et al. (2018) "Protein Phase Separation: A New Phase in Cell Biology," Trends Cell Biol 28:420-35. https://doi.org/10.1016/j.tcb.2018.02.004.
Boland et al. (2018) "Promoting the clearance of neurotoxic proteins in neurodegenerative disorders of aging," Nat Rev Drug Discov 17:660-88. https://doi.org/10.1038/nrd.2018.109.
Bolli et al. (1994) "α-Bicyclo-DNA: Synthesis, Characterization, and Pairing Properties of α-DNA-Analogues with Restricted

(56) References Cited

OTHER PUBLICATIONS

Conformational Flexibility in the Sugar-Phosphate Backbone," Chapter 7 in Carbohydrate Modifications in Antisense Research, Sanghvi and Cook, eds. pp. 100-117.

Bondeson et al. (2015) "Catalytic in vivo protein knockdown by small-molecule PROTACs," Nature Chemical Biology 11, 611-617.

Bonger et al. (2011) "Small-molecule displacement of a cryptic degron causes conditional protein degradation," Nat Chem Biol 7, 531-537.

Brangwynne (2013) "Phase transitions and size scaling of membrane-less organelles," J Cell Biol 2013;203:875-81. https://doi.org/10.1083/jcb.201308087.

Breaker (1997) "In Vitro Selection of Catalytic Polynucleotides," Chem. Rev. 97(2): 371-390.

Breaker et al. (1995) "Self-Incorporation of coenzymes by ribozymes," J. Mol. Evol. 40: 551-558.

Brinckerhoff et al. (1999) "Terminal modifications inhibit proteolytic degradation of an immunogenic mart-127-35 peptide: Implications for peptide vaccines," Int. J. Cancer 83(3): 326-334.

Brockhaus et al. (2007) "Thermodynamic studies on the interaction of antibodies with β-amyloid peptide," J Phys Chem B 2007;111:1238-43. https://doi.org/10.1021/jp0664059.

Broos et al. (2010) "Immunomodulatory nanoparticles as adjuvants and allergen-delivery system to human dendritic cells: Implications for specific immunotherapy," Vaccine, 28 (31), 5075-5085.

Broyer et al. (2008) "Designed Amino Acid ATRP Initiators for the Synthesis of Biohybrid Materials," J. Am. Chem. Soc. 130(3): 1041-1047.

Bulte et al. (2004) "Iron oxide MR contrast agents for molecular and cellular imaging," NMR Biomed. 17(7): 484-499.

Burke et al. (2010) "Synthesis and Characterization of Biodegradable HPMA-Oligolysine Copolymers for Improved Gene Delivery," Bioconjugate Chem. 21(1): 140-150.

Burslem et al. (2018) "The Advantages of Targeted Protein Degradation Over Inhibition: An RTK Case Study," Cell Chem Biol 25, 67-77.e63.

Burslem et al. (2020) "Proteolysis-Targeting Chimeras as Therapeutics and Tools for Biological Discovery," Cell 181:102-14. https://doi.org/10.1016/j.cell.2019.11.031.

Busseron et al. (May 2013) "Supramolecular self-assemblies as functional nanomaterials," Nanoscale 5: 7098-7140.

Cai et al. (2019) "Brusatol, an NRF2 inhibitor for future cancer therapeutic," Cell Biosci 9, 45. https://doi.org/10.1186/s13578-019-0309-8.

Cai et al. (2020) "Specific Degradation of Endogenous Tau Protein and Inhibition of Tau Fibrillation by Tanshinone IIA through the Ubiquitin-Proteasome Pathway," J Agric Food Chem 68:2054-62. https://doi.org/10.1021/acs.jafc.9b07022.

Caliceti et al. (2003) "Pharmacokinetic and biodistribution properties of poly(ethylene glycol)-protein conjugates," Adv. Drug Delivery Rev. 55(10): 1261-1277.

Callmann et al. (2015) "Therapeutic Enzyme-Responsive Nanoparticles for Targeted Delivery and Accumulation in Tumors," Adv Mater., 27(31):4611-4615. PMCID: PMC4699560.

Callmann et al. (Jan. 2020) "Poly(peptide): Synthesis, Structure, and Function of Peptide-Polymer Amphiphiles and Protein-like Polymers," Accounts Chem Res, 53 (2), 400-413.

Callmann et al. (Jul. 2019) "Antitumor Activity of 1,18-Octadecanedioic Acid-Paclitaxel Complexed with Human Serum Albumin," J Am Chem Soc., 141(30):11765-1769. DOI: 10.1021/jacs.9b04272. PMCID: PMC6676409.

Canning et al. (2015) "Structural basis of Keap1 interactions with Nrf2," Free Radic Biol Med, 88, part B, 101-107.

Canning et al. (2016) "A Critical Appraisal of RAFT-Mediated Polymerization-Induced SelfAssembly," Macromolecules, 49, 1985-2001.

Carbone et al. (2017) "First-line nivolumab in stage IV or recurrent non-small-cell lung cancer," New England Journal of Medicine, 376(25), 2415-2426. PMCID: PMC6487310.

Cardarelli (2011) "Quantitative Analysis of Tat Peptide Binding to Import Carriers Reveals Unconventional Nuclear Transport Properties," The Journal of Biological Chemistry 286(14): 12292-12299.

Carlini et al. (2019) "Enzyme-responsive progelator cyclic peptides for minimally invasive delivery to the heart post-myocardial infarction," Nat Commun 10:1-14. https://doi.org/10.1038/s41467-019-09587-y.

Carlini et al. (Mar. 2021) "pH-Responsive Charge-Conversion Progelator Peptides," Adv Funct Mater, 31(13), 2007733.

Carmean et al. (2017) "Ultra-High Molecular Weights via Aqueous Reversible-Deactivation Radical Polymerization," Chem, 2, 93-101.

Carreno et al. (2015) "A dendritic cell vaccine increases the breadth and diversity of melanoma neoantigen-specific T cells," Science, 348 (6236), 803-8.

Carrington et al. (2015) "Mussels as a Model System for Integrative Ecomechanics," Ann. Rev. Mar. Sci. 7, 443-469. https://doi.org/10.1146/ANNUREV-MARINE-010213-135049.

Cartier et al. (2002) "Utilization of synthetic peptides containing nuclear localization signals for nonviral gene transfer systems," Gene Ther. 9: 157-167.

Cavaco et al. (2020) "To What Extent Do Fluorophores Bias the Biological Activity of Peptides? A Practical Approach Using Membrane-Active Peptides as Models," Front. Bioeng. Biotechnol. 8, 552035.

Chang et al. (2014) "Functional Polyolefins Containing Disulfide and Phosphoester Groups: Synthesis and Orthogonal Degradation," Macromolecules. 47, 1344-1350.

Chang et al. (2015) "Blocking of the PD-1/PD-L1 Interaction by a D-Peptide Antagonist for Cancer Immunotherapy," Angew Chem Int Ed Engl, 54 (40), 11760-4.

Chartoumpekis et al. (2015) "Keap1/Nrf2 pathway in the frontiers of cancer and non-cancer cell metabolism," Biochem Soc Trans;43:639-44. https://doi.org/10.1042/BST20150049.

Chatterjee et al. (2008) "N-Methylation of Peptides: A New Perspective in Medicinal Chemistry," Acc. Chem. Res. 41(10): 1331-1342.

Chee et al. (Jul. 2018) "Biocompatible Peptide-Coated Ultrasmall Superparamagnetic Iron Oxide Nanoparticles for In Vivo Contrast-Enhanced Magnetic Resonance Imaging," ACS Nano, 12, 6480-6491.

Chen et al. (2005) "Biotin-Terminated Ruthenium Bipyridine Ring-Opening Metathesis Polymerization Copolymers: Synthesis and Self-Assembly with Streptavidin," Macromolecules, 38 (4), 1084-1090.

Chen et al. (2016) "Light-Controlled Radical Polymerization: Mechanisms, Methods, and Applications," Chem. Rev. 116, 10167-10211.

Chen et al. (2017) "Camptothecin suppresses NRF2-ARE activity and sensitises hepatocellular carcinoma cells to anticancer drugs," Br J Cancer, 117:1495-506. https://doi.org/10.1038/bjc.2017.317.

Chen et al. (2018) "Intrinsically Disordered Proteins: Structure, Function and Therapeutics," J Mol Biol 430, 2275-2277, doi:10.1016/j.jmb.2018.06.012.

Chen et al. (Feb. 2018) "RAFT polymerization of a RGD peptide-based methacrylamide monomer for cell adhesion," Polym. Chem., 9, 1780-1786.

Chen et al. (Jun. 2021) "High-Throughput Screening Test for Adhesion in Soft Materials Using Centrifugation," ACS Cent. Sci. acscentsci.1c00414. https://doi.org/10.1021/ACSCENTSCI.1C00414.

Cheng et al. (May 2019) "Endogenous Reactive Oxygen Species-Triggered Morphology Transformation for Enhanced Cooperative Interaction with Mitochondria," J. Am. Chem. Soc. 141, 7235-7239.

Chiappori et al. (Dec. 2018) "Randomized-controlled phase II trial of salvage chemotherapy after immunization with a TP53-transfected dendritic cell-based vaccine (Ad.p53-DC) in patients with recurrent small cell lung cancer," Cancer Immunol Immunother. PMID: 30591959.

Chien et al. (2010) "Programmable Shape-Shifting Micelles," Angew. Chem., Int. Ed. 49(30): 5076-5080.

Chien et al. (2012) "Fluorogenic enzyme-responsive micellar nanoparticles," Chem. Sci. 3(9): 2690-2694.

(56) References Cited

OTHER PUBLICATIONS

Chien et al. (Dec. 2013) "Enzyme-Directed Assembly of Nanoparticles in Tumors Monitored by in Vivo Whole Animal Imaging and ex Vivo Super-Resolution Fluorescence Imaging," J. Am. Chem. Soc. 135(50): 18710-18713.
Chien et al. (publicly available May 2013) "Enzyme-Directed Assembly of a Nanoparticle Probe in Tumor Tissue," Adv. Mater. (Jul. 2013), 25(26): 3599-3604.
Choi et al. (2003) "Controlled living ring-opening-metathesis polymerization by a fast-initiating ruthenium catalyst," Angew Chem Int Ed Engl, 42 (15), 1743-6.
Choi et al. (2009) "Human microtubule-associated-protein tau regulates the number of protofilaments in microtubules: A synchrotron X-ray scattering study," Biophys J 97:519-27. https://doi.org/10.1016/j.bpj.2009.04.047.
Choi et al. (2014) "Highly Purified Mussel Adhesive Protein to Secure Biosafety for in Vivo Applications," Microb. Cell Fact. 13 (1), 1-12. https://doi.org/10.1186/1475-2859-13-52.
Choi et al. (2020) "Biomolecular Densely Grafted Brush Polymers: Oligonucleotides, Oligosaccharides and Oligopeptides," Angew Chemie—Int Ed 59:19762-72. https://doi.org/10.1002/anie.202005379.
Choi et al. (2020) "Physical Principles Underlying the Complex Biology of Intracellular Phase Transitions," Annu Rev Biophys 49:107-33. https://doi.org/10.1146/annurev-biophys-121219-081629.
Chonn et al. (1995) "Recent advances in liposomal drug-delivery systems," Curr. Opin. Biotechnol. 6:698-708.
Chu (2019) "Pathological changes of tau related to alzheimer's disease," ACS Chem Neurosci 10:931-44. https://doi.org/10.1021/acschemneuro.8b00457.
Chu et al. (2012) "Cathepsin B-sensitive polymers for compartment-specific degradation and nucleic acid release," J. Controlled Release 157(3): 445-454.
Chu et al. (2015) "Multivalent display of pendant pro-apoptotic peptides increases cytotoxic activity," J. Control. Release., 205, 155-161.
Chu et al. (2016) "Specific Knockdown of Endogenous Tau Protein by Peptide-Directed Ubiquitin-Proteasome Degradation," Cell Chem Biol 23:453-61. https://doi.org/10.1016/j.chembiol.2016.02.016.
Chun et al. (2011) "Split GFP complementation assay for quantitative measurement of tau aggregation in situ," Methods Mol Biol 670, 109-123, doi:10.1007/978-1-60761-744-0_9.
Chung et al. (2015) "Direct force measurements reveal that protein Tau confers short-range attractions and isoform-dependent steric stabilization to microtubules," Proc Natl Acad Sci U S A 112:E6416-25. https://doi.org/10.1073/pnas.1513172112.
Chung et al. (2016) "Tau mediates microtubule bundle architectures mimicking fascicles of microtubules found in the axon initial segment," Nat Commun 7:1-9. https://doi.org/10.1038/ncomms12278.
Cieslewicz et al. (2013) "Targeted delivery of proapoptotic peptides to tumor-associated macrophages improves survival," Proc. Nat.l. Acad. Sci. USA, 110, 15919-15924.
Ciryam et al. (2013) "Neurodegenerative Diseases and Widespread Aggregation Are Associated with Supersaturated Proteins," Cell Rep 5:781-90. https://doi.org/10.1016/j.celrep.2013.09.043.
Ciryam et al. (2015) "Supersaturation is a major driving force for protein aggregation in neurodegenerative diseases," Trends Pharmacol Sci 36:72-7. https://doi.org/10.1016/j.tips.2014.12.004.
Clarke et al. (2000) "Characterization ofthe ovalbumin-specific TCR transgenic line OT-I: MHC elements for positive and negative selection," ImmunolCell Biol, 78(2), 110-7.
Cleveland et al. (1977) "Physical and chemical properties of purified tau factor and the role of tau in microtubule assembly," J Mol Biol 116:227-47. https://doi.org/10.1016/0022-2836(77)90214-5.
Cogan et al. (2017) "Topical Delivery of Anti-VEGF Drugs to the Ocular Posterior Segment Using Cell-Penetrating Peptides," IVOS., 58, 2578-2590.
Colarusso et al. (Nov. 2020) "Optimization of linear and cyclic peptide inhibitors of KEAP1-NRF2 protein-protein interaction," Bioorganic & Medicinal Chemistry. vol. 28, No. 21; DOI: 10.1016/j.bmc.2020.115738.
Conejo-Garcia et al. (2004) "Tumor infiltrating dendritic cell precursors recruited by a b-defensin contribute to vasculogenesis under the influence of Vegf-A," Nat Med; 10:950-958.
Congdon et al. (2018) "Tau-targeting therapies for Alzheimer disease," Nat Rev Neurol 14:399-415. https://doi.org/10.1038/s41582-018-0013-z.
Conicella et al. (2016) "ALS Mutations Disrupt Phase Separation Mediated by α-Helical Structure in the TDP-43 Low-Complexity C-Terminal Domain," Structure 24:1537-49. https://doi.org/10.1016/j.str.2016.07.007.
Conlon et al. (2013) "Mouse, but not human STING, binds and signals in response to the vascular disrupting agent 5,6-dimethylxanthenone-4-acetic acid," J Immunol, 190(10), 5216-25.
Conrad et al. (2009) "Tunable, Temperature-Responsive Polynorbornenes with Side Chains Based on an Elastin Peptide Sequence," Angew. Chem. Int. Edit. 48(44): 8328-8330.
Corrales et al. (2015) "Direct Activation of STING in the Tumor Microenvironment Leads to Potent and Systemic Tumor Regression and Immunity," CellRep, 11 (7), 1018-30.
Corrigan et al. (Apr. 2019) "Seeing the Light: Advancing Materials Chemistry through Photopolymerization," Chem. Int. Ed. 58, 5170-5189.
Cottet et al. (2008) "Separation of Synthetic (Co)Polymers by Capillary Electrophoresis Techniques," Methods Mol. Biol. 384, 541-567. https://doi.org/10.1007/978-1-59745-376-9_21.
Coulthard et al. (2015) "Is the Complement Activation Product C3a a Proinflammatory Molecule? Re-Evaluating the Evidence and the Myth," J. Immunol. 194 (8), 3542-3548. https://doi .org/10.4049/jimmunol.1403068.
Couly et al. (2018) "Improvement of BDNF Signaling by P42 Peptide in Huntington's Disease," Hum. Mol. Genet. 27 (17), 3012-3028.
Craik et al. (publicly available Dec. 2012) "The Future of Peptide-based Drugs," Chem. Biol. Drug Des. (Jan. 2013), 81(1): 136-147.
Creelan et al. (2015) "Safety and tolerability results from a phase I study of MEDI4736, a human IgG1 anti-programmed cell death-ligand-1 (PD-L1) antibody, combined with gefitinib in patients with non-small-cell lung cancer," Journal of Clinical Oncology 33, 15S: 3047.
Creelan et al. (Aug. 2013) "Phase II trial of a GM-CSF-producing and CD40L expressing bystander cell line combined with an allogeneic tumor cell-based vaccine for refractory lung adenocarcinoma." Journal of Immunotherapy. 36(8); 442-450. PMCID: PMC3846277.
Creelan et al. (Aug. 2017) "Safety, pharmacokinetics, and pharmacodynamics of oral omaveloxolone, a synthetic triterpenoid, in a first-in-human trial of patients with advanced solid tumors," Onco Targets Ther. 10:4239-50. PMCID: PMC5587199.
Creelan et al. (Aug. 2020) "Abstract CT056: Durable complete responses to adoptive cell transfer using tumor infiltrating lymphocytes (TIL) in nonsmall cell lung cancer (NSCLC): a phase I trial," AACR Annual meeting. Late Breaking and Clinical Trials. Cancer Res (2020) 80 (16_Supplement): CT056.
Creelan et al. (Mar. 2013) "Indoleamine 2,3-dioxygenase activity and clinical outcome following induction chemotherapy and concurrent chemoradiation in stage III non-small cell lung cancer," Oncolmmunology . 1;2(3). PMCID: PMC3661168.
Creelan et al. (May 2017) "Two phase I/II open label clinical trials evaluating the safety and efficacy of autologous T cells expressing enhanced TCRs specific for NY-ESO-1 or MAGE-A10 in subjects with stage IIIb or stage IV non-small cell lung cancer (NCT02588612/NCT02592577)," TPS3096 Journal of Clinical Oncology 35, No. 15_suppl.
Creelan et al. (Sep. 2018) "OA05. 03 Safety and Clinical Activity of Adoptive Cell Transfer Using Tumor Infiltrating Lymphocytes (TIL) Combined with Nivolumab in NSCLC," Journal of Thoracic Oncology, 13(10), pp. S330-S331.
Croy et al. (2004) "Biophysical characterization of the free IκBα ankyrin repeat domain in solution," Protein Science, 13, 1767.

(56) References Cited

OTHER PUBLICATIONS

Cuadrado et al. (2019) "Therapeutic targeting of the NRF2 and KEAP1 partnership in chronic diseases," Nat Rev Drug Discov, 295-317. https://doi.org/10.1038/s41573-018-0008-x.
Cubillos-Ruiz et al. (2009) "Polyethylenimine-based siRNA nanocomplexes reprogram tumor-associated dendritic cells via TLR5 to elicit therapeutic antitumor immunity," J Clin Invest; 119:2231-2244. PMC2719935.
Cubillos-Ruiz et al. (2015) "ER Stress Sensor XBP1 Controls Anti-tumor Immunity by Disrupting Dendritic Cell Homeostasis," Cell: 1527-1538. PMC4580135.
Cummings et al. (May 2021) "Alzheimer's disease drug development pipeline: 2021," Alzheimer's Dement Transl Res Clin Interv 2021;7:1-24. https://doi.org/10.1002/trc2.12179.
Curiel et al. (2004) "Specific recruitment of regulatory T cells in ovarian carcinoma fosters immune privilege and predicts reduced survival," Nat Med; 10:942-949.
Cutler et al. (2012) "Spherical Nucleic Acids," J. Am. Chem. Soc. 134(3): 1376-1391.
Dai et al. (2017) "Near-IR-induced dissociation of thermally-sensitive star polymers," Chem. Sci, 8, 1815-1821.
Dalsin et al. (2003) "Mussel Adhesive Protein Mimetic Polymers for the Preparatioono of Nonfouling Surfaces," J. Am. Chem. Soc. 125 (14), 4253-4258.
Dang (2012) "MYC on the path to cancer," Cell 149, 22-35.
Darden et al. (1993) "Particle mesh Ewald: An N•log(N) method for Ewald sums in large systems," J. Chem. Phys. 98(12): 10089-10092.
Davies et al. (2001) "Synthesis of nucleic-acid base containing norbornene derivatives as monomers for ring-opening-metathesis-polymerization," J. Chem. Soc., Perkin Trans. 1 24: 3365-3381.
Davis (2002) "Non-viral gene delivery systems," Curr. Opin. Biotechnol. 13(2): 128-131.
De et al. (2008) "Temperature-Regulated Activity of Responsive Polymer-Protein Conjugates Prepared by Grafting-from via RAFT Polymerization," J. Am. Chem. Soc. 130(34): 11288-11289.
De Gregorio et al. (2009) "Immunology of TLR-independent vaccine adjuvants," Curr OpinImmunol, 21 (3), 339-45.
De Jong et al. (2016) "Martini straight: Boosting performance using a shorter cutoff and GPUs," Comput. Phys. Commun. 199, 1-7.
Debelle et al. (1999) "Elastin: Molecular Description and Function," International Journal of Biochemistry and Cell Biology. Pergamon, pp. 261-272. https://doi.org/10.1016/S1357-2725(98)00098-3.
Debsharma et al. (Mar. 2019) "Ring-Opening Metathesis Polymerization of Biomass-Derived Levoglucosenol," Angew. Chem. Int. Edit. 58, 6718-6721.
Delplace et al. (2015) "Degradable vinyl polymers for biomedical applications," Nat. Chem. 7, 771-784.
Demaria et al. (2015) "STING activation of tumorendothelial cells initiates spontaneous and therapeutic antitumor immunity," Proc Natl Acad Sci U S A, 112(50), 15408-13.
Deming (1999) "Mussel Byssus and Biomolecular Materials," Curr. Opin. Chem. Biol. 3 (1), 100-105. https://doi.org/10.1016/S1367-5931(99)80018-0.
Deng et al. (2005) "DNA as Nanoscale Building Blocks," J. Nanosci. Nanotechnol. 5(12): 1954-1963.
Devos et al. (2018) "Tau reduction in the presence of amyloid-β prevents tau pathology and neuronal death in vivo," Brain 141:2194-212. https://doi.org/10.1093/brain/awy117.
Dietz et al. (2009) "Folding DNA into Twisted and Curved Nanoscale Shapes," Science 325(5941): 725-730.
Dinkova-Kostova et al. (2018) "The role of Nrf2 signaling in counteracting neurodegenerative diseases," FEBS J. 3576-3590.
Doherty et al. (2009) "Mechanisms of Endocytosis," Annu. Rev. Biochem. 78: 31.1-31.46 and Supplementary Information (69 pp. total).
Dominguez et al. (2017) "Exogenous IL-33 Restores Dendritic Cell Activation and Maturation in Established Cancer," J Immunol, 198 (3), 1365-1375.
Doncom et al. (2017) "Dispersity effects in polymer self-assemblies: a matter of hierarchical control," Chem. Soc. Rev. 46, 4119-4134.
Draeger et al. (1994) "Interaction of the bHLH-zip domain of c-Myc with H1-type peptides. Characterization of helicity in the H1 peptides by NMR," J Biol Chem 269, 1785-1793.
Drucker (Apr. 2020) "Advances in oral peptide therapeutics," Nat. Rev. Drug Discov. 19, 277-289.
Dubertret et al. (2001) "Single-mismatch detection using gold-quenched fluorescent oligonucleotides," Nat. Biotechnol. 19: 365-370.
Dumetz et al. (2008) "Protein phase behavior in aqueous solutions: Crystallization, liquid-liquid phase separation, gels, and aggregates," Biophys J 94:570-83. https://doi.org/10.1529/biophysj.107.116152.
Dutta et al. (2017) "Templated Self-Assembly of a Covalent Polymer Network for Intracellular Protein Delivery and Traceless Release," J. Am. Chem. Soc., 139, 5676-5679.
Dzuricky et al. (2020) "De novo engineering of intracellular condensates using artificial disordered proteins," Nat Chem 12:814-25. https://doi.org/10.1038/s41557-020-0511-7.
Eisenreich et al. (Jul. 2018) "A photoswitchable catalyst system for remote- controlled (co)polymerization in situ," Nat. Catal. 1, 516-522.
Elices et al. (2011) "Bioinspired Fibers Follow the Track of Natural Spider Silk," Macromolecules, 44 (5), 1166-1176. https://doi.org/10.1021/ma102291m.
Elling et al. (2020) "Degradable Polyacetals/Ketals from Alternating Ring-Opening Metathesis Polymerization," ACS Macro Lett. 9:180-4.
Engelhardt et al. (2000) "Capillary Electrophoresis in Polymer Analysis," Adv. Polym. Sci. 150, 189-217. https://doi.org/10.1007/3-540-48764-6_3.
Escriou et al. (2003) "NLS bioconjugates for targeting therapeutic genes to the nucleus," Adv. Drug Delivery Rev. 55(2): 295-306.
Essmann et al. (1995) "A smooth particle mesh Ewald method," J. Chem. Phys. 103(19): 8577-8593.
Evans et al. (Jul. 2018) "Seeded Growth of Single-Crystal Two-Dimensional Covalent Organic Frameworks," Science, 361(6397):52-57. PMID: 29930093. DOI: 10.1126/science.aar7883.
Evans et al. (Mar. 2022) "Protein complex prediction with AlphaFold-Multimer," bioRxiv, 2021.10.04.463034.
Extended European Search Report, dated May 3, 2024, corresponding to European Application No. 21797853, 9 pp.
Eyles et al. (1997) "Oral Delivery and Fate of Poly(lactic acid) Microsphere-encapsulated Interferon in Rats," J. Pharm. Pharmacol. 49: 669-674.
Fahnestock et al. (1997) "Production of Synthetic Spider Dragline Silk Protein in Pichia Pastoris," Appl. Microbiol. Biotechnol. 47 (1), 33-39. https://doi.org/10.1007/s002530050884.
Fairbanks et al.(2015) "Biomedical applications of polymers derived by reversible addition—fragmentation chain-transfer (RAFT)," Adv. Drug Deliver. Rev. 91, 141-152.
Falciani et al. (2007) "Molecular Basis of Branched Peptides Resistance to Enzyme Proteolysis," Chem. Biol. Drug Des. 69(3): 216-221.
Falo et al. (1992) "Serum proteases alter the antigenicity of peptides presented by class I major histocompatibility complex molecules," Proc Natl Acad Sci U S A, 89(17), 8347-50.
Fan et al. (2017) "Two-Dimensional Controlled Syntheses of Polypeptide Molecular Brushes via N-Carboxyanhydride Ring-Opening Polymerization and Ring-Opening Metathesis Polymerization," Acs Macro Lett. 6:1031-5.
Fantin et al. (2005) "A Bifunctional Targeted Peptide that Blocks HER-2 Tyrosine Kinase and Disables Mitochondrial Function in HER-2-Positive Carcinoma Cells," Cancer Res. 65, 6891-6900.
Farah et al. (2016) "Physical and mechanical properties of PLA, and their functions in widespread applications—A comprehensive review," Adv. Drug. Deliv. Rev. 107, 367-392.
Farokhzad et al. (2004) "Nanoparticle-Aptamer Bioconjugates: A New Approach for Targeting Prostate Cancer Cells," Cancer Res. 64(21): 7668-7672.

(56) References Cited

OTHER PUBLICATIONS

Farrell et al. (2014) "MYC degradation," Cold Spring Harb Perspect Med 4.
Fattah et al. (Aug. 21, 2022) "Mutant Huntingtin Mimetic Anti-Huntington's Protein-like Polymer Blocks Valosin Containing Protein Binding, Rescues HD Neurons, and Slows Onset of Neuropathology In Vivo," Presentation at the ACS Meetings & Expos, Chicago, IL.
Fattah et al. (Jun. 15, 2024 and Jun. 18, 2024) "Mutant Huntingtin Mimetic Anti-Huntington's Protein-like Polymer Blocks Valosin Containing Protein Binding, Rescues HD Neurons, and Slows Onset of Neuropathology In Vivo," Bioninspired materials gordon research seminar/conference, oral presentation and poster.
Fattah et al. (Oct. 29, 2022 and Oct. 31, 2022) "Mutant Huntingtin Mimetic Anti-Huntington's Protein-like Polymer Blocks Valosin Containing Protein Binding, Rescues HD Neurons, and Slows Onset of Neuropathology In Vivo," Chemistry and biology of peptides Gordon Research Seminar/Conference, oral presentation and poster.
Feig et al. (2018) "Biodegradable Polymeric Materials in Degradable Electronic Devices," ACS Cent. Sci. 4, 337-348.
Feist et al. (Dec. 2019) "Enol Ethers Are Effective Monomers for Ring-Opening Metathesis Polymerization: Synthesis of Degradable and Depolymerizable Poly(2,3-dihydrofuran)," J. Am. Chem. Soc. 142, 1186-1189.
Feng et al. (1988) "HIV-1 Tat Trans-Activation Requires the Loop Sequence within Tar," Nature, 334 (6178), 165-167. https://doi.org/10.1038/334165a0.
Fernández-Trillo et al. (2007) "Elastin-Based Side-Chain Polymers: Improved Synthesis via RAFT and Stimulus Responsive Behavior," Macromolecules, 40, 17, 6094-6099.
Ferrara et al. (2016) "Ten years of anti-vascular endothelial growth factor therapy," Nat Rev Drug Discov. 15(6), 385-403.
Fichman et al. (2014) "Seamless Metallic Coating and Surface Adhesion of Self-Assembled Bioinspired Nanostructures Based on Di-(3,4-Dihydroxy-I-Phenylalanine) Peptide Motif," ACS Nano, 8 (7), 7220-7228. https://doi.org/10.1021/nn502240r.
Figenschau et al. (Aug. 2018) "ICAM1 Expression is Induced by Proinflammatory Cytokines and Associated with TLS Formation in Aggressive Breast Cancer Subtypes," Sci Rep 8, 11720.
Figg et al. (2015) "Polymerization-induced thermal self-assembly (PITSA)," Chem. Sci. 6, 1230-1236.
Figg et al. (2017) "Tuning Hydrophobicity To Program Block Copolymer Assemblies from the Inside Out," Macromolecules, 50 (3), 935-943.
Fishman et al. (2013) "Synthesis of Functionalizable and Degradable Polymers by Ring-Opening Metathesis Polymerization," Angew. Chem. Int. Edit. 52, 5061-5064.
Fishman et al. (Jan. 2019) "Chemoselective, Postpolymerization Modification of Bioactive, Degradable Polymers," Biomacromolecules. 20, 1018-1027.
Flanders et al. (Apr. 2018) "Reversible-addition fragmentation chain transfer (RAFT) mediated depolymerization of brush polymers," Polym. Chem. 9, 2328-2335.
Fletcher et al. (2015) "Small-molecule inhibitors of the Myc oncoprotein," Biochim Biophys Acta 1849, 525-543.
Foret et al. (2019) "Effect of antioxidant supplements on lipid peroxidation levels in primary cortical neuron cultures," Free Radical Biology and Medicine, vol. 130, 471-477.
Fosgerau et al. (2015) "Peptide Therapeutics: Current Status and Future Directions," Drug Discovery Today. 20(1), 122-128. https://doi.org/10.1016/j.drudis.2014.10.003.
Foster et al. (Aug. 2018) "Ring-Opening Metathesis Polymerization in Aqueous Media Using a Macroinitiator Approach," Angew. Chem. Int. Ed. 57, 10672-10676.
Fraley et al. (2006) "Cationic Oligonucleotide-Peptide Conjugates with Aggregating Properties Enter Efficiently into Cells while Maintaining Hybridization Properties and Enzymatic Recognition," J. Am. Chem. Soc. 128(33): 10763-10771.
Franco-Iborra et al. (2018) "Mitochondrial Quality Control in Neurodegenerative Diseases: Focus on Parkinson's Disease and Huntington's Disease," Front. Neurosci. 12(342), 1-25.
Frank (2014) "Treatment of Huntington's Disease," Neurotherapeutics, 11 (1), 153-160.
Frankel et al. (1988) "Cellular uptake of the tat protein from human immunodeficiency virus," Cell 55(6): 1189-1193.
Fraser et al. (1995) "Degradable Cyclooctadiene Acetal Copolymers—Versatile Precursors to 1,4-Hydroxytelechelic Polybutadiene and Hydroxytelechelic Polyethylenem" Macromolecules. 28, 7256-7261.
Fu et al. (2015) "STING agonist formulated cancer vaccines can cure established tumors resistant to PD-1 blockade," Sci Transl Med, 7 (283), 283ra52.
Fu et al. (2016) "Photoacid-mediated ring opening polymerization driven by visible light," Chem. Commun. 52, 7126-7129.
Fu et al. (2018) "Relay Conjugation of Living Metathesis Polymers," J. Am. Chem. Soc. 140, 12181-12188.
Fu et al. (Sep. 2019) "Modular Approach to Degradable Acetal Polymers Using Cascade Enyne Metathesis Polymerization," Angew. Chem. Int. Edit. 58, 15726-15730.
Fukutomi et al. (2014) "Kinetic, Thermodynamic, and Structural Characterizations of the Association between Nrf2-DLGex Degron and Keap1," Mol. Cell. Biol., 34(5): 832-846.
Futaki et al. (2001) "Arginine-rich Peptides: An Abundant Source of Membrane-Permeable Peptides Having Potential as Carriers for Intracellular Protein Delivery," J. Biol. Chem. 276(8): 5836-5840.
Gabr et al. (2020) "Dual Targeting of Monomeric Tau and α-Synuclein Aggregation: A New Multitarget Therapeutic Strategy for Neurodegeneration," ACS Chem Neurosci 11:2051-7. https://doi.org/10.1021/acschemneuro.0c00281.
Gameiro et al. (2017) "Discovery of the first dual GSK3B inhibitor/Nrf2 inducer. A new multitarget therapeutic strategy for Alzheimer's disease," Scientific Reports vol. 7, Article No. 45701.
Gao et al. (1995) "Controlled Release of a Contraceptive Steroid from Biodegradable and Injectable Gel Formulations: In Vitro Evaluation," Pharm. Res. 12(6): 857-863.
Gao et al. (2017) "Hydrophobic tagging-mediated degradation of Alzheimer's disease related Tau," RSC Adv 7:40362-6. https://doi.org/10.1039/c7ra05347a.
Gaudet (2008) "A primer on ankyrin repeat function in TRP channels and beyond," Mol. BioSyst., 4, 372.
Gaylord et al. (2002) "DNA detection using water-soluble conjugated polymers and peptide nucleic acid probes," Proc. Natl. Acad. Sci. U.S.A. 99(17): 10954-10957.
Gentilucci et al. (2010) "Chemical Modifications Designed to Improve Peptide Stability: Incorporation of Non-Natural Amino Acids, Pseudo-Peptide Bonds, and Cyclization," Curr. Pharm. Design, 16, 3185-3203.
Georgakopoulos et al. (2018) "Modified Peptide Inhibitors of the Keap1-Nrf2 Protein-Protein Interaction Incorporating Unnatural Amino Acids," ChemBioChem, 19, 1810-1816.
Ghose et al. (2011) "Regulation of MIR-146a by RelA/NFKB and p53 in STHdh Q111 /Hdh Q111 Cells, a Cell Model of Huntington's Disease," PLoS One, 6 (8). https://doi.org/10.1371/journal.pone.0023837.
Giacomello et al. (Apr. 2020) "The cell biology of mitochondrial membrane dynamics," Nat. Rev. Mol. Cell Bio. 21, 204-224.
Gibbs et al. (2005) "Polymer-DNA Hybrids as Electrochemical Probes for the Detection of DNA," J. Am. Chem. Soc. 127(4): 1170-1178.
Gibson et al. (1997) "Thymine functionalised polymers via living ring-opening metathesis polymerisation," Chem. Commun. 12: 1095-1096.
Gibson et al. (Jun. 2021) "Lifetime Neuropsychiatric Symptoms in Huntington's disease: Implications for Psychiatric Nursing," Arch. Psychiatr. Nurs. 35 (3), 284-289.
Giorello et al. (1998) "Inhibition of cancer cell growth and c-Myc transcriptional activity by a c-Myc helix 1-type peptide fused to an internalization sequence," Cancer Res 58, 3654-3659.
Gnanasekaran et al. (2020) "In Situ Ni2+ Stain for Liposome Imaging by Liquid-Cell Transmission Electron Microscopy," (2020) Nano Lett 20:4292-7. https://doi.org/10.1021/acs.nanolett.0c00898.

(56) References Cited

OTHER PUBLICATIONS

Goa et al. (2020) "PROTAC Technology: Opportunities and Challenges," ACS Medicinal Chemistry Letters 11, 237-240.
Golder et al. (2018) "Brush-First and ROMP-Out with Functional (Macro)monomers: Method Development, Structural Investigations, and Applications of an Expanded Brush-Arm Star Polymer Platform," Macromolecules, 51 (23), 9861-9870.
Gorantla et al. (2018) Tau Protein Squired by Molecular Chaperones During Alzheimer's Disease. J Mol Neurosci 66:356-68. https://doi.org/10.1007/s12031-018-1174-3.
Gordon et al. (2001) "Inhibition of β-Amyloid(40) Fibrillogenesis and Disassembly of β-Amyloid(40) Fibrils by Short β-Amyloid Congeners Containing N-Methyl Amino Acids at Alternate Residues," Biochemistry 40(28): 8237-8245.
Gray et al. (Sep. 2018) "A phase I/randomized phase II study of GM.CD40L vaccine in combination with CCL21 in patients with advanced lung adenocarcinoma," Cancer Immunol Immunother. 67:1853-1862.
Grazon et al. (Oct. 2020) "Aqueous Ring-Opening Polymerization-Induced Self-Assembly (ROPISA) of N-Carboxyanhydrides," Angew. Chem. Int. Ed. 59, 622-626.
Green et al. (1988) "Autonomous functional domains of chemically synthesized human immunodeficiency virus tat trans-activator protein," Cell 55(6): 1179-1188.
Greenfield (2007) "Using circular dichroism spectra to estimate protein secondary structure," Nat Protoc 1:2876-90. https://doi.org/10.1038/nprot.2006.202.
Greenwald et al. (1996) "Drug Delivery Systems: Water Soluble Taxol 2'-Poly(ethylene glycol) Ester ProdrugsDesign and in Vivo Effectiveness," J. med. chem., 39, 424-431.
Griner et al. (2019) "Structure based inhibitors of amyloid beta core suggest a common interface with Tau," Elife 8:1-28. https://doi.org/10.7554/eLife.46924.
Gu et al. (2009) "Dynamic patterning programmed by DNA tiles captured on a DNA origami substrate," Nat. Nanotechnol. 4: 245-248.
Gu et al. (2010) "A proximity-based programmable DNA nanoscale assembly line," Nature 465: 202-205.
Gubin et al. (2014) "Checkpoint blockade cancer immunotherapy targets tumour-specific mutant antigens," Nature, 515 (7528), 577-81.
Guidotti et al. (2017) "Cell-Penetrating Peptides: From Basic Research to Clinics," Trends Pharmacol. Sci. 38, 406-424.
Guo et al. (2013) "Therapeutic cancer vaccines: past, present, and future," Adv Cancer Res, 119, 421-75.
Guo et al. (2016) "VCP Recruitment to Mitochondria Causes Mitophagy Impairment and Neurodegeneration in Models of Huntington's Disease," Nat. Commun. 7, 12646.
Guo et al. (2017) "VCP Cooperates with UBXD1 to Degrade Mitochondrial Outer Membrane Protein MCL 1 in Model of Huntington's Disease," Biochim. Biophys. Acta—Mo/. Basis Dis. 1863 (2), 552-559. https://doi.org/10.1016/j.bbadis.2016.11.026.
Guo et al. (Jul. 2018) Neoantigen Vaccine Delivery for Personalized Anticancer Immunotherapy, Front Immunol. 9:1499.
Gupta et al. (Aug. 2021) "Demethyleneberberine : A Possible Treatment for Huntington's disease," Medical Hypotheses. 153, 110639.
Hahn et al. (Apr. 2013) "Polymerization of a peptide-based enzyme substrate," Chem Commun (Camb) 49(28): 2873-2875 (8 pp.).
Hamamoto et al. (2002) "Antimicrobial Activity and Stability to Proteolysis of Small Linear Cationic Peptides with D-Amino Acid Substitutions," Microbiol. Immunol. 46(11): 741-749.
Hamley (2012) "The amyloid beta peptide: A chemist's perspective. role in Alzheimer's and fibrillization," Chem Rev 112:5147-92. https://doi.org/10.1021/cr3000994.
Han et al. (2019) "Small-Molecule MYC Inhibitors Suppress Tumor Growth and Enhance Immunotherapy," Cancer Cell 36, 483-497. e415.
Han et al. (Oct. 2021) "Proteolysis targeting chimera technology : a novel strategy for treating diseases of the central nervous system" Neural Regeneration Research 16:1944-9.
Hanahan (Jan. 2022) "Hallmarks of Cancer: New Dimensions," Cancer Discov 12, 31-46, doi:10.1158/2159-8290.CD-21-1059.
Hanahan et al. (2011) "Hallmarks of cancer: the next generation," Cell, 144(5), 646-674.
Hancock et al. (2012) "Peptide inhibitors of the Keap1-Nrf2 protein-protein interaction," Free Radical Biology & Medicine 52, 444-451.
Hancock et al. (2013) "Peptide inhibitors of the Keap1-Nrf2 protein-protein interaction with improved binding and cellular activity," Org. Biomol. Chem., 11, 3553.
Hanlon et al. (2017) "Scalable Synthesis of Single-Chain Nanoparticles under Mild Conditions," Macromolecules 50:2996-3003. https://doi.org/10.1021/acs.macromol.7b00497.
Hanover et al. (1984) "Kinetics of transit of transferrin and epidermal growth factor through clathrin-coated membranes," Cell 39(2): 283-293.
Hansson et al. (1999) "Transgenic Mice Expressing a Huntington's Disease Mutation Are Resistant to Quinolinic Acid-Induced Striatal Excitotoxicity," Proc. Natl. Acad.Sci. 96 (15), 8727-8732. https://doi.org/10.1073/pnas.96.15.8727.
Harris et al. (1990) "Bioadhesive Polymers in Peptide Drug Delivery," Biomaterials, 11 (9), 652-658. https://doi.org/10.1016/0142-9612(90)90023-J.
Hartley et al. (1999) "Protofibrillar intermediates of amyloid β-protein induce acute electrophysiological changes and progressive neurotoxicity in cortical neurons," J Neurosci 19:8876-84. https://doi.org/10.1523/jneurosci.19-20-08876.1999.
Hastings et al. (2011) "Disulfide reduction in the endocytic pathway: immunological functions of gamma-interferon-inducible lysosomal thiol reductase," Antioxid Redox Signal, 15 (3), 657-68.
He et al. (2009) "Synthesis of Surface-Anchored DNA-Polymer Bioconjugates Using Reversible Addition-Fragmentation Chain Transfer Polymerization," Biomacromolecules 10(7): 1804-1809.
Heidebrecht et al. (2013) "Recombinant Production of Spider Silk Proteins," In Advances in Applied Microbiology; Academic Press Inc., vol. 82, pp. 115-153. https://doi.org/10.1016/B978-0-12-407679-2.00004-1.
Heitz et al. (2009) "Twenty years of cell-penetrating peptides: from molecular mechanisms to therapeutics," Br. J. Pharmacol. 157(2): 195-206.
Hejl et al. (2005) "Ring-opening metathesis polymerization of functionalized low-strain monomers with ruthenium-based catalysts," Macromolecules. 38, 7214- 7218.
Hellmann et al. (2014) "Smoking History and Response to Nivolumab in Patients with Advanced NSCLC," Annals of Oncology 25, S4 426-70, 1229PD.
Hellmann et al. (Apr. 2018) "Genomic Features of Response to Combination Immunotherapy in Patients with Advanced Non-Small-Cell Lung Cancer," Cancer Cell. pii: S1535-6108(18)30123-5. PMCID: PMC5953836.
Henikoff et al. (1992) "Amino acid substitution matrices from protein blocks," Proc. Nat'l Acad. Sci. USA 89(22): 10915-10919.
Henninot et al. (Feb. 2018) "The Current State of Peptide Drug Discovery: Back to the Future?," J. Med. Chem. 61, 1382-1414.
Herdewijn et al. (1994) "Hexopyranosyl-Like Oligonucleotides," Chapter 6 in Carbohydrate Modifications in Antisense Research, Sanghvi and Cook, eds. pp. 80-99.
Heredia et al. (2005) "In Situ Preparation of Protein-'Smart' Polymer Conjugates with Retention of Bioactivity," J. Am. Chem. Soc. 127(48): 16955-16960.
Hermann et al. (2000) "Adaptive Recognition by Nucleic Acid Aptamers," Science 287(5454): 820-825.
Hess et al. (2008) "GROMACS 4: Algorithms for Highly Efficient, Load Balanced, and Scalable Molecular Simulation," J. Chem. Theory Comput. 4, 435-447.
Hilf et al. (2008) "End capping ring-opening olefin metathesis polymerization polymers with vinyl lactones," J Am Chem Soc 130, 11040-11048, doi:10.1021/ja8022863.
Hilf et al. (2009) "Functional end groups for polymers prepared using ring-opening metathesis polymerization," Nature Chemistry, 1 (7), 537-546.

(56)     References Cited

OTHER PUBLICATIONS

Hill et al. (2015) "Expanding the Scope of RAFT Polymerization: Recent Advances and New Horizons," Macromolecules, 48, 5459-5469.

Hill et al. (2018) "Alternating Radical Ring-Opening Polymerization of Cyclic Ketene Acetals: Access to Tunable and Functional Polyester Copolymers," Macromolecules. 51, 5079-5084.

Hillmyer et al. (2014) "Aliphatic Polyester Block Polymers: Renewable, Degradable, and Sustainable," Acc. Chem. Res. 47, 2390-2396.

Hlil et al. (2017) "Ring Opening Metathesis Polymerization (ROMP) of Five-to Eight-Membered Cyclic Olefins: Computational, Thermodynamic, and Experimental Approach," J. Polym. Sci. Pol. Chem. 55, 3137-3145.

Hong et al. (2020) "Behavior control of membrane-less protein liquid condensates with metal ion-induced phase separation," Nat Commun 11:1-12. https://doi.org/10.1038/s41467-020-19391-8.

Hopewell et al. (1995) "The nerve growth factor-responsive PC12 cell line does not express the Myc dimerization partner Max," Mol Cell Biol 15, 3470-3478.

Horsch et al. (2018) "Polymerizing Like Mussels Do: Toward Synthetic Mussel Foot Proteins and Resistant Glues," Angew. Chemie, 130 (48), 15954-15958. https://doi.org/10.1002/ange.201809587.

Houston et al. (2017) "Development of β-Hairpin Peptides for the Measurement of SCF-Family E3 Ligase Activity in Vitro via Ornithine Ubiquitination," ACS Omega 2, 1198-1206.

Hua et al. (Jul. 2018) "Current Trends and Challenges in the Clinical Translation of Nanoparticulate Nanomedicines: Pathways for Translational Development and Commercialization," Front Pharmacol. 9, 790.

Huang et al. (2017) "Single Molecule Study of Force-Induced Rotation of Carbon-Carbon Double Bonds in Polymers," ACS Nano. 11, 194-203.

Huang et al. (2018) "Radical Cascade-Triggered Controlled Ring-Opening Polymerization of Macrocyclic Monomers," J. Am. Chem. Soc. 140, 10402-10406.

Huang et al. (Jan. 2017) "CHARMM36m: An Improved Force Field for Folded and Intrinsically Disordered Proteins," Nat. Meth. 14 (1), 71-73.

Huang et al. (May 2017) "Mimicking Melanosomes: Polydopamine Nanoparticles as Artificial Microparasols," ACS Cent Sci., 3(6):564-569. https://doi.org/10.1021/acscentsci.6b00230.

Hubbers et al. (2007) "Pathological Consequences of VCP Mutations on Human Striated Muscle," Brain, 130 (2), 381-393.https://doi.org/10.1093/brain/aw1238.

Huemmerich et al. (2004) "Novel Assembly Properties of Recombinant Spider Dragline Silk Proteins," Curr. Biol. 14 (22), 2070-2074. https://doi.org/10.1016/j.cub.2004.11.005.

Huh et al. (2005) "In Vivo Magnetic Resonance Detection of Cancer by Using Multifunctional Magnetic Nanocrystals," J. Am. Chem. Soc. 127(35): 12387-12391.

Huh et al. (2016) "Maintenance of age in human neurons generated by microRNA-based neuronal conversion of fibroblasts," Elife 5:1-14. https://doi.org/10.7554/eLife.18648.

Humphrey et al. (1996) "VMD: Visual Molecular Dynamics," J. Malec. Graphics 14: 33-38.

Hundal et al. (2016) "pVAC-Seq: A genome-guided in silico approach to identifying tumor neoantigens," Genome Med, 8 (1), 11.

Husted et al. (Jun. 2021) "Molecularly Designed Additives for Chemically Deconstructable Thermosets without Compromised Thermomechanical Properties" ACS Macro Lett. 10, 805-810, DOI: 10.1021/acsmacrolett.1c00255.

Hwang et al. (2007) "Practical Recombinant Hybrid Mussel Bioadhesive Fp-151," Biomaterials, 28 (24), 3560-3568. https://doi.org/10.1016/j.biomaterials.2007.04.039.

International Search Report and Written Opinion, dated Oct. 27, 2021, corresponding to International Application No. PCT/US2021/029829, (from which the present application claims priority,) 16 pp.

Isenberg et al. (2007) "Thrombospondin-1 Inhibits Nitric Oxide Signaling via CD36 by Inhibiting Myristic Acid Uptake," J. Bio. Chem. 282(21), 15404-15415.

Itoh et al. (Jan. 2020) "Solid-Phase Total Synthesis of Yaku'amide B Enabled by Traceless Staudinger Ligation," Angew. Chem. Int. Ed. 59, 4564-4571.

Ivin et al. (2000) "Thermodynamics of Addition Polymerization," J. Polym. Sci., Part A: Polym. Chem. 38 (12), 2137-2146.

Jacobs et al. (1998) "Structure of an IκBα/NF-κB Complex," Cell, 95, 749.

Jadhav et al. (2019) "A walk through tau therapeutic strategies," Acta Neuropathol Commun 7:22. https://doi.org/10.1186/s40478-019-0664-z.

Jakalian et al. (2000) "Fast, efficient generation of high-quality atomic charges. AM1-BCC model: I. Method," J. Comput. Chem. 21(2): 132-146.

Jakalian et al. (2002) "Fast, efficient generation of high-quality atomic charges. AM1-BCC model: II. Parameterization and validation," J. Comput. Chem. 23(16):1623-1641.

James et al. (Jul. 2014) "Poly(oligonucleotides)," Journal of the American Chemical Society 136: 11216-11219.

Jeong et al. (2001) "Novel Polymer-DNA Hybrid Polymeric Micelles Composed of Hydrophobic Poly(D,L-lactic-co-glycolic Acid) and Hydrophilic Oligonucleotides," Bioconjugate Chem. 12(6): 917-923.

Jernigan et al. (2015) "Tandem-Repeat Protein Domains across the Tree of Life," PeerJ, 3e732. https://doi.org/10.7717/peerj.732.

Ji et al. (2011) "Digesting New Information About the Role of Trypsin in Pancreatitis," Gastroenterology, 141, 1972-1975.

Jia et al. (Jan. 2017) "Effect of PEG Architecture on the Hybridization Thermodynamics and Protein Accessibility of PEGylated Oligonucleotides," Angew. Chem. Int. Ed. 56, 1239-1243.

Jia et al. (Jul. 2017) "Depth-Profiling the Nuclease Stability and the Gene Silencing Efficacy of Brush-Architectured Poly(ethylene glycol)-DNA Conjugates," J. Am. Chem. Soc. 139, 10605-10608.

Jiang et al. (2018) "Identification of a novel small-molecule Keap1-Nrf2 PPI inhibitor with cytoprotective effects on LPS-induced cardiomyopathy," Journal of Enzyme Inhibition and Medicinal Chemistry, 33:1, 833-841, DOI: 10.1080/14756366.2018.1461856.

Jiang et al. (Jan. 2020) "Single-chain heteropolymers transport protons selectively and rapidly," Nature, 577 (7789), 216-220.

Jimenez-Sanchez et al. (2017) "Huntington's disease: Mechanisms of pathogenesis and therapeutic strategies," Cold Spring Harb Perspect Med 7:1-22. https://doi.org/10.1101/cshperspect.a024240.

Jin et al. (2020) "The peptide PROTAC modality: A novel strategy for targeted protein ubiquitination," Theranostics 10:10141-53. https://doi.org/10.7150/thno.46985.

Jin et al. (Feb. 2021) "Development of an α-synuclein knockdown peptide and evaluation of its efficacy in Parkinson's disease models," Commun Biol 4, 232.

Johnson (Apr. 2021) "Isothermal Titration Calorimetry," Methods Mol Biol 2263:135-59. https://doi.org/10.1007/978-1-0716-1197-5_5.

Johnson et al. (2010) "Drug-Loaded, Bivalent-Bottle-Brush Polymers by Graft-through ROMP," Macromolecules 43(24): 10326-10335.

Johnson et al. (2010) "Synthesis of Statistical Copolymers Containing Multiple Functional Peptides for Nucleic Acid Delivery," Biomacromolecules 11(11): 3007-3013.

Johnson et al. (2011) "Core-Clickable PEG-Branch-Azide Bivalent-Bottle-Brush Polymers by ROMP: Grafting-Through and Clicking-To," J. Am. Chem. Soc. 133(3): 559-566.

Johnson et al. (2015) "Nrf2—a therapeutic target for the treatment of neurodegenerative diseases," Free Radical Biology and Medicine 88, 253-267.

Joyce (1994) "In vitro evolution of nucleic acids," Curr. Opin. Struct. Biol. 4(3): 331-336.

Jun et al. (2005) "Nanoscale Size Effect of Magnetic Nanocrystals and Their Utilization for Cancer Diagnosis via Magnetic Resonance Imaging," J. Am. Chem. Soc. 127(16): 5732-5733.

Kajava (2012) "Tandem repeats in proteins: From sequence to structure," J. Struct. Bio, 179, 279-288.

(56) References Cited

OTHER PUBLICATIONS

Kakkar et al. (2017) "Evolution of macromolecular complexity in drug delivery systems," Nat. Rev. Chem., 1, 0063.
Kalkat et al. (2017) "MYC Deregulation in Primary Human Cancers," Genes (Basel) 8, doi:10.3390/genes8060151.
Kamimura et al. (Mar. 2021) "Chemical insights into liquid-liquid phase separation in molecular biology," Bull Chem Soc Jpn 2021;94:1045-58. https://doi.org/10.1246/BCSJ.20200397.
Kammeyer et al. (2013) "Polymerization of protecting-group-free peptides via ROMP," Polymer Chemistry 4(14): 3929-3933.
Kana et al. (2019) "Elucidating the druggability of the human proteome with eFindSite," J Comput Aided Mol Des 33, 509-519.
Kanaan et al. (2020) "Liquid-liquid phase separation induces pathogenic tau conformations in vitro," Nat Commun 11:. https://doi.org/10.1038/s41467-020-16580-3.
Kansanen et al. (2013) "The Keap1-Nrf2 pathway: Mechanisms of activation and dysregulation in cancer," Redox Biol:45-9. https://doi.org/10.1016/j.redox.2012.10.001.
Kaplan et al. (2005) "Cationic TAT peptide transduction domain enters cells by macropinocytosis," J. Controlled Release 102(1): 247-253.
Kargbo (2019) "Treatment of Alzheimer's by PROTAC-Tau Protein Degradation," ACS Med Chem Lett 1:699-700. https://doi.org/10.1021/acsmedchemlett.9b00083.
Karttunen et al. (2018) "Prediction of Binding Energy of Keap1 Interaction Motifs in the Nrf2 Antioxidant Pathway and Design of Potential High-Affinity Peptides," J. Phys. Chem. B, 122, 5851-5859.
Kaspar et al. (Sep. 2013) "Future directions for peptide therapeutics development," Drug Discovery Today 18(17-18): 807-817.
Kasper et al. (May 2019) "Vinylphosphonites for Staudinger-induced chemoselective peptide cyclization and functionalization," Chem Sci, 10, 6322-6329.
Kaur et al. (2018) "Direct Observation of the Interplay of Catechol Binding and Polymer Hydrophobicity in a Mussel-Inspired Elastomeric Adhesive," ACS Cent. Sci. 4, 10, 1420-1429. https://doi.org/10.1021/acscentsci.8b00526.
Kawai et al. (2010) "The role of pattern-recognition receptors in innate immunity: update on Toll-like receptors," Nature Immunology, 11 (5), 373-384.
Kebriaei et al. (Jun. 2018) "A phase 1 multicenter study evaluating the safety and efficacy of MHC class II-restricted MAGE-A3/A6 T-cell receptor engineered T cells (KITE-718) in patients with advanced cancer," Journal of Clinical Oncology 2018 36:15_suppl, TPS3104.
Kershner et al. (2009) "Placement and orientation of individual DNA shapes on lithographically patterned surfaces," Nat. Nanotechnol. 4: 557-561.
Keskin et al. (Jan. 2019) "Neoantigen vaccine generates intratumoral T cell responsesin phase lb glioblastoma trial," Nature, 565 (7738), 234-239.
Khalil et al. (2016) "The future of cancer treatment:immunomodulation, CARs and combination immunotherapy," Nat Rev Clin Oncol, 13(5): 273-290.
Khan et al. (2011) "Ring-Closing Metathesis Approaches for the Solid-Phase Synthesis of Cyclic Peptoids" Org. Lett. 13, 7, 1582-1585 DOI: 10.1021/01200226z.
Khan et al. (2013) "Readily Accessible and Easily Modifiable Ru-Based Catalysts for Efficient and Z-Selective Ring-Opening Metathesis Polymerization and Ring-Opening/Cross-Metathesis," J. Am. Chem. Soc., 135 (28), 10258-10261.
Kikis et al. (2010) "Protein homeostasis in models of aging and age-related conformational disease," Adv Exp Med Biol 694:138-59. https://doi.org/10.1007/978-1-4419-7002-2_11.
Kim et al. (2011) "Synthesis of all-hydrocarbon stapled α-helical peptides by ring-closing olefin metathesis," Nat. Protoc. 6(6): 761-771.
Kim et al. (2013) "Mussel Adhesive Protein-Based Whole Cell Array Biosensor for Detection of Organophosphorus Compounds," Biosens. Bioelectron. 41 (1), 199-204. https://doi.org/10.1016/j.bios.2012.08.022.
Kinkead et al. (Oct. 2018) "Combining STING-based neoantigen-targeted vaccine with checkpoint modulators enhances antitumorimmunity in murine pancreatic cancer," Jci Insight, 3 (20).
Kirkin et al. (1999) "Establishment of gp100 and MART-1/Melan-A-specific cytotoxic T lymphocyte clones using in vitro immunization against preselected highly immunogenic melanoma cell clones," Cancer Immunol Immunother, 48 (5), 239-46.
Kitamura et al. (2014) "Dysregulation of the proteasome increases the toxicity of ALS-linked mutant SOD1," Genes to Cells 19:209-24. https://doi.org/10.1111/gtc.12125.
Knutson et al. (2005) "Tumor antigen-specific T helper cells in cancer immunity and immunotherapy," Cancer Immunol Immunother. 54(8):721-8.
Kolonko et al. (2008) "A Polymeric Domain That Promotes Cellular Internalization," J. Am. Chem. Soc. 130(17): 5626-5627.
Kolonko et al. (2009) "General Synthetic Route to Cell-Permeable Block Copolymers via Romp," J. Am. Chem. Soc. 131(21): 7327-7333.
Kolpashchikov et al. (2005) "Boolean Control of Aptamer Binding States," J. Am. Chem. Soc. 127(32): 11348-11351.
Koppelhus et al. (2003) "Cellular delivery of peptide nucleic acid (PNA)," Adv. Drug Delivery Rev. 55(2): 267-280.
Kord Forooshani et al. (2017) "Recent Approaches in Designing Bioadhesive Materials Inspired by Mussel Adhesive Protein," Journal of Polymer Science, Part A: Polymer Chemistry. John Wiley and Sons Inc. pp 9-33. https://doi.org/10.1002/pola.28368.
Kordasiewicz et al. (2012) "Sustained Therapeutic Reversal of Huntington's Disease by Transient Repression of Huntingtin Synthesis," Neuron, 74 (6), 1031-1044.
Koren et al. (2012) "Cell-penetrating peptides: breaking through to the other side," Trends Mol. Med. 18(7): 385-393.
Kottisch et al. (2016) "Cationic Polymerization of Vinyl Ethers Controlled by Visible Light," J. Am. Chem. Soc. 138, 15535-15538.
Kottisch et al. (May 2018) "Enhancing Temporal Control and Enabling Chain-End Modification in Photoregulated Cationic Polymerizations by Using Iridium-Based Catalysts," Angew. Chem. Int. Ed. 130, 8392-8396.
Kraft et al. (2004) "Nuclear Factor E2-Related Factor 2-Dependent Antioxidant Response Element Activation by tert-Butylhydroquinone and Sulforaphane Occurring Preferentially in Astrocytes Conditions Neurons against Oxidative Insult," The Journal of Neuroscience, 24(5):1101-1112.
Krainer et al. (2021) "Reentrant liquid condensate phase of proteins is stabilized by hydrophobic and non-ionic interactions," Nat Commun 12:1-14. https://doi.org/10.1038/s41467-021-21181-9.
Kreiter et al. (2015) "Mutant MHC class II epitopes drive therapeutic immune responses to cancer," Nature, 520 (7549), 692-U269.
Ku et al. (2011) "Controlling and Switching the Morphology of Micellar Nanoparticles with Enzymes," J. Am. Chem. Soc. 133: 8392-8395.
Kueny-Stotz et al. (2012) "Manganese-enhanced MRI contrast agents: From small chelates to nanosized hybrids," Eur J Inorg Chem 1987-2005 https://doi.org/10.1002/ejic.201101163.
Kuhn et al. (2010) "Low Catalyst Loadings in Olefin Metathesis: Synthesis of Nitrogen Heterocycles by Ring-Closing Metathesis" Org. Lett. 12, 5, 984-987, DOI: 10.1021/019029808.
Kumar et al. (2015) "Huntington's Disease: An Update of Therapeutic Strategies," Gene, 556 (2), 91-97.https://doi.org/10.1016/j.gene.2014.11.022.
Kuykendall et al. (2015) "Distribution of Immune Markers and Their Association with Overall Survival and Time to Progression in Non-Small-Cell Lung Cancer," Journal of Thoracic Oncology. 10, S2, 9, S268, Mini oral session, Sep. 7, 2015, Abstract.
Kwak et al. (2010) "Nucleic Acid/Organic Polymer Hybrid Materials: Synthesis, Superstructures, and Applications," Angew. Chem., Int. Ed. 49(46): 8574-8587.
Kwak et al. (2020) "Amyloid-β42/40 ratio drives tau pathology in 3D human neural cell culture models of Alzheimer's disease," Nat Commun 11:1-14. https://doi.org/10.1038/s41467-020-15120-3.

(56) References Cited

OTHER PUBLICATIONS

Labbadia et al. (2013) "Huntington's disease: Underlying molecular mechanisms and emerging concepts," Trends Biochem Sci 38:378-85. https://doi.org/10.1016/j.tibs.2013.05.003.
Lafontaine et al. (2021) "The nucleolus as a multiphase liquid condensate," Nat Rev Mol Cell Biol 22:165-82. https://doi.org/10.1038/s41580-020-0272-6.
Lakey et al. (1998) "Measuring protein-protein interactions," Curr Opin Struct Biol 8:119-23. https://doi.org/10.1016/S0959-440X(98)80019-5.
Lam et al. (2016) "Stabilization of α-Synuclein Fibril Clusters Prevents Fragmentation and Reduces Seeding Activity and Toxicity," Biochemistry 55:675-85. https://doi.org/10.1021/acs.biochem.5b01168.
Lam et al. (Oct. 2018) "LBA38 Safety and anti-tumor effects of MAGE-A10c796 TCR T-cells in two clinical trials," Annals of Oncology, vol. 29, Issue suppl_8, 1.
Lange et al. (2007) "Classical Nuclear Localization Signals: Definition, Function, and Interaction with Importin α," J. Biol. Chem. 282(8): 5101-5105.
Le et al. (Feb. 2019) "Straightforward access to biocompatible poly(2-oxazoline)-coated nanomaterials by polymerization-induced self-assembly," Chem. Commun, 55, 3741-3744.
Le et al. (Mar. 2019) "Ultra-Fast Synthesis of Multivalent Radical Nanoparticles by Ring-Opening Metathesis Polymerization-Induced Self-Assembly," Angew. Chem. In. Ed. 58, 4725-4731.
Lee et al. (2001) "Nrf2-Dependent Activation of the Antioxidant Responsive Element by tert-Butylhydroquinone Is Independent of Oxidative Stress in IMR-32 Human Neuroblastoma Cells," Biochemical and Biophysical Research Communications 280, 286-292.
Lee et al. (2003) "N-Terminal Site-Specific Mono-PEGylation of Epidermal Growth Factor," Pharm. Res. 20(5): 818-825.
Lee et al. (2007) "Mussel-Inspired Surface Chemistry for Multifunctional Coatings," Science, 318 (5849), 426-430. https://doi.org/10.1126/science.1147241.
Lee et al. (2009) "Polymeric ADAM Protein Mimics Interrogate Mammalian Sperm-Egg Binding," ChemBioChem 10(5): 929-937.
Lee et al. (2011) "Inspired Adhesives and Coatings," Annu. Rev. Mater. Res. 41 (1), 99-132. https://doi.org/10.1146/annurev-matsci-062910-100429.
Lee et al. (2016) "CHARMM-GUI Input Generator for Namd, Gromacs, Amber, OpenMM, and CHARMM/OpenMM Simulations Using the CHARMM36 Additive Force Field," J. Chem. Theory Comput. 12 (1), 405-413.
Lee et al. (2017) Interactions between Membranes and "Metaphilic Polypeptide Architectures with Diverse Side-Chain Populations," ACS Nano, 11 (3), 2858-2871.https://doi.org/10.1021 /acsnano.6b07981.
Lee et al. (Apr. 2020) "Nrf2 activation through the inhibition of Keap1-Nrf2 protein-protein interaction," Medicinal Chemistry Research, 29:846-867.
Lee et al. (Feb. 2017) "Interactions between Membranes and 'metaphilic' Polypeptide Architectures with Diverse Side-Chain Populations," ACS Nano 11:2858-71. https://doi.org/10.1021/acsnano.6b07981.
Lee et al. (Jan. 2017) "Polymer Structure and Conformation Alter the Antigenicity of Virus-like Particle-Polymer Conjugates," J. Am. Chem. Soc. 139, 3312-3315.
Lee et al. (Jan. 2020) "Stimuli-Responsive Conformational Transformation of Peptides for Tunable Cytotoxicity," Bioconjug. Chem. 31, 43-50.
Lei et al. (1995) "Structure-Function Analysis of Human Glucose-6-phosphatase, the Enzyme Deficient in Glycogen Storage Disease Type 1a," J. Biol. Chem. 270(20): 11882-11886.
Leicher et al. (1998) "Coexpression of the KCNA3B Gene Product with Kv1.5 Leads to a Novel A-type Potassium Channel," J. Biol. Chem. 273(52):35095-35101.
Lele et al. (2005) "Synthesis of Uniform Protein-Polymer Conjugates," Biomacromolecules 6(6): 3380-3387.
Lesignoli et al. (2001) "Recognition and strand displacement of DNA oligonucleotides by peptide nucleic acids (PNAs): High-performance ion-exchange chromatographic analysis," J. Chromatogr. A 922(1-2) 177-185.
Lewis et al. (2010) "Nrf2, a Guardian of Healthspan and Gatekeeper of Species Longevity," pp. 829-843. Integrative and Comparative Biology. vol. 50, No. 5; DOI: 10.1093/icb/icq034.
Li et al. (1987) "Monte Carlo-minimization approach to the multiple-minima problem in protein folding," Proc Natl Acad Sci U S A 84:6611-5. https://doi.org/10.1073/pnas.84.19.6611.
Li et al. (2002) "Preparation and characterization of PEGylated adducts of recombinant human tumor necrosis factor-α from *Escherichia coli*," Biotechnol. 92(3): 251-258.
Li et al. (2006) "Ankyrin Repeat: A Unique Motif Mediating Protein-Protein Interactions," Biochemistry, 45, 15168.
Li et al. (2014) "Self-assembly of random copolymers," Chem. Commun. 50, 13417-13432.
Li et al. (2016) "Structure and Function of Iron-Loaded Synthetic Melanin," ACS Nano, 10(11):10186-10194. PMCID: PMC5295137.
Li et al. (2017) "CD54-NOTCH1 Axis Controls Tumor Initiation and Cancer Stem Cell Functions in Human Prostate Cancer," Theranostics. 7(1):67-8.
Li et al. (Jun. 2018) "A facile approach to enhance antigen response for personalized cancer vaccination," Nat Mater, 17 (6), 528-534.
Liang et al. (Sep. 2020) "Degradable Polyphosphoramidate via Ring-Opening Metathesis Polymerization," ACS Macro Letters, 9, 10, 1417-1422.
Lin et al. (2021) "Liquid-Liquid Phase Separation of Tau Driven by Hydrophobic Interaction Facilitates Fibrillization of Tau," J Mol Biol 433:166731. https://doi.org/10.1016/j.jmb.2020.166731.
Lindorff-Larsen et al. (2010) "Improved side-chain torsion potentials for the Amber ff99SB protein force field," Proteins 78(8): 1950-1958.
Liou et al. (1993) "Regulation of the NF-ηB/rel transcription factor and IηB inhibitor system," Curr. Opin. Cell Biol. 5(3): 477-487.
Lipschutz et al. (1999) "High density synthetic oligonucleotide arrays," Nat. Genet. 21: 20-24.
Liu et al. (1979) "New procedures for preparation and isolation of conjugates of proteins and a synthetic copolymer of D-amino acids and immunochemical characterization of such conjugates," Biochemistry 18(4): 690-697.
Liu et al. (Aug. 2018) "Polymerization Induced Self-Assembly of a Site-Specific Interferon α-Block Copolymer Conjugate into Micelles with Remarkably Enhanced Pharmacology," J. Am. Chem. Soc. 140(33), 10435-10438.
Liu et al. (Oct. 2019) "Discovery of low-molecular weight anti-PD-L1 peptides for cancer immunotherapy," J Immunother Cancer, 7 (1), 270.
Livant et al. (2000) "The PHSRN sequence induces extracellular matrix invasion and accelerates wound healing in obese diabetic mice," J. Clin. Invest. 105(11):1537-1545.
Llombart et al. (Jan. 2022) "Therapeutic targeting of "undruggable" MYC," EBioMedicine 75, 103756.
Lockhart et al. (1996) "Expression monitoring by hybridization to high-density oligonucleotide arrays," Nat. Biotechnol. 14: 1675-1680.
Lohrmann et al. (1984) "New solid supports for DNA synthesis," DNA 3: 122-122.
Lopez et al. (2011) "Molecular Mechanism of Cyclodextrin Mediated Cholesterol Extraction," PLoS Comp. Biol. 7(3): e1002020, pp. 1-11.
Louage et al. (2016) "Well-Defined Polymer-Paclitaxel Prodrugs by a Grafting-from-Drug Approach," Angew. Chem. Int. Ed., 55, 11791-11796.
Louage et al. (2017) "Micellar Paclitaxel-Initiated RAFT Polymer Conjugates with Acid-Sensitive Behavior," ACS Macro Lett., 6, 272-276.
Love et al. (2002) "A practical and highly active ruthenium-based catalyst that effects the cross metathesis of acrylonitrile," Angew. Chem. 114, 4207-4209.
Love et al. (2003) "Synthesis, Structure, and Activity of Enhanced Initiators for Olefin Metathesis," J. Am. Chem. Soc. 125(33): 10103-10109.

(56) References Cited

OTHER PUBLICATIONS

Lu et al. (2009) "One-Pot Synthesis of Brush-Like Polymers via Integrated Ring-Opening Metathesis Polymerization and Polymerization of Amino Acid N-Carboxyanhydrides," JACS 131(38): 13582-13583.
Lu et al. (2015) "Binding thermodynamics and kinetics guided optimization of potent Keap1-Nrf2 peptide inhibitors," RSC Advances, 5:85983-7.
Lu et al. (Dec. 2020) "Discovery of 2-oxy-2-phenylacetic acid substituted naphthalene sulfonamide derivatives as potent KEAP1-NRF2 protein-protein interaction inhibitors for inflammatory conditions," European Journal of Medicinal Chemistry, 207, 112734.
Lu et al. (Feb. 2018) "Discovery of a Keap1-dependent peptide PROTAC to knockdown Tau by ubiquitination-proteasome degradation pathway," Eur J Med Chem, 146:251-9. https://doi.org/10.1016/j.ejmech.01.063.
Lu et al. (Jan. 2018) "Discovery of a head-to-tail cyclic peptide as the Keap1-Nrf2 protein-protein interaction inhibitor with high cell potency," European Journal of Medicinal Chemistry, 143, 1578-1589.
Luckerath et al. (Apr. 2020) "DNA-Polymer Nanostructures by RAFT Polymerization and Polymerization-Induced Self-Assembly," Angew. Chem. Int. Ed. doi: 10.1002/anie.201916177.
Lutz et al. (2005) "Preparation by controlled radical polymerization and self-assembly via base-recognition of synthetic polymers bearing complementary nucleobases," J. Polym. Sci., Part A: Polym. Chem. 43(20): 4805-4818.
Lv et al. (2016) "Thermally Degradable Polyesters with Tunable Degradation Temperatures via Postpolymerization Modification and Intramolecular Cyclization," Macromolecules. 49, 8449-8458.
Lynn et al. (Mar. 2020) "Peptide-TLR-7/8a conjugate vaccines chemically programmed for nanoparticle self-assembly enhanceCD8 T-cell immunity to tumor antigens," Nat Biotechnol, 38 (3), 320-332.
Lytle et al. (Nov. 2018) "Stem cell fate in cancer growth, progression and therapy resistance," Nat Rev Cancer. Nov. 2018;18(11):669-680.
Lytton-Jean et al. (2009) "Highly Cooperative Behavior of Peptide Nucleic Acid-Linked DNA-Modified Gold-Nanoparticle and Comb-Polymer Aggregates," Adv. Mater. 21(6): 706-709.
Ma et al. (2017) "Synergistic antitumor activity of a self-assembling camptothecin and capecitabine hybrid prodrug for improved efficacy," Control Release, 263, 102-111.
Mackerell et al. (1998) "All-Atom Empirical Potential for Molecular Modeling and Dynamics Studies of Proteins," J. Phys. Chem. B, 102 (18), 3586-3616.
Macri et al. (2016) "Targeting dendritic cells: a promising strategy to improve vaccine effectiveness," Clin Transl Immunology, 5 (3), e66.
Madden et al. (Jan. 2021) "Taking the Myc out of cancer: toward therapeutic strategies to directly inhibit c-Myc," Molecular Cancer 20, 3.
Madden et al. (Jul. 2020) "Structural and mechanistic insights into the Keap1-Nrf2 system as a route to drug discovery," BBA—Proteins and Proteomics 1868, 140405.
Madkour et al. (2010) "End-Functionalized ROMP Polymers for Biomedical Applications," Macromolecules, 43 (10), 4557-4561.
Mae et al. (2006) "Cell-Penetrating Peptides as Vectors for Peptide, Protein and Oligonucleotide Delivery," Curr. Opin. Pharmacol. 6 (5), 509-514.https://doi.org/10.1016/j.coph.2006.04.004.
Maeda et al. (2019) "Tau Oligomers," Adv Exp Med Biol 1184:373-80. https://doi.org/10.1007/978-981-32-9358-8_27.
Mai et al. (2012) "Self-assembly of block copolymers," Chem. Soc. Rev. 41(18): 5969-5985.
Maier et al. (2015) "Adaptive Synergy between Catechol and Lysine Promotes Wet Adhesion by Surface Salt Displacement," Science (80 -. ). 349 (6248), 628-632. https://doi.org/10.1126/science.aab0556.
Main et al. (2003) "The folding and design of repeat proteins: reaching a consensus," Curr. Opinion in Struct. Bio, 13, 482.
Maisha et al. (2020) "Development of a Sensitive Assay to Screen Nanoparticles in Vitro for Complement Activation," ACS Biomater. Sci. Eng. 6 (9),4903-4915. https:/ /doi .org/10.1021 /acsbiomaterials. 0c00722.
Mallick et al. (2018) "Oxadiazabicyclooctenone as a versatile monomer for the construction of pH sensitive functional polymers via ROMP," Polym Chem-Uk. 9:372-7.
Mammen et al. (1998) "Polyvalent Interactions in Biological Systems: Implications for Design and Use of Multivalent Ligands and Inhibitors," Angew. Chem., Int. Ed. 37(20): 2754-2794.
Mangold et al. (2008) "Synthesis of Fluorogenic Polymers for Visualizing Cellular Internalization," Organic Letters, 10 (14), 2997-3000.
Marelli et al. (2016) "The P42 Peptide and Peptide-Based Therapies for Huntington's Disease," Orphanet J. Rare Dis. 11:24.
Marrink et al. (2007) "The Martini Force Field: Coarse Grained Model for Biomolecular Simulations," J. Phys. Chem. B, 111 (27), 7812-7824. 19.
Marrink et al. (2013) "Perspective on the Martini model," Chem. Soc. Rev. 42 (16), 6801-6822.
Marsico et al. (2012) "Unsaturated Polyphosphoesters via Acyclic Diene Metathesis Polymerization," Macromolecules, vol. 45, pp. 8511-8518.
Martin et al. (2002) "(Z)-1,4-diamino-2-butene as a vector of boron, fluorine, or iodine for cancer therapy and imaging: Synthesis and biological evaluation," Bioorg. Med. Chem. 10, 2863-2871.
Martinez et al. (Sep. 2020) "A Thermodynamic Roadmap for the Grafting-through Polymerization of PDMS11MA" ACS Macro Lett. 9, 1303-1309.
Martinez Rodriguez et al. (2015) "Mussel Adhesive Protein Provides Cohesive Matrix for Collagen Type-1α," Biomaterials, 51, 51-57. https://doi.org/10.1016/J.BIOMATERIALS.2015.01.033.
Mateyak et al. (1997) "Phenotypes of c-Myc-deficient rat fibroblastsisolated by targeted homologous recombination," Cell Growth Differ 8, 1039-1048.
Matson et al. (2010) "Monotelechelic Poly(oxa)norbornenes by Ring-Opening Metathesis Polymerization using Direct End-Capping and Cross Metathesis," Macromolecules 43(1): 213-221.
Maynard et al. (2000) "Synthesis of Norbornenyl Polymers with Bioactive Oligopeptides by Ring-Opening Metathesis Polymerization," Macromolecules 33(17):6239-6248.
Maynard et al. (2001) "Inhibition of Cell Adhesion to Fibronectin by Oligopeptide-Substituted Polynorbornenes," J. Am. Chem. Soc. 123, 1275-1279.
Mcgregor (2008) "Discovering and improving novel peptide therapeutics," Curr. Opin. Pharmacol. 8(5): 616-619.
Mcguire et al. (Aug. 2019) "Divergent Catalytic Strategies for the Cis/Trans Stereoselective Ring-Opening Polymerization of a Dual Cyclic Carbonate/Olefin Monomer," J. Am. Chem. Soc. 141, 13301-13305.
McHale et al. (2012) "Nucleobase Containing Synthetic Polymers: Advancing Biomimicry via Controlled Synthesis and Self-Assembly," Macromolecules 45(19): 7665-7675.
Meeth et al. (2016) "The YUMM lines: a series of congenic mouse melanoma cell lines with defined genetic alterations," Pigm Cell Melanoma R, 29 (5), 590-597.
Mellman et al. (2011) Cancer immunotherapy comes of age. Nature, 480 (7378),480-9.
Melvin et al. (2013) "A Comparative Analysis of the Ubiquitination Kinetics of Multiple Degrons to Identify an Ideal Targeting Sequence for a Proteasome Reporter," PLOS One 8, e78082.
Menacho-Melgar et al. (Feb. 2019) "A review of lipidation in the development of advanced protein and peptide therapeutics," J. Control Release, 295, 1-12.
Merrifield (1963) "Solid Phase Peptide Synthesis. I. The Synthesis of a Tetrapeptide," J. Am. Chem. Soc. 85 (14), 2149-2154. https://doi.org/10.1021/ja00897a025.
Michaudel et al. (2017) "Cationic Polymerization: From Photoinitiation to Photocontrol," Angew. Chem. Int. Ed. 56, 9670-9679.
Mihov et al. (2005) "Polyphenylene Dendrimers as Scaffolds for Shape-Persistent Multiple Peptide Conjugates," Bioconjugate Chem. 16(2): 283-293.

(56) References Cited

OTHER PUBLICATIONS

Millar et al. (Apr. 2020) "Antibody-mediated delivery of viral epitopes to tumors harnesses CMV-specific T cells for cancer therapy," Nat Biotechnol. 38(4):420-425.
Miller et al. (1994) "Proteolytic studies of homologous peptide and N-substituted glycine peptoid oligomers," Bioorg. Med. Chem. Lett. 4(22): 2657-2662.
Min et al. (2015) "Clinical Translation of Nanomedicine," Chem. Rev., 115, 11147-11190.
Mirkin et al. (1996) "A DNA-based method for rationally assembling nanoparticles into macroscopic materials," Nature 382: 607-609.
Mitchell et al. (2000) "Polyarginine enters cells more efficiently than other polycationic homopolymers," J. Pept. Res. 56(5): 318-325.
Miyamoto et al. (1992) "Settle: An Analytical Version of the Shake and Rattle Algorithm for Rigid Water Models," J. Comput. Chem. 13, 952-962.
Moad (2017) "RAFT polymerization to form stimuli-responsive polymers," Polym. Chem., 8, 177-219.
Mok et al. (2018) "Mapping interactions with the chaperone network reveals factors that protect against tau aggregation," Nat Struct Mol Biol 25:384-93. https://doi.org/10.1038/s41594-018-0057-1.
Molla et al. (Jun. 2018) "Dynamic actuation of glassy polymersomes through isomerization of a single azobenzene unit at the block copolymer interface," Nat. Chem. 10, 659-666.
Mondal et al. (2020) "Total degradation of extracellular amyloids by miniature artificial proteases," Chem Commun 56:2348-51. https://doi.org/10.1039/c9cc09409a.
Monfardini et al. (1995) "A Branched Monomethoxypoly(ethylene glycol) for Protein Modification," Bioconjugate Chem. 6(1): 62-69.
Monnard et al. (2003) "Eutectic Phase Polymerization of Activated Ribonucleotide Mixtures Yields Quasi-Equimolar Incorporation of Purine and Pyrimidine Nucleobases," J. Am. Chem. Soc. 125(45): 13734-13740.
Mori et al. (2013) "Valosin-Containing Protein Immunoreactivity in Tauopathies, Synucleinopathies, Polyglutamine Diseases and Intranuclear Inclusion Body Disease," Neuropathology, 33 (6), 637-644. https://doi.org/10.1111/neup.12050.
Morimoto et al. (2014) "Proteostasis and the aging proteome in health and disease," Journals Gerontol—Ser A Biol Sci Med Sci 69:S33-8. https://doi.org/10.1093/gerona/glu049.
Mosavi et al.(2002) "Consensus-derived structural determinants of the ankyrin repeat motif," PNAS, 99, 16029.
Mou et al. (Sep. 2020) "Recent progress in Keap1-Nrf2 protein-protein interaction inhibitors," European Journal of Medicinal Chemistry 202, 112532.
Mougel et al. (Mar. 2019) "Therapeutic Cancer Vaccine and Combinations With Antiangiogenic Therapies and Immune Checkpoint Blockade," Front Immunol, 10.
Moynihan et al. (Sep. 2018) "Enhancement of Peptide Vaccine Immunogenicity by Increasing Lymphatic Drainage and Boosting Serum Stability," Cancer Immunol Res, 6 (9), 1025-1038.
Murata et al. (1997) "Syntheses and Radical Polymerization Behavior of Methacrylamides Having Peptide Moieties: Effect of the Methylene Chain Introduced between the Methacrylamide and Peptide Moieties on the Polymerizability and Polymer Structure," Macromolecules 30(10): 2902-2906.
Mutlu et al. (2016) "Green chain-shattering polymers based on a self-immolative azobenzene motif," Polym Chem-Uk. 7:2272-9.
Nagarkar et al. (2012) "Efficient Amine End-Functionalization of Living Ring-Opening Metathesis Polymers," Macromolecules. 45, 4447-4453.
Naing et al. (Jul. 2018) "Epacadostat plus durvalumab in patients with advanced solid tumors: preliminary results of the ongoing, open-label, phase I/II ECHO-203 study," AACR; Cancer Res 2018 Abstract CT177.
Nakase et al. (2004) "Cellular Uptake of Arginine-Rich Peptides: Roles for Macropinocytosis and Actin Rearrangement," Mol. Ther. 10(6): 1011-1022.
Nalawansha et al. (2022) "Hijacking Methyl Reader Proteins for Nuclear-Specific Protein Degradation," Journal of the American Chemical Society 144, 5594-5605.
Navaratna et al. (Jan. 2020) "Directed Evolution Using Stabilized Bacterial Peptide Display," J. Am. Chem. Soc. 142, 1882-1894.
Neary et al. (2017) "Variable Temperature ROMP: Leveraging Low Ring Strain Thermodynamics to Achieve Well-Defined Polypentenamers," Macromolecules. 50, 4935-4941.
Neary et al. (Aug. 2019) "Depolymerization of Bottlebrush Polypentenamers and Their Macromolecular Metamorphosis," J. Am. Chem. Soc. 141, 14220-14229.
Needleman et al. (1970) "A general method applicable to the search for similarities in the amino acid sequence of two proteins," J. Mol. Biol. 48: 443-453.
Newberg et al. (1996) "Importance of MHC class 1 alpha2 and alpha3 domains in the recognition of self and non-self MHC molecules," J Immunol, 156 (7), 2473-80.
Ng et al. (Oct. 2018) "Pushing the Limits of High Throughput PET-RAFT Polymerization," Macromolecules, 51, 7600-7607.
Ngambenjawong et al. (2017) "Multivalent Polymers Displaying M2 Macrophage-Targeting Peptides Improve Target Binding Avidity and Serum Stability,"ACS Biomater. Sci. Eng. 2017, 3, 2050-2053.
Nguyen et al. (2015) "Enzyme-responsive Nanoparticles for Targeted Accumulation and Prolonged Scaffold Retention in Heart Tissue After Myocardial Infarction," Adv Mater., 27(37):5547-5552. PMID: PMC4699559.
Nicklisch et al. (2012) "Mini-Review: The Role of Redox in Dopa-Mediated Marine Adhesion," Biofouling, 28 (8), 865-877. https://doi.org/10.1080/08927014.2012.719023.
Nielsen et al. (1991) "Sequence-selective recognition of DNA by strand displacement with a thymine-substituted polyamide," Science 254(5037): 1497-1500, (Machine Generated Copy).
Nischan et al. (publicly available Aug. 2013) "Stabilization of Peptides for Intracellular Applications by Phosphoramidate-Linked Polyethylene Glycol Chains," Angew. Chem., Int. Ed. (Nov. 2013), 52(45): 11920-11924.
Niu et al. (2017) "Engineering live cell surfaces with functional polymers via cytocompatible controlled radical polymerization," Nat. Chem. 9, 537-545.
Nizynski et al. (2017) "Amyloidogenesis of Tau protein," Protein Sci 26:2126-50. https://doi.org/10.1002/pro.3275.
Nomura et al. (1996) "Preparation of 'Sugar-Coated' Homopolymers and Multiblock ROMP Copolymers," Macromolecules 29(2): 540-545.
Nomura et al. (2010) "Precise Synthesis of Polymers Containing Functional End Groups by Living Ring-Opening Metathesis Polymerization (ROMP): Efficient Tools for Synthesis of Block/Graft Copolymers," Polymer, 51 (9), 1861-1881. https://doi.org/10.1016/J.POLYMER.2010.02.028.
North et al. (2017) "High Strength Underwater Bonding with Polymer Mimics of Mussel Adhesive Proteins," ACS Appl. Mater. Interfaces, 9 (8), 7866-7872. https://doi.org/10.1021/acsami.7b00270.
Nowalk et al. (2019) "Sequence-Controlled Polymers Through Entropy-Driven Ring-Opening Metathesis Polymerization: Theory, Molecular Weight Control, and Monomer Design," J Am Chem Soc. 141:5741-52.
O'Brien-Simpson et al. (1997) "Polymerization of Unprotected Synthetic Peptides: A View toward Synthetic Peptide Vaccines," J. Am. Chem. Soc. 119(6):1183-1188.
Ogawa, et al. (2015) "Metal-Free Ring-Opening Metathesis Polymerization," J. Am. Chem. Soc. 137, 1400-1403.
Ogba et al. (2018) "Recent advances in ruthenium-based olefin metathesis," Chem. Soc. Rev. 47, 4510-4544.
Oliver et al. (Dec. 2018) "Scalable Fiber-like Micelles and Block Co-micelles by Polymerization-Induced Crystallization-Driven Self-Assembly," J. Am. Chem. Soc. 140, 18104-18114.
Ontoria et al. (Apr. 2020) "Combined Peptide and Small-Molecule Approach towards Nonacidic THIQ Inhibitors of the KEAP1/NRF2 Interaction," ACS Med. Chem. Lett. 11, 5, 740-746.
Orum et al. (1993) "Single base pair mutation analysis by PNA directed PCR clamping," Nucleic Acids Res. 21(23): 5332-5336.

(56) References Cited

OTHER PUBLICATIONS

Osapay et al. (1997) "Lanthionine-somatostatin analogs: synthesis, characterization, biological activity, and enzymatic stability studies," J. Med. Chem. 40(14): 2241-2251.
Ostankovitch et al. (1998) "A partially modified retro-inverso pseudopeptide modulates the cytokine profile ofCTL specific for an influenza virus epitope," J Immunol, 161 (1), 200-8.
Ostro (1989) "Use of liposomes as injectable-drug delivery systems ," Am. J. Hosp. Pharm.46:1576-1587.
Ott et al. (2017) "An immunogenic personal neoantigen vaccine for patients with melanoma," Nature, 547 (7662), 217-221.
Otvos et al. (2014) "Current Challenges in Peptide-Based Drug Discovery," Front. Chem. 2(62).
Ouyang et al. (2010) "Simultaneous Visualization of Protumorigenic Src and MT1-MMP Activities with Fluorescence Resonance Energy Transfer," Cancer Res. 70(6): 2204-2212.
Overwijk et al. (1998) "gp100/pmel 17 is a murine tumor rejection antigen: induction of "self"-reactive, tumoricidal T cells using high-affinity, altered peptide ligand," J Exp Med, 188 (2), 277-86.
Owen et al. (2002) "Synthesis and Applications of End-Labeled Neoglycopolymers," Organic Letters, 4 (14), 2293-2296.
Owens III et al. (2006) "Opsonization, biodistribution, and pharmacokinetics of polymeric nanoparticles," Int. J. Pharm., 307, 93-102.
Pan et al. (2016) "Mechanism of Photoinduced Metal-Free Atom Transfer Radical Polymerization: Experimental and Computational Studies," J. Am. Chem. Soc. 138, 2411-2425.
Pan et al. (2017) "Automated Synthesis of Well-Defined Polymers and Biohybrids by Atom Transfer Radical Polymerization Using a DNA Synthesizer," Angew. Chem. Int. Ed. 56, 2740-2743.
Pan et al. (Feb. 2021) "Huntington's Disease: New Frontiers in Therapeutics," Curr. Neurol. Neurosci. Rep. 21 (3).
Pandey et al. (2020) "Modulation of tau protein aggregation using 'Trojan' sequences," Biochim Biophys Acta—Gen Subj 1864:129569. https://doi.org/10.1016/j.bbagen.2020.129569.
Panganiban et al. (2018) "Random Heteropolymers Preserve Protein Function in Foreign Environments," Science, 359 (6381), 1239-1243.
Panieri et al. (2019) "Potential applications of NRF2 inhibitors in cancer therapy," Oxid Med Cell Longev, vol. 2019, 8592348, https://doi.org/10.1155/2019/8592348.
Pappu (2020) "Phase Separation—A Physical Mechanism for Organizing Information and Biochemical Reactions," Dev Cell 2020;55:1-3. https://doi.org/10.1016/j.devcel.2020.09.023.
Parent et al. (2017) "Directly Observing Micelle Fusion and Growth in Solution by Liquid-Cell Transmission Electron Microscopy," J Am Chem Soc 139:17140-51. https://doi.org/10.1021/jacs.7b09060.
Parent et al. (Oct. 2018) "Hierarchical Spidroin Micellar Nanoparticles as the Fundamental Precursors of Spider Silks," Proc Nat Acad Sci U S A, 115(45):11507-11512. PMCID: PMC6233143.
Park et al. (2008) "DNA-programmable nanoparticle crystallization," Nature 451: 553-556.
Parkhurst et al. (2014) "Synthesis of poly(sulfonate ester)s by ADMET polymerization," Rsc Adv. 4:53967-74.
Patel et al. (2007) "Cell Penetrating Peptides: Intracellular Pathways and Pharmaceutical Perspectives," Pharm. Res. 24(11): 1977-1992.
Patel et al. (2012) "Synthesis and Cell Adhesive Properties of Linear and Cyclic RGD Functionalized Polynorbornene Thin Films," Biomacromolecules 13(8): 2546-2553.
Patil et al. (2005) "DNA-based therapeutics and DNA delivery systems: A comprehensive review," AAPS J. 7(1): E61-E77.
Patterson et al. (2015) "Observing the Growth of Metal-Organic Frameworks by In Situ Liquid Cell Tem," J Am Chem Soc., 137(23):7322-7328. https://doi.org/10.1021/jacs.5b00817.
Payne et al. (Aug. 2020) "BTN3A1 governs antitumor responses by coordinating ab and gd T cells," Science 369, 942-949.
Pazgier et al. (2009) "Structural basis for high-affinity peptide inhibition of p53 interactions with MDM2 and MDMX," Proc Natl Acad Sci U S A 106, 4665-4670.
Pazos et al. (2009) "Peptide-based fluorescent biosensors," Chem. Soc. Rev. 38(12): 3348-3359.
Pearce et al. (2019) "Recent developments in entropy-driven ring-opening metathesis polymerization: Mechanistic considerations, unique functionality, and sequence control," J Polym Sci Pol Chem. 57:1621-34.
Pearson et al. (1988) "Improved tools for biological sequence comparison," Proc. Nat'l. Acad. Sci. USA 85(8):2444-2448.
Pena-Francesch et al. (2019) "Squid-Inspired Tandem Repeat Proteins: Functional Fibers and Films," Frontiers in Chemistry. Frontiers Media S.A. 7, 69. https://doi.org/10.3389/fchem.2019.00069.
Penfold et al. (Aug. 2019) "Emerging Trends in Polymerization-Induced Self-Assembly," ACS Macro Lett, 8, 1029-1054.
Peng et al. (2006) "Characterization of HLA-A2-restricted HPV-16 E7-specific CD8(+) T-cell immune responses induced by DNA vaccines in HLA-A2 transgenic mice," Gene Ther, 13 (1), 67-77.
Peng et al. (2015) "Exceptionally abundant exceptions: comprehensive characterization of intrinsic disorder in all domains of life," Cell Mol Life Sci 72, 137-151, doi:10.1007/s00018-014-1661-9.
Perales-Puchalt et al. (2016) "Follicle-stimulating hormone receptor is expressed by most ovarian cancer subtypes and is a safe and effective immunotherapeutic target," Clin. Cancer Res. 23:441-53. PMC5241180.
Periole et al. (2009) "Combining an Elastic Network With a Coarse-Grained Molecular Force Field: Structure, Dynamics, and Intermolecular Recognition," J. Chem. Theory Comput. 5 (9), 2531-2543.
Perrier (2017) "50th Anniversary Perspective: RAFT Polymerization—A User Guide," Macromolecules, 50, 19, 7433-7447.
Pescarolo et al. (2001) "A retro-inverso peptide homologous to helix 1 of c-Myc is a potent and specific inhibitor of proliferation in different cellular systems," Faseb J., 15, 31-33.
Peters et al. (2017) "Impact of tumor mutation burden on the efficacy of first-line nivolumab in stage iv or recurrent non-small cell lung cancer: An exploratory analysis ofCheckMate 026," Cancer Res;77(13 Suppl): Abstract nr CT082.
Phillips et al. (2005) "Scalable molecular dynamics with NAMD," Journal of Computational Chemistry 26(16): 1781-1802.
Pianowski et al. (2008) "Nucleic acid encoding to program self-assembly in chemical biology," Chem. Soc. Rev. 37(7): 1330-1336.
Pini et al. (2008) "Branched Peptides as Therapeutics," Curr. Protein Pept. Sci. 9(5): 468-477.
Plückthun (2015) "Designed Ankyrin Repeat Proteins (DARPins): Binding Proteins for Research, Diagnostics, and Therapy," Annu. Rev. Pharmacol. Toxicol. 55, 489.
Poelma et al. (2016) "Controlled drug release to cancer cells from modular one-photon visible light-responsive micellar system," Chem. Commun., 52, 10525-10528.
Pohl et al. (1999) "Scope of Multivalent Ligand Function: Lactose-Bearing Neoglycopolymers By Ring-Opening Metathesis Polymerization," Synthesis 1999(SI): 1515-1519.
Pooga et al. (1998) "Cell penetrating PNA constructs regulate galanin receptor levels and modify pain transmission in vivo," Nat. Biotechnol. 16: 857-861.
Popiel et al. (2007) "Protein Transduction Domain-Mediated Delivery of QBP1 Suppresses Polyglutamine-Induced Neurodegeneration in Vivo," Mol. Ther. 15 (2), 303-309.
Popiel et al. (2009) "Delivery of the Aggregate Inhibitor Peptide QBP1 into the Mouse Brain Using PTDs and Its Therapeutic Effect on Polyglutamine Disease Mice," Neurosci. Lett. 449 (2), 87-92.
Popov et al. (2019) "Insight into the Structure of the "Unstructured" Tau Protein," Structure 27:1710-1715.e4. https://doi.org/10.1016/j.str.2019.09.003.
Poropatich et al. (2017) "Comprehensive T-cell immunophenotyping and next-generation sequencing of human papillomavirus (HPV)-positive and HPV-negative head and neck squamous cell carcinomas," J Pathol, 243 (3), 354-365.
Portz et al. (2021) "FUS and TDP-43 Phases in Health and Disease," Trends Biochem Sci 46:550-63. https://doi.org/10.1016/j.tibs.2020.12.005.

(56) References Cited

OTHER PUBLICATIONS

Powell et al. (1993) "Peptide Stability in Drug Development. II. Effect of Single Amino Acid Substitution and Glycosylation on Peptide Reactivity in Human Serum," Pharm. Res. 10(9): 1268-1273.
Prahlad et al. (2009) "Integrating the stress response: lessons for neurodegenerative diseases from C. elegans," Trends Cell Biol 19:52-61. https://doi.org/10.1016/j.tcb.2008.11.002.
Prasad et al. (2017) "Fabrication of nanostructures through self-assembly of non-ionic amphiphiles for biomedical applications," RSC Adv., 7, 22121-22132.
Price et al. (2004) "A modified TIP3P water potential for simulation with Ewald summation," J. Chem. Phys. 121(20): 10096-10103.
Proetto et al. (2016) "Cellular Delivery of Nanoparticles Revealed with Combined Optical and Isotopic Nanoscopy," ACS Nano, 10 (4),4046-54.
Proetto et al. (Jan. 2019) "Phosphorescent Pt(ii) complexes spatially arrayed in micellar polymeric nanoparticles providing dual readout for multimodal imaging," Chem. Commun., 55, 501-504.
Pronk et al. (publicly available Feb. 2013) "GROMACS 4.5: a high-throughput and highly parallel open source molecular simulation toolkit," Bioinformatics (Apr. 2013) 29(7): 845-854.
Puglisi et al. (1995) "Solution Structure of a Bovine Immunodeficiency Virus Tat-TAR Peptide-RNA Complex," Science 270(5239): 1200-1203, (Machine Generated Copy).
Qi et al. (May 2021) "PROTAC: An Effective Targeted Protein Degradation Strategy for Cancer Therapy," Front Pharmacol 12, 692574.
Qiao et al. (2019) "Water Follows Polar and Nonpolar Protein Surface Domains," Proc. Natl. Acad. Sci. U. S. A. 116, 19274-19281.
Qiao et al. (Apr. 2019) ""Mirror"-Like Protein Dimers Stabilized by Local Heterogeneity at Protein Surfaces," J. Phys. Chem. B, 123 (18), 3907-3915.
Qiao et al. (Aug. 2020) "Enhanced Binding of SARS-COV-2 Spike Protein to Receptor by Distal Polybasic Cleavage Sites," ACS Nano, 14, 10616-10623.
Qu et al. (2020) "Specific Knockdown of α-Synuclein by Peptide-Directed Proteasome Degradation Rescued Its Associated Neurotoxicity," Cell Chem Biol 27, 751-762.e754.
Ramon et al. (2005) "PEGylated Interferon-α2b: A Branched 40K Polyethylene Glycol Derivative," Pharm. Res. 22(8): 1374-1386.
Ramsey et al. (2007) "Expression of Nrf2 in Neurodegenerative Diseases," J Neuropathol Exp Neurol;66:75-85. https://doi.org/10.1097/nen.0b013e31802d6da9.
Ramshaw et al. (2014) "Bioengineered Collagens," Bioengineered, 5 (4), 227-233. https://doi.org/10.4161/BIOE.28791.
Rankin et al. (2007) "The controlled homogeneous organic solution polymerization of new hydrophilic cationic exo-7-oxanorbornenes via ROMP with RuCl2(PCy3)2CHPh in a novel 2,2,2-trifluoroethanol/methylenechloride solvent mixture," J. Polym. Sci. A Polym. Chem. 45(11): 2113-2128.
Rao (1995) "Recent developments of collagen-based materials for medical applications and drug delivery systems," Biomater Sci. Polym. Ed. 7:623-645.
Rao et al. (2012) "Norbornene Derived Doxorubicin Copolymers as Drug Carriers with pH Responsive Hydrazone Linker," Biomacromolecules 13(1): 221-230.
Raus et al. (2014) "ATRP of POSS Monomers Revisited: Toward High-Molecular Weight Methacrylate-POSS (Co)Polymers," Macromolecules, 47 (21), 7311-7320.
Rawlins et al. (2016) "The Prevalence of Huntington's Disease," Neuroepidemio/ogy, 46 (2), 144-153. https://doi.org/10.1159/000443738.
Regenbrecht et al. (2008) "Stemming cancer: functional genomics of cancer stem cells in solid tumors," Stem Cell Rev. 4(4):319-28.
Reissmann et al. (2000) "The LHRH antagonist Cetrorelix: a review," Human Reproduction Update 6(4): 322-331.
Richard et al. (2003) "Cell-penetrating Peptides: A Reevaluation of the Mechanism of Cellular Uptake," J. Biol. Chem. 278(1): 585-590.
Rizzuti et al. (2015) "Therapeutic Applications of the Cell-Penetrating HIV-1 Tat Peptide," Drug Discovery Today. 20 (1), 76-85. https://doi.org/10.1016/j.drudis.2014.09.017.
Roberts et al. (2012) "Chemistry for peptide and protein PEGylation," Adv. Drug Deliv. Rev. 64, 116-127.
Rodal et al. (1999) "Extraction of Cholesterol with Methyl-β-Cyclodextrin Perturbs Formation of Clathrin-coated Endocytic Vesicles," Mol. Biol. Cell 10(4): 961-974.
Röder et al. (2018) "Energy Landscapes for the Aggregation of AB17-42," J Am Chem Soc 140:4018-27. https://doi.org/10.1021/jacs.7b12896.
Roloff et al. (2017) "Micellar Thrombin-Binding Aptamers: Reversible Nanoscale Anticoagulants," J Am Chem Soc., 139(46):16442-16445. PMID: 29135251. DOI: 10.1021/jacs.7b07799.
Roloff et al. (Jan. 2018) "Self-Transfecting Micellar RNA: Modulating Nanoparticle Cell Interactions via High Density Display of Small Molecule Ligands on Micelle Coronas," Bioconjug Chem., 29(1):126-135. PMCID: PMC5993044.
Rosemalen et al. (2017) "Tuning the Flexibility of Glycine, Serine Linkers To Allow Rational Design of Multidomain Proteins," pp. 6565-6574. Biochemistry. vol. 56, No. 50; DOI: 10.1021/acs.biochem.7b00902.
Rosi et al. (2006) "Oligonucleotide-Modified Gold Nanoparticles for Intracellular Gene Regulation," Science 312(5776): 1027-1030.
Rothemund (2006) "Folding DNA to create nanoscale shapes and patterns," Nature 440: 297-302.
Rouse et al. (2010) "A Review of Keratin-Based Biomaterials for Biomedical Applications," Materials (Basel). 3 (2), 999-1014. https://doi.org/10.3390/ma3020999.
Rozek et al. (2003) "Structure-Based Design of an Indolicidin Peptide Analogue with Increased Protease Stability," Biochemistry 42(48): 14130-14138.
Ruijtenbeek et al. (2001) "Peptoid-Peptide Hybrids That Bind Syk SH2 Domains Involved in Signal Transduction," ChemBioChem 2(3): 171-179.
Rush et al. (2013) "Nuclease-resistant DNA via High Density Packing in Polymeric Micellar Nanoparticle Coronas," ACS Nano, 7(2):1379-1387. PMCID: PMC3608424.
Rush et al. (May 2014) "Intracellular mRNA Regulation with Self-Assembled Locked Nucleic Acid Polymer Nanoparticles," J. Am. Chem. Soc. 136: 7615-7618.
Rutkowski et al. (2015) "Microbially driven TLR-dependent signalling governs distal malignant progression through tumor-promoting inflammation," Cancer Cell; 27: 27-40. PMC4293269.
Ruttekolk et al. (2011) "Coupling to Polymeric Scaffolds Stabilizes Biofunctional Peptides for Intracellular Applications," Mol. Pharmacol. 79(4): 692-700.
Sabo et al. (2014) "Genome recognition by MYC," Cold Spring Harb Perspect Med 4, doi:10.1101/cshperspect.a014191.
Sahin et al. (Mar. 2018) "Personalized vaccines for cancer immunotherapy," Science. 359. 1355-1360.
Sahu et al. (2017) "Charged Macromolecular Rhenium Bipyridine Catalysts with Tunable CO2 Reduction Potentials," Chemistry—A European Journal, 23 (36), 8619-8622.
Saiki (1985) "Enzymatic amplification of beta-globin genomic sequences and restriction site analysis for diagnosis of sickle cell anemia," Science 230(4732): 1350-1354, (Machine Generated Copy).
Sakamoto et al. (2020) "Generation of KS-58 as the first K-Ras(G12D)-inhibitory peptide presenting anti-cancer activity in vivo," Scientific Reports 10, 21671.
Salim et al. (Feb. 2020) "Development of a Cell-Permeable Cyclic Peptidyl Inhibitor against the Keap1-Nrf2 Interaction," J. Org. Chem. 85, 1416-1424.
Samarajeewa et al. (publicly available Dec. 2013) "Programmed hydrolysis of nanoassemblies by electrostatic interaction-mediated enzymatic-degradation," Chem. Commun. (Jan. 2014), 50(8): 968-970.
Sánchez-Paulete et al. (Dec. 2017) "Antigen cross-presentation and T-cell cross-priming in cancer immunology and immunotherapy," Ann Oncol. 28(suppl_12):xii44-xii55.

(56) References Cited

OTHER PUBLICATIONS

Sanford et al. (2001) "A Versatile Precursor for the Synthesis of New Ruthenium Olefin Metathesis Catalysts," Organometallics 20(25): 5314-5318.
Savastano et al. (2021) "Disease-Associated Tau Phosphorylation Hinders Tubulin Assembly within Tau Condensates," Angew Chemie—Int Ed 60:726-30. https://doi.org/10.1002/anie.202011157.
Scarlett et al. (2012) "Ovarian cancer progression is controlled by phenotypic changes in dendritic cells," J Exp Med; 209:495-506. PMC3302234.
Schabath et al. (2016) "Differential association of STK11 and TP53 with KRAS mutation-associated gene expression, proliferation and immune surveillance in lung adenocarcinoma," Oncogene 35(24): 3209-3216, PMCID: PMC4837098.
Schafmeister et al. (2000) "An All-Hydrocarbon Cross-Linking System for Enhancing the Helicity and Metabolic Stability of Peptides," J. Am. Chem. Soc. 122(24): 5891-5892.
Schaub et al. (2018) "Pan-cancer Alterations of the MYC Oncogene and Its Proximal Network across the Cancer Genome Atlas," Cell Syst 6, 282-300 e282, doi:10.1016/j.cels.2018.03.003.
Scheller et al. (2001) "Production of Spider Silk Proteins in Tobacco and Potato," Nat. Biotechnol. 19 (6), 573-577. https://doi.org/10.1038/89335.
Schellinger et al. (Jul. 2013) "Block Copolymers Containing a Hydrophobic Domain of Membrane-Lytic Peptides Form Micellar Structures and Are Effective Gene Delivery Agents," ACS Macro Lett. 2(8): 725-730.
Scheutz et al. (Feb. 2021) "Probing Thermoresponsive Polymerization-Induced Self-Assembly with Variable-Temperature Liquid-Cell Transmission Electron Microscopy," Matter 4:722-36. https://doi.org/https://doi.org/10.1016/j.matt.2020.11.017.
Schleyer et al. (1970) "Evaluation of Strain in Hydrocarbons—Strain in Adamantane and Its Origin," J. Am. Chem. Soc. 92, 2377-2386.
Schmidlin et al. (2019) "Redox regulation by NRF2 in aging and disease," Free Radic Biol Med:702-7. https://doi.org/10.1016/j.freeradbiomed.2019.01.016.
Schmidt et al. (Jan. 2021) "Ubiquitin signalling in neurodegeneration: mechanisms and therapeutic opportunities," Cell Death Differ 28:570-90. https://doi.org/10.1038/s41418-020-00706-7.
Scholl et al. (1999) "Synthesis and Activity of a New Generation of Ruthenium-Based Olefin Metathesis Catalysts Coordinated with 1,3-Dimesityl-4,5-dihydroimidazol-2-ylidene Ligands," Org. Lett. 1(6): 953-956.
Schuster et al. (1997) "Neoglycopolymers produced by aqueous ring-opening metathesis polymerization: decreasing saccharide density increases activity," J. Mol. Catal. 116(1-2): 209-216.
Scott et al. (2016) "Small molecules, big targets: drug discovery faces the protein-protein interaction challenge," Nature Reviews Drug Discovery 15, 533-550.
Sears et al. (2000) "Multiple Ras-dependent Phosphorylation Pathways Regulate Myc Protein Stability," Genes Dev 14, 2501-2514.
Seeman (2010) "Structural DNA Nanotechnology: Growing Along with Nano Letters," Nano Lett. 10(6): 1971-1978.
Selkoe et al. (2016) "The amyloid hypothesis of Alzheimer's disease at 25 years," EMBO Mol Med 8:595-608. https://doi.org/10.15252/emmm.201606210.
Semsarilar et al. (2010) "'Green' reversible addition-fragmentation chain-transfer (RAFT) polymerization," Nat. Chem. 2, 811-820.
Senapati et al. (2018) "Controlled drug delivery vehicles for cancer treatment and their performance," Signal Transduct. Tar., 3, 7.
Shae et al. (Mar. 2019) "Endosomolytic polymersomes increase the activity of cyclic dinucleotide STING agonists to enhance cancer immunotherapy," Nat Nanotechnol, 14 (3), 269-278.
Shahpasand et al. (2018) "Tau immunotherapy: Hopes and hindrances," Hum Vaccines Immunother 2018;14:277-84. https://doi.org/10.1080/21645515.2017.1393594.
Shanmugam (2016) "Aqueous RAFT Photopolymerization with Oxygen Tolerance," Macromolecules, 49, 24, 9345-9357, doi: 10.1021/acs.macromol.6b02060.
Shannon et al. (2001) "Novel cyclic peptide inhibits intercellular adhesion molecule-1-mediated cell aggregation," J Pept Res. 58(2):140-50.
Shao et al. (2006) "Advances in methods and algorithms in a modern quantum chemistry program package," Phys. Chem. Chem. Phys. 8, 3172-3191.
Sharp et al. (2009) "Uptake of particulate vaccine adjuvants by dendritic cells activates the NALP3 inflammasome," P Natl Acad Sci USA, 106 (3), 870-875.
Shearouse et al. (2015) "Sustainable Polyesters Derived from Glucose and Castor Oil: Building Block Structure Impacts Properties," ACS Macro Lett. 4, 284-288.
Shi et al. (Oct. 2013) "Engineering biodegradable and multifunctional peptide-based polymers for gene delivery," J. Biol. Eng. 7: 25, pp. 1-10.
Shieh et al. (Jul. 2020) "Cleavable comonomers enable degradable, recyclable thermoset plastics," Nature. 583:542-7.
Shieh et al. (Oct. 2019) "Tailored silyl ether monomers enable backbone-degradable polynorbornene-based linear, bottlebrush and star copolymers through ROMP," Nat. Chem. 11, 1124-1132.
Silverman et al. (2007) "Understanding Marine Mussel Adhesion," Marine Biotechnology. Springer, pp. 661-681. https://doi.org/10.1007/s10126-007-9053-x.
Simov et al. (Nov. 2021) "Discovery and characterization of novel peptide inhibitors of the NRF2/MAFG/DNA ternary complex for the treatment of cancer," European Journal of Medicinal Chemistry, 224, 113686.
Singh et al. (2016) "Small Molecule Inhibitor of NRF2 Selectively Intervenes Therapeutic Resistance in KEAP1-Deficient NSCLC Tumors," ACS Chem Biol;11:3214-25. https://doi.org/10.1021/ACSCHEMBIO.6B00651.
Sionkowska et al. (2017) "The Review of Versatile Application of Collagen," Polym. Adv. Technol. 28 (1), 4-9. https://doi.org/10.1002/pat.3842.
Sivick et al. (Dec. 2018) "Magnitude of Therapeutic STING Activation Determines CD8(+) T Cell-Mediated Anti-tumor Immunity," Cell Rep, 25 (11), 3074-3085 e5.
Słabicki et al. (2020) "The CDK inhibitor CR8 acts as a molecular glue degrader that depletes cyclin K," Nature 585, 293-297, doi:10.1038/s41586-020-2374-x.
Smirnova et al. (2011) "Development of Neh2-luci-ferase reporter and its application for high throughput screening and real-time monitoring of Nrf2 Activators," Chemistry & Biology, 18, 752-765.
Smith et al. (1981) "Comparison of Biosequences," Adv. Appl. Math. 2:482-489.
Smith et al. (2017) "MET:GRB2 Signaling-Associated Complexes Correlate with Oncogenic MET Signaling and Sensitivity to MET kinase inhibitors," Clin Cancer Res. PMCID: PMC5833309.
Smith et al. (Jan. 2019) "Radical Approach to Thioester-Containing Polymers," J. Am. Chem. Soc. 141, 1446-1451.
Smyth et al. (2016) "Combination cancer immunotherapies tailored to the tumour microenvironment," Nat Rev Clin Oncol, 13 (3), 143-58.
Som et al. (2011) "Self-Activation in De Novo Designed Mimics of Cell-Penetrating Peptides," Angew. Chem., Int. Ed. 123: 6271-6274.
Song et al. (Aug. 2019) "Highly active ruthenium metathesis catalysts enabling ring-opening metathesis polymerization of cyclopentadiene at low temperatures," Nat. Commun. 10, 3860.
Song et al. (Jan. 2019) "pH-Sensitive morphological transitions in polymeric tadpole assemblies for programmed tumor therapy," J. Control Release, 293, 1-9.
Song et al. (Oct. 2018) "IRE1α-XBP1 controls T cell function in ovarian cancer by regulating mitochondrial activity," Nature. 562:423-8. PMC6237282.
Spicer et al. (Feb. 2018) "Peptide and protein nanoparticle conjugates: versatile platforms for biomedical applications," Chem. Soc. Rev. 47, 3574-3620.
Spijker et al. (2007) "Atom Transfer Radical Polymerization of Adenine, Thymine, Cytosine, and Guanine Nucleobase Monomers," Macromolecules 40(1): 12-18.

(56) References Cited

OTHER PUBLICATIONS

Spring et al. (publicly available May 2014) "The preparation of well-controlled poly(N-cyclohexyl-exo-norbornene-5, 6-dicarboximide) polymers," Polymer Journal (Sep. 2014) 46: 576-583.
Sprott et al. (2001) "Ring-closing metathesis strategies to amino acid-derived P-heterocycles," Synthesis-Stuttgart. 4, 612-620.
Steel et al. (2012) "Anti-inflammatory Effect of a Cell-Penetrating Peptide Targeting the Nrf2/Keapl Interaction," ACS Med. Chem. Lett. 3, 407-410.
Steer et al. (2002) "β-Amino Acids: Versatile Peptidomimetics," Curr. Med. Chem. 9(8): 811-822.
Steinbach et al. (2013) "Unsaturated poly(phosphoester)s via ring-opening metathesis polymerization," Polym. Chem. 4, 3800-3806.
Steinbach et al. (2014) "Poly(phosphonate)s via Olefin Metathesis: Adjusting Hydrophobicity and Morphology," Macromolecules. 47:4884-93.
Steinmann (2013) "Reactive Polyphosphoeslers via Acyclic Diene Metathesis Polymerization," Graduate Thesis, Johannes Gutenberg-Universitat Mainz. p. 11.
Stephen et al. (2014) "Transforming Growth Factor-beta-Mediated Suppression of Antitumor T Cells Requires FoxP1 Transcription Factor Expression," Immunity; 41:427-39. PMC4174366.
Stephen et al. (2017) "SATB1 expression governs epigenetic repression of PD-1 in tumor-reactive T cells," Immunity; 46: 51-64. PMC5336605.
Stickle et al. (1992) "Hydrogen bonding in globular proteins," J. Mol. Biol. 226(4): 1143-1159.
Storhoff et al. (1999) "Programmed Materials Synthesis with DNA," Chem. Rev. 99(7): 1849-1862.
Su et al. (1991) "In Vitro Stability of Growth Hormone Releasing Factor (GRF) Analogs in Porcine Plasma," Horm. Metab. Res. 23(1): 15-21.
Su et al. (2014) "Resilin: Protein-Based Elastomeric Biomaterials," Acta Biomaterialia. Elsevier BV, pp. 1601-1611. https://doi.org/10.1016/j.actbio.2013.06.038.
Sui et al. (Jul. 2020) "Alternating Cascade Metathesis Polymerization of Enynes and Cyclic Enol Ethers with Active Ruthenium Fischer Carbenes," J Am Chem Soc. 142:12942-7.
Suma et al. (2017) "Modulated Fragmentation of Proapoptotic Peptide Nanoparticles Regulates Cytotoxicity," J. Am. Chem. Soc. 139, 4009-4018.
Sumerlin (2012) "Proteins as Initiators of Controlled Radical Polymerization: Grafting-from via ATRP and RAFT," ACS Macro Lett. 1: 141-145.
Sun et al. (2012) "A novel mouse CD133 binding-peptide screened by phage display inhibits cancer cell motility in vitro," Clin Exp Metastasis, 29, 185-196.
Sun et al. (2017) "Macromolecular metamorphosis via stimulus-induced transformations of polymer architecture," Nat. Chem., 9, 817-823.
Sun et al. (Dec. 2021) "Origin of Proteolytic Stability of Peptide-Brush Polymers as Globular Proteomimetics," ACS Cent. Sci. 7 (12), 2063-2072.
Sun et al. (Feb. 2019) "Architecture-transformable polymers: Reshaping the future of stimuli-responsive polymers," Prog. Polym. Sci.89, 61-75.
Sun et al. (Nov. 2019) "Bioactive Peptide Brush Polymers via Photoinduced Reversible-Deactivation Radical Polymerization," Angewandte Chemie International Edition in English. vol. 58, No. 48; pp. 17359-17364; DOI: 10.1002/anie.201908634.
Sun et al. (Oct. 2020) "Direct inhibition of Keap1-Nrf2 Protein-Protein interaction as a potential therapeutic strategy for Alzheimer's disease," Bioorg Chem; 103:104172. https://doi.org/10.1016/j.bioorg.2020.104172.
Sun et al. (Oct. 2020) "Proapoptotic Peptide Brush Polymer Nanoparticles via Photoinitiated Polymerization-Induced Self-Assembly," Angew. Chem. 59, 19136-19142.
Sun et al. (Sep. 2021) "Degradable Polymers via Olefin Metathesis Polymerization", Progress in Polymer Science, vol. 120, 101427, doi:10.1016/j.progpolymsci.2021.101427.
Sutthasupa et al. (2010) "Recent advances in ring-opening metathesis polymerization, and application to synthesis of functional materials," Polymer Journal 42: 905-915.
Svoronos et al. (2017) "Tumor cell-independent estrogen signaling drives malignant progression through MDSC mobilization," Cancer Discovery. 7: 72-85. PMC5222699.
Sweeney et al. (2018) "Blood-brain barrier breakdown in Alzheimer disease and other neurodegenerative disorders," Nat Rev Neurol 14:133-50. https://doi.org/10.1038/nrneurol.2017.188.
Tan et al. (Apr. 2015) "Light-Triggered, Self-Immolative Nucleic Acid-Drug Nanostructures," J. Am. Chem. Soc., 137, 6112-6115.
Tan et al. (Jun. 2019) "Expanding the Materials Space of DNA via Organic-Phase Ring-Opening Metathesis Polymerization," Chem. 5, 1584-1596.
Tan et al. (Oct. 2015) "Photo-PISA: Shedding Light on Polymerization-Induced Self-Assembly," ACS Maacro Lett. 4, 1249-1253.
Tang et al. (2011) "Luteolin inhibits Nrf2 leading to negative regulation of the Nrf2/ARE pathway and sensitization of human lung carcinoma A549 cells to therapeutic drugs," Free Radic Biol Med;50:1599-1609. https://doi.org/10.1016/J.FREERADBIOMED.2011.03.008.
Tanji et al. (2013) "Keapl Is Localized in Neuronal and Glial Cytoplasmic Inclusions in Various Neurodegenerative Diseases," J Neuropathol Exp Neurol; 72:18-28. https://doi.org/10.1097/NEN.0b013e31827b5713.
Tapia-Rojas et al. (2019) "It's all about tau," Prog Neurobiol 175:54-76. https://doi.org/10.1016/j.pneurobio.2018.12.005.
Tardy et al. (2017) "Radical Ring-Opening Polymerization: Scope, Limitations, and Application to (Bio) Degradable Materials," Chem. Rev. 117, 1319-1406.
Taylor et al. (2016) "Biophysical characterization of organelle-based RNA/protein liquid phases using microfluidics," Soft Matter 12:9142-50. https://doi.org/10.1039/C6SM01087C.
Tee (Apr. 2019) "Polyphosphoesters: A Degradable Alternative to Polyolefins and Poly(elhyleneglycol)," Doctoral Thesis, Johannes Gutenberg-Universitat Mainz. p. 1-268.
Tee et al. (Jan. 2019) "Aliphatic Long-Chain Polypyrophosphates as Biodegradable Polyethylene Mimics," Macromolecules. 52:1166-72.
Tesone et al. (2016) "Satb1 Overexpression Drives Tumor-Promoting Activities in Cancer-Associated Dendritic Cells," Cell Reports.14: 1774-1786. PMC4767618.
Thies et al. (2013) "2013 Alzheimer's disease facts and figures." Alzheimer's & dementia 9, No. 2: 208-245.
Thomas et al. (2003) "Conditions for Facile, Controlled RAFT Polymerization of Acrylamide in Water," Macromolecules, 36, 1436-1439.
Thomas et al. (2004) "Hydrolytic Susceptibility of Dithioester Chain Transfer Agents and Implications in Aqueous RAFT Polymerizations," Macromolecules, 37, 1735-1741.
Thompson et al. (publicly available Dec. 2013) "Labelling Polymers and Micellar Nanoparticles via Initiation, Propagation and Termination with ROMP," Polym Chem, Mar. 2014 5(6):1954-1964.
Thundimadathil (Dec. 2012) "Cancer Treatment Using Peptides: Current Therapies and Future Prospects," Journal of Amino Acids 2012(967347): 1-13.
Tijssen (1993) "Overview of principles of hybridization and the strategy of nucleic acid probe assays," in Techniques in Biochemistry and Molecular Biology—Hybridization with Nucleic Probes, 19-78.
Ting et al. (2020) "Targeting c-Myc with a novel Peptide Nuclear Delivery Device," Scientific Reports 10, 17762.
Toft et al. (2012) "Coassembled Cytotoxic and Pegylated Peptide Amphiphiles Form Filamentous Nanostructures with Potent Anti-tumor Activity in Models of Breast Cancer," ACS Nano, 6, 7956-7965.
Tomita (2011) "Transgenic Silkworms That Weave Recombinant Proteins into Silk Cocoons," Biotechnology Letters. Springer, pp. 645-654. https://doi.org/10.1007/s10529-010-0498-z.
Tomoshige et al. (2021) "PROTACs and Other Chemical Protein Degradation Technologies for the Treatment of Neurodegenerative Disorders," Angew. Chem. Int. Ed. 60, 3346-3354.

(56) References Cited

OTHER PUBLICATIONS

Toti et al. (2010) "Interfacial Activity Assisted Surface Functionalization: A Novel Approach To Incorporate Maleimide Functional Groups and cRGD Peptide on Polymeric Nanoparticles for Targeted Drug Delivery," Mol Pharm. 7(4): 1108-1117.
Touve et al. (Apr. 2018) "Polymerization-Induced Self-Assembly of Micelles Observed by Liquid Cell Transmission Electron Microscopy," ACS Central Sci. 4, 543-547.
Trabulo et al. (2010) "Cell-Penetrating Peptides-Mechanisms of Cellular Uptake and Generation of Delivery Systems," Pharmaceuticals 3(4): 961-993.
Tran et al. (2019) "A Comparative Assessment Study of Known Small-Molecule Keap1-Nrf2 Protein-Protein Interaction Inhibitors: Chemical Synthesis, Binding Properties, and Cellular Activity," J. Med. Chem. 62, 17, 8028-8052.
Trettel et al. (2000) "Dominant Phenotypes Produced by the HD Mutationin STHdh(Q111) Striatal Cells," Hum. Mo/. Genet. 9 (19), 2799-2809. https://doi.org/10.1093/hmg/9.19.2799.
Trnka et al. (2001) "The Development of L2X2RuCHR Olefin Metathesis Catalysts: An Organometallic Success Story," Acc. Chem. Res. 34(1): 18-29.
Tsai et al. (2015) "ICAM1 Is a Potenital Cancer Stem Cell Marker of Esophageal Squamous Cell Carcinoma," PLOS One 10(11): e0142834.
Tuba et al. (2013) "Ruthenium catalyzed equilibrium ring-opening metathesis polymerization of cyclopentene," Polym. Chem. 4, 3959-3962.
Turbant et al. (2009) "Cynomolgus macaques immunized with two HIV-1 Tat stabilized proteins raise strong and long-lasting immune responses with a pattern of Th1/Th2response differing from that in mice," Vaccine, 27 (39), 5349-56.
Tyagi et al. (1996) "Molecular Beacons: Probes that Fluoresce upon Hybridization," Nat. Biotechnol. 14: 303-308.
Tymoczko ed. (2010) Biochemistry: A Short Course, 2nd ed., W.H. Freeman and Company: 13-15.
Ungerleider et al. (2017) "Enzyme-Targeted Nanoparticles for Delivery to Ischemic Skeletal Muscle," Polym Chem., 8(34):5212-5219. PMCID: PMC5662209.
Uto et al. (2009) "Modulation of innate and adaptive immunity by biodegradable nanoparticles," Immunol Lett, 125 (1), 46-52.
Valdebenito et al. (2010) "Effect of solvent on the free radical polymerization of N,N-dimethylacrylamide," Polym. Int. 59, 1246-1251.
Van Der Burg et al. (2016) "Vaccines for established cancer: overcoming the challenges posed by immune evasion," Nat Rev Cancer. 16(4):219-33.
Van Der Kant et al. (2020) "Amyloid-β-independent regulators of tau pathology in Alzheimer disease," Nat Rev Neurosci 21:21-35. https://doi.org/10.1038/s41583-019-0240-3.
Vandevrede et al. (2020) "Targeting tau: Clinical trials and novel therapeutic approaches," Neurosci. Lett. 731:134919. https://doi.org/10.1016/j.neulet.2020.134919.
Vanommeslaeghe et al. (2010) "CHARMM general force field: A force field for drug-like molecules compatible with the CHARMM all-atom additive biological force fields," J. Comput. Chem. 31(4): 671-690.
Vanommeslaeghe et al. (Nov. 2012) "Automation of the CHARMM General Force Field (CGenFF) I: Bond Perception and Atom Typing," J. Chem. Inf. Model. 52(12): 3144-3154.
Vanommeslaeghe et al. (Nov. 2012) "Automation of the CHARMM General Force Field (CGenFF) II: Assignment of Bonded Parameters and Partial Atomic Charges," J. Chem. Inf Model. 52(12): 3155-3168.
Varlas et al. (Aug. 2018) "Photoinitiated Polymerization-Induced Self-Assembly in the Presence of Surfactants Enables Membrane Protein Incorporation into Vesicles," Macromolecules, 51, 6190-6201.
Varlas et al. (Nov. 2019) "Polymerization-Induced Polymersome Fusion," J. Am. Chem. Soc. 141, 20234-20248.
Verdine et al. (2012) "Chapter one—Stapled Peptides for Intracellular Drug Targets," Methods Enzymol. 503: 3-33.
Vincent et al. (Aug. 2021) "The Combination of Morphology and Surface Chemistry Defines the Immunological Identity of Nanocarriers in Human Blood," Adv. Ther. 4 (8), 2100062.
Vinciguerra et al. (Feb. 2019) "Heterotelechelic polymer prodrug nanoparticles: Adaptability to different drug combinations and influence of the dual functionalization on the cytotoxicity," J. Control Release, 295, 223-236.
Vlieghe et al. (2010) "Synthetic therapeutic peptides: science and market," Drug Discovery Today 15(1-2): 40-56.
Voisine et al. (2010) "Chaperone networks: Tipping the balance in protein folding diseases," Neurobiol Dis 40:12-20. https://doi.org/10.1016/j.nbd.2010.05.007.
Von Bergen et al. (2000) "Assembly of T protein into Alzheimer paired helical filaments depends on a local sequence motif (306VQIVYK311) forming β structure," Proc Natl Acad Sci U S A 97:5129-34. https://doi.org/10.1073/pnas.97.10.5129.
Von Bergen et al. (2001) "Mutations of Tau Protein in Frontotemporal Dementia Promote Aggregation of Paired Helical Filaments by Enhancing Local B-Structure," J Biol Chem 276:48165-74. https://doi.org/10.1074/jbc.M105196200.
Von Bergen et al. (2005) "Tau aggregation is driven by a transition from random coil to beta sheet structure," Biochim Biophys Acta—Mol Basis Dis 1739:158-66. https://doi.org/10.1016/j.bbadis.2004.09.010.
Vonderheit et al. (2005) "Rab7 Associates with Early Endosomes to Mediate Sorting and Transport of Semliki Forest Virus to Late Endosomes," PLoS Biol. 3(7): 1225-1238.
Vukovic et al. (2011) "Structure and Dynamics of Highly PEGylated Sterically Stabilized Micelles in Aqueous Media," J. Am. Chem. Soc. 133(34): 13481-13488.
Vukovic et al. (Nov. 2013) "Solubilization of Therapeutic Agents in Micellar Nanomedicines," Langmuir 29(51): 15747-15754.
Wagener el al. (1991) "Acyclic Diene Metathesis (ADMET) Polymerization," Macromolecules, vol. 24(10), pp. 2649-2657.
Waite (2017) "Mussel Adhesion—Essential Footwork," Journal of Experimental Biology. Company of Biologists Ltd, pp. 517-530. https://doi.org/10.1242/jeb.134056.
Wales (2005) "The energy landscape as a unifying theme in molecular science," Philos Trans R Soc A Math Phys Eng Sci 363:357-77. https://doi.org/10.1098/rsta.2004.1497.
Wales et al. (1997) "Global optimization by basin-hopping and the lowest energy structures of Lennard-Jones clusters containing up to 110 atoms," J Phys Chem A 101:5111-6. https://doi.org/10.1021/jp970984n.
Wales et al. (1999) "Global optimization of clusters, crystals, and biomolecules," Science, 285:1368-72. https://doi.org/10.1126/science.285.5432.1368.
Walz et al. (2014) "Activation and repression by oncogenic MYC shape tumour-specific gene expression profiles," Nature 511, 483-487, doi: 10.1038/nature13473.
Wang et al. (1999) "Phase I trial of a MART-1 peptide vaccine with incomplete Freund's adjuvant for resected high-risk melanoma," ClinCancer Res, 5 (10), 2756-65.
Wang et al. (2004) "Development and testing of a general amber force field," J. Comput. Chem. 25(9): 1157-1174.
Wang et al. (2014) "Recent progress of cell-penetrating peptides as new carriers for intracellular cargo delivery," J. Controlled Release (Jan. 2014) 174: 126-136.
Wang et al. (2015) "Enzyme-regulated topology of a cyclic peptide brush polymer for tuning assembly," Chemical Communications, 51 (96), 17108-17111.
Wang et al. (Dec. 2017) "Preclinical development of drug delivery systems for paclitaxel-based cancer chemotherapy," J. Control Release, 267, 100-118.
Wang et al. (Feb. 2017) "Polyphosphoramidates That UndergoAcid-Triggered Backbone Degradation," ACS Macro Lett. 6, 219-223.
Wang et al. (Jan. 2021) "Small molecule therapeutics for tauopathy in Alzheimer's disease: Walking on the path of most resistance," Eur J Med Chem 209:112915. https://doi.org/10.1016/j.ejmech.2020.112915.

(56) References Cited

OTHER PUBLICATIONS

Wang et al. (May 2019) "Rational vaccinology with spherical nucleic acids," Proc Natl Acad Sci U S A, 116(21), 10473-10481.
Wanker et al. (2019) "The Pathobiology of Perturbed Mutant Huntingtin Protein-Protein Interactions in Huntington's Disease," J.Neurochem. 151 (4 ), 507-519. https://doi.org/10.1111/jnc.14853.
Warren et al. (2000) "APC Stimulated by CpG Oligodeoxynucleotide Enhance Activation of MHC Class I-Restricted T Cells," J. Immunol. 165 (11), 6244-6251. https://doi.org/10.4049/JIMMUNOL.165.11.6244.
Webber et al. (2016) "Supramolecular PEGylation of biopharmaceuticals," Proc. Natl. Acad. Sci. USA, 113, 14189-14194.
Weinstock et al. (2012) "Protease-resistant peptide design-empowering nature's fragile warriors against HIV," Pept. Sci. 98(5): 431-442.
Weiss et al. (2015) "Sequence-Controlled Copolymers Prepared via Entropy-Driven Ring-Opening Metathesis Polymerization," Acs Macro Lett. 4:1039-43.
Weiss et al. (2017) "The STING agonist DMXAA triggers a cooperation between T lymphocytes and myeloid cells that leads to tumor regression," Oncoimmunology, 6 (10),e1346765.
Wen et al. (Aug. 2021) "Conformational Expansion of Tau in Condensates Promotes Irreversible Aggregation," J Am Chem Soc 2021. https://doi.org/10.1021/jacs.1c03078.
Wender et al. (2000) "The design, synthesis, and evaluation of molecules that enable or enhance cellular uptake: Peptoid molecular transporters," Proc. Natl. Acad. Sci. U. S. A. 97(24): 13003-13008.
Whitfield et al. (2017) "Strategies to Inhibit Myc and Their Clinical Applicability," Front Cell Dev Biol 5, 10.
Widmann et al. (1991) "Differential stability of antigenic MHC class I restricted synthetic peptides," J Immunol, 147 (11), 3745-51.
Willaert (2018) "Cell Immobilization and Its Applications in Biotechnology: Current Trends and Future Prospects," Ferment. Microbiol. Biotechnol. Fourth Ed. 323-358. https://doi.org/10.1201/9780429506987-17.
Williamson et al. (2012) "Discovery of Potent, Novel Nrf2 Inducers Via Quantum Modeling, Virtual Screening, and In Vitro Experimental Validation," Chem Biol Drug Des; 80: 810-820.
Wilson et al. (1991) "Restriction and Modification Systems," Annu. Rev. Genet. 25: 585-627.
Wilson et al. (2018) "Magnesium Catalyzed Polymerization of End Functionalized Poly(propylene maleate) and Poly(propylene fumarate) for 3D Printing of Bioactive Scaffolds," J. Am. Chem. Soc. 140, 277-284.
Wolchok et al. (2007) "Safety and immunogenicity of tyrosinase DNA vaccines in patients with melanoma," Mol Ther, 15 (11), 2044-50.
Woodley (1994) "Enzymatic barriers for GI peptide and protein delivery," Crit. Rev. Ther. Drug Carrier Syst. 11(2-3): 61-95.
Wright et al. (Apr. 2018) "Aqueous-Phase Ring-Opening Metathesis Polymerization-Induced Self-Assembly," ACS Macro Lett, 7, 401-405.
Wright et al. (Apr. 2019) "Ring-opening metathesis polymerization-induced self-assembly (ROMPISA) of a cisplatin analogue for high drug-loaded nanoparticles," Polym. Chem. 10 (23), 2996-3000.
Wu et al. (2017) "Targeting the Genome-Stability Hub Ctf4 by Stapled-Peptide Design," Angew. Chem. Int. Ed. 56, 12866-12872.
Xiao et al. (2015) "Bioinspired Structural Colors Produced via Self-Assembly of Synthetic Melanin Nanoparticles," ACS Nano, 9(5):5454-5460. https://doi.org/10.1021/acsnano.5b01298.
Xiao et al. (2017) "Bio-Inspired Bright Non-Iridescent Photonic Melanin Supraballs," Science Advances, 3(9): e1701151. DOI: 10.1126/sciadv.1701151.
Xie et al. (2020) "Enhanced nuclear delivery of H1-S6A, F8A peptide by NrTP6-modified polymeric platform," Int J Pharm 580, 119224.
XU at al. (2016) "Selective Photoactivation: From a Single Unit Monomer Insertion Reaction to Controlled Polymer Architectures," J. Am. Chem. Soc. 138 (9), 3094-3106.
Xu et al. (2007) "Construct Synthetic Gene Encoding Artificial Spider Dragline Silk Protein and Its Expression in Milk of Transgenic Mice," Anim. Biotechnol. 18 (1), 1-12. https://doi.org/10.1080/10495390601091024.
Xu et al. (2013) "Cytomegalovirus-based cancer vaccines expressing TRP2 induce rejection of melanoma in mice," Biochem Biophys Res Commun, 437 (2), 287-91.
Xu et al. (2014) "A Robust and Versatile Photoinduced Living Polymerization of Conjugated and Unconjugated Monomers and Its Oxygen Tolerance," J. Am. Chem. Soc. 136, 5508-5519.
Xu et al. (2017) "Mussel-Inspired Polyesters with Aliphatic Pendant Groups Demonstrate the Importance of Hydrophobicity in Underwater Adhesion," Adv. Mater. Interfaces, 4 (22), 1700506. https://doi.org/10.1002/admi.201700506.
Xu et al. (Feb. 2021) "Injectable and Biocompatible Mussel-Inspired Adhesive for Enhanced Reendothelialization of Injured Artery," Adv. Mater. Interfaces, 8 (7), 2001955. https://doi.org/10.1002/ADMI.202001955.
Yadav et al. (2014) "Predicting immunogenic tumour mutations by combining mass spectrometry and exome sequencing," Nature, 515(7528), 572-6.
Yamaguchi et al. (2003) "Effect of α,α-Dialkyl Amino Acids on the Protease Resistance of Peptides," Biosci., Biotechnol., Biochem. 67(10): 2269-2272.
Yang et al. (2016) "Development of a Robust Photocatalyzed ATRP Mechanism Exhibiting Good Tolerance to Oxygen and Inhibitors," Macromolecules, 49, 7653-7666.
Yang et al. (2018) "Self-assembled aptamer-hyperbranched polymer nanocarrier for targeted and photoresponsive drug delivery," Angew. Chem. Int. Ed., 57, 17048-17052.
Yang et al. (2020) "Amelioration of aggregate cytotoxicity by catalytic conversion of protein oligomers into amyloid fibrils," Nanoscale 2020;12:18663-72. https://doi.org/10.1039/d0nr01481h.
Yasir et al. (2019) "Catalytic living ring-opening metathesis polymerization with Grubbs' second- and third-generation catalysts," Nat Chem. 11:488-94.
Yeo et al. (2016) "Valosin-Containing Protein (VCP): Structure, Functions, and Implications in Neurodegenerative Diseases," Animal Cells Syst. (Seoul). 20 (6), 303-309. https://doi.org/10.1080/19768354.2016.1259181.
Yeow et al. (2017) "Photoinitiated Polymerization-Induced Self-Assembly (Photo-PISA): New Insights and Opportunities," Adv. Sci. 4, 1700137.
Yhnell et al. (2016) "A Longitudinal Operant Assessment of Cognitiveand Behavioural Changes in the HdhQ111 Mouse Model of Huntington's Disease," PLoSOne, 11 (10), 1-19. https://doi.org/10.1371/journal.pone.0164072.
Yin et al. (2016) "Mitochondria-Targeted Molecules MitoQ and SS31 Reduce Mutant Huntingtin-Induced Mitochondrial Toxicity and Synaptic Damage in Huntington's Disease," Hum. Mol. Genet. 25 (9), 1739-1753.
Yu et al. (2018) "Ring-Closing Metathesis in Pharmaceutical Development: Fundamentals, Applications, and Future Directions" Org. Process Res. Dev. 22, 8, 918-946, DOI:10.1021/acs.oprd.8b00093.
Yu et al. (Feb. 2019) "A Hybrid Platform Based on a Bispecific Peptide-Antibody Complex for Targeted Cancer Therapy," Angew. Chem. Int. Ed. 58, 2005-2010.
Yu et al. (May 2019) "Tau protein aggregates inhibit the protein-folding and vesicular trafficking arms of the cellular proteostasis network," J Biol Chem 294:7917-30. https://doi.org/10.1074/jbc.RA119.0075.
Zeng et al. (Jan. 2021) "Proteolysis targeting chimera (PROTAC) in drug discovery paradigm: Recent progress and future challenges," Eur J Med Chem 210:112981. https://doi.org/10.1016/j.ejmech.2020.112981.
Zeng et al. (Oct. 2021) "The structure and phase of tau: from monomer to amyloid filament," Cell Mol Life Sci 78:1873-86. https://doi.org/10.1007/s00018-020-03681-x.
Zhang et al. (2003) "Intratumoral T cells, recurrence and survival in epithelial ovarian cancer," N Engl J Med; 348:201-211.
Zhang et al. (2007) "Thrombospondin-based antiangiogenic therapy," Microvasc Res. 74(2-3), 90-99.

(56) References Cited

OTHER PUBLICATIONS

Zhang et al. (2012) "Rapid and Versatile Constructionof Diverse and Functional Nanostructures Derived froma Polyphosphoester-Based Biomimetic Block Copolymer System," J. Am. Chem. Soc. 134, 18467-18474.
Zhang et al. (2015) "Polyelectrolyte Multilayers Assembled Entirely from Immune Signals on Gold Nanoparticle Templates Promote Antigen-Specific T Cell Response," ACS Nano, 9 (6), 6465-77.
Zhang et al. (Apr. 2020) "Emerging Substrate Proteins of Kelch-like ECH Associated Protein 1 (Keap1) and Potential Challenges for the Development of Small-Molecule Inhibitors of the Keap1-Nuclear Factor Erythroid 2-Related Factor 2 (Nrf2) Protein-Protein Interaction," J. Med. Chem. 63, 7986-8002.
Zhang et al. (Aug. 2021) "Strategies for targeting undruggable targets," Expert Opin Drug Discov 17, 55-69.
Zhang et al. (Mar. 2021) "DCAF11 Supports Targeted Protein Degradation by Electrophilic Proteolysis-Targeting Chimeras," J Am Chem Soc 143, 5141-5149.
Zhao et al. (2007) "Chemical Chaperone and Inhibitor Discovery: Potential Treatments for Protein Conformational Diseases," Perspect Medicin Chem 1:PMC.S212. https://doi.org/10.4137/pmc.s212.
Zhao et al. (2016) "Prognostic value of the expression of cancer stem cell-related markers CD133 and CD44 in hepatocellular carcinoma: From patients to patient-derived tumor xenograft models," Oncotarget. 7(30):47431-47443.
Zhao et al. (publicly available Aug. 2013) "Mimicry of High-Density Lipoprotein: Functional Peptide-Lipid Nanoparticles Based on Multivalent Peptide Constructs," J. Am. Chem. Soc. (Sep. 2013) 135(36): 13414-13424.
Zheng et al. (2011) "Macrocyclic β-sheet peptides that inhibit the aggregation of a tau-protein-derived hexapeptide," J Am Chem Soc 133:3144-57. https://doi.org/10.1021/ja110545h.
Zhou et al. (Apr. 2015) "Aqueous Polymerization-Induced Self-Assembly for the Synthesis of Ketone-Functionalized Nano-Objects with Low Polydispersity," ACS Macro Lett. 4, 495-499.
Zhou et al. (Jan. 2015) "Adhesion Properties of Catechol-Based Biodegradable Amino Acid-Based Poly(Ester Urea) Copolymers Inspired from Mussel Proteins," Biomacromolecules, 16 (1), 266-274. https://doi.org/10.1021/bm501456g.
Zhou et al. (May 2015) "Regulation Mechanism of Fbxw7-related Signaling Pathways (Review)," Oncol Rep 34, 2215-2224.
Zhu et al. (May 2020) "Paclitaxel-terminated peptide brush polymers," Chem. Commun., 56, 6778-6781.
Zidovetzki et al. (2007) "Use of cyclodextrins to manipulate plasma membrane cholesterol content: Evidence, misconceptions and control strategies," Biochim. Biophys. Acta 1768(6): 1311-1324.
Zielińska et al. (2020) "Polymeric Nanoparticles: Production, Characterization, Toxicology and Ecotoxicology," Molecules, 25: 3731.
Zilong et al. (publicly available Jun. 2013) "A Controlled-Release Nanocarrier with Extracellular pH Value Driven Tumor Targeting and Translocation for Drug Delivery," Angew. Chem., Int. Ed. (Jul. 2013), 52(29): 7487-7491.
Zou et al. (2015) "Well-defined diblock brush polymer-drug conjugates for sustained delivery of paclitaxel," Biomaterials Science, 3 (7), 1078-1084.
Zou et al. (2017) "Progress in Research and Application of HIV-1TAT-Derived Cell-Penetrating Peptide," J. Membr. Biol. 250 (2), 115-122.https://doi.org/10.1007/s00232-016-9940-z.

* cited by examiner

I + II III PTX

Poly(amino acid sequence)-Dye-PTX

Norbornene-peptide monomers

Nor-GGSGSGR

Nor-GGSGSGRR

Crude Poly(GGSGSGS) (monomer Nor-GGSGSGS)

Crude Poly(GGSGSGK) (monomer Nor-GGSGSGK)

Crude Poly(GGSGSGR) (monomer Nor-GGSGSGR)

Crude Poly(GGSGSGRR) (monomer Nor-GGSGSGRR)

Cis-Butene Termination Agents

A1 can be a carbon atom(s) or oxygen atom or linker molecule
A2 can be a carbon atom(s) or oxygen atom or linker molecule
X1 is a therapeutic
X2 is a therapeutic Linker molecules we have used but there are many variations that can be used Enol Ether Termination Agents $B^1$ can be a linker molecule
$R^1$ is a therapeutic

SEQUENCE LISTING

```
<160> NUMBER OF SEQ ID NOS: 5

<210> SEQ ID NO 1
<211> LENGTH: 7
<212> TYPE: PRT
<213> ORGANISM: Artificial sequence
<220> FEATURE:
<223> OTHER INFORMATION: Synthetic construct

<400> SEQUENCE: 1

Gly Gly Ser Gly Ser Gly Ser
1               5


<210> SEQ ID NO 2
<211> LENGTH: 7
<212> TYPE: PRT
<213> ORGANISM: Artificial sequence
<220> FEATURE:
<223> OTHER INFORMATION: Synthetic construct

<400> SEQUENCE: 2

Gly Gly Ser Gly Ser Gly Glu
1               5


<210> SEQ ID NO 3
<211> LENGTH: 7
<212> TYPE: PRT
<213> ORGANISM: Artificial sequence
<220> FEATURE:
```

-continued

```
<223> OTHER INFORMATION: Synthetic construct

<400> SEQUENCE: 3

Gly Gly Ser Gly Ser Gly Lys
1               5


<210> SEQ ID NO 4
<211> LENGTH: 7
<212> TYPE: PRT
<213> ORGANISM: Artificial sequence
<220> FEATURE:
<223> OTHER INFORMATION: Syntehtic construct

<400> SEQUENCE: 4

Gly Gly Ser Gly Ser Gly Arg
1               5


<210> SEQ ID NO 5
<211> LENGTH: 8
<212> TYPE: PRT
<213> ORGANISM: Artificial sequence
<220> FEATURE:
<223> OTHER INFORMATION: Synthetic construct

<400> SEQUENCE: 5

Gly Gly Ser Gly Ser Gly Arg Arg
1               5
```

DRUG LOADED PEPTIDE BRUSH POLYMERS

CROSS-REFERENCE TO RELATED APPLICATIONS

This application is a U.S. National Stage Application under 35 U.S.C. § 371 of International Application No. PCT/US2021/029829, filed Apr. 29, 2021, which claims the benefit of priority to U.S. Provisional Patent Application No. 63/018,991, filed May 1, 2020, which is hereby incorporated by reference in its entirety, and this application also incorporates by reference in its entirety, to the extent not inconsistent herewith, each of the following applications: U.S. Non-Provisional application Ser. No. 15/502,166 filed Aug. 10, 2015, and U.S. Non-Provisional application Ser. No. 15/329,526 filed Jul. 28, 2015.

REFERENCE TO A SEQUENCE LISTING

A sequence listing containing SEQ ID NOs: 1-5, created Apr. 27, 2021, 2 kB, is provided herewith in a computer-readable nucleotide/amino acid .txt file and is specifically incorporated by reference.

BACKGROUND OF INVENTION

Small molecule therapeutics commonly used in the treatment of human diseases, such as cancer, often suffer from poor solubility and stability in aqueous solutions or blood.

Systems for improving drug delivery often rely on covalent-conjugation to carrier species or encapsulation by carrier species. Covalent conjugation generally involves attaching drugs via chemical bonds, such as esters and disulfides, that facilitate release. Covalent conjugation has received increasing interest because it confers the drug delivery system with enhanced stability during blood circulation. This approach not only precludes premature release of therapeutics, but also allows for specific stimuli-triggered drug release in diseased tissues. In the case of polymeric carriers, drugs are typically tethered as side chains via direct polymerization of drug-modified monomers or via post-polymerization modifications. In each case, a statistical average of drugs is incorporated per polymer chain because of the dispersity of the polymer, which limits controllability of therapeutic dosage.

Other issues with polymeric therapeutics include hydrophobicity, poor resistance to proteolysis, poor cellular uptake, or inconsistent or incomplete therapeutic attachment, thereby requiring extra purification steps and/or limiting controllability of drug dosage.

To overcome these issues and to prepare polymer-based drug delivery systems in a more precise and well-defined fashion, new approaches are needed. These issues, and others, are addressed by the polymers, and associated methods, disclosed herein, which include one or more therapeutic moieties.

SUMMARY OF THE INVENTION

Included herein are polymers that comprise one or more non-peptide therapeutic moieties, such as small molecule therapeutics. In certain embodiments, the polymers contain one non-peptide therapeutic moiety per polymer, optionally at the chain end of the polymer, providing for precise and accurate control of drug delivery and dosing. In certain embodiments, the polymers comprise peptide-containing side chains which increases cellular uptake. In certain embodiments, the polymers are positively charged, which further facilitates cellular uptake. In certain embodiments, the polymers are water soluble. A tunable range of compositions of these polymers are disclosed, including tunable compositions and distribution of the peptide moieties, the therapeutic moieties, and the charge, which in turn provides for tunability of characteristics such as cellular uptake, potency, cytotoxicity, and water-solubility. Also disclosed herein are methods for synthesizing these polymers and methods for treating patients using these polymers, or aqueous solutions comprising these polymers. In certain embodiments, the polymers are formed by ring-opening metathesis polymerization. In certain embodiments, the polymers and synthesis steps are free of drug-containing substituted or unsubstituted norbornene or norbornene derivative monomers, including but not limited to norbornenyl monomers. Applications of the polymers and methods disclosed herein include small molecule therapeutic delivery systems. For example, in embodiments, a peptide-containing polymer provided herein is a carrier for a non-peptide therapeutic (e.g., small molecule drug), whereby the peptide-containing polymer as a carrier provides for, facilitates, or improves (compared to providing said non-peptide therapeutic without the polymer as a carrier): stability of the non-peptide therapeutic in biological fluids and biological systems, cellular uptake of the non-peptide therapeutic, and accurate and reproducible dosing of the therapeutic. Advantages of the polymers and methods disclosed herein include: ability to incorporate a single drug moiety onto the end of a ROMP polymer; tunability of charge of the polymer for tunable cellular uptake; end-labelled and non-labelled polymers can be separated; drug-end-labelled polymers are can be dispersed as single chains in aqueous environments; the polymers show resistance to proteolysis; and the polymers show enhanced cellular internalization.

Aspects of the invention include a polymer comprising: a plurality of repeating units, each repeating unit comprising a polymer backbone group directly or indirectly covalently linked to one or two side chain moieties, the polymer being characterized by formula FX1: $Q^1$-$[M(Z)_u]_n$-$Q^2$ (FX1); wherein: n is an integer selected from the range of 2 to 1000; u is 1 or 2; each M is independently the polymer backbone group of one of the repeating units and each M is independently a ROMP-polymerized monomer; each Z is independently one of the one or two side chain moieties of a repeating unit and each Z independently comprises a peptide moiety or a non-peptide therapeutic moiety; wherein the polymer comprises a plurality of peptide moieties; each Z is independently directly or indirectly covalently attached to an M; each M is covalently attached to at least one other M and 100% of the ROMP-polymerized monomers are each individually attached to the one or two side chain moieties of the respective repeating unit; $Q^1$ is a first polymer-terminating group; $Q^2$ is a second polymer-terminating group; and at least one Z of the polymer comprises a non-peptide therapeutic moiety, $Q^1$ comprises a non-peptide therapeutic moiety, and/or $Q^2$ comprises a non-peptide therapeutic moiety.

Aspects of the invention include a polymer comprising: a plurality of repeating units, each repeating unit comprising a polymer backbone group directly or indirectly covalently linked to one or two side chain moieties, the polymer being characterized by formula FX1: $Q^1$-$[M(Z)_u]_n$-$Q^2$ (FX1); wherein: n is an integer selected from the range of 2 to 1000; u is 1 or 2; each M is independently the polymer backbone group of one of the repeating units and each M is independently a ROMP-polymerized monomer; each Z is independently one of the one or two side chain moieties of a repeating unit and each Z independently comprises a peptide moiety or a non-peptide therapeutic moiety; wherein the polymer comprises a plurality of peptide moieties; each Z is independently directly or indirectly covalently attached to an M; each M is covalently attached to at least one other M and each M is independently directly or indirectly covalently attached to one or two of Z, such that 100% of the ROMP-polymerized monomers are each individually attached to one or two side chain moieties; $Q^1$ is a first polymer-terminating group; $Q^2$ is a second polymer-terminating group; and at least one Z of the polymer comprises a non-peptide therapeutic moiety, $Q^1$ comprises a non-peptide therapeutic moiety, and/or $Q^2$ comprises a non-peptide therapeutic moiety. Optionally in any of the polymers, methods, and liquid compositions disclosed herein, n and a fraction (“P”) of all side chain moieties in the polymer that are side chain moieties comprising a peptide moiety are selected to provide for cellular uptake. Optionally, cellular uptake refers to cellular uptake of or penetration of a biological by at least a portion of the polymer, the majority of the polymer, or the entirety of the polymer. Cellular uptake can be measured or quantified, such as via absorbance or fluorescence signal unique to a portion of the polymer (such as the drug) using different cellular assays, UV-Vis absorption spectroscopy, fluorescence spectroscopy, radio labeling, mass-spectroscopy, and/or inductively coupled plasma mass spectrometry. Preferably, in any of the polymers and methods disclosed herein, $Q^1$ comprises a non-peptide therapeutic moiety and/or $Q^2$ comprises a non-peptide therapeutic moiety. Optionally in any of the polymers, methods, and liquid compositions disclosed herein, $Q^1$ comprises a non-peptide therapeutic moiety. Optionally in any of the polymers, methods, and liquid compositions disclosed herein, $Q^2$ comprises a non-peptide therapeutic moiety. Optionally in any of the polymers, methods, and liquid compositions disclosed herein, only one of $Q^1$ and $Q^2$ comprises a non-peptide therapeutic moiety. Preferably, for some applications, in Preferably, for some applications, in any of the polymers, methods, and liquid compositions disclosed herein, each Z is independently a side chain moiety not comprising a non-peptide therapeutic moiety such that the polymer does not comprise a non-peptide therapeutic moiety between $Q^1$ and $Q^2$; and wherein $Q^1$ and/or $Q^2$ comprises a non-peptide therapeutic moiety. For example, optionally for some applications, a non-peptide therapeutic moiety is only at one or both of the polymer-terminating groups of the polymer. Preferably, for some applications, in any of the polymers, methods, and liquid compositions disclosed herein, only one of $Q^1$ and $Q^2$ comprises a therapeutic moiety and the polymer does not comprise a therapeutic moiety between $Q^1$ and $Q^2$ (such that the polymer comprises only one non-peptide therapeutic moiety). Optionally in any of the polymers, methods, and liquid compositions disclosed herein, each non-peptide therapeutic moiety is identical to each other non-peptide therapeutic moiety. Optionally in any of the polymers, methods, and liquid compositions disclosed herein, each Z is independently a side chain moiety comprising a peptide moiety. Optionally in any of the polymers, methods, and liquid compositions disclosed herein, each Z independently comprises a peptide moiety, a non-peptide therapeutic moiety, or a dye moiety. For clarity, each $-[M(Z)_u]—$ of a polymer characterized by formula FX1 independently corresponds to a repeating unit of the polymer.

Optionally in any of the polymers, methods, and liquid compositions disclosed herein, each peptide moiety of the polymer is identical to each other peptide moiety of the polymer. Optionally in any of the polymers, methods, and liquid compositions disclosed herein, the peptide comprises at least two peptide moieties; wherein the at least two peptide moieties include at least two unique peptide moieties. For example, optionally for some application, the polymer comprises at least two different peptide moieties or sequences. Optionally in any of the polymers, methods, and liquid compositions disclosed herein, the peptide comprises at least three peptide moieties; wherein the at least three peptide moieties include at least three unique peptide moieties. Optionally in any of the polymers, methods, and liquid compositions disclosed herein, at least one of the plurality of peptide moieties is a therapeutic peptide moiety. Optionally in any of the polymers, methods, and liquid compositions disclosed herein, the polymer comprises one, two, or more than two different therapeutic peptide moieties. Optionally in any of the polymers, methods, and liquid compositions disclosed herein, the polymer comprises one, two, or more than two different non-peptide therapeutic moieties. Optionally in any of the polymers, methods, and liquid compositions disclosed herein, at least one of the plurality of peptide moieties is a non-cell-penetrating peptide. Optionally in any of the polymers, methods, and liquid compositions disclosed herein, each peptide moiety of at least a majority of the plurality of peptide moieties is a non-cell-penetrating peptide. Optionally in any of the polymers, methods, and liquid compositions disclosed herein, cellular uptake of the polymer is provided by a combination of parameters n, P, and peptide moiety charge. Optionally in any of the polymers, methods, and liquid compositions disclosed herein, cellular uptake of the polymer is not (or, not necessarily) provided by a sequence of each individual peptide moiety. Optionally in any of the polymers, methods, and liquid compositions disclosed herein, at least one of the plurality of peptide moieties comprises a sequence having 80% or greater sequence homology of GGSGSGS (SEQ ID NO:1), GGSGSGE (SEQ ID NO:2), GGSGSGK (SEQ ID NO:3), GGSGSGR (SEQ ID NO:4), GGSGSGRR (SEQ ID NO:5), or a combination of these. Optionally in any of the polymers, methods, and liquid compositions disclosed herein, the polymer has a net positive charge. The presence of a positive charge can increase or otherwise enhance the therapeutic activity or function of the polymer, or portions thereof such as of the non-peptide therapeutic(s) and any therapeutic peptides, if present. The presence of a positive charge on the polymer can increase or otherwise enhance the therapeutic activity or function of the polymer, or portions thereof at least because of the enhanced or improved cellular uptake efficiency of the polymer due to the presence of the positive charge. Preferably, the net positive charge of the polymer is present at least when the polymer is exposed to physiological conditions, including normal physiological conditions. Preferably, any positive charge of the polymer is present at least when the polymer is exposed to physiological conditions, including normal physiological conditions. Optionally in any of the polymers, methods, and liquid compositions disclosed herein, at least one of the plurality of peptide moieties has a positive charge. Optionally in any of the polymers, methods, and liquid compositions disclosed herein, at least one side chain moiety Z comprises a positive charge. A positive charge of a peptide moiety can be present at any portion of the sequence of the peptide having the positive charge. A polymer including a positive charge can include cations that are not pH dependent. Optionally in any of the polymers, methods, and liquid compositions disclosed herein, each of a number of peptide moieties corresponding to at least 5% of the plurality of peptide moieties comprises a positive charge. Optionally in any of the polymers, methods, and liquid compositions disclosed herein, each peptide moiety of at least 5% of the plurality of peptide moieties comprises a positive charge. Optionally in any of the polymers, methods, and liquid compositions disclosed herein, each of a number of peptide moieties corresponding to at least 1%, at least 5%, at least 10%, optionally at least 20%, of the plurality of peptide moieties comprises a positive charge. Optionally in any of the polymers, methods, and liquid compositions disclosed herein, each peptide moiety having a positive charge has a sequence comprising at least one arginine (R) group and/or at least one lysine (K) group. Optionally in any of the polymers, methods, and liquid compositions disclosed herein, a cell uptake efficiency of the polymer is higher due to the presence of at least one positively charged peptide moiety, compared to a cell uptake efficiency of an equivalent polymer free of a positively charged group. Optionally in any of the polymers, methods, and liquid compositions disclosed herein, each of a number of peptide moieties corresponding to at least a fraction of the plurality of peptide moieties is a hydrophilic peptide such that the polymer is hydrophilic. Optionally in any of the polymers, methods, and liquid compositions disclosed herein, each of a number of peptide moieties corresponding to at least 30%, at least 50%, at least 75%, optionally at least 90%, of the plurality of peptide moieties is a hydrophilic peptide such that the polymer is hydrophilic. Optionally in any of the polymers, methods, and liquid compositions disclosed herein, each peptide moiety of the polymer is a hydrophilic peptide. Optionally in any of the polymers, methods, and liquid compositions disclosed herein, each peptide moiety comprises at least 2 amino acids. Optionally in any of the polymers, methods, and liquid compositions disclosed herein, each peptide moiety comprises at least 2 and less than or equal to 50 amino acids. Optionally in any of the polymers, methods, and liquid compositions disclosed herein, each peptide moiety is a branched polypeptide, a linear polypeptide or a cross-linked polypeptide. Optionally in any of the polymers, methods, and liquid compositions disclosed herein, the polymer is a brush polymer.

Preferably, for some applications, in any of the polymers, methods, and liquid compositions disclosed herein, each M is independently a ROMP-polymerized substituted or unsubstituted norbornene or a ROMP-polymerized substituted or unsubstituted oxanorbornene monomer. Preferably, for some applications, in any of the polymers, methods, and liquid compositions disclosed herein, each M is independently a ROMP-polymerized substituted or unsubstituted norbornene dicarboximide monomer. Preferably, for some applications, in any of the polymers, methods, and liquid compositions disclosed herein, the polymer is characterized by formula FX2a or FX2b:

(FX2a)

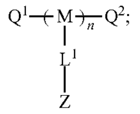

(FX2b)

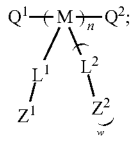

wherein: each of $L^1$ and $L^2$ is independently a covalent linking group; each of Z, $Z^1$, and $Z^2$ is independently the side chain moiety; and w is 1 or 0. Preferably, for some applications, in any of the polymers, methods, and liquid compositions disclosed herein, each M covalently attached to one or two side chain moieties through a covalent linking group is characterized by formula FX3a, FX3b, FX3c, FX3d, FX3e, FX3f, FX3g, or FX3h:

(FX3a)

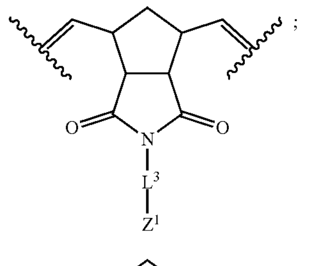

(FX3b)

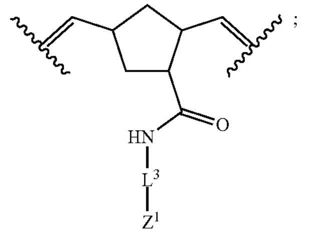

(FX3c)

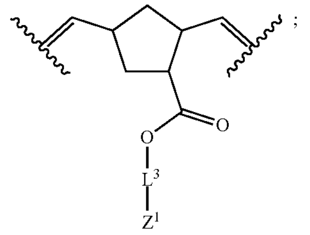

(FX3d)

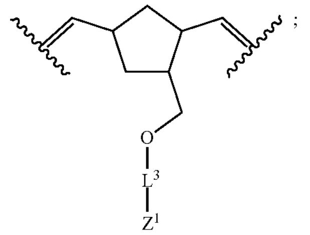

(FX3e)

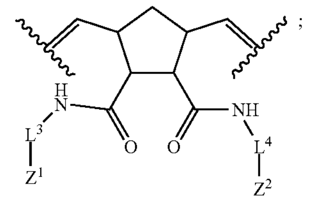

(FX3f)

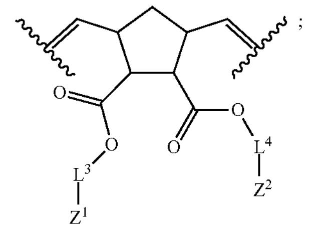

-continued (FX3g)

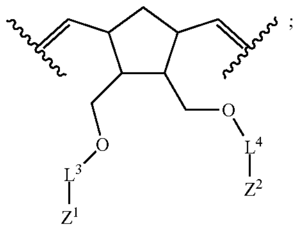

or (FX3h)

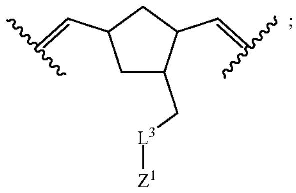

wherein each of $L^3$ and $L^4$ is independently the covalent linking group; and wherein each of $Z^1$ and $Z^2$ is independently the side chain moiety. Preferably, for some applications, in any of the polymers, methods, and liquid compositions disclosed herein, each M covalently attached to one or two side chain moieties is characterized by formula FX3i, FX3j, FX3k, FX3l, FX3m, FX3n, FX3o, or FX3p:

(FX3i)

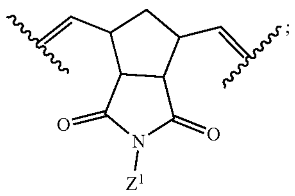

(FX3j)

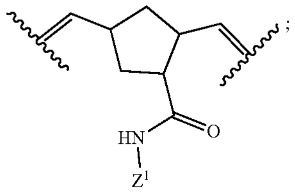

(FX3k)

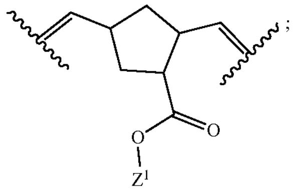

(FX3l)

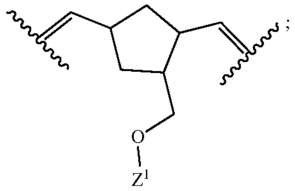

-continued (FX3m)

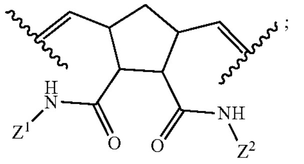

(FX3n)

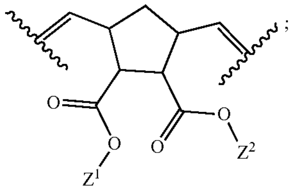

(FX3o)

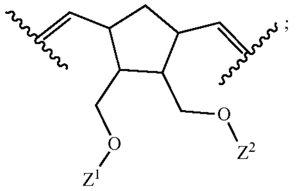

or (FX3o)

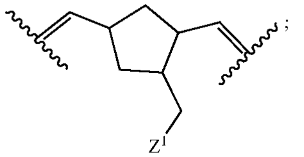

wherein each of $Z^1$ and $Z^2$ is independently the side chain moiety. Optionally in any of the polymers, methods, and liquid compositions disclosed herein, each of $L^1$, $L^2$, $L^3$, and $L^4$ is independently selected from a single bond, an oxygen, and one or more substituted or substituted groups having an alkyl group, an alkenylene group, an arylene group, an alkoxy group, an acyl group, a carboxyl group, an aliphatic group, an amide group, an aryl group, an amine group, an ether group, a ketone group, an ester group, a triazole group, a diazole group, a pyrazole group, or combinations thereof. Optionally in any of the polymers, methods, and liquid compositions disclosed herein, each of $L^1$, $L^2$, $L^3$, and $L^4$ is independently selected from a single bond, —O—, $C_1$-$C_{10}$ alkyl, $C_2$-$C_{10}$ alkenylene, $C_3$-$C_{10}$ arylene, $C_1$-$C_{10}$ alkoxy, $C_1$-$C_{10}$ acyl and combinations thereof.

Optionally in any of the polymers, methods, and liquid compositions disclosed herein, $Q^1$ and/or $Q^2$ is characterized by the formula FX4a or FX4b:

(FX4a)

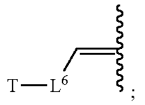

(FX4b)

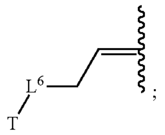

wherein: T is a non-peptide therapeutic moiety; and $L^6$ is a covalent linking group selected from a single bond, an oxygen, and one or more substituted or substituted groups having an alkyl group, an alkenylene group, an arylene group, an alkoxy group, an acyl group, a carboxyl group, an aliphatic group, an amide group, an aryl group, an amine group, an ether group, a ketone group, an ester group, a triazole group, a diazole group, a pyrazole group, or combinations thereof. Optionally in any of the polymers, methods, and liquid compositions disclosed herein, $L^1$ is characterized by the formula FX5a, FX5b, FX5c, FX5d, FX5e, FX5f, FX5g, or any combination thereof:

(FX5a)

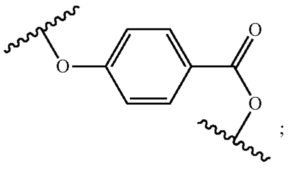

(FX5b)

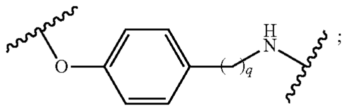

(FX5c)

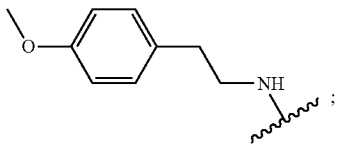

(FX5d)

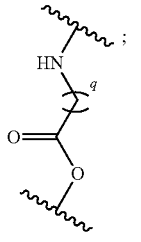

(FX5e)

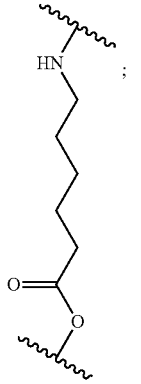

(FX5f)

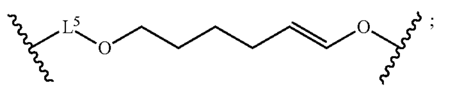

or (FX5g)

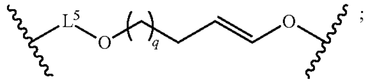

wherein: q is an integer selected from the range of 1 to 10; and $L^5$ is a covalent linking group. In any of the polymers, $Q^1$ and/or $Q^2$ is characterized by the formula FX6a, FX6b, FX6c, or FX6d:

(FX6a)

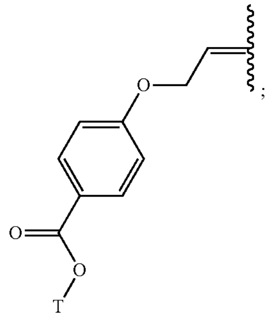

(FX6b)

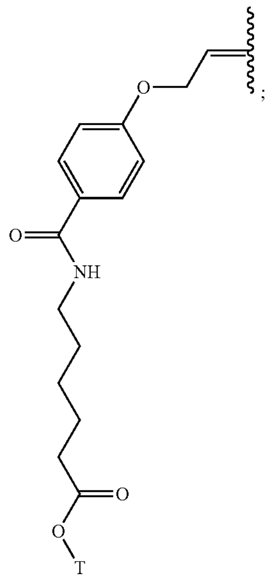

FX6c

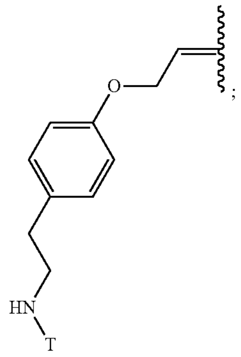

or

FX6d

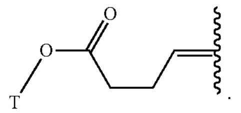

Optionally in any of the polymers, methods, and liquid compositions disclosed herein, each non-peptide therapeutic moiety of the polymer is identical to each other non-peptide therapeutic moiety of the polymer. Optionally in any of the polymers, methods, and liquid compositions disclosed herein, the polymer comprises at least two non-peptide therapeutic moieties; wherein the at least two non-peptide therapeutic moieties include at least two unique non-peptide therapeutic moieties. Optionally in any of the polymers, methods, and liquid compositions disclosed herein, the non-peptide therapeutic moiety is a therapeutic agent and is not a diagnostic agent. Optionally in any of the polymers, methods, and liquid compositions disclosed herein, the therapeutic moiety has a molecular weight selected from the range of 100 to 4500 Da. Optionally in any of the polymers, methods, and liquid compositions disclosed herein, the therapeutic moiety has a molecular weight selected from the range of 100 to 2000 Da, optionally less than 1000 Da, optionally less than 650 Da, optionally less than 500 Da, optionally selected from the range of 100 to 1000 Da. Preferably, but not necessarily, the non-peptide therapeutic is characterized (in the art) as a small molecule drug. Optionally in any of the polymers, methods, and liquid compositions disclosed herein, the non-peptide therapeutic moiety is a cell growth or proliferation inhibitory agent, an anti-inflammatory agent, an anti-tumor or anti-cancer agent, an anti-apoptotic agent, anti-diabetic agent, anti-obesity agent, anti-infective agent, anti-bacterial agent, anti-viral agent, an agent for promoting cell growth and differentiation, an agent for preventing pain, an agent for preventing or treating neural degeneration, an agent for promoting neurogenesis; an immunosuppressant agent, an immunostimulant agent, an MMP-inhibitor agent, a corticosteroid, an anti-angiogenic agent, a pro-angiogenic agent, an NSAID, paclitaxel, or any combination of these. Optionally in any of the polymers, methods, and liquid compositions disclosed herein, each non-peptide therapeutic moiety is therapeutically active when attached to the polymer and/or when released from the polymer. Optionally in any of the polymers, methods, and liquid compositions disclosed herein, each non-peptide therapeutic moiety is released from the polymer when the polymer is exposed to an acidic solution.

Optionally in any of the polymers, methods, and liquid compositions disclosed herein, the polymer is characterized by a polydispersity index less than 1.5. Optionally in any of the polymers, methods, and liquid compositions disclosed herein, the polymer exhibits no peptide cleavage after at least 3 hours of exposure to pronase. Optionally in any of the polymers, methods, and liquid compositions disclosed herein, the peptides on the polymer exhibit less than 25% of the proteolytic cleavage after at least 3 hours of exposure to normally proteolytic enzymes compared to the degradation observed for a linear peptide alone.

Aspects of the invention include a liquid composition comprising an aqueous plurality of polymers, each polymer being according to any one or any combination of the embodiments disclosed herein, wherein the therapeutic formulation is free of polymers that do not include the non-peptide therapeutic moiety. Optionally, each polymer of the aqueous plurality of polymers is individually solvated by water.

Optionally, the liquid composition being free of aggregates or particles having a plurality of polymers. Optionally, the liquid composition is a therapeutic formulation having a therapeutically effective concentration of the aqueous polymers.

Aspects of the invention include a liquid composition comprising: water; and a plurality of aqueous polymers, wherein aqueous polymer is independently solvated by water and each aqueous polymer independently comprises: a plurality of repeating units, each repeating unit comprising a polymer backbone group directly or indirectly covalently linked to one or two side chain moieties, the polymer being characterized by formula FX1: $Q^1$-$[M(Z)_u]_n$-$Q^2$ (FX1); wherein: n is an integer selected from the range of 2 to 1000; u is 1 or 2; each M is independently the polymer backbone group of one of the repeating units and each M is independently a ROMP-polymerized monomer; each Z is independently one of the one or two side chain moieties and each Z independently comprises a peptide moiety or a non-peptide therapeutic moiety; wherein the polymer comprises a plurality of peptide moieties; each Z is independently directly or indirectly covalently attached to an M; each M is covalently attached to at least one other M and each M is independently directly or indirectly covalently attached to one or two of Z, such that 100% of the ROMP-polymerized monomers are each individually attached to the respective one or two side chain moieties; $Q^1$ is a first polymer-terminating group; $Q^2$ is a second polymer-terminating group; and at least one Z comprises of the polymer a non-peptide therapeutic moiety, $Q^1$ comprises a non-peptide therapeutic moiety, and/or $Q^2$ comprises a non-peptide therapeutic moiety. Optionally, the concentration of the plurality of aqueous polymers is selected from the range of 1 pM to 1 M. Optionally, the liquid composition is a therapeutic formulation having a therapeutically effective concentration of the aqueous polymers. Preferably, the liquid composition is free of aggregates or particles having a plurality of polymers.

Aspects of the invention include a method of treating or managing a condition in a subject comprising: administering to a subject an effective amount of a polymer comprising: a plurality of repeating units, each repeating unit comprising a polymer backbone group directly or indirectly covalently linked to one or two side chain moieties, the polymer being characterized by formula FX1: $Q^1$-$[M(Z)_u]_n$-$Q^2$ (FX1); wherein: n is an integer selected from the range of 2 to 1000; u is 1 or 2; each M is independently the polymer backbone group of one of the repeating units and each M is independently a ROMP-polymerized monomer; each Z is independently one of the one or two side chain moieties and each Z independently comprises a peptide moiety or a non-peptide therapeutic moiety; wherein the polymer comprises a plurality of peptide moieties; each Z is independently directly or indirectly covalently attached to an M; each M is covalently attached to at least one other M and each M is independently directly or indirectly covalently attached to one or two of Z, such that 100% of the ROMP-polymerized monomers are each individually attached to the one or two side chain moieties of the respective repeating unit; $Q^1$ is a first polymer-terminating group; $Q^2$ is a second polymer-terminating group; and at least one Z comprises of the polymer a non-peptide therapeutic moiety, $Q^1$ comprises a non-peptide therapeutic moiety, and/or $Q^2$ comprises a non-peptide therapeutic moiety.

Aspects of the invention include a method of treating or managing a condition in a subject comprising: administering to the subject an effective amount of a liquid composition having water and a plurality of aqueous polymers; wherein each of the aqueous polymers independently comprises: a plurality of repeating units, each repeating unit comprising a polymer backbone group directly or indirectly covalently linked to one or two side chain moieties, the polymer being characterized by formula FX1: $Q^1$-$[M(Z)_u]_n$-$Q^2$ (FX1); wherein: n is an integer selected from the range of 2 to 1000; u is 1 or 2; each M is independently the polymer backbone group of one of the repeating unit and each M is independently a ROMP-polymerized monomer; each Z is independently one of the one or two side chain moieties and each Z independently comprises a peptide moiety or a non-peptide therapeutic moiety; wherein the polymer comprises a plurality of peptide moieties; each Z is independently directly or indirectly covalently attached to an M; each M is covalently attached to at least one other M and each M is independently directly or indirectly covalently attached to one or two of Z, such that 100% of the ROMP-polymerized monomers are each individually attached to the one or two side chain moieties of the respective repeating unit; $Q^1$ is a first polymer-terminating group; $Q^2$ is a second polymer-terminating group; and at least one Z comprises of the polymer a non-peptide therapeutic moiety, $Q^1$ comprises a non-peptide therapeutic moiety, and/or $Q^2$ comprises a non-peptide therapeutic moiety.

Optionally in any of the methods and liquid compositions disclosed herein, each aqueous polymer is independently solvated by water. Optionally in any of the methods and liquid compositions disclosed herein, the condition is myocardial ischemia, acute myocardial infarction, heart failure, rheumatoid arthritis, articular cartilage damage, acute and/or chronic epidermal wound, liver failure, nerve damage, acute brain injury, spinal disk injury, or any combination of these.

Aspects of the invention include a method for synthesizing a polymer, the method comprising steps of: ROMP-polymerizing of a plurality of monomers, each monomer being directly or indirectly covalently attached to at least one side chain moiety; terminating ROMP-polymerization using a chain termination agent, wherein the chain termination agent comprises a non-peptide therapeutic moiety; wherein the polymer comprises: a plurality of repeating units, each repeating unit comprising a polymer backbone group directly or indirectly covalently linked to one or two side chain moieties, the polymer being characterized by formula FX1: $Q^1$-$[M(Z)_u]_n$-$Q^2$ (FX1); wherein: n is an integer selected from the range of 2 to 1000; u is 1 or 2; each M is independently the polymer backbone group of one of the repeating units and each M is independently a ROMP-polymerized monomer; each Z is independently one of the one or two side chain moieties and each Z independently comprises a peptide moiety or a non-peptide therapeutic moiety; wherein the polymer comprises a plurality of peptide moieties; each Z is independently directly or indirectly covalently attached to an M; each M is covalently attached to at least one other M and each M is independently directly or indirectly covalently attached to one or two of Z, such that 100% of the ROMP-polymerized monomers are each individually attached to the one or two side chain moieties of the respective repeating unit; $Q^1$ is a first polymer-terminating group; $Q^2$ is a second polymer-terminating group; and $Q^1$ comprises a non-peptide therapeutic moiety and/or $Q^2$ comprises a non-peptide therapeutic moiety. Optionally, the chain termination agent is characterized by formula FX7a or FX7b:

(FX7a)

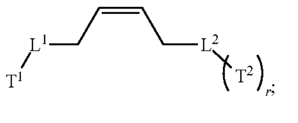

or (FX7b)

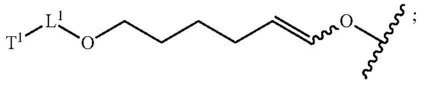

wherein: r is 0 or 1; each of $L^1$ and $L^2$ is independent a covalent linker group selected from a single bond, —O—, oxygen, $C_1$-$C_{10}$ alkyl, $C_2$-$C_{10}$ alkenylene, $C_3$-$C_{10}$ arylene, $C_1$-$C_{10}$ alkoxy, $C_1$-$C_{10}$ acyl, and one or more substituted or substituted groups having an alkyl group, an alkenylene group, an arylene group, an alkoxy group, an acyl group, a carboxyl group, an aliphatic group, an amide group, an aryl group, an amine group, an ether group, a ketone group, an ester group, a triazole group, a diazole group, a pyrazole group, or combinations thereof; and each of $T^1$ and $T^2$ is independently a non-peptide therapeutic moiety. Optionally, the chain termination agent is characterized by formula FX7c, FX7d, FX7e, FX7f, FX7g, FX7h, FX7i, or FX7j:

(FX7c)

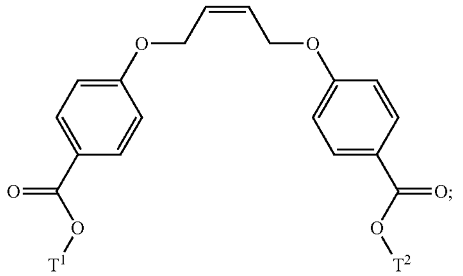

(FX7d)

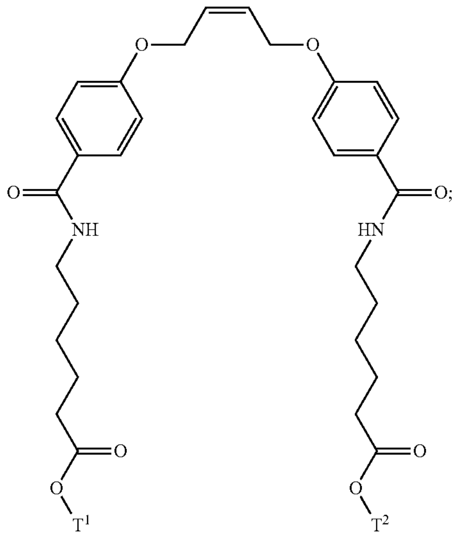

(FX7e)

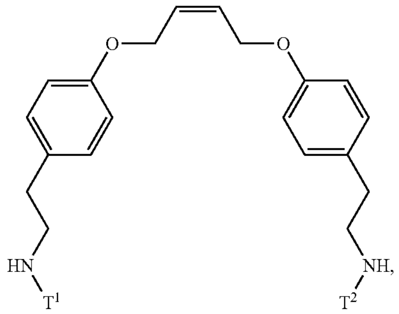

(FX7f)

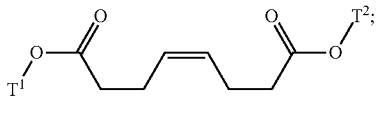

-continued (FX7g)

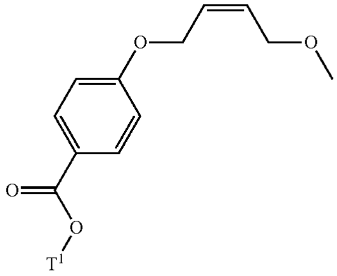

;

(FX7h)

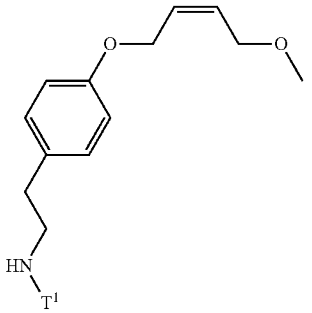

;

(FX7i)

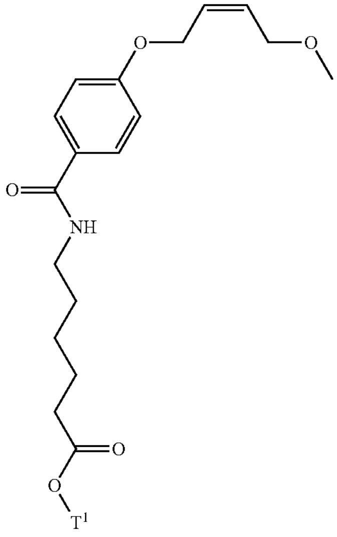

; or (FX7j)

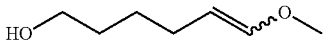

.

Optionally a method of synthesizing includes a step of making the chain termination agent. Optionally a method of synthesizing includes synthesizing a plurality of polymers and a step of purifying to remove at least a fraction of polymers not having the non-peptide therapeutic moiety, such that each of the plurality of polymers is independently the polymer. Optionally, the plurality of polymers are free of polymers not comprising the non-peptide therapeutic moiety.

Also include herein are polymers, liquid compositions, and methods according to any one of any combination of embodiments of polymers, liquid compositions, and methods disclosed herein.

BRIEF DESCRIPTION OF THE DRAWINGS

Variants of the following peptide monomers are disclosed throughout the figures and description of the figures: GGSGSGS (SEQ ID NO:1), GGSGSGE (SEQ ID NO:2), GGSGSGK (SEQ ID NO:3), GGSGSGR (SEQ ID NO:4), GGSGSGRR (SEQ ID NO:5).

FIG. 16A. Nor-GGSGSGS polymerization. FIG. 16B. Nor-GGSGSGE polymerization. FIG. 16C. Nor-GGSGSGK polymerization. FIG. 16D. Nor-GGSGSGR polymerization. FIG. 16E. Nor-GGSGSGRR polymerization.

FIG. 32A. After 1 hr pronase treatment. FIG. 32B. After 2 hrs pronase treatment. FIG. 32C. After 3 hrs pronase treatment. FIG. 32D. After 4 hrs pronase treatment. Those spectra were used to determine the extent of intact peptide of polymers except spectrum D, whose S/N was too low for quantification.

STATEMENTS REGARDING CHEMICAL COMPOUNDS AND NOMENCLATURE

Figure 1:
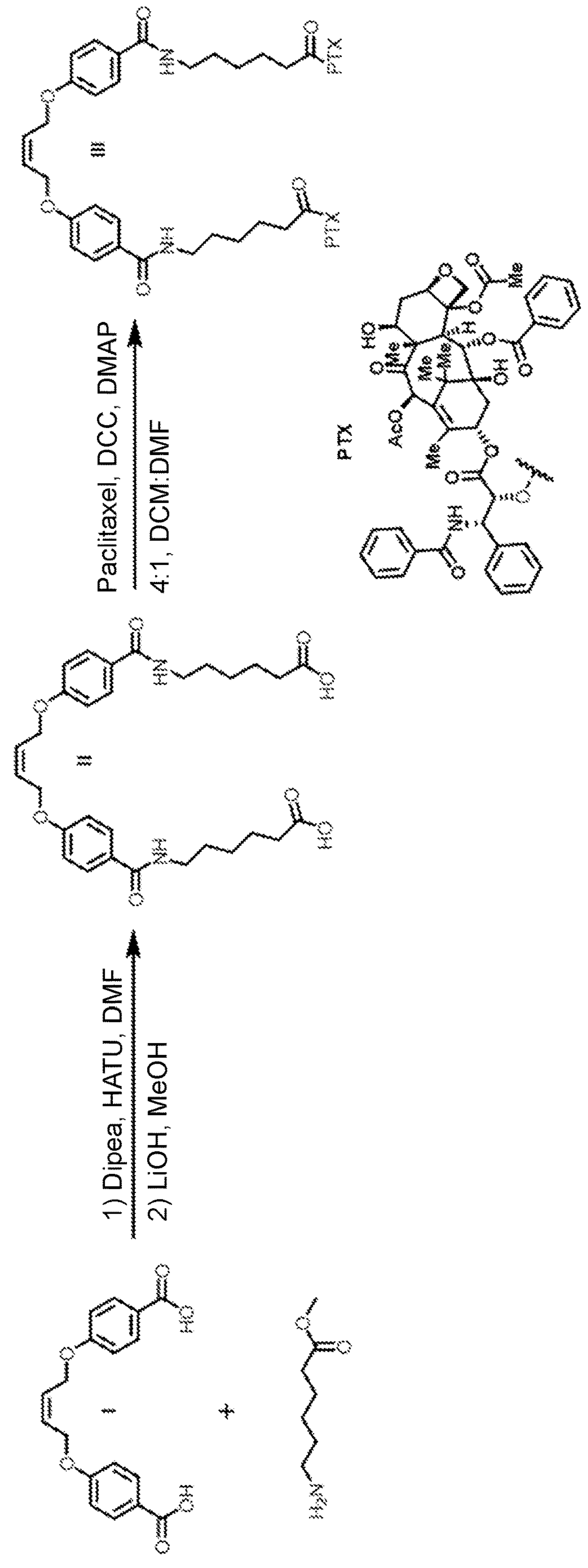
FIG. 1. Synthesis of PTX-chain termination agent.

In general, the terms and phrases used herein have their art-recognized meaning, which can be found by reference to standard texts, journal references and contexts known to those skilled in the art. The following definitions are provided to clarify their specific use in the context of the invention.

The following abbreviations are used herein: MBHA refers to 4-methylbenzylhydrylamine; DMF refers to dimethylformaide; Acm refers to acetamidomethyl; TFA refers to trifluoroacetic acid; TIPS refers to triisopropyl silyl; RP-HPLC refers to reverse-phase high performance liquid chromatography; ESI-MS refers to electrospray ionization mass spectrometry; SEC-MALS refers to size-exclusion chromatography coupled with multiangle light scattering; and DP refers to degree of polymerization.

In an embodiment, a composition or compound of the invention is isolated or purified. In an embodiment, an isolated or purified compound is at least partially isolated or purified as would be understood in the art. In an embodiment, the composition or compound of the invention has a chemical purity of at least 95%, optionally for some applications at least 99%, optionally for some applications at least 99.9%, optionally for some applications at least 99.99%, and optionally for some applications at least 99.999% pure. The invention includes isolated and purified compositions of any of the polymers described herein.

As used herein, the term "polymer" refers to a molecule composed of repeating structural units connected by covalent chemical bonds often characterized by a number of repeating units, also referred to as base units (e.g., greater than or equal to 2 base units). As used herein, a term "polymer" is inclusive of an "oligomer" (i.e., an oligomer is a polymer; i.e., a polymer is optionally an oligomer). An "oligomer" refers to a molecule composed of repeating structural units, also referred to as base units, connected by covalent chemical bonds often characterized by a number of repeating units less such that the oligomer is a low molecular weight polymer. Preferably, but not necessarily, for example, an oligomer has equal to or less than 100 repeating units. Preferably, but not necessarily, for example, an oligomer has a lower molecular weight less than or equal to 10,000 Da. Oligomers may be the polymerization product of one or more monomer precursors. Polymerization of one or more monomers, or monomer precursors, resulting in formation of an oligomer may be referred to as oligomerization. An oligomer optionally includes 100 or less, 50 or less, 15 or less, 12 or less, 10 or less, or 5 or less repeating units (or, "base units"). An oligomer may be characterized has having a molecular weight of 10,000 Da or less, 5,000 Da or less, 1,000 Da or less, 500 Da or less, or 200 Da or less. A dimer, a trimer, a tetramer, or a pentamer is an oligomer having two, three, four, or five, respectively, repeating units, or base units. Polymers can have, for example, greater than 100 repeating units. Polymers can have, for example, a high molecular weight, such as greater than 10,000 Da, in some embodiments greater than or equal to 50,000 Da or greater than or equal to 100,000 Da. The term polymer includes homopolymers, or polymers consisting essentially of a single repeating monomer subunit. The term polymer also includes copolymers which are formed when two or more different types of monomers are linked in the same polymer. Copolymers may comprise two or more monomer subunits, and include random, block, brush, brush block, alternating, segmented, grafted, tapered and other architectures. Useful polymers include organic polymers or inorganic polymers that may be in amorphous, semi-amorphous, crystalline or semi-crystalline states. Polymer side chains capable of cross linking polymers (e.g., physical cross linking) may be useful for some applications. The invention provides polymers comprising therapeutic agents, such as brush polymers having at least a portion of the repeating units comprising side chains having therapeutic peptides and/or non-peptide therapeutic moieties. The polymers disclosed herein include one or more non-peptide therapeutic moieties.

Except where otherwise specified, the term "molecular weight" refers to an average molecular weight. Except where otherwise specified, the term "average molecular weight," refers to number-average molecular weight. Number average molecular weight is defined as the total weight of a sample volume divided by the number of molecules within the sample. As is customary and well known in the art, peak average molecular weight and weight average molecular weight may also be used to characterize the molecular weight of the distribution of polymers within a sample.

The term "weight-average molecular weight" ($M_w$) refers to the average molecular weight defined as the sum of the products of the molecular weight of each polymer molecule ($M_i$) multiplied by its weight fraction ($w_i$): $M_w=\Sigma w_i M_i$. As is customary and well known in the art, peak average molecular weight and number average molecular weight may also be used to characterize the molecular weight of the distribution of polymers within a sample.

A "polypeptide" or "oligopeptide" herein are used interchangeably and refer to a polymer of repeating structural units connected by a peptide bond. Typically, the repeating structural units of the polypeptide are amino acids including naturally occurring amino acids, non-naturally occurring amino acids, analogues of amino acids or any combination of these. The number of repeating structural units of a polypeptide, as understood in the art, are typically less than a "protein", and thus the polypeptide often has a lower molecular weight than a protein. Peptides and peptide moieties, as used and described herein, comprise two or more amino acid groups connected via peptide bonds.

Amino acids and amino acid groups refer to naturally-occurring amino acids, unnatural (non-naturally occurring) amino acids, and/or combinations of these. Naturally-occurring amino acids are those encoded by the genetic code, as well as those amino acids that are later modified, e.g., hydroxyproline, γ-carboxyglutamate, and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gin), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" can be unnatural amino acids that have the same basic chemical structure as naturally-occurring amino acids (i.e., a carbon that is bonded to a hydrogen, a carboxyl group, an amino group) but have modified side-chain groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid. Amino acids may be referred to herein by either the commonly known three letter symbols or by the one-letter symbols recommended by the IUPAC-IUB Biochemical Nomenclature Commission.

"Block copolymers" are a type of copolymer comprising blocks or spatially segregated domains, wherein different domains comprise different polymerized monomers, for example, including at least two chemically distinguishable blocks. Block copolymers may further comprise one or more other structural domains, such as hydrophobic groups, hydrophilic groups, etc. In a block copolymer, adjacent blocks are constitutionally different, i.e. adjacent blocks comprise constitutional units derived from different species of monomer or from the same species of monomer but with a different composition or sequence distribution of constitutional units. Different blocks (or domains) of a block copolymer may reside on different ends or the interior of a polymer (e.g. [A][B]), or may be provided in a selected sequence ([A][B][A][B]). "Diblock copolymer" refers to block copolymer having two different polymer blocks. "Triblock copolymer" refers to a block copolymer having three different polymer blocks, including compositions in which two non-adjacent blocks are the same or similar. "Pentablock" copolymer refers to a copolymer having five different polymer including compositions in which two or more non-adjacent blocks are the same or similar.

"Polymer backbone group" refers to groups that are covalently linked to make up a backbone of a polymer, such as a block copolymer. Polymer backbone groups may be linked to side chain groups, such as polymer side chain groups. Some polymer backbone groups useful in the present compositions are derived from polymerization of a monomer selected from the group consisting of a substituted or unsubstituted, olefin, vinyl, acrylate, acrylamide, cyclic olefin, norbornene, norbornene anhydride, cyclooctene, cyclopentadiene, styrene and acrylate. Some polymer backbone groups useful in the present compositions are obtained from metal-free photoinduced reversible-deactivation radical polymerization (photo-RDRP), photo-electron transfer reversible addition-fragmentation transfer polymerization (PET-RAFT), and/or photoinitiated polymerization-induced self-assembly (photo-PISA). Polymer backbones may terminate (e.g., by coupling, disproportionation, or chain transfer) in a range of backbone terminating groups including, but not limited to, hydrogen, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ acyl, $C_1$-$C_{10}$ hydroxyl, $C_1$-$C_{10}$ alkoxy, $C_2$-$C_{10}$ alkenyl, $C_2$-$C_{10}$ alkynyl, $C_5$-$C_{10}$ alkylaryl, —$CO_2R^{30}$, —$CONR^{31}R^{32}$, —$COR^{33}$, —$SOR^{34}$, —$OSR^{35}$, —$SO_2R^{36}$, —$OR^{37}$, —$SR^{38}$, —$NR^{39}R^{40}$, —$NR^{41}COR^{42}$, $C_1$-$C_{10}$ alkyl halide, phosphonate, phosphonic acid, silane, siloxane, acrylate, catechol, or any combinations thereof; wherein each of $R^{30}$-$R^{42}$ is independently hydrogen, $C_1$-$C_{10}$ alkyl or $C_5$-$C_{10}$ aryl. A polymer backbone may terminate in backbone terminating groups that is a portion or moiety from a chain transfer used during polymerization of the polymer. A backbone terminating group may be a polymer-terminating group. A "polymer-terminating group" is a group or moiety at a terminal end of a polymer and which terminates a polymer backbone.

As used herein, the term "chain transfer agent" refers to a compound that reacts with a growing polymer chain to interrupt growth and transfer the reactive species to a different compound (e.g., different polymer chain, monomer, or polymerizable monomer). The chain transfer agent can help regulate the average molecular weight of a polymer by terminating polymerization. The terms "chain transfer agent" and "chain termination agent" are intended to be equivalent and interchangeable. Exemplary chain transfer agents include, but are not limited to, compounds comprising a dimethoxybutene group (e.g., dimethoxybut-2-ene), a diphenoxybutene group (e.g., diphenoxybut-2-ene). Exemplary chain transfer agents include, but are not limited to, (Z)-6,6'-((4,4'-(but-2-ene-1,4-diylbis(oxy))bis(benzoyl))bis(azanediyl))dihexanoic acid and any compound characterized by formula FX7a, FX7b, FX7c, FX7d, FX7e, FX7f, FX7g, FX7h, FX7i, or FX7j.

""Polymer side chain group" refers to a group covalently linked (directly or indirectly) to a polymer backbone group that comprises a polymer side chain, optionally imparting steric properties to the polymer. In an embodiment, for example, a polymer side chain group is characterized by a plurality of repeating units having the same, or similar, chemical composition. A polymer side chain group may be directly or indirectly linked to the polymer backbone groups. In some embodiments, polymer side chain groups provide steric bulk and/or interactions that result in an extended polymer backbone and/or a rigid polymer backbone. Some polymer side chain groups useful in the present compositions include unsubstituted or substituted polypeptide groups. Some polymers useful in the present compositions comprise repeating units obtained via anionic polymerization, cationic polymerization, free radical polymerization, group transfer polymerization, a photopolymerization, a ring-opening polymerization, metal-free photoinduced reversible-deactivation radical polymerization (photo-RDRP), photo-electron transfer reversible addition-fragmentation transfer polymerization (PET-RAFT), and/or photoinitiated polymerization-induced self-assembly (photo-PISA). A polymer side chain may terminate in a wide range of polymer side chain terminating groups including hydrogen, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ acyl, $C_1$-$C_{10}$ hydroxyl, $C_1$-$C_{10}$ alkoxy, $C_2$-$C_{10}$ alkenyl, $C_2$-$C_{10}$ alkynyl, $C_5$-$C_{10}$ alkylaryl, —$CO_2R^{30}$, —$CONR^{31}R^{32}$, —$COR^{33}$, —$SOR^{34}$, —$OSR^{35}$, —$SO_2R^{36}$, —$OR^{37}$, —$SR^{38}$, —$NR^{39}R^{40}$, —$NR^{41}COR^{42}$, $C_1$-$C_{10}$ alkyl halide, phosphonate, phosphonic acid, silane, siloxane acrylate, or catechol; wherein each of $R^{30}$-$R^{42}$ is independently hydrogen or $C_1$-$C_5$ alkyl.

As used herein, the term "brush polymer" refers to a polymer comprising repeating units each independently comprising a polymer backbone group directly or indirectly covalently linked to at least one polymer side chain group. A brush polymer may be characterized by brush density, which refers to the percentage of the repeating units in a brush polymer that comprise a polymer side chain group. Brush polymers of certain aspects are characterized by a brush density greater than or equal to 50% (e.g., greater than or equal to 60%, greater than or equal to 65%, greater than or equal to 70%, greater than or equal to 75%, greater than or equal to 80%, greater than or equal to 85%, or greater than or equal to 90%), optionally for some embodiments a density greater than or equal to 70%, or optionally for some embodiments a density greater than or equal to 90%. Brush polymers of certain aspects are characterized by a brush density selected from the range 50% to 100%, optionally some embodiments a density selected from the range of 75% to 100%, or optionally for some embodiments a density selected from the range of 90% to 100%.

The terms "monomer" or "polymerizable monomer" can be used interchangeably and refer to a monomer precursor capable of undergoing polymerization as described herein to form a polymer according to embodiments described herein. The term "polymerizable monomer" is also interchangeably referred to herein as a "monomer precursor." Generally, the "monomer" or "polymerizable monomer" comprises an olefin capable of undergoing polymerization as described herein.

The term "ROMP-polymerized monomer" refers to a group or moiety resulting from or produced by ring opening metathesis polymerization (ROMP) of a ROMP-polymerizable monomer or monomeric group or moiety. A ROMP-polymerizable monomer or monomeric group comprises a strained olefin group and may be, but is not necessarily, a cyclic (including bicyclic, tricyclic, etc.) monomer or monomeric group. For example, a ROMP-polymerizable monomer or monomeric group may be or comprise a substituted or unsubstituted norbornene, cyclic olefin, bicyclic olefin, norbornene anhydride, cyclooctene, cyclopentadiene, or any combination of these. In embodiments, for example, a monomer comprising a cyclopentene and/or cycloheptene group may be ROMP-polymerized resulting in a ROMP-polymerized monomer having a cyclopentane and/or cycloheptane group.

The term "strained" in reference to a chemical species or group, such as a "strained olefin group", refers to a chemical species or group that has a higher internal energy, due to strain, compared to a strain-free reference. Strain refers to a form of deformation. In an embodiment, strain refers to a compression or expansion of one or more bonds compared the lowest internal energy state equilibrium state of the bond. In an embodiment, a strain-free reference is the chemical species or group in its lowest internal energy equilibrium state.

The terms "monomer unit," "repeating monomer unit," "repeating unit," and "polymerized monomer" can be used interchangeably and refer to a monomeric portion of a polymer described herein which is derived from or is a product of polymerization of one individual "monomer" or "polymerizable monomer." Each individual monomer unit of a polymer is derived from or is a product of polymerization of one polymerizable monomer. Each individual "monomer unit" or "repeating unit" of a polymer comprises one (polymerized) polymer backbone group. For example, in a polymer that comprises monomer units X and Y arranged as X-Y-X-Y-X-Y-X-Y (where each X is identical to each other X and each Y is identical to each other Y), each X and each Y is independently can be referred to as a repeating unit or monomer unit.

As used herein, the term "degree of polymerization" refers to the average number of monomer units or repeating units per polymer chain. The term "degree of polymerization" may be used to characterized number of repeating units defining an entire polymer, a polymer block thereof, or a polymerized chain moiety thereof, such as a side chain moiety or a (poly)peptide moiety. For example, in embodiments, a degree of polymerization of a polymer defined by formula FX1 ($Q^1$-$[M(Z)_u]_n$-$Q^2$), refers to the average number of $[M(Z)_u]$ repeating monomer units. For example, a degree of polymerization of a peptide or polypeptide refers to the number of amino acids forming the peptide. For example, a peptide whose amino acid sequence consists of the sequence GGSGSGK (SEQ ID NO:3), has a degree of polymerization of 7 because the amino acid sequence GGSGSGK (SEQ ID NO:3) has 7 amino acids. Since the degree of polymerization can vary from polymer to polymer, the degree of polymerization is generally represented by an average which can be determined by, for example, gel permeation chromatography with a multi-angle light scattering detector (GPC-MALS). The degree of polymerization can be calculated by the number-average molecular weight of polymer (e.g., determined by GPC-MALS) dividing by the molar mass of the monomer.

As used herein, the terms "peptide density" and "peptide graft density" interchangeably refer to the percentage of monomer units in the polymer chain which have a peptide covalently linked thereto. The percentage is based on the overall sum of monomer units in the polymer chain. For example, for certain polymers described herein, each $P^1$ is the polymer side chain comprising the peptide, each $P^2$ is a polymer side chain having a composition different from that of $P^1$, and each S is independently a repeating unit having a composition different from $P^1$ and $P^2$. Thus, the peptide density of $P^1$, or percentage of monomer units comprising the peptide of $P^1$ (i.e., $P^1$ for this particular example) would be represented by the formula:

$$\frac{P^1}{P^1 + P^2 + S} \times 100,$$

where each variable refers to the number of monomer units of that type in the polymer chain.

In an aspect, the polymer side chain groups can have any suitable spacing on the polymer backbone. Typically, the space between adjacent polymer side chain groups is from 3 angstroms to 30 angstroms, and optionally 5 to 20 angstroms and optionally 5 to 10 angstroms. By way of illustration, in certain embodiments having a brush density of 100%, the polymer side chain groups typically are spaced 6±5 angstroms apart on the polymer backbone. In some embodiments the brush polymer has a high a brush density (e.g. greater than 70%), wherein the polymer side chain groups are spaced 5 to 20 angstroms apart on the polymer backbone.

The terms "analog" and "analogue" are used interchangeably and are used in accordance with their plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound. The analogue can be a natural analogue or a synthetic analogue. In embodiments, a peptide analogue has five or fewer substituted or unsubstituted amino acids, or derivatives thereof, that are different, removed, added, or any combination of these, with respect to the reference peptide.

The term "sequence homology" or "sequence identity" means the proportion of amino acid matches between two amino acid sequences. When sequence homology is expressed as a percentage, e.g., 50%, the percentage denotes the fraction of matches over the length of sequence that is compared to some other sequence. Gaps (in either of the two sequences) are permitted to maximize matching; for example, wherein gap lengths of 5 amino acids or less, optionally 3 amino acids or less, are usually used.

The term "fragment" refers to a portion, but not all of, a composition or material, such as a polypeptide composition or material. In an embodiment, a fragment of a polypeptide refers to 50% or more of the sequence of amino acids, optionally 70% or more of the sequence of amino acids and optionally 90% or more of the sequence of amino acids.

As used herein, the term "group" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to their valence state. The present invention includes groups characterized as monovalent, divalent, trivalent, etc. valence states.

The term "moiety" refers to a group, such as a functional group, of a chemical compound or molecule. A moiety is a collection of atoms that are part of the chemical compound or molecule. The present invention includes moieties characterized as monovalent, divalent, trivalent, etc. valence states. Generally, but not necessarily, a moiety comprises more than one functional group. A "peptide moiety" is a moiety or group that comprises or consists of a peptide.

As used herein, the term "substituted" refers to a compound wherein one or more hydrogens is replaced by another functional group, provided that the designated atom's normal valence is not exceeded. An exemplary substituent includes, but is not limited to: a halogen or halide, an alkyl, a cycloalkyl, an aryl, a heteroaryl, an acyl, an alkoxy, an alkenyl, an alkynyl, an alkylaryl, an arylene, a heteroarylene, an alkenylene, a cycloalkenylene, an alkynylene, a hydroxyl (—OH), a carbonyl (RCOR'), a sulfide (e.g., RSR'), a phosphate ($ROP(=O)(OH)_2$), an azo (RNNR'), a cyanate (ROCN), an amine (e.g., primary, secondary, or tertiary), an imine (RC(=NH)R'), a nitrile (RCN), a pyridinyl (or pyridyl), a diamine, a triamine, an azide, a diimine, a triimine, an amide, a diimide, or an ether (ROR'); where each of R and R' is independently a hydrogen or a substituted or unsubstituted alkyl group, aryl group, alkenyl group, or a combination of these. Optional substituent functional groups are also described below. In some embodiments, the term substituted refers to a compound wherein each of more than one hydrogen is replaced by another functional group, such as a halogen group. For example, when the substituent is oxo (i.e., =O), then two hydrogens on the atom are replaced. The substituent group can be any substituent group described herein. For example, substituent groups can include one or more of a hydroxyl, an amino (e.g., primary, secondary, or tertiary), an aldehyde, a carboxylic acid, an ester, an amide, a ketone, nitro, an urea, a guanidine, cyano, fluoroalkyl (e.g., trifluoromethane), halo (e.g., fluoro), aryl (e.g., phenyl), heterocyclyl or heterocyclic group (i.e., cyclic group, e.g., aromatic (e.g., heteroaryl) or non-aromatic where the cyclic group has one or more heteroatoms), oxo, or combinations thereof. Combinations of substituents and/or variables are permissible provided that the substitutions do not significantly adversely affect synthesis or use of the compound.

As used herein, the term "derivative" refers to a compound wherein an atom or functional group is replaced by another atom or functional group (e.g., a substituent function group as also described below), including, but not limited to: a hydrogen, a halogen or halide, an alkyl, a cycloalkyl, an aryl, a heteroaryl, an acyl, an alkoxy, an alkenyl, an alkynyl, an alkylaryl, an arylene, a heteroarylene, an alkenylene, a cycloalkenylene, an alkynylene, a hydroxyl (—OH), a carbonyl (RCOR'), a sulfide (e.g., RSR'), a phosphate ($ROP(=O)(OH)_2$), an azo (RNNR'), a cyanate (ROCN), an amine (e.g., primary, secondary, or tertiary), an imine (RC(=NH)R'), a nitrile (RCN), a pyridinyl (or pyridyl), a diamine, a triamine, an azide, a diimine, a triimine, an amide, a diimide, or an ether (ROR'); where each of R and R' is independently a hydrogen or a substituted or unsubstituted alkyl group, aryl group, alkenyl group, or a combination of these. Optional substituent functional groups are also described below. Preferably, the term "derivative" refers to a compound wherein one or two atoms or functional groups are independently replaced by another atom or functional group. Preferably, the term derivative does not refer to or include replacement of a chalcogen atom (S, Se) that is a member of a heterocyclic group. Preferably, the term derivative does not refer to or include replacement of a chalcogen atom (S, Se) nor a N (nitrogen) where the chalcogen atom and the N are members same heterocyclic group. Preferably, but not necessarily, the term derivative does not include breaking a ring structure, replacement of a ring member, or removal of a ring member.

Unless otherwise specified, the term "average molecular weight," refers to number average molecular weight. Number average molecular weight is the defined as the total weight of a sample volume divided by the number of molecules within the sample. As is customary and well known in the art, peak average molecular weight and weight average molecular weight may also be used to characterize the molecular weight of the distribution of polymers within a sample.

As is customary and well known in the art, hydrogen atoms in formulas presented throughout herein, such as, but not limited to formulas FX3a, FX3b, FX3c, FX3d, FX3e, FX3f, FX3g, and FX3h are not always explicitly shown, for example, hydrogen atoms bonded to the carbon atoms of aromatic, heteroaromatic, and alicyclic rings are not always explicitly shown in formulas presented herein. The structures provided herein, for example in the context of the description of formulas just listed and schematics and structures in the drawings, are intended to convey to one of reasonable skill in the art the chemical composition of compounds of the methods and compositions of the invention, and as will be understood by one of skill in the art, the structures provided do not indicate the specific positions and/or orientations of atoms and the corresponding bond angles between atoms of these compounds.

As used herein, the terms "alkylene" and "alkylene group" are used synonymously and refer to a divalent group derived from an alkyl group as defined herein. The invention includes compounds having one or more alkylene groups. Alkylene groups in some compounds function as linking and/or spacer groups. Compounds of the invention may have substituted and/or unsubstituted $C_1$-$C_{20}$ alkylene, $C_1$-$C_{10}$ alkylene and $C_1$-$C_5$ alkylene groups, for example, as one or more linking groups (e.g. $L^1$-$L^2$).

As used herein, the terms "cycloalkylene" and "cycloalkylene group" are used synonymously and refer to a divalent group derived from a cycloalkyl group as defined herein. The invention includes compounds having one or more cycloalkylene groups. Cycloalkyl groups in some compounds function as linking and/or spacer groups. Compounds of the invention may have substituted and/or unsubstituted $C_3$-$C_{20}$ cycloalkylene, $C_3$-$C_{10}$ cycloalkylene and $C_3$-$C_5$ cycloalkylene groups, for example, as one or more linking groups (e.g. $L^1$-$L^2$).

As used herein, the terms "arylene" and "arylene group" are used synonymously and refer to a divalent group derived from an aryl group as defined herein. The invention includes compounds having one or more arylene groups. In some embodiments, an arylene is a divalent group derived from an aryl group by removal of hydrogen atoms from two intra-ring carbon atoms of an aromatic ring of the aryl group.

Arylene groups in some compounds function as linking and/or spacer groups. Arylene groups in some compounds function as chromophore, fluorophore, aromatic antenna, dye and/or imaging groups. Compounds of the invention include substituted and/or unsubstituted $C_3$-$C_{30}$ arylene, $C_3$-$C_{20}$ arylene, $C_3$-$C_{10}$ arylene and $C_1$-$C_5$ arylene groups, for example, as one or more linking groups (e.g. $L^1$-$L^2$).

As used herein, the terms "heteroarylene" and "heteroarylene group" are used synonymously and refer to a divalent group derived from a heteroaryl group as defined herein. The invention includes compounds having one or more heteroarylene groups. In some embodiments, a heteroarylene is a divalent group derived from a heteroaryl group by removal of hydrogen atoms from two intra-ring carbon atoms or intra-ring nitrogen atoms of a heteroaromatic or aromatic ring of the heteroaryl group.

Heteroarylene groups in some compounds function as linking and/or spacer groups. Heteroarylene groups in some compounds function as chromophore, aromatic antenna, fluorophore, dye and/or imaging groups. Compounds of the invention include substituted and/or unsubstituted $C_3$-$C_{30}$ heteroarylene, $C_3$-$C_{20}$ heteroarylene, $C_1$-$C_{10}$ heteroarylene and $C_3$-$C_5$ heteroarylene groups, for example, as one or more linking groups (e.g. $L^1$-$L^2$).

As used herein, the terms "alkenylene" and "alkenylene group" are used synonymously and refer to a divalent group derived from an alkenyl group as defined herein. The invention includes compounds having one or more alkenylene groups. Alkenylene groups in some compounds function as linking and/or spacer groups. Compounds of the invention include substituted and/or unsubstituted $C_2$-$C_{20}$ alkenylene, $C_2$-$C_{10}$ alkenylene and $C_2$-$C_5$ alkenylene groups, for example, as one or more linking groups (e.g. $L^1$-$L^2$).

As used herein, the terms "cycloalkenylene" and "cycloalkenylene group" are used synonymously and refer to a divalent group derived from a cycloalkenyl group as defined herein. The invention includes compounds having one or more cycloalkenylene groups. Cycloalkenylene groups in some compounds function as linking and/or spacer groups. Compounds of the invention include substituted and/or unsubstituted $C_3$-$C_{20}$ cycloalkenylene, $C_3$-$C_{10}$ cycloalkenylene and $C_3$-$C_5$ cycloalkenylene groups, for example, as one or more linking groups (e.g. $L^1$-$L^2$).

As used herein, the terms "alkynylene" and "alkynylene group" are used synonymously and refer to a divalent group derived from an alkynyl group as defined herein. The invention includes compounds having one or more alkynylene groups. Alkynylene groups in some compounds function as linking and/or spacer groups. Compounds of the invention include substituted and/or unsubstituted $C_2$-$C_{20}$ alkynylene, $C_2$-$C_{10}$ alkynylene and $C_2$-$C_5$ alkynylene groups, for example, as one or more linking groups (e.g. $L^1$-$L^2$).

As used herein, the term "halo" refers to a halogen group such as a fluoro (—F), chloro (—Cl), bromo (—Br), iodo (—I) or astato (—At).

The term "heterocyclic" refers to ring structures containing at least one other kind of atom, in addition to carbon, in the ring. Examples of such heteroatoms include nitrogen, oxygen and sulfur. Heterocyclic rings include heterocyclic alicyclic rings and heterocyclic aromatic rings. Examples of heterocyclic rings include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. Atoms of heterocyclic rings can be bonded to a wide range of other atoms and functional groups, for example, provided as substituents.

The term "carbocyclic" refers to ring structures containing only carbon atoms in the ring. Carbon atoms of carbocyclic rings can be bonded to a wide range of other atoms and functional groups, for example, provided as substituents.

The term "alicyclic ring" refers to a ring, or plurality of fused rings, that is not an aromatic ring. Alicyclic rings include both carbocyclic and heterocyclic rings.

The term "aromatic ring" refers to a ring, or a plurality of fused rings, that includes at least one aromatic ring group. The term aromatic ring includes aromatic rings comprising carbon, hydrogen and heteroatoms. Aromatic ring includes carbocyclic and heterocyclic aromatic rings. Aromatic rings are components of aryl groups.

The term "fused ring" or "fused ring structure" refers to a plurality of alicyclic and/or aromatic rings provided in a fused ring configuration, such as fused rings that share at least two intra ring carbon atoms and/or heteroatoms.

As used herein, the term "alkoxyalkyl" refers to a substituent of the formula alkyl-O-alkyl.

As used herein, the term "polyhydroxyalkyl" refers to a substituent having from 2 to 12 carbon atoms and from 2 to 5 hydroxyl groups, such as the 2,3-dihydroxypropyl, 2,3,4-trihydroxybutyl or 2,3,4,5-tetrahydroxypentyl residue.

As used herein, the term "polyalkoxyalkyl" refers to a substituent of the formula alkyl-(alkoxy)$_n$-alkoxy wherein n is an integer from 1 to 10, preferably 1 to 4, and more preferably for some embodiments 1 to 3.

Amino acids include glycine, alanine, valine, leucine, isoleucine, methionine, proline, phenylalanine, tryptophan, asparagine, glutamine, glycine, serine, threonine, serine, rhreonine, asparagine, glutamine, tyrosine, cysteine, lysine, arginine, histidine, aspartic acid and glutamic acid. As used herein, reference to "a side chain residue of a natural α-amino acid" specifically includes the side chains of the above-referenced amino acids. Peptides are comprised of two or more amino acids connected via peptide bonds.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. The term cycloalkyl specifically refers to an alky group having a ring structure such as ring structure comprising 3-30 carbon atoms, optionally 3-20 carbon atoms and optionally 2-10 carbon atoms, including an alkyl group having one or more rings. Cycloalkyl groups include those having a 3-, 4-, 5-, 6-, 7-, 8-, 9- or 10-member carbon ring(s) and particularly those having a 3-, 4-, 5-, 6-, or 7-member ring(s). The carbon rings in cycloalkyl groups can also carry alkyl groups. Cycloalkyl groups can include bicyclic and tricycloalkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups. As used herein MeO— refers to $CH_3O$—. Compositions of some embodiments of the invention comprise alkyl groups as terminating groups, such as polymer backbone terminating groups and/or polymer side chain terminating groups.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those in which a double bond is in the ring or in an alkenyl group attached to a ring. The term cycloalkenyl specifically refers to an alkenyl group having a ring structure, including an alkenyl group having a 3-, 4-, 5-, 6-, 7-, 8-, 9- or 10-member carbon ring(s) and particularly those having a 3-, 4-, 5-, 6- or 7-member ring(s). The carbon rings in cycloalkenyl groups can also carry alkyl groups. Cycloalkenyl groups can include bicyclic and tricyclic alkenyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogen atoms replaced with one or more fluorine atoms. Compositions of some embodiments of the invention comprise alkenyl groups as terminating groups, such as polymer backbone terminating groups and/or polymer side chain terminating groups.

Aryl groups include groups having one or more 5-, 6- or 7-member aromatic rings, including heterocyclic aromatic rings. The term heteroaryl specifically refers to aryl groups having at least one 5-, 6- or 7-member heterocyclic aromatic rings. Aryl groups can contain one or more fused aromatic rings, including one or more fused heteroaromatic rings, and/or a combination of one or more aromatic rings and one or more nonaromatic rings that may be fused or linked via covalent bonds. Heterocyclic aromatic rings can include one or more N, O, or S atoms in the ring. Heterocyclic aromatic rings can include those with one, two or three N atoms, those with one or two O atoms, and those with one or two S atoms, or combinations of one or two or three N, O or S atoms. Aryl groups are optionally substituted. Substituted aryl groups include among others those which are substituted with alkyl or alkenyl groups, which groups in turn can be optionally substituted. Specific aryl groups include phenyl, biphenyl groups, pyrrolidinyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocyclic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic group, including monovalent, divalent and polyvalent groups, of the aromatic and heterocyclic aromatic groups listed herein are provided in a covalently attached configuration in the compounds of the invention at any suitable point of attachment. In embodiments, aryl groups contain between 5 and 30 carbon atoms. In embodiments, aryl groups contain one aromatic or heteroaromatic six-membered ring and one or more additional five- or six-membered aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents. Compositions of some embodiments of the invention comprise aryl groups as terminating groups, such as polymer backbone terminating groups and/or polymer side chain terminating groups.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl groups having one or more hydrogens replaced with one or more fluorine atoms, chlorine atoms, bromine atoms and/or iodine atoms. Compositions of some embodiments of the invention comprise arylalkyl groups as terminating groups, such as polymer backbone terminating groups and/or polymer side chain terminating groups.

As to any of the groups described herein which contain one or more substituents, it is understood that such groups do not contain any substitution or substitution patterns which are sterically impractical and/or synthetically non-feasible. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for any alkyl, alkenyl and aryl group includes substitution with one or more of the following substituents, among others:

halogen, including fluorine, chlorine, bromine or iodine;

pseudohalides, including —CN;

—COOR where R is a hydrogen or an alkyl group or an aryl group and more specifically where R is a methyl, ethyl, propyl, butyl, or phenyl group all of which groups are optionally substituted;

—COR where R is a hydrogen or an alkyl group or an aryl group and more specifically where R is a methyl, ethyl, propyl, butyl, or phenyl group all of which groups are optionally substituted;

—CON(R)$_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—OCON(R)$_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—N(R)$_2$ where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring which can contain one or more double bonds and can contain one or more additional carbon atoms;

—SR, where R is hydrogen or an alkyl group or an aryl group and more specifically where R is hydrogen, methyl, ethyl, propyl, butyl, or a phenyl group, which are optionally substituted;

—SO$_2$R, or —SOR where R is an alkyl group or an aryl group and more specifically where R is a methyl, ethyl, propyl, butyl, or phenyl group, all of which are optionally substituted;

—OCOOR where R is an alkyl group or an aryl group;

—SO$_2$N(R)$_2$ where each R, independently of each other R, is a hydrogen, or an alkyl group, or an aryl group all of which are optionally substituted and wherein R and R can form a ring which can contain one or more double bonds and can contain one or more additional carbon atoms; and —OR where R is H, an alkyl group, an aryl group, or an acyl group all of which are optionally substituted. In a particular example R can be an acyl yielding —OCOR" where R" is a hydrogen or an alkyl group or an aryl group and more specifically where R" is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

As to any of the above groups which contain one or more substituents, it is understood that such groups do not contain any substitution or substitution patterns which are sterically impractical and/or synthetically non-feasible.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or D- or L-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

Many of the molecules disclosed herein contain one or more ionizable groups. Ionizable groups include groups from which a proton can be removed (e.g., —COOH) or added (e.g., amines) and groups that can be quaternized (e.g., amines). All possible ionic forms of such molecules and salts thereof are intended to be included individually in the disclosure herein. With regard to salts of the compounds herein, one of ordinary skill in the art can select from among a wide variety of available counterions that are appropriate for preparation of salts of this invention for a given application. In specific applications, the selection of a given anion or cation for preparation of a salt can result in increased or decreased solubility of that salt.

As used herein, the term "isomers" refers to compounds having the same number and kind of atoms, and hence the same molecular weight, but differing in respect to the structural arrangement or configuration of the atoms. Isomers include structural isomers and stereoisomers such as enantiomers.

The term "tautomer," as used herein, refers to one of two or more structural isomers which exist in equilibrium and which are readily converted from one isomeric form to another. It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present invention, whether radioactive or not, are encompassed within the scope of the present invention.

The symbol " " denotes the point of attachment of one or more chemical moieties, one or more functional groups, one or more atoms, one or more ions, an unpaired electron, or one or more other chemical species to the represented molecule, compound, or chemical formula. For example, in the formula

,

"X" represents a molecule or compound, the symbol " " denotes a point of attachment of one or more chemical moieties, one or more functional groups, one or more atoms, one or more ions, an unpaired electron, or one or more other chemical species to X (where X corresponds to the represented molecule, compound, or chemical formula) via covalent bonding, wherein the covalent bonding can be any feasible covalent bond, including, but not limited to, a single bond, a double bond, or a triple bond. As an illustrative example, in the moiety

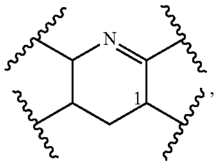 [SMILES: *C1=NC(*)C(*)CC1*], the carbon labeled "1" has point of attachment which can be a double bond to another species, such a double bond to an oxygen, or two single bonds to two independent species, such as two distinct single bonds each to a hydrogen. As another illustrative example, when two points of attachment are shown on a single atom of a molecule, such as in the moiety

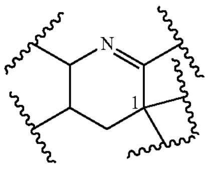

where the carbon labeled "1" has two points of attachment shown, the shown points of attachment on the same single atom (e.g., carbon 1), can be interpreted as representing either a preferable embodiment of two distinct bonds to that same single atom (e.g., two hydrogens bonded to carbon 1) or an optional embodiment of a single point of attachment to said same single atom (e.g., the two points of attachment on carbon 1 can optionally be consolidated as representing one double to carbon 1, such as a double bond to oxygen). As used herein, the various functional groups represented will be understood to have a point of attachment at the functional group having the hyphen or dash (-) or a dash used in combination with an asterisk (*). In the case of $—CH_2CH_2CH_3$, it will be understood that the point of attachment is the $CH_2$ group at the far left. If a group is recited without an asterisk or a dash, then the attachment point is indicated by the plain and ordinary meaning" of the recited group.

Where substituent groups are specified by their conventional chemical formulae, written from left to right, they equally encompass the chemically identical substituents that would result from writing the structure from right to left, e.g., $—CH_20$- is equivalent to $—OCH_2—$.

Where used, a bond represented by " " (a squiggly or wavy line) refers to a bond having any angle or geometry, such as in the case of a chemical species exhibiting stereochemistry such as chirality. For example, the compound characterized by formula (FX100):

(FX100)

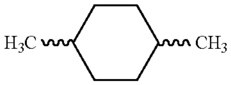

may correspond to one or more compounds, such as those characterized by the formulas (FX100a), (FX100b), (FX100c), and (FX100d):

(FX100a)

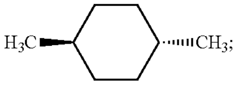;

(FX100b)

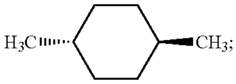;

(FX100c)

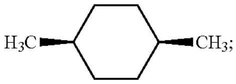;

(FX100d)

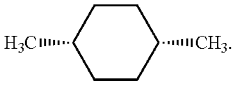.

It must also be noted that a bond represented as a non-wavy or non-squiggly line, such as a "——", may exhibit more than one stereochemical configuration, such as chirality. In other words, the compound characterized by formula (FX100e):

(FX100e)

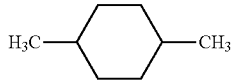

may correspond to one or more compounds, such as those characterized by the formulas (FX100a), (FX100b), (FX100c), and (FX100d).

When referring to a material, such as a polymer, being aqueous, the term "aqueous" refers to said material being dispersed, dissolved, or otherwise solvated by water. An "aqueous solution" refers to a solution that comprises water as solvent and one or more solute species dispersed, dissolved, or otherwise solvated by the water. Optionally, but not necessarily, an aqueous solution or an aqueous solvent includes 20 vol. % or less, optionally 15 vol. % or less, optionally 10 vol. % or less, preferably 5 vol. % or less, of a non-aqueous or organic solvent.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to a subject, such as a patient in need of treatment; slowing in the rate of degeneration or decline; making the final point of degeneration less debilitating; improving a subject's physical or mental well-being. The treatment or amelioration of symptoms can be based on objective or subjective parameters; including the results of a physical examination, neuropsychiatric exams, and/or a psychiatric evaluation. The term "treating," and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, increase enzyme activity, reduce transcriptional activity, increase transcriptional activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist (inhibitor) required to decrease the activity of an enzyme or protein (e.g. transcription factor) relative to the absence of the antagonist. An "activity increasing amount," as used herein, refers to an amount of agonist (activator) required to increase the activity of an enzyme or protein (e.g. transcription factor) relative to the absence of the agonist. A "function disrupting amount," as used herein, refers to the amount of antagonist (inhibitor) required to disrupt the function of an enzyme or protein (e.g. transcription factor) relative to the absence of the antagonist. A "function increasing amount," as used herein, refers to the amount of agonist (activator) required to increase the function of an enzyme or protein (e.g. transcription factor) relative to the absence of the agonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

As defined herein, the term "inhibition", "inhibit", "inhibiting" and the like in reference to a protein-inhibitor (e.g. antagonist) interaction means negatively affecting (e.g. decreasing) the activity or function of the protein relative to the activity or function of the protein in the absence of the inhibitor. In some embodiments inhibition refers to reduction of a disease or symptoms of disease. In some embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein The term "modulator" refers to a composition that increases or decreases the level of a target molecule or the function of a target molecule.

"Patient", "subject", or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In some embodiments, a patient is human. In some embodiments, a patient is a mammal. In some embodiments, a patient is a mouse. In some embodiments, a patient is an experimental animal. In some embodiments, a patient is a rat. In some embodiments, a patient is a test animal.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). In embodiments, administration includes direct administration to a tumor. Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent or chemotherapeutic). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

As used herein, the term "conjugated" when referring to two moieties means the two moieties are bonded, wherein the bond or bonds connecting the two moieties may be covalent or non-covalent. In embodiments, the two moieties are covalently attached to each other (e.g. directly or through a covalently attached intermediary). In embodiments, the two moieties are non-covalently attached (e.g. through ionic bond(s), van der waal's bond(s)/interactions, hydrogen bond (s), polar bond(s), or combinations or mixtures thereof).

The term "non-peptide therapeutic moiety" refers to a therapeutic moiety that is not a peptide or a polypeptide having at least 2 amino acids. A "therapeutic moiety" refers to a chemical moiety that: (i) can function as a therapeutic agent (or perform a therapeutic function), such as for a treatment when administered to or otherwise provided to a patient or subject; and (ii) is covalently attached to host or carrier compound or molecule, such as a polymer according to any of the embodiments disclosed herein. A therapeutic moiety is optionally a monovalent moiety. The therapeutic moiety is a therapeutic agent that is a therapeutically or pharmaceutically active therapeutic agent when attached to the polymer, when released from the polymer (such as via a chemical reaction), or both. A therapeutic agent is capable of treating or managing a condition, such as a disease, in a living patient or subject, such as a human or animal. A non-peptide therapeutic moiety is optionally a small molecule having a molecular weight below 4500 Da, optionally below 2000 Da, optionally below 1000 Da. Unless otherwise stated, a peptide or polypeptide of the invention can be a therapeutic peptide, which is a therapeutic moiety that is or that comprises a peptide or polypeptide. Optionally the term "peptide" can refer to a polypeptide.

Optionally in any of the polymers, methods, and liquid compositions disclosed herein, n and a fraction ("P") of all side chain moieties in the polymer that are side chain moieties comprising a peptide moiety are selected to provide for cellular uptake. Optionally, cellular uptake refers to cellular uptake of or penetration of a biological by at least a portion of the polymer, the majority of the polymer, or the entirety of the polymer. Cellular uptake can be measured or quantified, such as via absorbance or fluorescence signal unique to a portion of the polymer (such as the drug) using different cellular assays, UV-Vis absorption spectroscopy, fluorescence spectroscopy, radio labeling, mass-spectroscopy, and/or inductively coupled plasma mass spectrometry. Optionally in any of the polymers, methods, and liquid compositions disclosed herein, at least one of the plurality of peptide moieties is a non-cell-penetrating peptide. Optionally in any of the polymers, methods, and liquid compositions disclosed herein, each peptide moiety of at least a majority of the plurality of peptide moieties is a non-cellpenetrating peptide. Optionally in any of the polymers, methods, and liquid compositions disclosed herein, the polymer has a net positive charge. Preferably, the net positive charge of the polymer is present at least when the polymer is exposed to physiological conditions, including normal physiological conditions. Preferably, any positive charge of the polymer is present at least when the polymer is exposed to physiological conditions, including normal physiological conditions. Preferably in any of the polymers, methods, and liquid compositions disclosed herein, at least one of the plurality of peptide moieties has a positive charge. The presence of a positive charge can increase or otherwise enhance the therapeutic activity or function of the polymer, or portions thereof such as of the non-peptide therapeutic(s) and any therapeutic peptides, if present. In embodiments, the presence of a positive charge on the polymer can increase or otherwise enhance the therapeutic activity or function of the polymer, or portions thereof at least because of the enhanced or improved cellular uptake efficiency of the polymer due to the presence of the positive charge. Preferably, polymers disclosed herein can penetrate or be taken up by a biological cell even when any, a majority, or even when all of the peptide sequences on said polymer do not correspond to cell-penetrating peptides. This is because peptide sequences that are not cell-penetrating peptides but that have at least a single positive charge are able to enter cells (cellular uptake) once polymerized as a high density brush of peptides, wherein, in contrast, the monomeric peptide alone would be unable to enter the cell. See also Blum, et al. ("Activating peptides for cellular uptake via polymerization into high density brushes." A. P. Blum, J. K. Kammeyer and N. C. Gianneschi, Chem. Sci., 2016, 7, 989-994), which is incorporated herein by reference in its entirety to the extent not inconsistent herewith.

The term "cellular uptake" refers to any process or mechanism that results in a molecule, peptide, therapeutic agent, compound, polymer, or portion thereof, or material being transported either actively of passively across the cellular membrane of a biological cell.

The terms "cell" and "biological cell" are used interchangeably are refer to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells. A "viable cell" is a living biological cell.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The term "substantially" refers to a property, condition, or value that is within 20%, 10%, within 5%, within 1%, optionally within 0.1%, or is equivalent to a reference property, condition, or value. The term "substantially equal", "substantially equivalent", or "substantially unchanged", when used in conjunction with a reference value describing a property or condition, refers to a value that is within 20%, within 10%, optionally within 5%, optionally within 1%, optionally within 0.1%, or optionally is equivalent to the provided reference value. For example, a diameter is substantially equal to 100 nm (or, "is substantially 100 nm") if the value of the diameter is within 20%, optionally within 10%, optionally within 5%, optionally within 1%, within 0.1%, or optionally equal to 100 nm. The term "substantially greater", when used in conjunction with a reference value describing a property or condition, refers to a value that is at least 1%, optionally at least 5%, optionally at least 10%, or optionally at least 20% greater than the provided reference value. The term "substantially less", when used in conjunction with a reference value describing a property or condition, refers to a value that is at least 1%, optionally at least 5%, optionally at least 10%, or optionally at least 20% less than the provided reference value. As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value. In embodiments, the terms "about" and "substantially" are interchangeable and have identical means. For example, a particle having a size of about 1 μm may have a size is within 20%, optionally within 10%, optionally within 5%, optionally within 1%, optionally within 0.1%, or optionally equal to 1 μm.

Additional useful background information, terminology (to the extent not inconsistent with the terms as defined herein), and embodiments (to the extent not inconsistent with the embodiments described herein) may be found in International Patent Publication No. WO 2021/030326 A1, filed Aug. 11, 2020 (Gianneschi, et al.; PCT/US2020/045729), which is incorporated herein by reference in its entirety to the extent not inconsistent herewith.

DETAILED DESCRIPTION OF THE INVENTION

In the following description, numerous specific details of the devices, device components and methods of the present invention are set forth in order to provide a thorough explanation of the precise nature of the invention. It will be apparent, however, to those of skill in the art that the invention can be practiced without these specific details.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

Small molecule therapeutics commonly used in the treatment of human diseases such as cancer often suffer from poor solubility and stability in blood. Systems for improving drug delivery often rely on covalent-conjugation to or encapsulation by carriers. In the case of polymeric carriers therapeutics are often incorporated directly as a monomer or through a post polymerization conjugation reaction and result in systems with a statistical average of the therapeutic. To address these issues a polymer-drug conjugate was designed and synthesized by ring-opening metathesis polymerization incorporating a single drug moiety on the chain end of a water-soluble polymer. A chain termination agent containing Paclitaxel (PTX) for ROMP was designed and synthesized then used to add a single PTX moiety to the end of water soluble peptide based ROMP polymers with different overall charges. Polymers end-labelled by PTX could be separated from unlabeled polymers and polymers carrying positive charges were shown to have greater cytotoxicity compared with the neutral and negatively charged polymers.

Applications of the polymers and methods disclosed herein include small molecule therapeutic delivery systems. Advantages of the polymers and methods disclosed herein include: ability to incorporate a single drug moiety onto the end of a ROMP polymer; tunability of charge of the polymer for tunable cellular uptake; end-labelled and non-labelled polymers can be separated; drug-end-labelled polymers are can be dispersed as single chains in aqueous environments; the polymers show resistance to proteolysis; and the polymers show enhanced cellular internalization.

According to certain embodiments disclosed herein, a paclitaxel chain termination agent was used to add a single drug moiety to the end of a number of peptide containing polymers with different overall charges that were synthesized by ROMP. Polymers end-labelled with the drug were separated from the un-labelled polymers by HPLC. Drug-terminated peptide brush polymers carrying positive charges exhibited enhanced cell uptake and cytotoxicity as compared to their neutral and negatively charged analogues.

Figure 2:
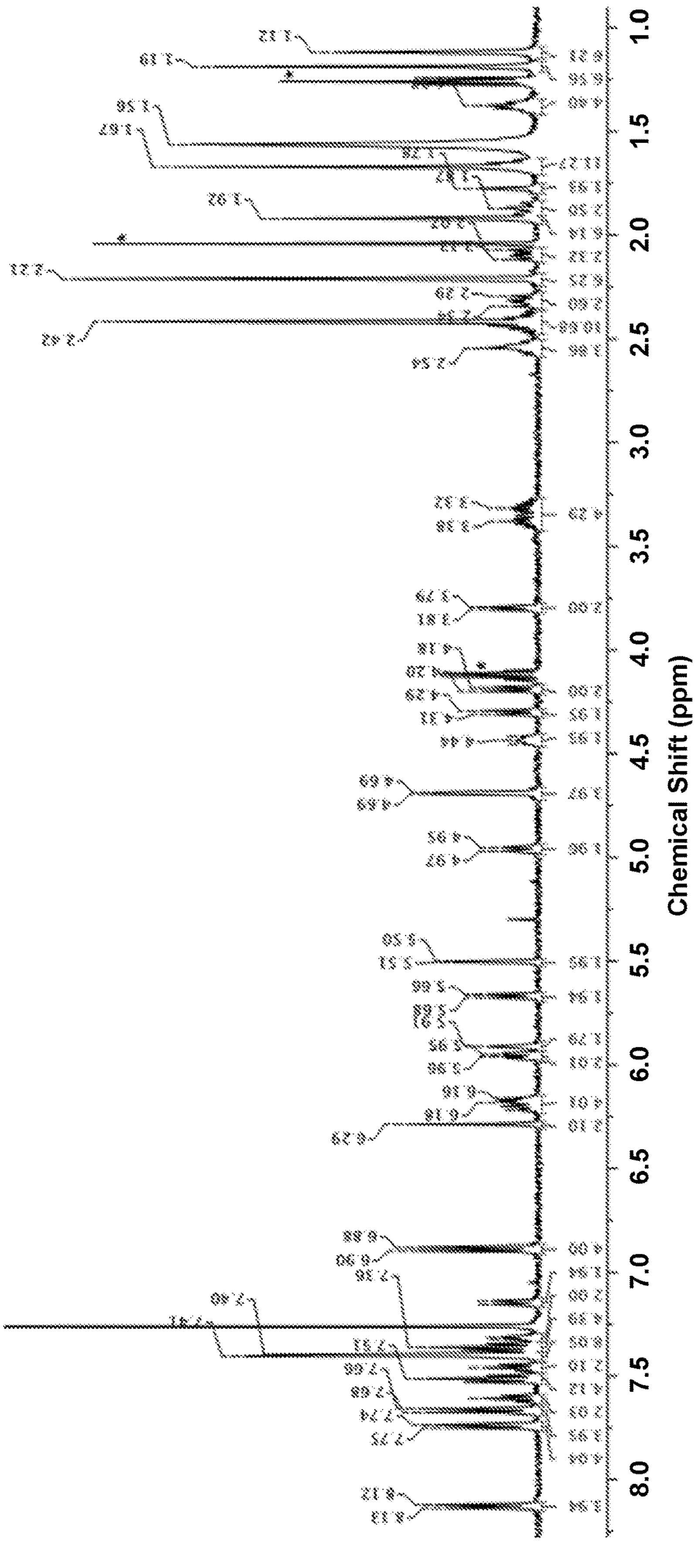
FIG. 2. $^{1}H$ NMR spectrum of PTX-containing chain transfer agent (III) (*remaining Ethyl Acetate).
Figure 3:
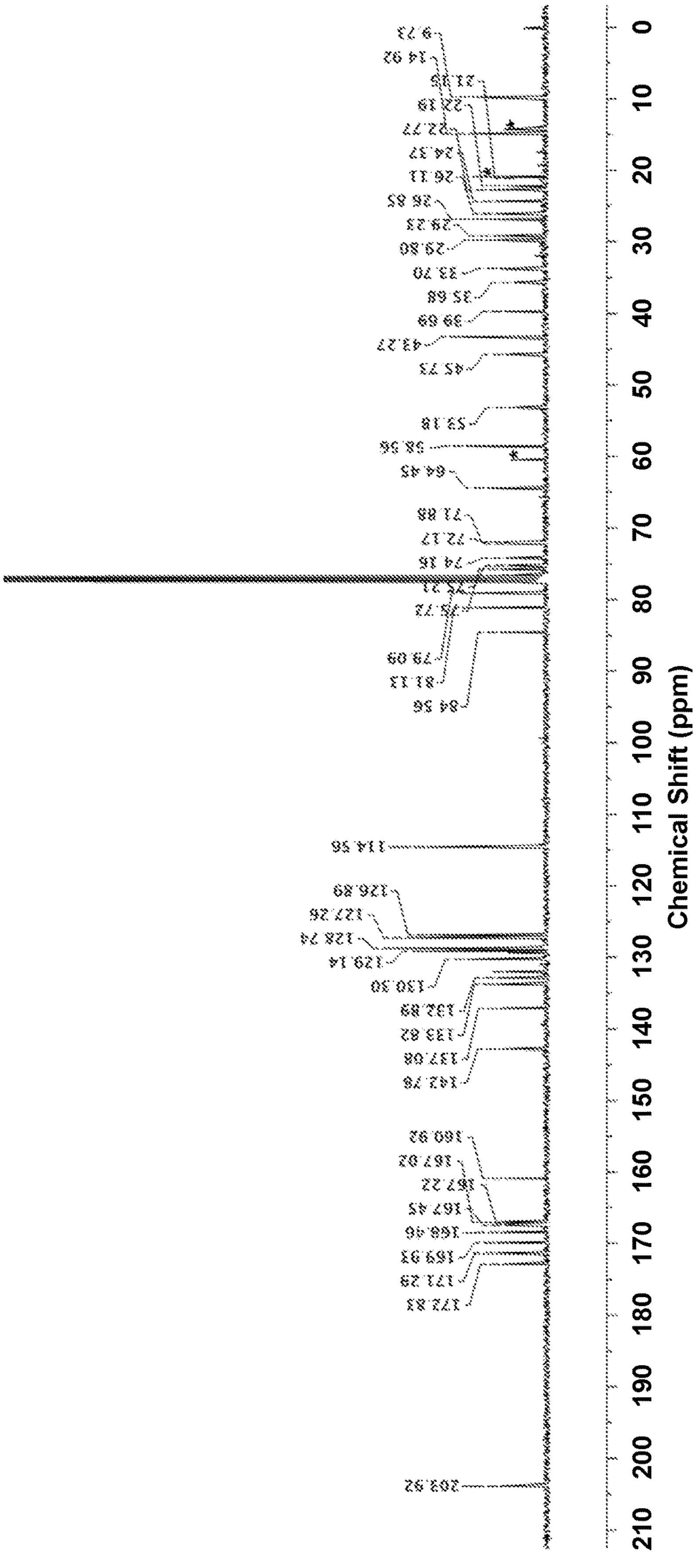
FIG. 3. $^{13}C$ NMR spectrum of PTX-containing chain transfer agent (III).
Figure 4:
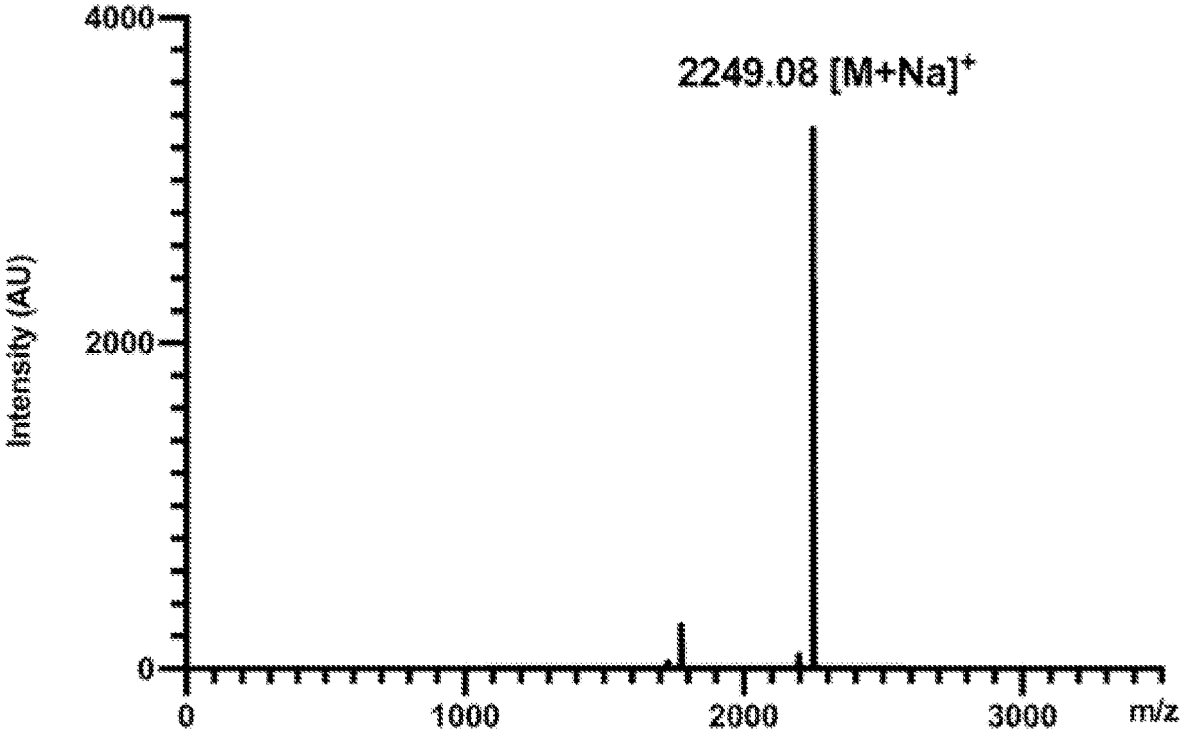
FIG. 4. Mass Spectrum of PTX-containing chain transfer agent (III).

According to certain embodiments disclosed herein, a Paclitaxel chain termination agent (III, FIG. 1) for ROMP was synthesized in two steps from known dicarboxylic acid I. Methyl 6-aminohexanoate was added to the carboxylic acid moieties using standard HATU coupling conditions to give diester II. Subsequent base hydrolysis of the methyl esters gave the target PTX-chain termination agent III. The termination agent was characterized by proton and carbon NMR and mass spectrometry (FIGS. 2-4).

Figure 5A:
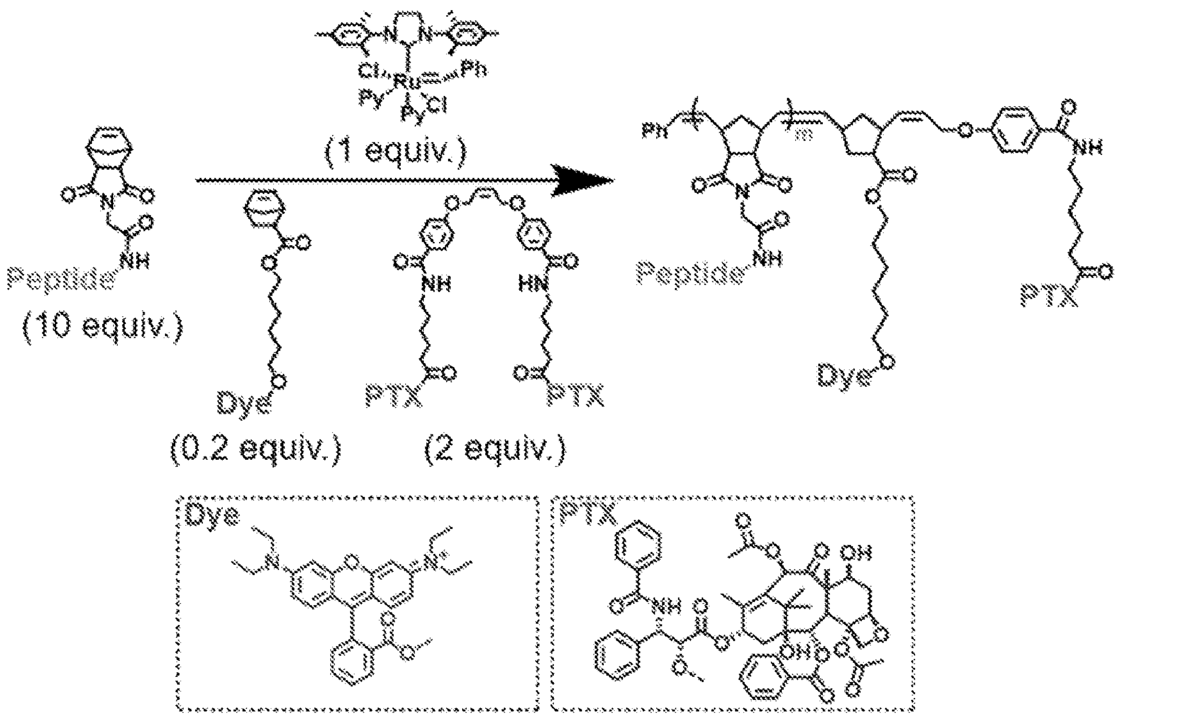
FIG. 5A. ROMP approach to dye-labeled and paclitaxel end-capped peptide brush polymers, denoted as poly(amino acid sequence)-Dye-PTX.
Figure 5B:
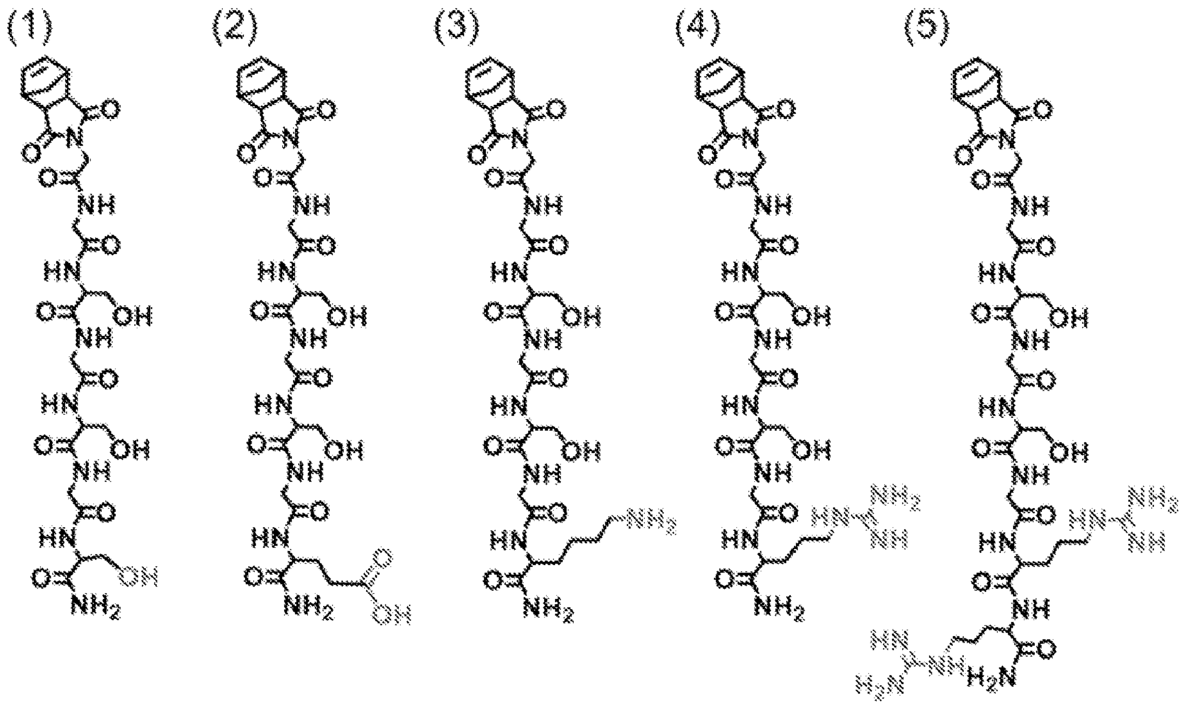
FIG. 5B. Chemical structures of various peptide norbornene monomers in this study: (1) Nor-GGSGSGS; (2) Nor-GGSGSGE; (3) Nor-GGSGSGK; (4) Nor-GGSGSGR; (5) Nor-GGSGSGRR.

To assess the utility of labelling ROMP polymers with a single PTX moiety, peptide brush polymers are presented. A series of peptides bearing different charges and number of charges were synthesized, including GGSGSGS (SEQ ID NO:1), GGSGSGE (SEQ ID NO:2), GGSGSGK (SEQ ID NO:3), GGSGSGR (SEQ ID NO:4), GGSGSGRR (SEQ ID N0:5). These amino acid sequences were anchored with a carboxylic acid-functionalized norbornenes through solid phase peptide synthesis (FIGS. 5A-5B). The sequence GGSGSG endows hydrophilicity to the norbornene monomers and resulting peptide brush polymers. Moreover, four different amino acids including lysine (K), serine (S), arginine (R), and glutamic acid (E) were appended to the C terminus, giving rise to monomers possessing positive, negative, and neutral charges, respectively.

Figure 6:
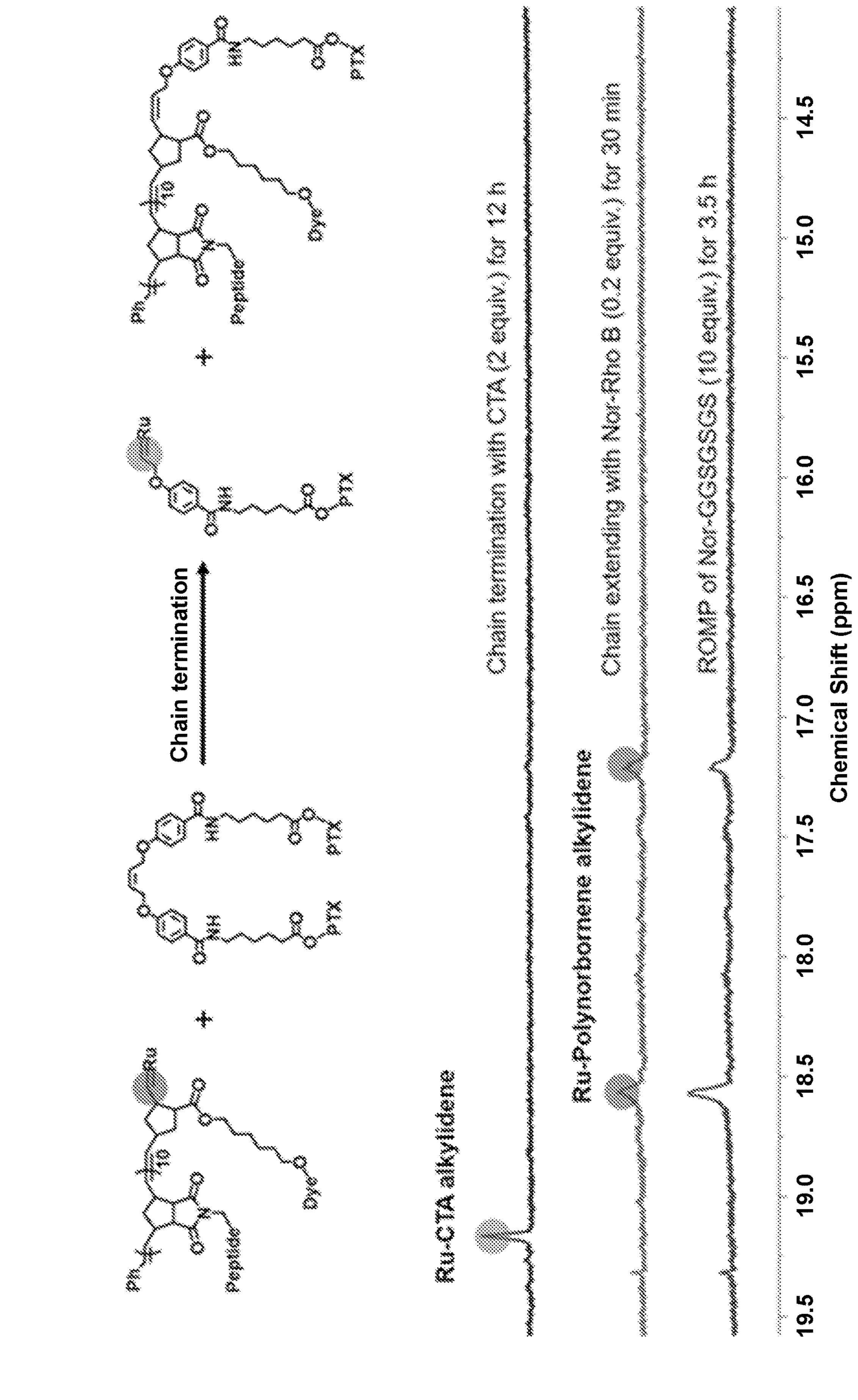
FIG. 6. $^{1}H$ NMR spectra of ROMP of Nor-GGSGSGS, chain extension with dye monomer (0.2 equiv.), and termination with PTX-CTA (2 equiv.).

ROMP of peptide monomers was conducted in the presence of a modified $2^{nd}$ generation Grubbs catalyst (FIGS. 5A-5B), targeting a degree of polymerization (DP) of 10 for all peptide brush polymers. Upon the full consumption of monomers as confirmed by NMR, a rhodamine B-functionalized norbornene monomer (0.2 equiv. with respect to catalyst) was added to incorporate a fluorophore into a portion of polymers. Finally, the polymerization reactions were terminated using a paclitaxel-modified chain termination agent, resulting in drug-loaded, and dye-labelled peptide brush polymers. The progress of the polymerizations and chain termination was monitored by $^{1}$HNMR and showed complete termination of active polymer chains (FIG. 6).

Figure 7:
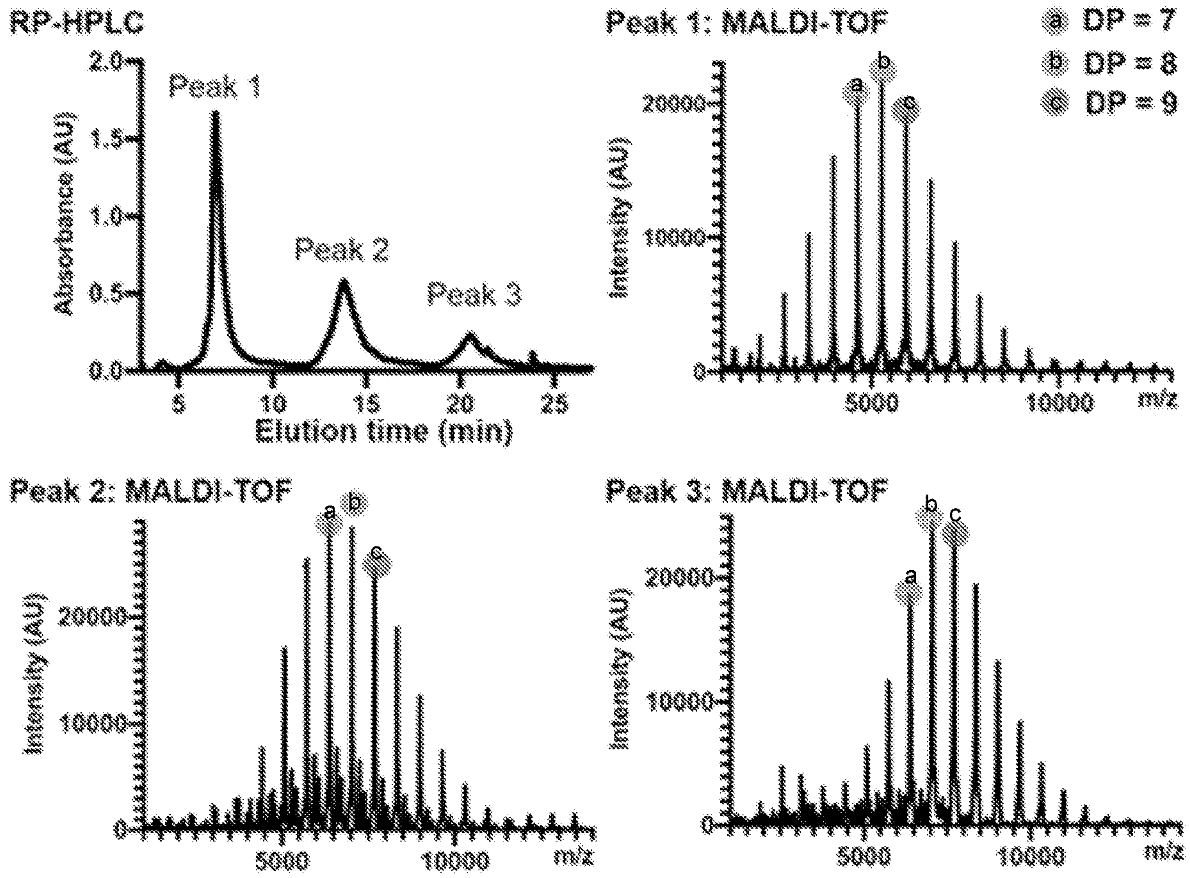
FIG. 7. RP-HPLC enabled efficient separation of crude poly(GGSGSGS), leading to three distinct peaks. MALDI-TOF mass spectroscopy further identified those three peaks. Peak 1 (51% of total polymers) was attributed to polymer without dye and drug, denoted as poly(GGSGSGS); Peak 2 (35% of total polymers) was assigned to polymer only with drug, denoted as poly(GGSGSGS)-PTX; Peak 3 (14% of total polymers) was the dye-labeled and drug terminated polymer, denoted as poly(GGSGSGS)-Dye-PTX.

The polymers successfully labelled with PTX could be separated from unlabelled polymers by reverse phase HPLC due to the difference in hydrophobicity. The three main peaks were further identified by MALDI-TOF mass spectroscopy as polymers without dye or drug, polymers with drug only, and polymers with both dye and drug (FIG. 7). These results prove the feasibility of purifying peptide brush polymer-drug conjugates by HPLC.

Figure 8:
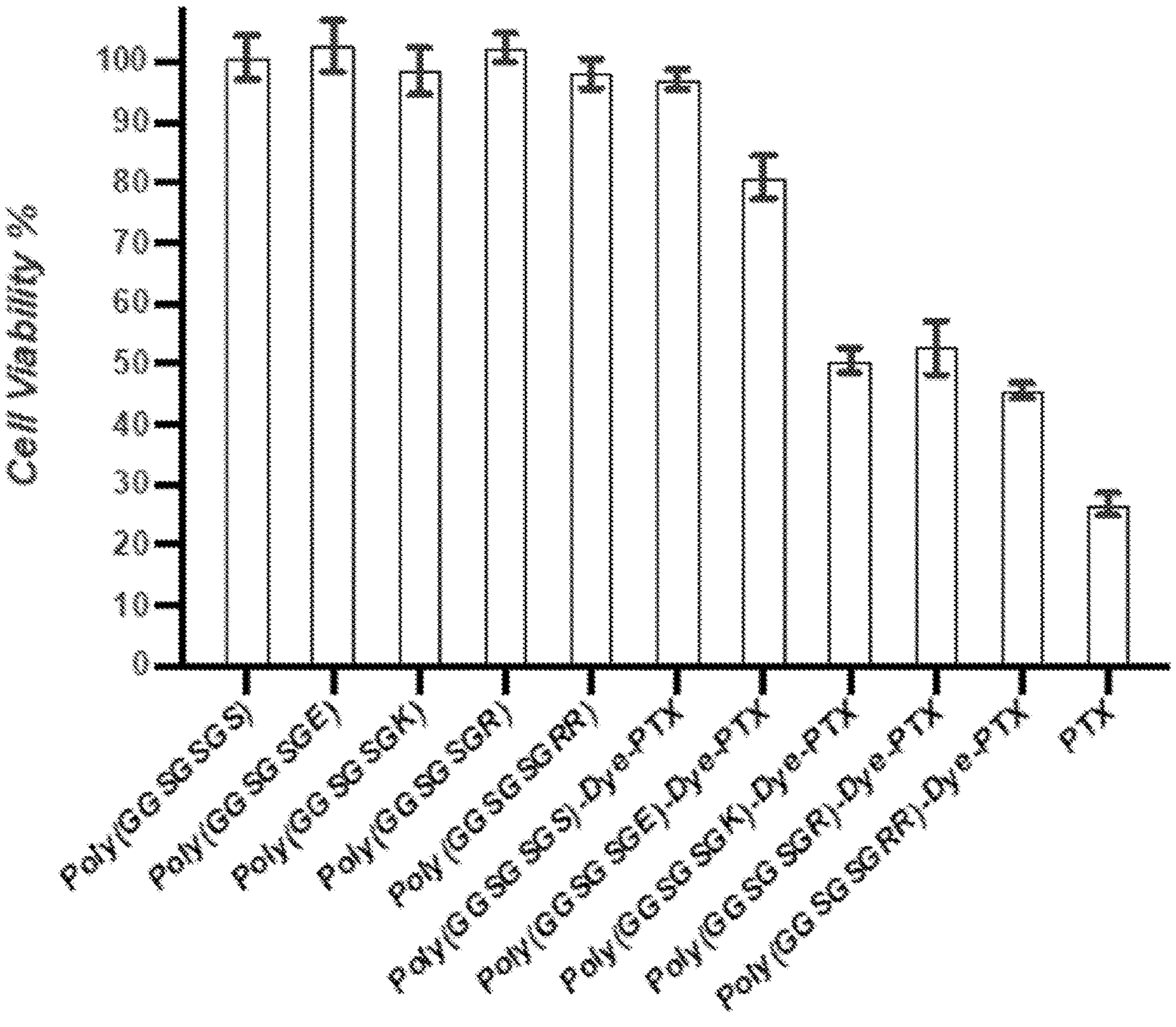
FIG. 8. Cytotoxicity of purified peptide brush polymer-drug conjugates (columns 6-10 from left to right) and polymers without loading drug (columns 1-5). A549 lung carcinoma cells were treated with 4 μM of each polymer sample for 4 hours, washed twice with PBS, and incubated for an additional 72 h.

According to certain embodiments disclosed herein, the cytotoxicity of polymer-drug conjugates was assessed in A549 lung carcinoma cells. All peptide brush polymers without paclitaxel exhibited no toxicity, showing near 100% cell viability after incubation for 3 days, indicative of excellent cytocompatibility of peptide brush polymers (FIG. 8). In the case of purified polymer-drug conjugates, cytotoxicity of positively charged polymer-drug conjugates was markedly higher than their neutral and negatively charged analogues. It is worth noting that purified polymer-drug conjugates showed higher cytotoxicity than that of their corresponding crude products, regardless of the nature of charges. This can be attributed to the higher drug loading of pure polymer-drug conjugates than crude product, which contains some polymer species that lack drug. These results demonstrate the feasibility of using drug containing chain termination agents to form well defined drug-terminated ROMP polymers that can be separated from unlabelled polymers. In addition drug-terminated peptide brush polymers carrying positive charges exhibited enhanced cytotoxicity as compared to their neutral and negatively charged analogues.

Experimental methods, according to certain embodiments disclosed herein:

Peptide monomers were synthesized on a Biotage Alstra peptide synthesizer. Analytical RP-HPLC analysis was performed on a Waters Symmetry column (150×4.60 mm) using a Waters 1525 Binary HPLC pump equipped with Waters 2998 Photodiode Array Detector. Peptide monomers were purified on a Semi-Prep RP-HPLC using a Waters SunFire column (250×19 mm). The solvent system for both HPLC instruments consists of 0.1% TFA in water (buffer A) and 0.1% TFA in acetonitrile (buffer B). $^{1}$H and $^{13}$C NMR spectra were recorded on a Bruker 400 MHz NMR spectrometer. Chemical shifts were reported in ppm relative to the residual solvent peak or TMS peak. ESI-MS spectra were performed on a LCQ-Advantage mass spectrometer. MALDI-TOF-MS spectra were performed on a Bruker Ultraflextreme mass spectrometer. MALDI-TOF-MS spectra of polymers were performed using a matrix solution of 2,5-dihydroxybenzoic acid in 1:3 water:acetonitrile with 0.1% TFA (30 mg/ml), and polymer solutions in water (1 mg/ml). The solutions were mixed in a 10:1 ratio (matrix: polymer). Absorbance at 570 nm was measured in 96 well plates using a TECAN Spark 10M microplate reader. Flow cytometry measurements were performed using a BD Accuri $C_6$ Plus.

Experimental, according to certain embodiments disclosed herein:

Synthesis of (Z)-6,6'-((4,4'-(but-2-ene-1,4-diylbis(oxy))bis(benzoyl))bis(azanediyl))dihexanoic acid (II): To a solution of (I) (182.4 mg, 1.0 equiv.) in 10 mL DMF, HATU (472 mg, 2.2 equiv.) and DIPEA (450 μL, 4.6 equiv.) were added. The mixture was stirred at room temperature for 30 minutes. To the mixture 6-Aminocaproic acid methyl ester hydrochloride (237 mg, 2.3 equiv.) and DIPEA (240 μL, 2.5 equiv.) were added. The reaction was stirred for another 48 hours and then concentrated to dryness. The residue was resuspended in $CH_2Cl_2$ and washed by water (×1) and HCl (aq) (1M) (×3). The organic layer was collected and dried by $Na_2SO_4$, filtered and concentrated. The obtained solid was then purified by flash chromatography (4:1 Ethyl Acetate: Petroleum Ether) to give dimethyl 6,6'-((4,4'-(but-2-ene-1,4-diylbis(oxy))bis(benzoyl))bis(azanediyl))(Z)-dihexanoate as a white solid.

To a container charged with dimethyl 6,6'-((4,4'-(but-2-ene-1,4-diylbis(oxy))bis(benzoyl))bis(azanediyl))(Z)-dihexanoate (100.6 mg, 1 equiv.) was added 4:1 MeOH:$H_2O$ (100 mL) containing LiOH (85.4 mg, 20.6 equiv.). The mixture was stirred at 35° C. for 6 h and then MeOH was removed by rotary evaporation until a white precipitate formed. The mixture was diluted by water and acidified with HCl (conc.). The resulting white solid was collected by vacuum filtration, washed with water and dried under vacuum.

Synthesis of PTX-containing chain transfer agent (III): To a solution of (3) (60.1 mg, 1 equiv.), paclitaxel (260.2 mg, 3 equiv.) and DMAP (2.65 mg, 0.2 equiv.) in 4:1 DCM:DMF (10 mL) in a 0° C. ice bath was added DCC (53.8 mg, 2.4 equiv.) slowly. The reaction was stirred for 30 minutes and then the ice bath was removed and the reaction was stirred for another 8 h. The mixture was filtered and washed with water (×1) and HCl (aq) (1M) (×2), then dried ($Na_2SO_4$), filtered and concentrated to dryness. The white crude material was purified by flash chromatography (3:1 Ethyl Acetate:Petroleum Ether to 100% Ethyl Acetate).

Synthesis of peptide monomers: Peptide monomers were synthesized via standard FMOC-based solid phase peptide synthesis using Rink Amide MBHA resin. FMOC was deprotected using a solution of 20% piperidine in DMF. Amino acid couplings were carried out using HBTU and DIPEA (resin/amino acid/HBTU/DIPEA 1:3:2.95:6) for 45 mins. Norbornenyl-glycine (1.2 equiv.) coupling was carried out using HATU (1.15 equiv.) and DIPEA (2.4 equiv.) for 6 hrs. The final peptide monomers were cleaved from the resin using a mixture of TFA/H2O/TIPS (95:2.5:2.5) for 2 hrs and precipitated from cold ether. The crude products were further purified by semi-prep HPLC using UV-Vis detector at 214 nm.

Synthesis of polymers: To stirred solutions of peptide monomers (10 equiv., 0.03 mmol/L) in DMF-$d_7$ (0.5 mL) were added modified $2^{rd}$ Generation Grubbs initiator (1 equiv.) in a small volume of DMF-$d_7$. The polymerizations were stirred for 4 to 5 h, after which a solution of the dye monomer (0.2 equiv.) in a small volume DMF-$d_7$ was added to the reactions and left to stir for 1 hour. To each reaction PTX-containing chain transfer agent (4) in a small volume of dry DMF (2 equiv.) was added. After 12 h, ethyl vinyl ether was added to ensure full termination. The polymers were precipitated into a cold 1:2 dichloromethane:ether solution (×3) and then purified by RP-HPLC with the UV-Vis detector monitoring at 214 nm. Each peak obtained from HPLC was characterized by MALDI-TOF-MS.

Cytotoxicity Assay: The cytotoxicity of all polymers was assessed using the MTT metabolic assay. A549 cells were plated at a density of 2,000 cells/well in a 96-well plate 18 hrs prior to treatment. Materials at 10× the desired concentration (with respect to polymer) were diluted with PBS, added to the appropriate wells, and the plates incubated for 4 hrs at 37° C. Following incubation, the materials were removed, cells were washed twice with PBS, supplemented with 100 μL Ham's F-12K media, and incubated for an additional 48 or 72 hrs.

De Geest and coworkers developed a paclitaxel-containing chain transfer agent for reversible addition-fragmentation polymerization to prepare well-defined terminal drug-labeled polymers. The resulting polymers contained one drug per modified polymer chain end; although it must be noted that not all chain ends contained a drug moiety because of inherent features of the RAFT mechanism including the use of initiators. These polymers also formed micellar structures with the drug in the core of the micelles.

To the best of our knowledge no other groups are working on chain terminating agents for functionalizing ROMP polymers of peptides.

REFERENCES CORRESPONDING TO ABOVE DESCRIPTION

1. Thompson, M. P.; Randolph, L. M.; James, C. R.; Davalos, A. N.; Hahn, M. E.; Gianneschi, N. C., Labelling polymers and micellar nanoparticles via initiation, propagation and termination with ROMP. Polymer Chemistry 2014, 5 (6), 1954-1964.
2. Golder, M. R.; Nguyen, H. V. T.; Oldenhuis, N. J.; Grundler, J.; Park, E. J.; Johnson, J. A., Brush-First and ROMP-Out with Functional (Macro)monomers: Method Development, Structural Investigations, and Applications of an Expanded Brush-Arm Star Polymer Platform. Macromolecules 2018, 51 (23), 9861-9870.
3. Zou, J.; Yu, Y.; Li, Y.; Ji, W.; Chen, C.-K.; Law, W.-C.; Prasad, P. N.; Cheng, C., Well-defined diblock brush polymer—drug conjugates for sustained delivery of paclitaxel. Biomaterials Science 2015, 3 (7), 1078-1084.
4. Hilf, S.; Kilbinger, A. F. M., Functional end groups for polymers prepared using ring-opening metathesis polymerization. Nature Chemistry 2009, 1 (7), 537-546.
5. Madkour, A. E.; Koch, A. H. R.; Lienkamp, K.; Tew, G. N., End-Functionalized ROMP Polymers for Biomedical Applications. Macromolecules 2010, 43 (10), 4557-4561.
6. Chen, B.; Metera, K.; Sleiman, H. F., Biotin-Terminated Ruthenium Bipyridine Ring-Opening Metathesis Polymerization Copolymers: Synthesis and Self-Assembly with Streptavidin. Macromolecules 2005, 38 (4), 1084-1090.
7. Kolonko, E. M.; Kiessling, L. L., A Polymeric Domain That Promotes Cellular Internalization. Journal of the American Chemical Society 2008, 130 (17), 5626-5627.
8. Mangold, S. L.; Carpenter, R. T.; Kiessling, L. L., Synthesis of Fluorogenic Polymers for Visualizing Cellular Internalization. Organic Letters 2008, 10 (14), 2997-3000.
9. Matson, J. B.; Grubbs, R. H., Monotelechelic Poly(oxa) norbornenes by Ring-Opening Metathesis Polymerization Using Direct End-Capping and Cross-Metathesis. Macromolecules 2010, 43 (1), 213-221.
10. Owen, R. M.; Gestwicki, J. E.; Young, T.; Kiessling, L. L., Synthesis and Applications of End-Labeled Neoglycopolymers. Organic Letters 2002, 4 (14), 2293-2296.
11. Sahu, S.; Cheung, P. L.; Machan, C. W.; Chabolla, S. A.; Kubiak, C. P.; Gianneschi, N. C., Charged Macromolecular Rhenium Bipyridine Catalysts with Tunable CO2 Reduction Potentials. Chemistry—A European Journal 2017, 23 (36), 8619-8622.
12. Wang, Z.; Li, Y.; Huang, Y.; Thompson, M. P.; LeGuyader, C. L. M.; Sahu, S.; Gianneschi, N. C., Enzyme-regulated topology of a cyclic peptide brush polymer for tuning assembly. Chemical Communications 2015, 51 (96), 17108-17111.
13. Kammeyer, J. K.; Blum, A. P.; Adamiak, L.; Hahn, M. E.; Gianneschi, N. C., Polymerization of protecting-group-free peptides via ROMP. Polym. Chem. 2013, 4 (14), 3929-3933.
14. Blum, A. P.; Kammeyer, J. K.; Yin, J.; Crystal, D. T.; Rush, A. M.; Gilson, M. K.; Gianneschi, N. C., Peptides Displayed as High Density Brush Polymers Resist Proteolysis and Retain Bioactivity. J. Am. Chem. Soc. 2014, 136 (43), 15422-15437.
15. Blum, A. P.; Kammeyer, J. K.; Gianneschi, N. C., Activating peptides for cellular uptake via polymerization into high density brushes. Chem. Sci. 2016, 7 (2), 989-994.
16. Adamiak, L.; Touve, M. A.; LeGuyader, C. L. M.; Gianneschi, N. C., Peptide Brush Polymers and Nanoparticles with Enzyme-Regulated Structure and Charge for Inducing or Evading Macrophage Cell Uptake. ACS Nano 2017, 11 (10), 9877-9888
17. 4. Sun, H.; Choi, W.; Zang, N.; Battistella, C.; Thompson, M. P.; Cao, W.; Zhou, X.; Forman, C.; Gianneschi, N.C., "Bioactive Peptide Brush Polymers via Photoinduced Reversible-Deactivation Radical Polymerization", Angew. Chem. Int. Ed., 2019, 58, 17359-17364

The invention can be further understood by the following non-limiting examples.

Example 1: Paclitaxel-Terminated Peptide Brush Polymers

Included in this section are certain embodiments of polymers and methods disclosed herein, including preparation of paclitaxel-terminated peptide brush polymers wherein cell uptake and toxicity are tunable based on peptide sequence. Synthesis was enabled using a new paclitaxel-containing chain termination agent for ring-opening metathesis polymerization (ROMP). Importantly, reverse phase HPLC could be used to efficiently separate peptide brush polymers consisting of one fluorophore and one terminal paclitaxel from crude polymer mixtures. These purified terminally-modified polymers showed greater potency than the original mixtures. Drug-terminated peptide brush polymers carrying positive charges exhibited enhanced cell uptake and cytotoxicity as compared to their neutral and negatively charged analogues.

The loading of therapeutics to and within carriers is achieved by either physical encapsulation or covalent conjugation.[1-4] The latter generally involves attaching drugs via chemical bonds, such as esters and disulfides, that facilitate release.[5,6] Covalent conjugation has received increasing interest because it confers the drug delivery system with enhanced stability during blood circulation. This approach not only precludes premature release of therapeutics, but also allows for specific stimuli-triggered drug release in diseased tissues.[7-9] In the case of polymeric carriers, drugs are typically tethered as side chains via direct polymerization of drug-modified monomers or via post-polymerization modifications.[2] In each case, a statistical average of drugs is incorporated per polymer chain because of the inherent dispersity of the polymer. To overcome this issue and to prepare polymer-based drug delivery systems in a more precise and well-defined fashion, new approaches are needed.[10]

Recently, De Geest and coworkers developed a paclitaxel-containing chain transfer agent for reversible addition-fragmentation polymerization to prepare well-defined terminal drug-labeled polymers. The resulting polymers contained one drug per modified polymer chain end; although it must be noted that not all chain ends contained a drug moiety because of inherent features of the RAFT mechanism including the use of initiators.[11-13] The resulting polymers spontaneously assembled, with the hydrophobic drug at the core, anchoring the amphiphilic molecules as micelles.[14-17]

Figure 9:
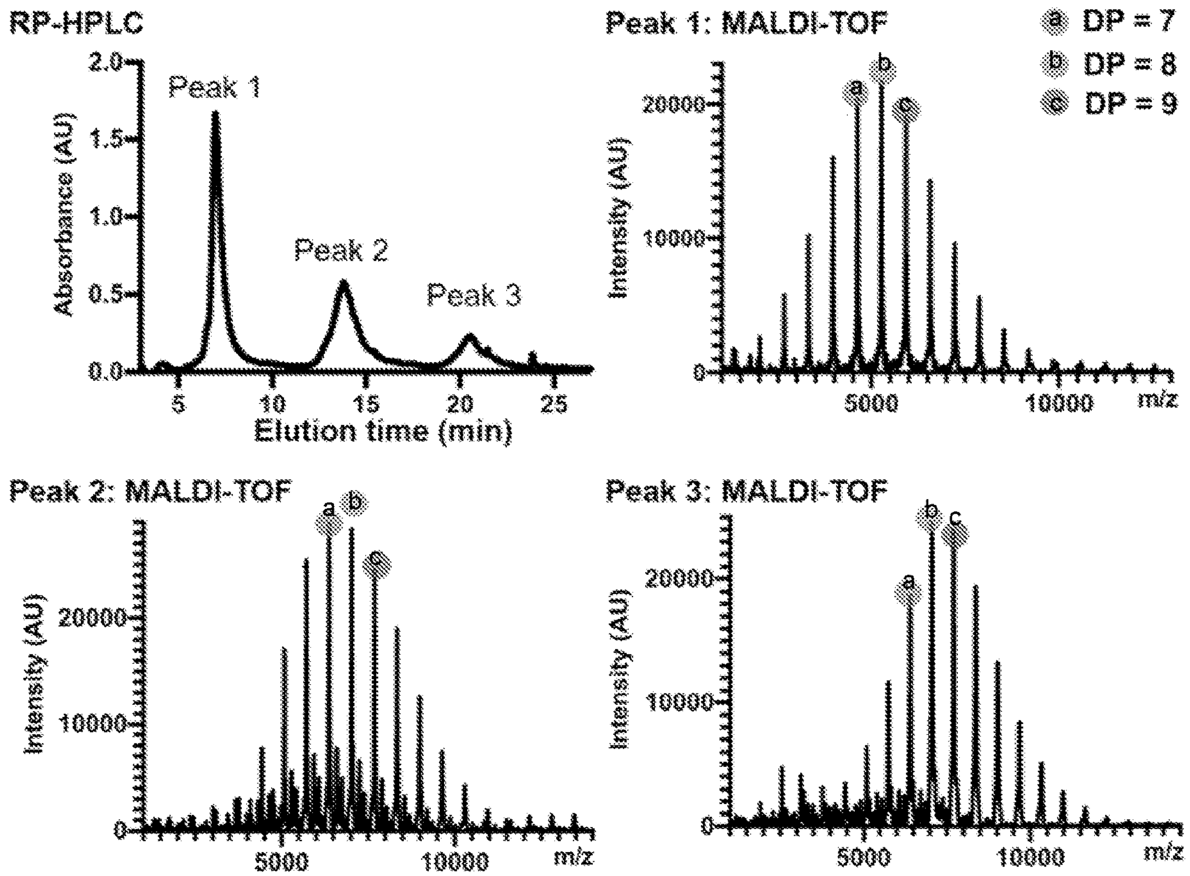
FIG. 9. RP-HPLC enabled efficient separation of crude poly(GGSGSGS), leading to three distinct peaks. MALDI-TOF mass spectroscopy further identified those three peaks. Peak 1 (51% of total polymers) was attributed to polymer without dye and drug, denoted as poly(GGSGSGS); Peak 2 (35% of total polymers) was assigned to polymer only with drug, denoted as poly(GGSGSGS)-PTX; Peak 3 (14% of total polymers) was the dye-labeled and drug terminated polymer, denoted as poly(GGSGSGS)-Dye-PTX. Only 49% of polymers were functionalized with drug because of the livingness of ROMP under reaction conditions in this study.

Contemplated herein are water soluble peptide-based polymers that are resistant to proteolysis and capable of cell internalization.[18-22] These polymers can be tuned in terms of aggregated state and overall charge. Indeed, when dispersed as individual chains, we have shown that the polymers avoid macrophage uptake,[18] a drawback inherent to nanoparticle formulations.[23] Inspired by the concept of the chain end-modified polymers by De Geest and our observations regarding the benefits of single-chain polymers,[18] here we designed a polymer-drug conjugate with one drug residing on a water-soluble polymer chain end and an easily adjustable overall charge. The goal was to incorporate a drug to water soluble polymers via ring-opening metathesis polymerization (ROMP),[5,24] where only a single drug per polymer chain was introduced. As such, the design employed herein avoids drug-containing norbornene monomers. We designed and synthesized a new paclitaxel-containing chain termination agent for ROMP (FIGS. 5A-5B), which was used to terminate the polymerization and concomitantly install one paclitaxel at the ω-terminus of polymers. Targeted polymers consisted of poly(GGSGSGS)-Dye-PTX, poly (GGSGSGE)-Dye-PTX, poly(GGSGSGK)-Dye-PTX, poly (GGSGSGR)-Dye-PTX and poly(GGSGSGRR)-Dye-PTX. Peptide based norbornene monomers easily confer hydrophilicity and enable the introduction of specific chemical functionality, including net charge.[18,19] Furthermore, the crude peptide brush polymer-drug conjugates could be purified via reverse-phase high performance liquid chromatography (RP-HPLC) under normal peptide purification procedures, giving rise to well-defined and highly pure polymer-drug conjugates, consisting of one paclitaxel and one dye (FIG. 9). The efficient purification process enabled us to directly compare the bioactivity of well-defined peptide-drug polymer conjugates, polymers not containing the drug, and the crude polymer mixtures. Variants of the following peptide monomers are disclosed throughout herein: GGSGSGS (SEQ ID NO:1), GGSGSGE (SEQ ID NO:2), GGSGSGK (SEQ ID NO:3), GGSGSGR (SEQ ID NO:4), GGSGSGRR (SEQ ID NO:5).

Figure 11:
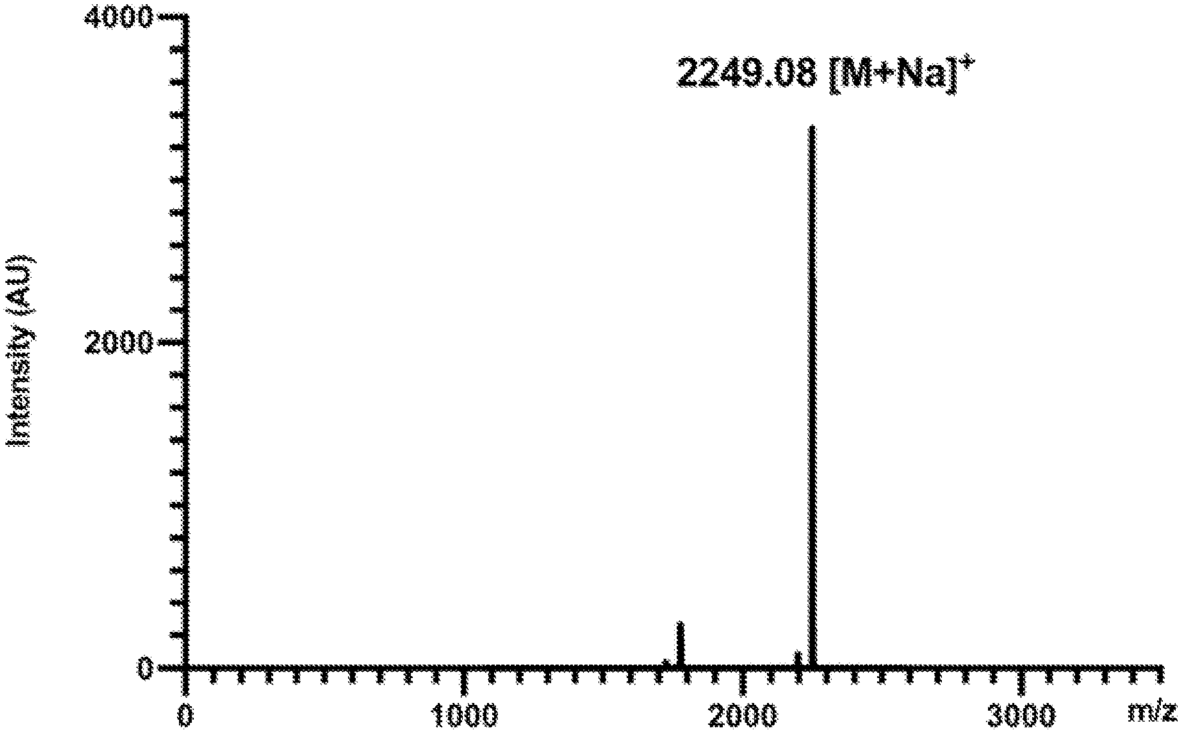
FIG. 11. Mass Spectrum of PTX-containing chain transfer agent (4).
Figure 12:
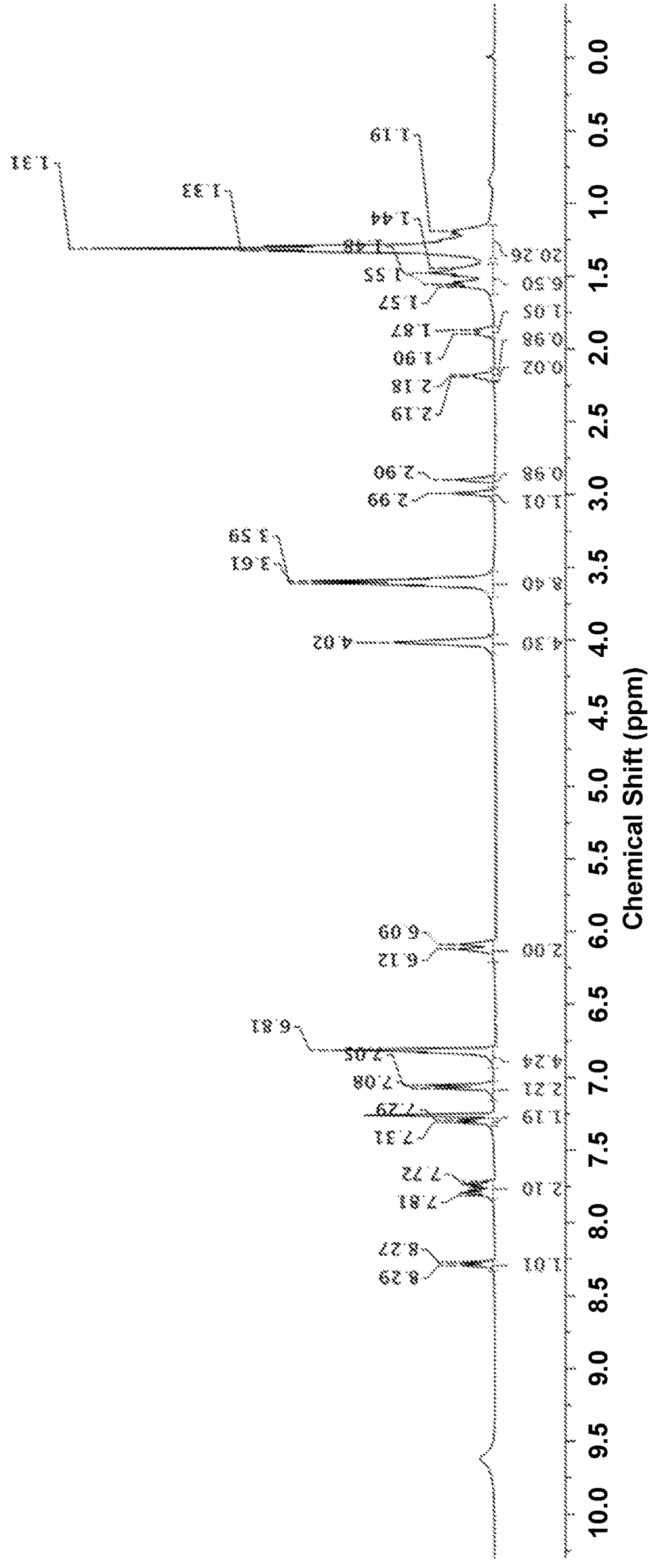
FIG. 12. $^{1}H$ NMR spectrum of dye monomer (6).
Figure 13:
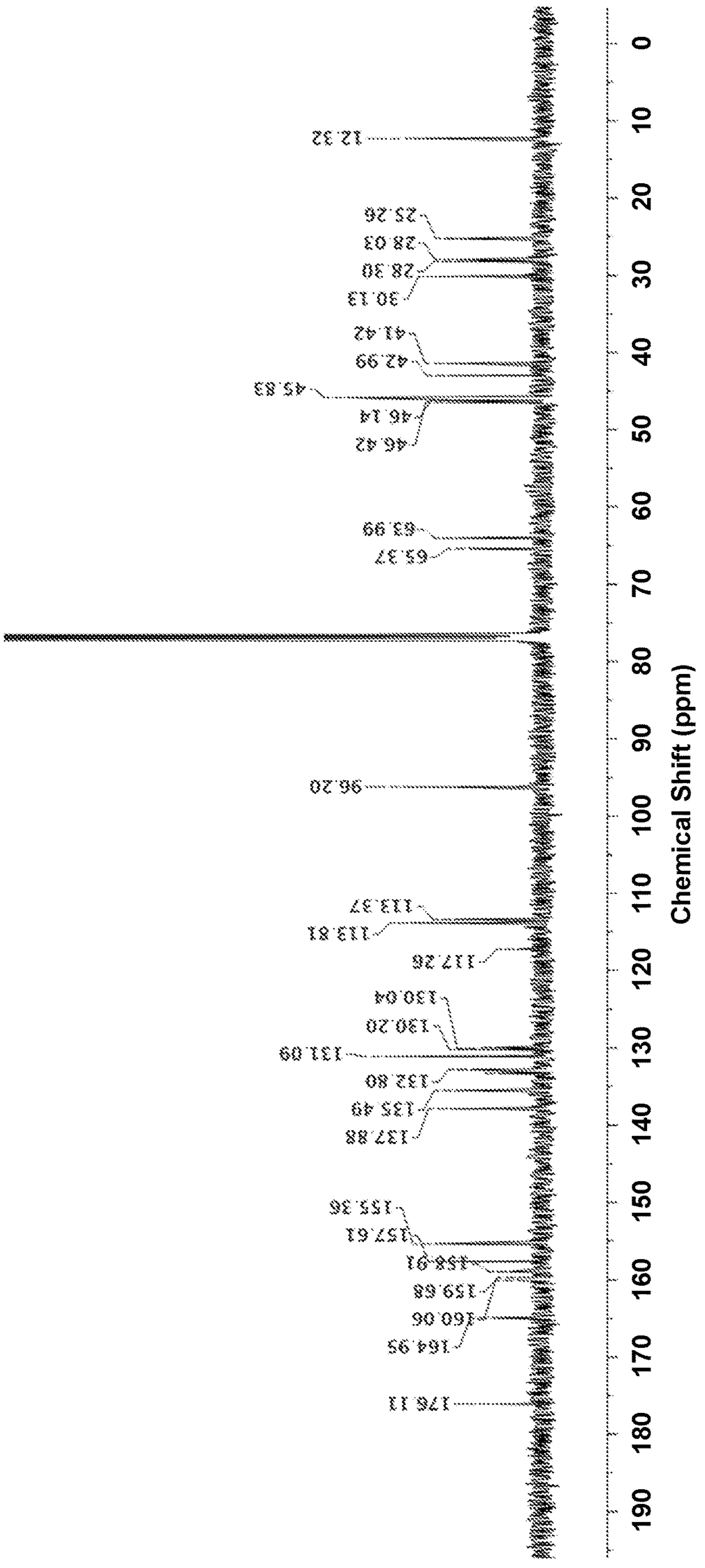
FIG. 13. $^{13}C$ NMR spectrum of dye monomer (6).
Figure 14:
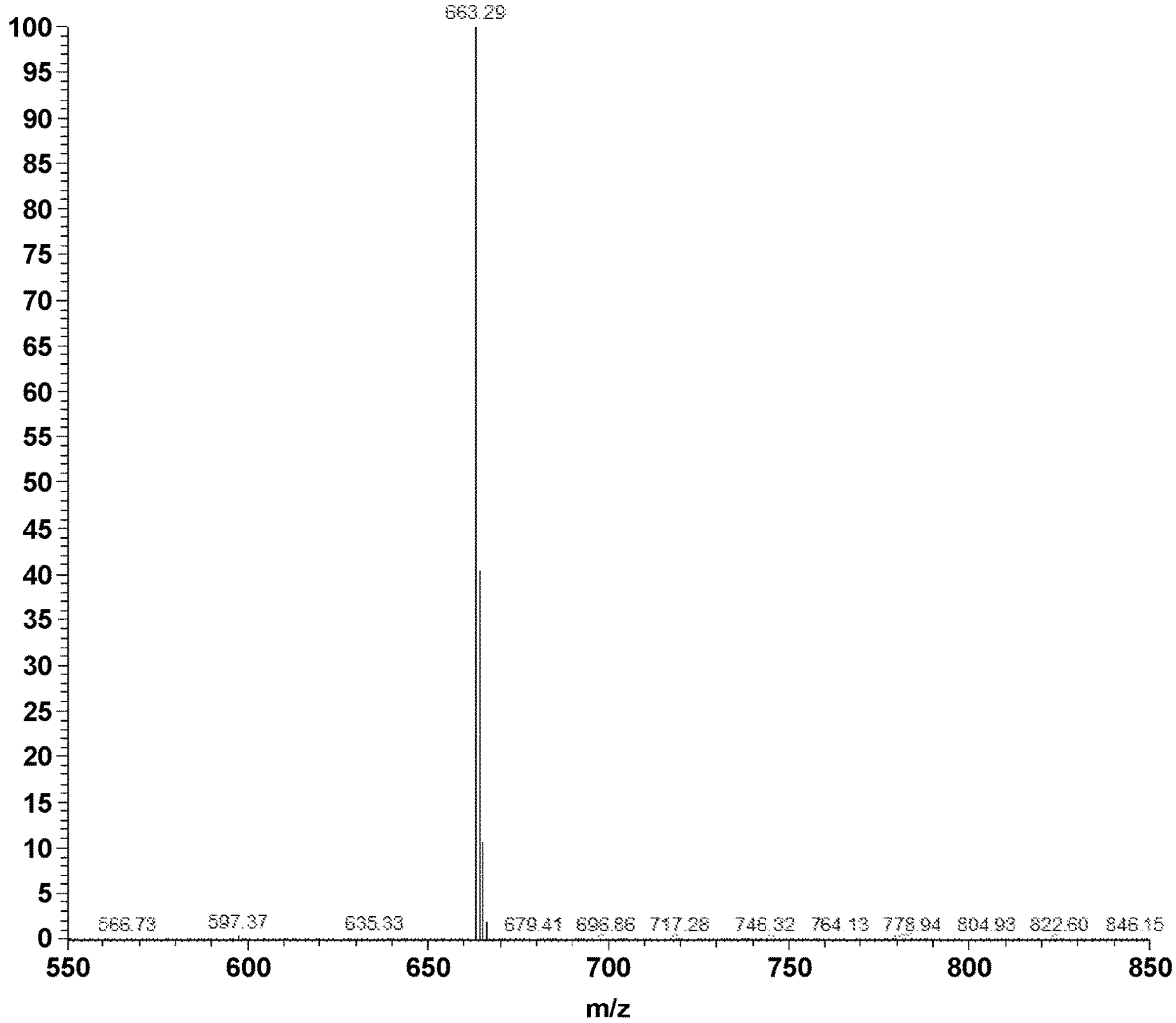
FIG. 14. Mass spectrum of dye monomer (6).

Paclitaxel serves as a potent anticancer agent used in the treatment of many solid tumors. However, its poor solubility in aqueous solution poses a long-lasting challenge in clinical applications.[16,25] In view of this, chemical modifications of paclitaxel involving the attachment of hydrophilic moieties to the drug have been extensively investigated. Specifically, the relatively high reactivity of the 2'-hydroxyl group in paclitaxel allows for selective conjugation with carboxylic functionalities through formation of an ester bond,[26] which is cleavable in the presence of esterases or acidic environment facilitating drug release. In our design, a chain termination agent that contains two carboxylic acids was conjugated to paclitaxel through the 2'-hydroxyl, generating a new chain termination agent consisting of two drugs. This agent can be used to terminate ROMP and attach the drug covalently to the polynorbornene chain end. It is worth noting that a linker based on six methylene carbons was added between the termination agent and drug to overcome steric hinderance and increase the overall synthetic efficiency (FIGS. 2, 3, and 11).

Figure 15:
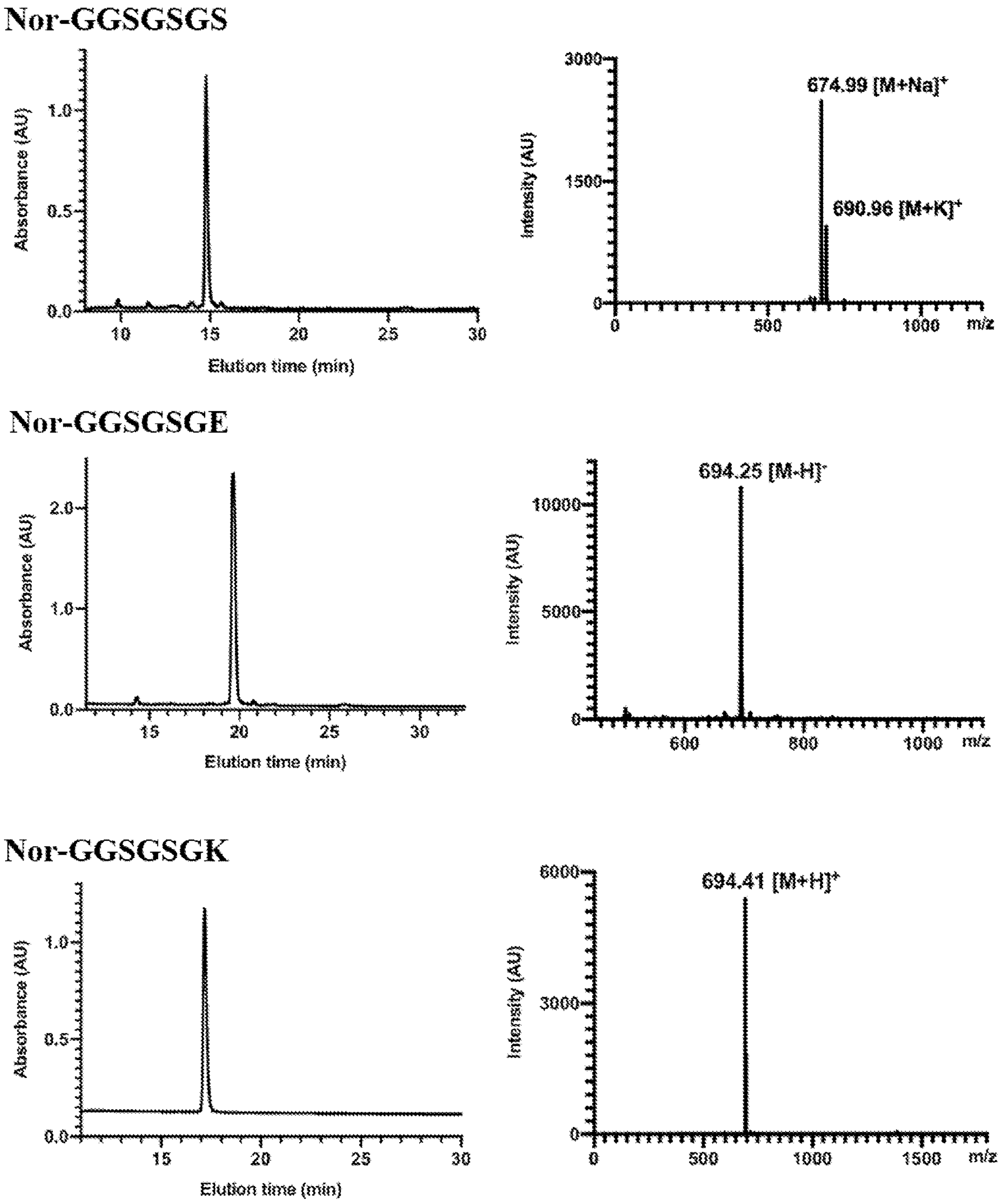
FIG. 15. RP-HPLC traces and mass spectra (MALDI-TOF-MS) of all peptide monomers in this study.
Figure 15:
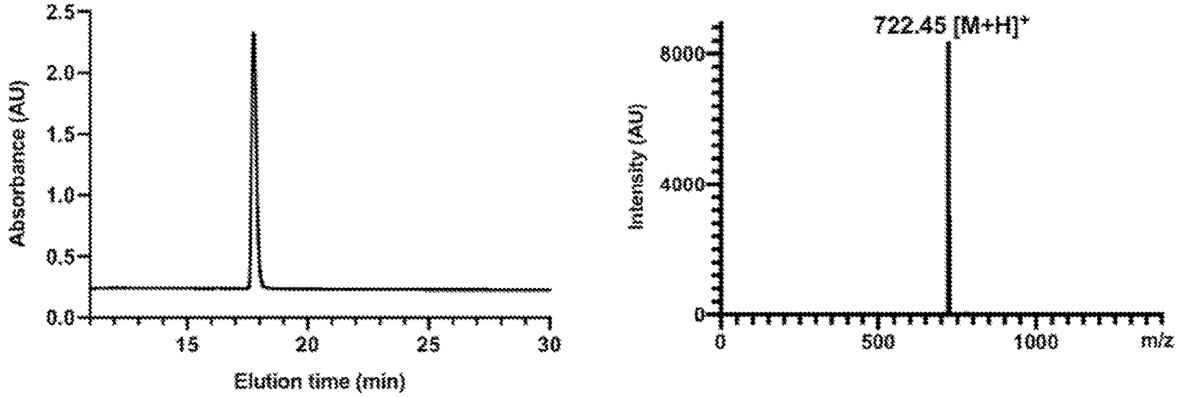
Figure 15:
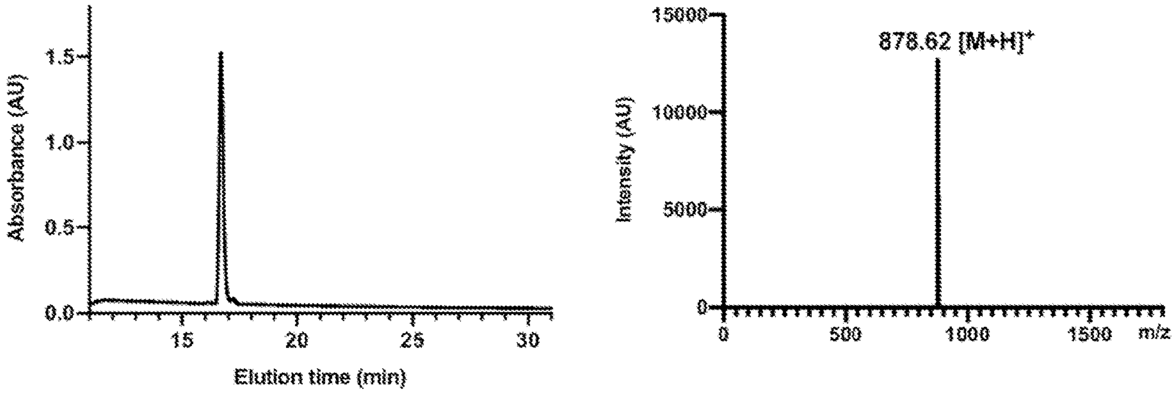
Figure 16A:
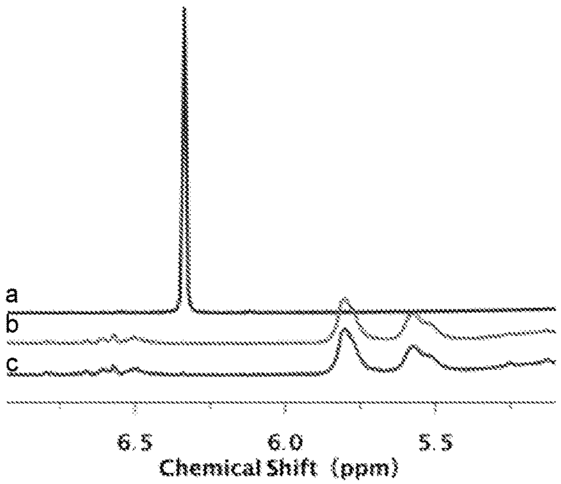
FIGS. 16A-16E. $^{1}H$ NMR spectra of ROMP polymerization of peptide norbornene monomers. Blue spectra (labeled "a") are taken before addition of initiator; Green spectra (labeled "b") are recorded after the polymerization of peptide monomers; Red spectra (labeled "c") are recorded at the end of polymerization of the dye monomer. Resonance at δ 6.34 ppm corresponds to the norbornene olefin protons of the monomer. The new resonance at ~δ 5.5-6 ppm corresponds to the cis-trans olefin protons of the polymerized material.
Figure 16B:
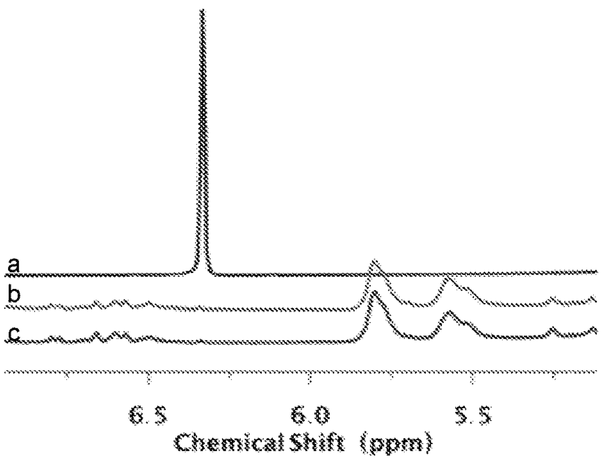
Figure 16C:
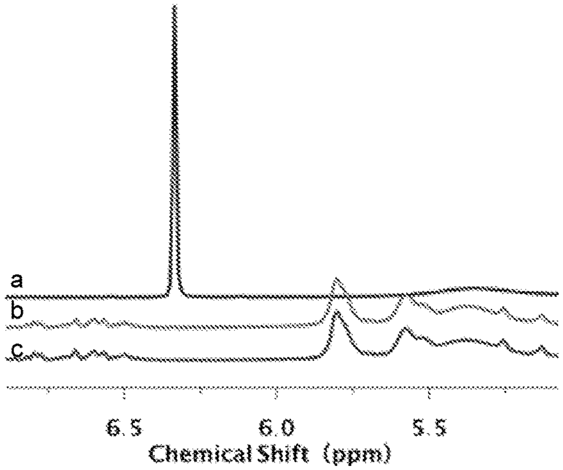
Figure 16D:
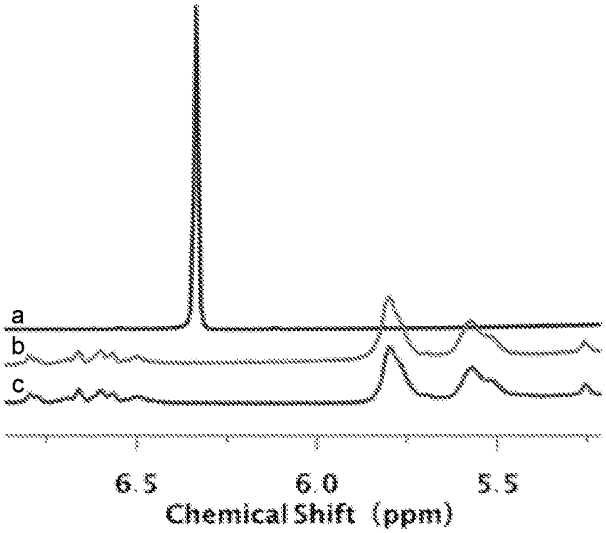
Figure 16E:
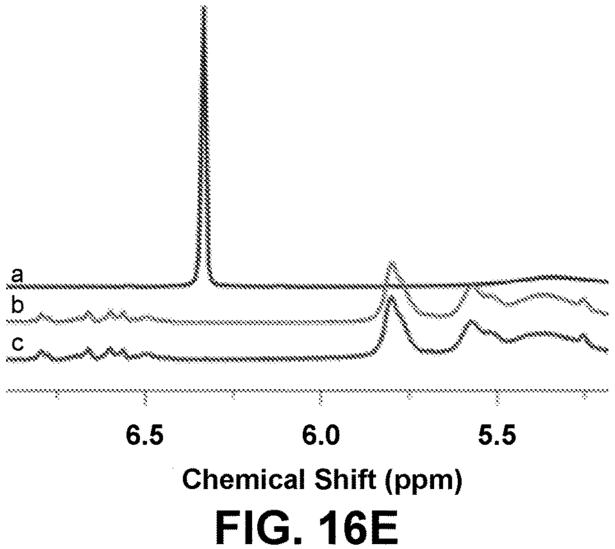

An important property governing the efficacy of nanomedicines is their ability to enter cells, which governs their bioactivity towards cell organelles.[18,19,27,28] Since the cell membrane is negatively charged, we contemplated that positively charged peptide brush polymers would possess a higher performance in cell penetration than their neutral and negatively charged analogues. To verify this, a series of peptides bearing different charges and number of charges were synthesized, including GGSGSGS (SEQ ID NO:1), GGSGSGE (SEQ ID NO:2), GGSGSGK (SEQ ID NO:3), GGSGSGR (SEQ ID NO:4), GGSGSGRR (SEQ ID NO:5). These amino acid sequences were anchored with a carboxylic acid-functionalized norbornenes through solid phase peptide synthesis (FIGS. 5A-5B). The sequence GGSGSG endows hydrophilicity to the norbornene monomers and resulting peptide brush polymers. Moreover, four different amino acids including lysine (K), serine (S), arginine (R), and glutamic acid (E) were appended to the C terminus, giving rise to monomers possessing positive, negative, and neutral charges, respectively. The identity and purity of these monomers were confirmed by mass spectrometry and RP-HPLC (FIG. 15).

Figure 17:
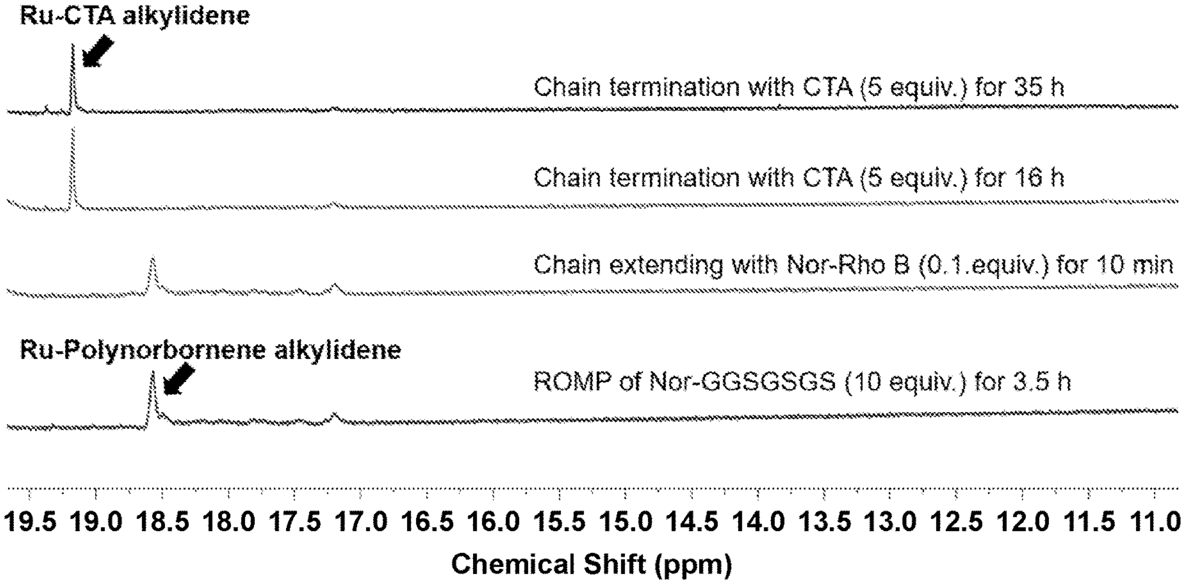
FIG. 17. $^1$H NMR spectra of ROMP of Nor-GGSGSGS, chain extension with dye monomer (0.1 equiv.), and termination with PTX-CTA (5 equiv.).
Figure 18:
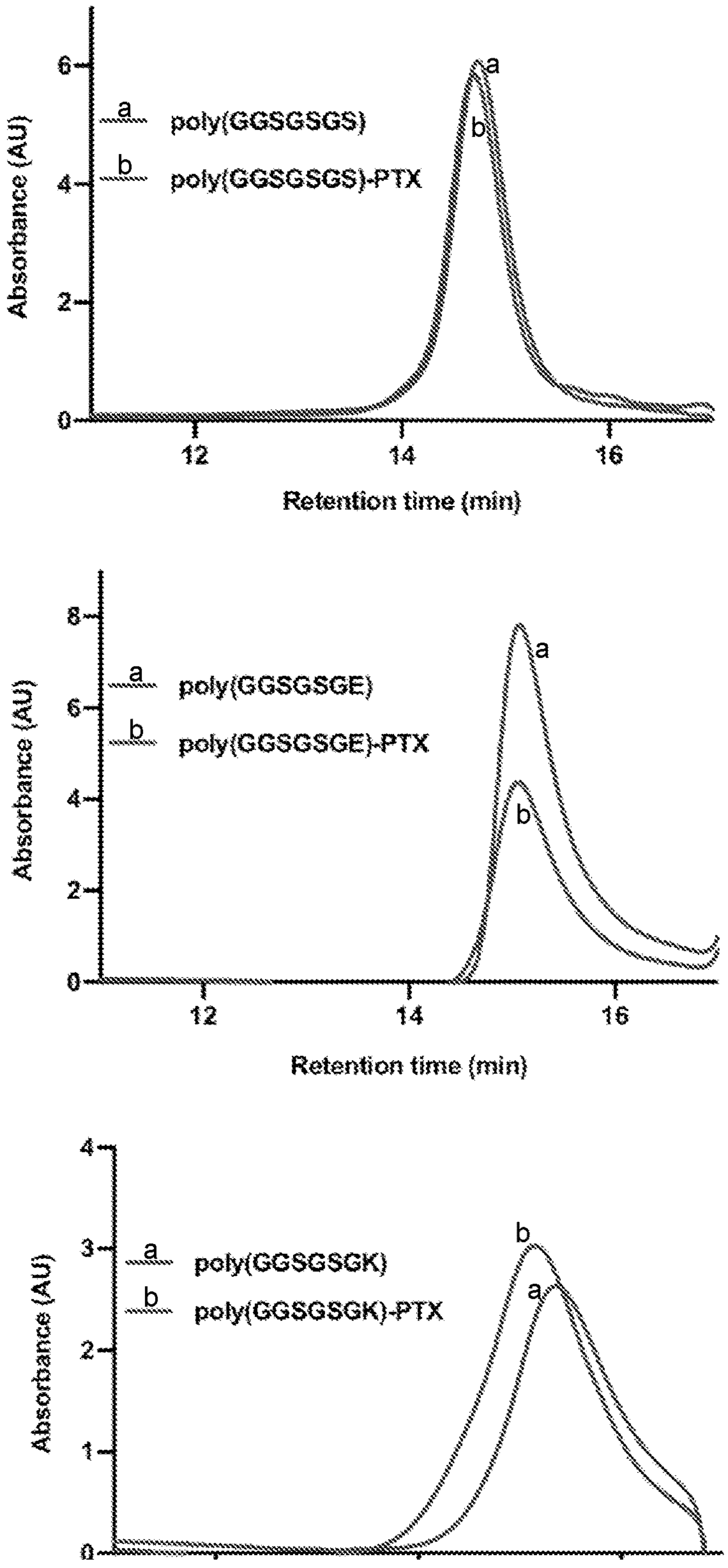
FIG. 18. GPC measurements of representative peptide brush polymers. Poly(amino acid sequence) represented the polymer that was only quenched by ethyl vinyl ether. Poly(amino acid sequence)-PTX represented the polymer that was only terminated by PTX without RP-HPLC purification.
Figure 19:
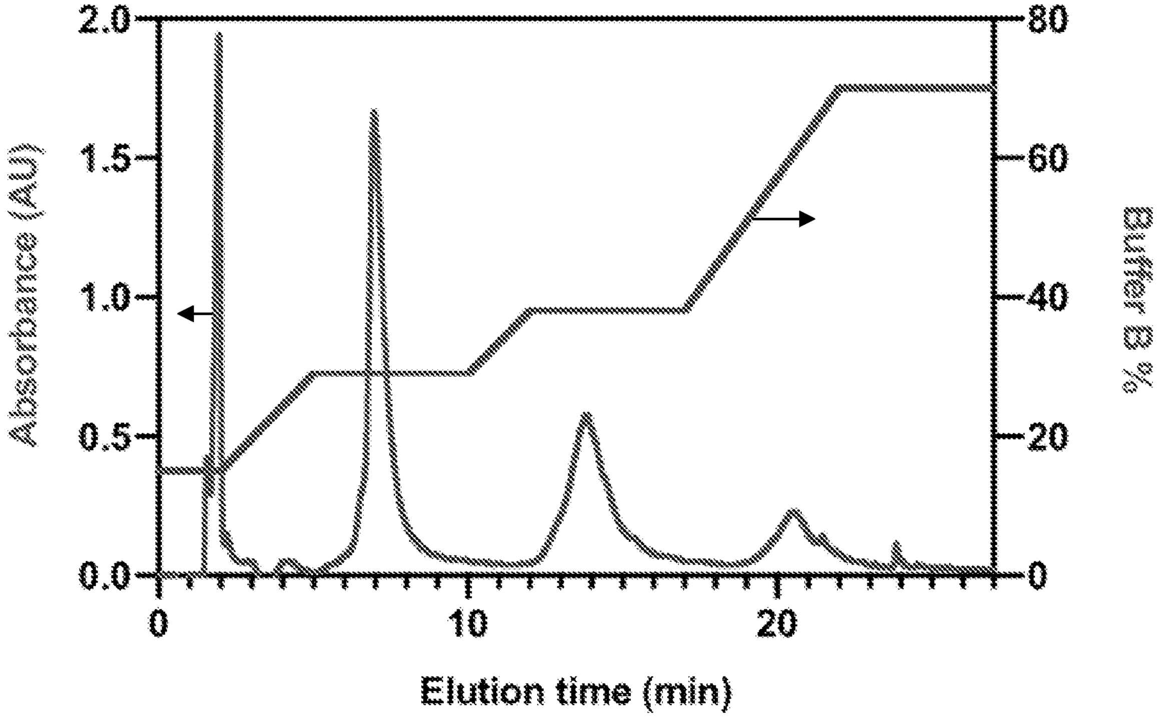
FIG. 19. RP-HPLC separation of crude Poly(GGSGSGS) (monomer Nor-GGSGSGS). Arrows in the plot point to the y-axis corresponding to the data adjacent to the arrow.

ROMP of peptide monomers was conducted in the presence of a modified $2^{nd}$ generation Grubbs catalyst (FIGS. 5A-5B), targeting a degree of polymerization (DP) of 10 for all peptide brush polymers. Upon the full consumption of monomers as confirmed by NMR, a rhodamine B-functionalized norbornene monomer (0.2 equiv. with respect to catalyst) was added to incorporate a fluorophore into a portion of polymers (FIGS. 16A-16E). Finally, the polymerization reactions were terminated using a paclitaxel-modified chain termination agent, resulting in drug-loaded, and dye-labelled peptide brush polymers. $^1$H NMR analysis exhibited the full disappearance of polyolefin-Ru alkylidene signal (17-19 ppm) and appearance of a new peak at 19.2 ppm which was attributed to PTX-Ru alkylidene proton (FIGS. 6 and 17). This result indicated a quantitative metathesis reaction in the course of chain termination. While Gel permeation chromatography (GPC) verified low dispersity (Đ<1.2) of the polymers, it is difficult to discern their purity because of the technique's inherent low resolution in distinguishing polymer species with similar molecular weights. This is particularly true in the case of peptide brush polymers with and without end-capped small molecule paclitaxel (FIG. 18).

Figure 20:
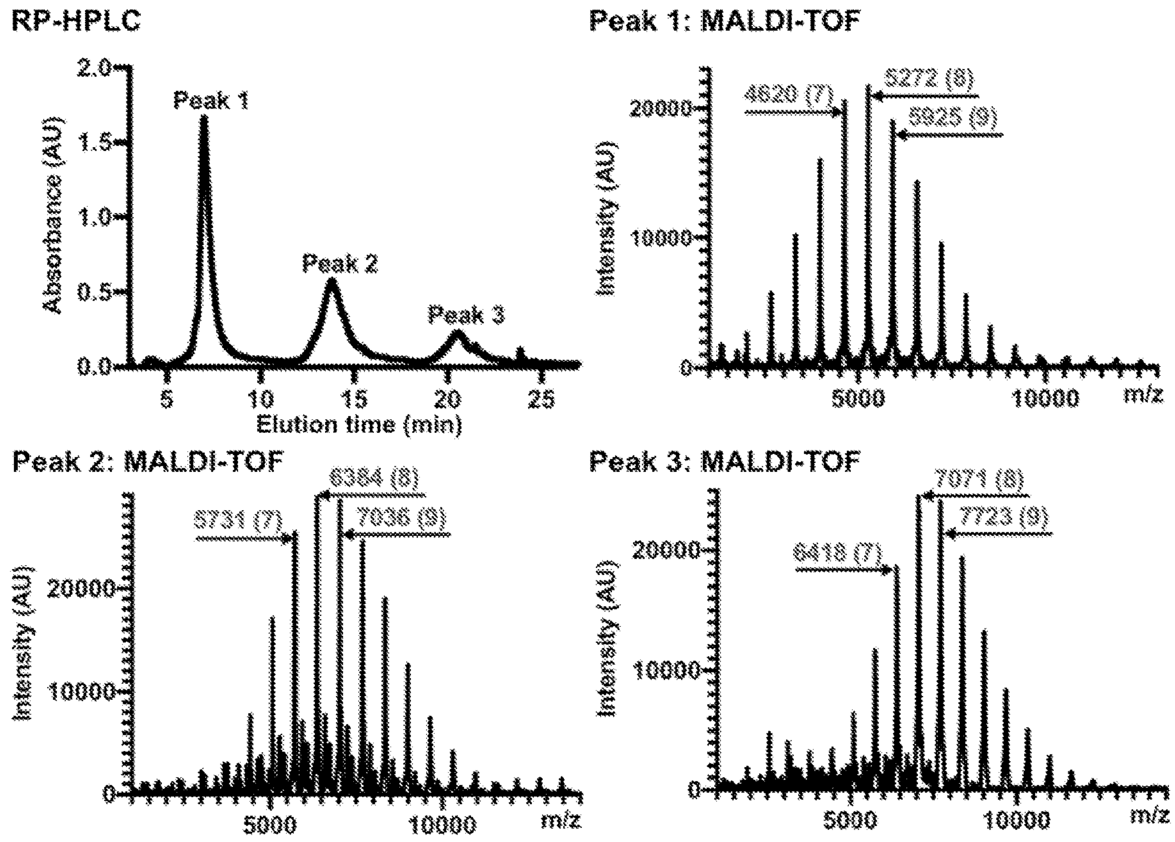
FIG. 20. RP-HPLC separation of crude Poly(GGSGSGS) and MALDI-TOF-MS spectra of all the separated peaks. Peak 1, ~51%, was attributed to polymer without dye or drug, denoted as poly(GSGSGS); Peak 2, ~35%, was assigned to polymer with only drug incorporation, denoted as poly(GGSGSGS)-PTX. Peak 3, ~14%, corresponds to the dye-labeled and drug terminated polymer, denoted as poly (GGSGSGS)-Dye-PTX. The numbers in brackets indicates the DP of the polymer.
Figure 21:
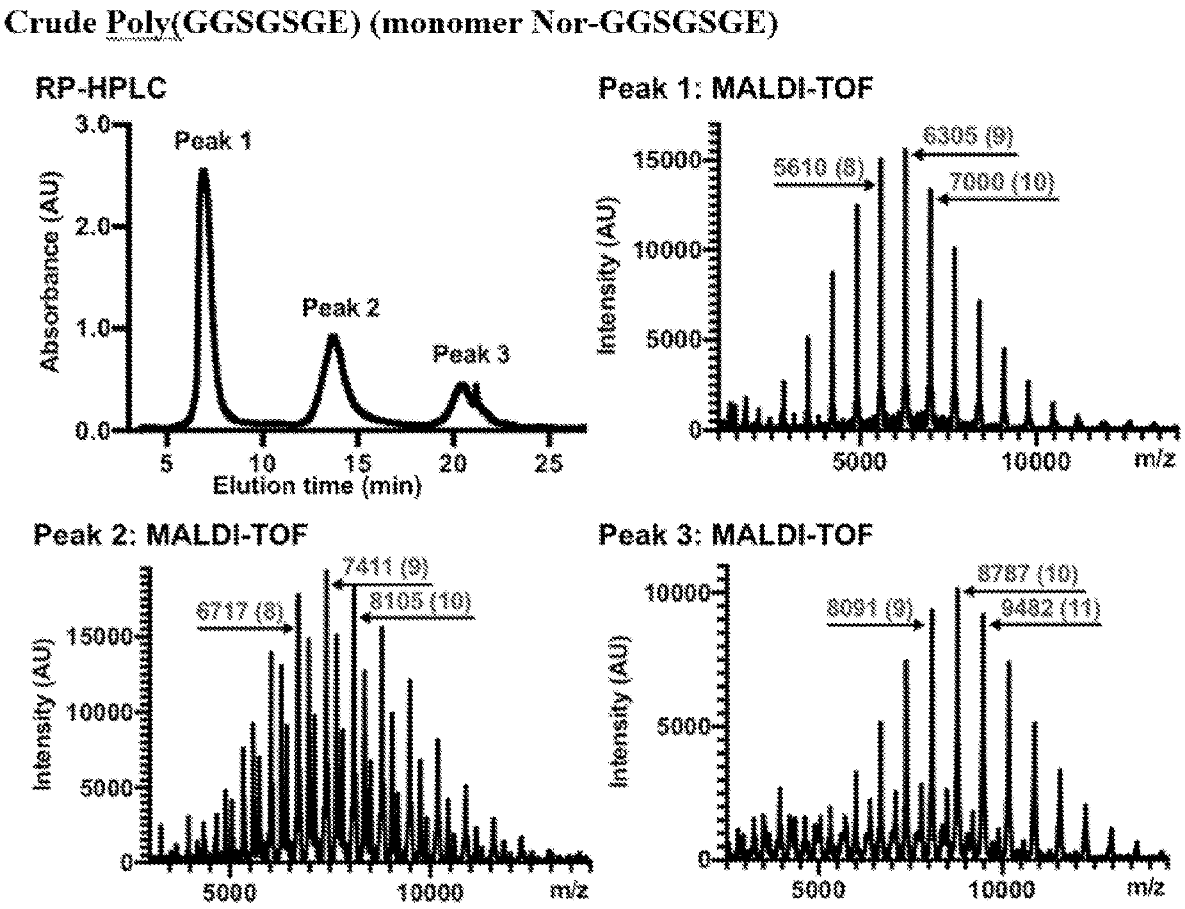
FIG. 21. RP-HPLC separation of crude Poly(GGSGSGE) and MALDI-TOF-MS spectra of all the separated peaks. Peak 1, p~53%, was attributed to polymer without dye or drug, denoted as poly(GGSGSGE); Peak 2, ~31%, was mainly assigned as polymer with drug only, denoted as poly(GGSGSGE)-PTX. Peak 3, ~16%, was the dye-labeled and drug terminated polymer, denoted as poly(GGSGSGE)-Dye-PTX. The numbers in brackets indicates the degree of polymerization.
Figure 22:
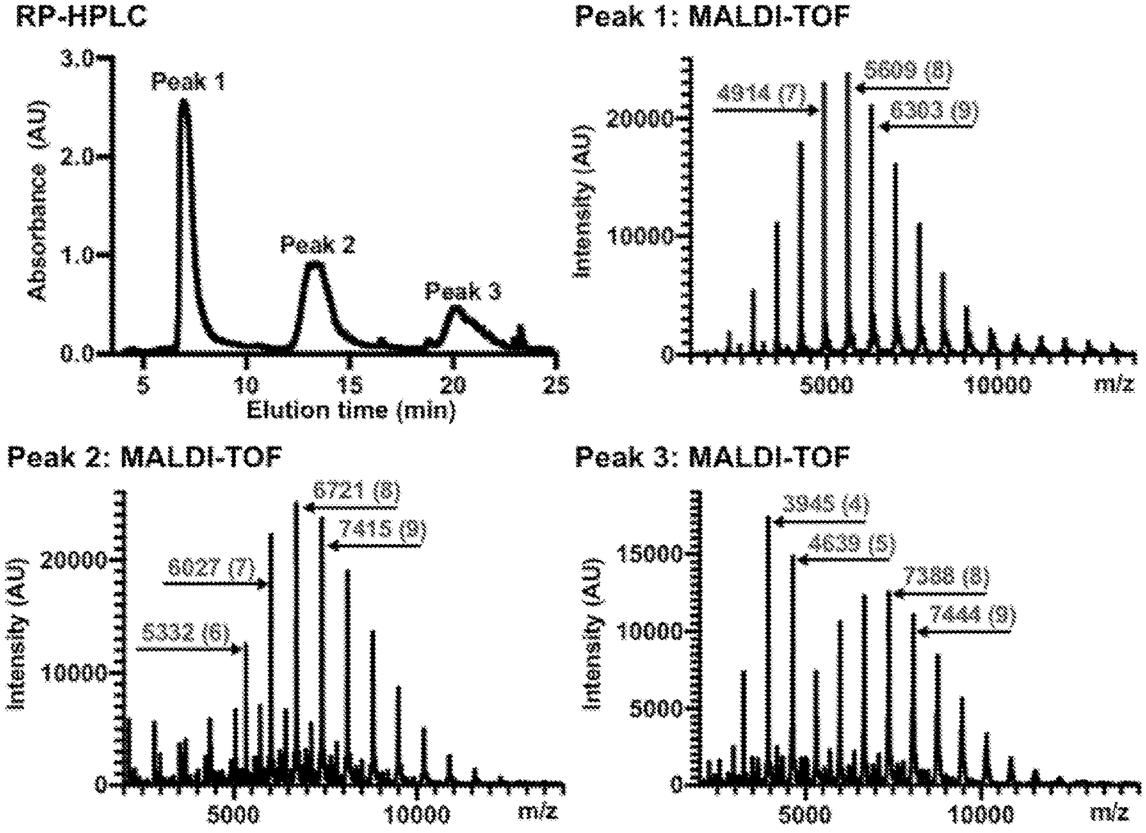
FIG. 22. RP-HPLC separation of crude Poly(GGSGSGK) and MALDI-TOF-MS spectra of all the separated peaks. Peak 1, ~52%, was attributed to polymer without dye or drug, denoted as poly(GGSGSGK); Peak 2, ~33%, was mainly assigned as polymer with drug only, denoted as poly(GGSGSGK)-PTX. Peak 3, ~15%, consisted mainly of the dye-labeled and drug terminated polymer (~83%), denoted as poly(GGSGSGK)-Dye-PTX. The numbers in brackets indicates the degree of polymerization. Blue-labelled peaks are assigned as polymers containing drug only.
Figure 23:
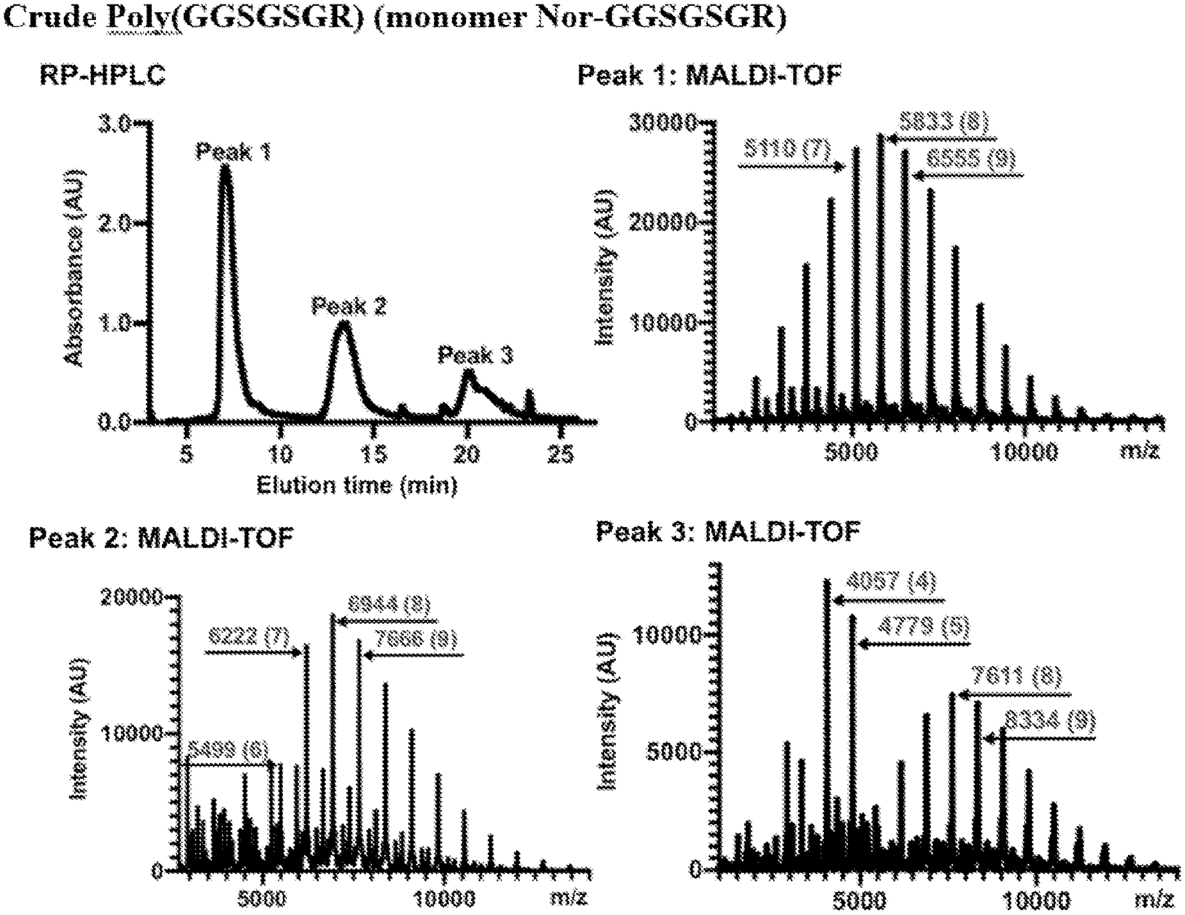
FIG. 23. RP-HPLC separation of crude Poly(GGSGSGR) and MALDI-TOF-MS spectra of all the separated peaks. Peak 1, ~53%, was attributed to polymer without dye or drug, denoted as poly(GGSGSGR); Peak 2, ~32%, was mainly assigned to polymer with drug only, still denoted as poly(GGSGSGR)-PTX. Peak 3, ~15%, consisted mainly of the dye-labeled and drug terminated polymer (~81%), still denoted as poly(GGSGSGR)-Dye-PTX. The numbers in brackets indicates degree of polymerization. Blue-labelled peaks are assigned as polymers with drug only.
Figure 24:
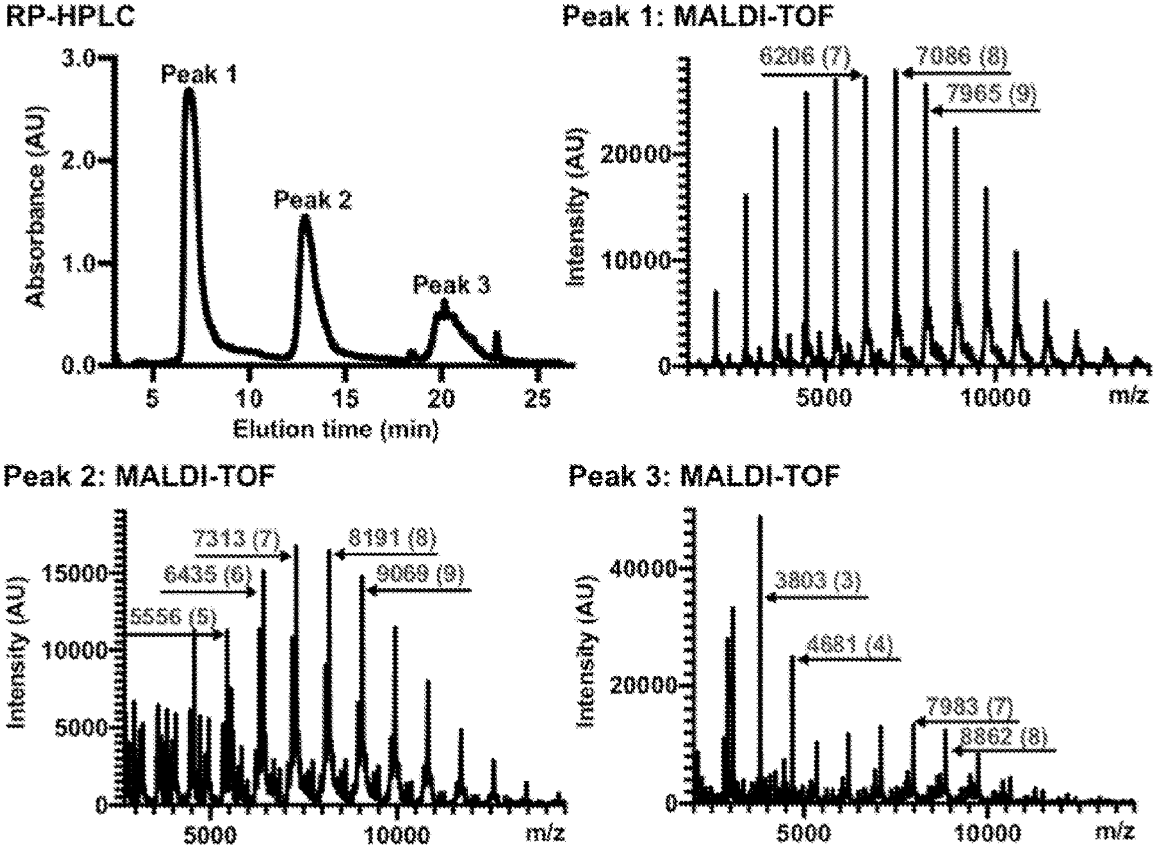
FIG. 24. RP-HPLC separation of crude Poly(GGSGSGRR) and MALDI-TOF-MS spectra of all the separated peaks. Peak 1, ~53%, was attributed to polymer without dye or drug, denoted as poly(GGSGSGRR); Peak 2, ~30%, was mainly assigned to polymer with drug only, still denoted as poly(GGSGSGRR)-PTX. Peak 3, ~17%, consisted mainly of dye-labeled and drug terminated polymer (~83%), still denoted as poly(GGSGSGRR)-Dye-PTX. The numbers in brackets indicates the degree of polymerization. Blue-labelled peaks are assigned as polymers with drug only.
Figure 25:
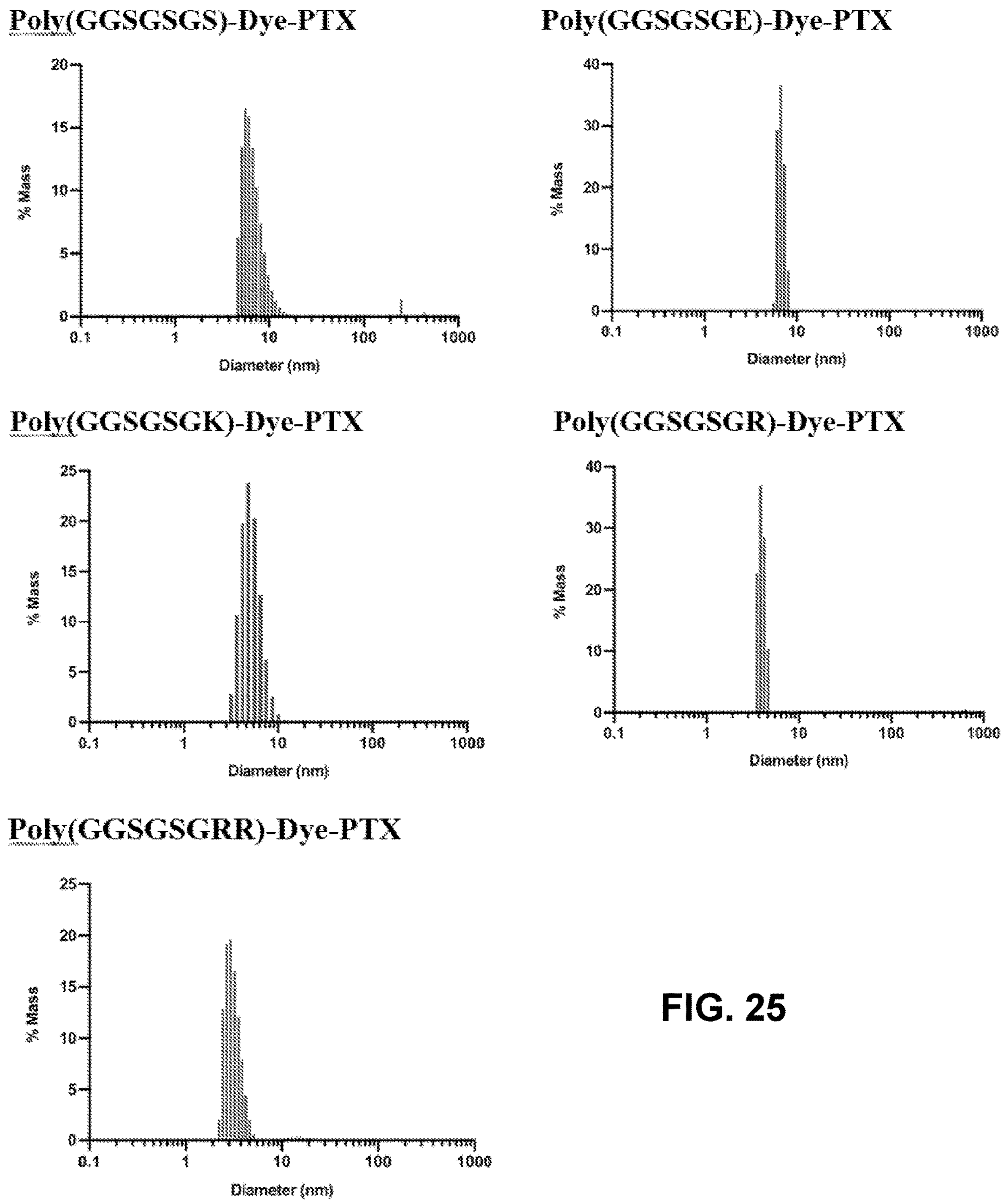
FIG. 25. Representative DLS measurements of drug-terminated peptide brush polymers.

We contemplated that successfully drug end-capped peptide brush polymers would be more hydrophobic than polymers without drug. Similarly, Du Prez et al. demonstrated the utilization of HPLC in separating polymers of different hydrophobicity.[29] The neutral version of drug end-capped peptide brush polymers consisting of amino acid sequence GGSGSGS (denoted as poly(GGSGSGS)) was assessed by HPLC (FIGS. 9 and 20). Three distinct peaks could be discerned and were ascribed to three species, including polymer lacking both dye and drug (peak 1), polymer with drug but without dye (peak 2), and polymer bearing both drug and dye (peak 3). The HPLC peaks were collected and examined by MALDI-TOF mass spectrometry. Based on MALDI-MS spectra, we observed that the molecular weights of the three polymer species had an increasing trend from peak 1 to peak 3, which is in good agreement with our assignments of polymers to those HPLC peaks (FIG. 9). More importantly, the mass differences of polymers from peaks 1-3 can be clearly assigned to the molecular weights of dye and paclitaxel moieties when polymers of the same DP are compared (FIG. 20). These results prove the feasibility of purifying peptide brush polymer-drug conjugates by HPLC. Similarly, other crude polymer-drug conjugates, including three cationic polymers (denoted as poly (GGSGSGK), poly(GGSGSGR), and poly(GGSGSGRR)) and one anionic polymer (denoted as poly(GGSGSGE)) were efficiently purified and characterized using the same method (FIGS. 21-24, Table 1). Moreover, dynamic light scattering (DLS) confirmed that all polymers after purification were dissolved in solution and not present as assembled nanostructures or particles in water (FIG. 25).

TABLE 1

Summary of theoretical and experimentally determined molecular weights and dispersities of polymers by MALDI-TOF-MS

| | Mn(Theor) (DP = 10) | $Mn^a$ | $Mw^b$ | Mw/ Mn | $Mn^c$ (peak 3) |
|---|---|---|---|---|---|
| Poly(GSGSGS) | 6612 | 5696 | 5999 | 1.05 | |
| Poly(GSGSGS)-Dye-PTX | 8375 | 7892 | 8092 | 1.03 | 7892 |
| Poly(GSGSGE) | 7033 | 6660 | 7075 | 1.06 | |
| Poly(GSGSGE)-Dye-PTX | 8796 | 9253 | 9481 | 1.02 | 9253 |
| Poly(GSGSGK) | 7023 | 6258 | 6793 | 1.09 | |
| Poly(GSGSGK)-Dye-PTX | 8786 | 7940 | 8211 | 1.03 | 7281 |
| Poly(GSGSGR) | 7303 | 6589 | 7130 | 1.08 | |
| Poly(GSGSGR)-Dye-PTX | 9066 | 8433 | 8743 | 1.04 | 7651 |
| Poly(GSGSGRR) | 8864 | 7410 | 8163 | 1.10 | |
| Poly(GSGSGRR)-Dye-PTX | 10627 | 8011 | 8338 | 1.04 | 7310 |

[a]Mn = ΣNiMi/ΣNi
[b]Mw = $\Sigma NiMi^2/\Sigma NiMi$
Mi refers to the mass of each peak, Ni refers to the area of each peak. Only the main peaks in the spectra were calculated.
[c]The Mn (peak 3) of each polymer was determined by the average molecular weight and portion of each part.

Figure 10A:
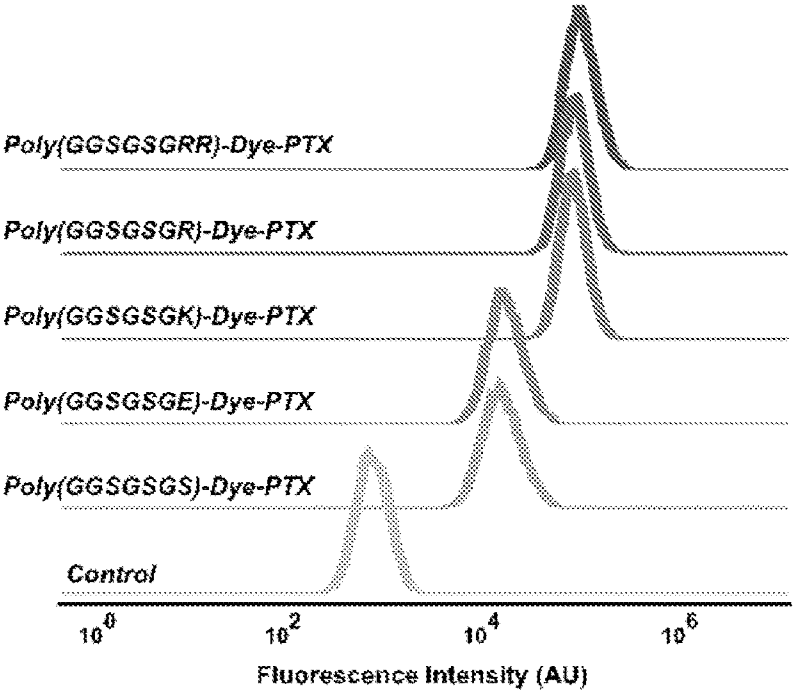
FIG. 10A. Flow cytometry of A549 lung carcinoma cells after treated with poly(amino acid sequence)-Dye-PTX at a concentration of 4 μM (with respect to polymer) for 4 h. Polymer-drug conjugates containing positively charged amino acids (K and R) possess a higher cell uptake efficiency than those with neutral and negative amino acids (S and E).
Figure 10B:
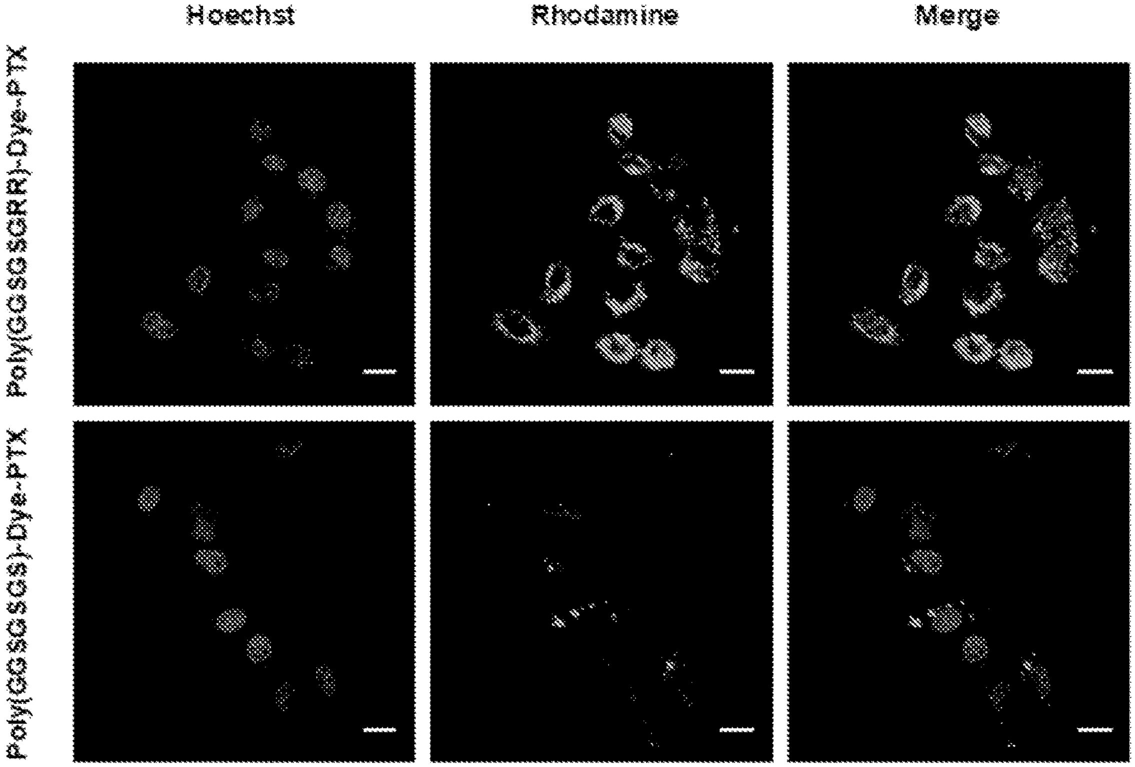
FIG. 10B. Confocal microscopy images of A549 lung carcinoma cells after treatment with 4 μM poly(GGSGSGRR)-Dye-PTX and poly(GGSGSGS)-Dye-PTX for 4 h. Scale bar: 20 μm.
Figure 26:
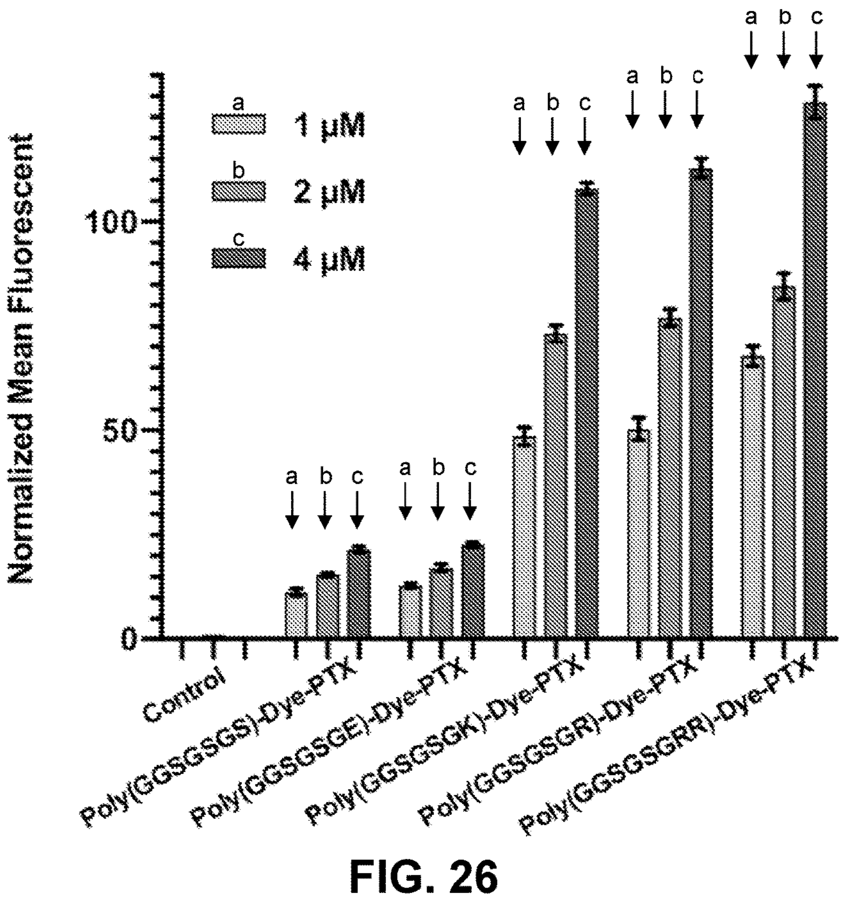
FIG. 26. Flow cytometry assay of poly(amino acid sequence)-Dye-PTX with respect to 1, 2 and 4 μM of polymers. Normalized mean fluorescence refers to the mean fluorescence (PE-A) detected for the material divided by the mean fluorescence exhibited by the vehicle control (PBS).
Figure 27:
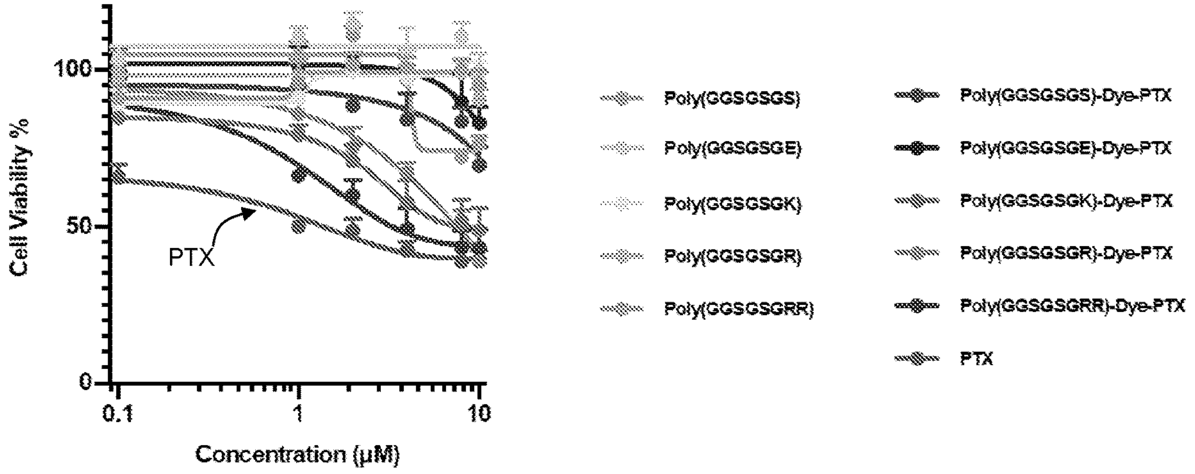
FIG. 27. Cytotoxicity of purified polymer-drug conjugates and polymers without drugs. Cell viability was measured relative to vehicle control. Cells were incubated for 72 hrs after treatment with the polymers.
Figure 28:
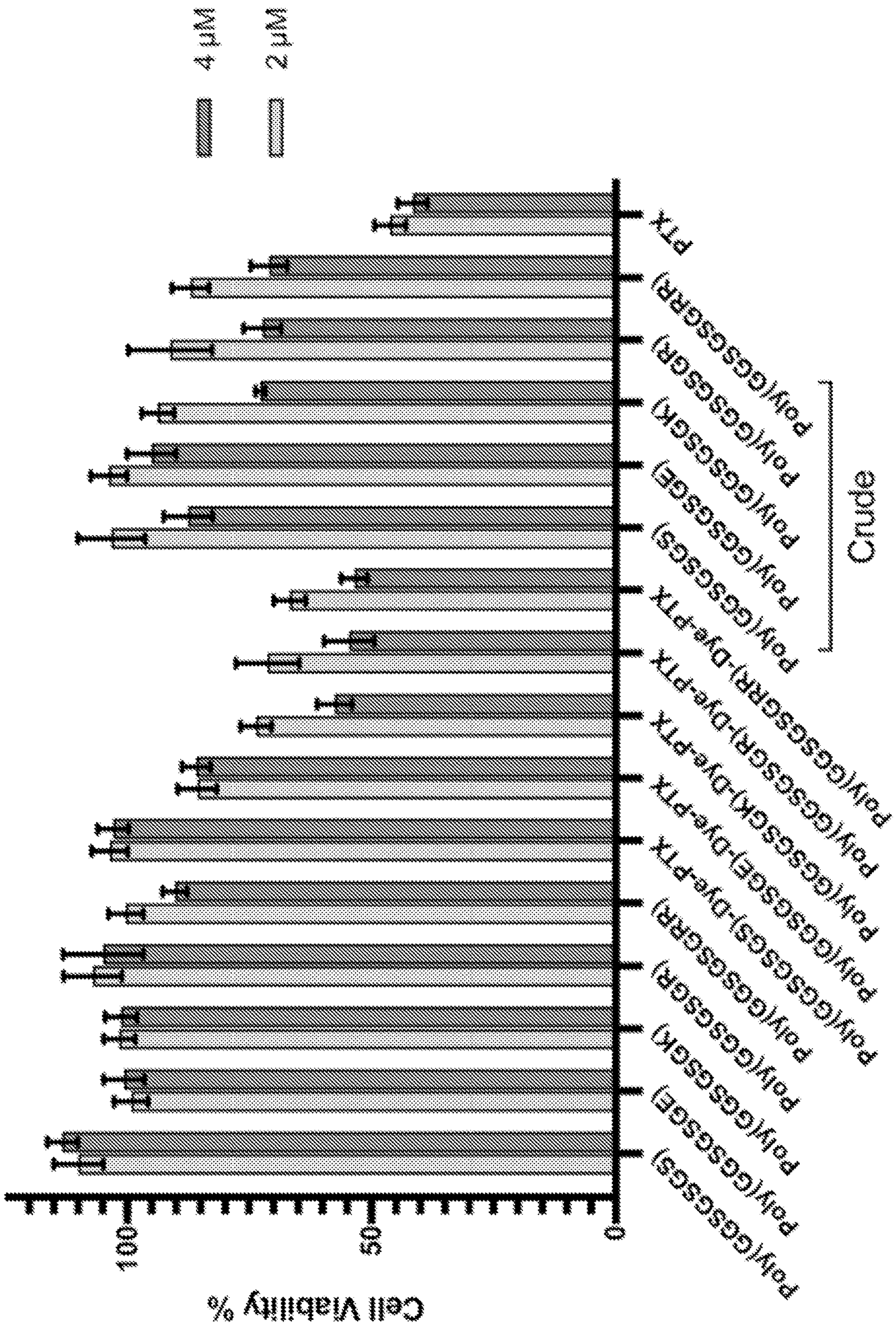
FIG. 28. Cytotoxicity of purified polymer-drug conjugates, polymers without drugs, and crude polymers. Cell viability was measured relative to vehicle control. Cells were incubated for 48 hrs after treatment with the polymers.
Figure 29:
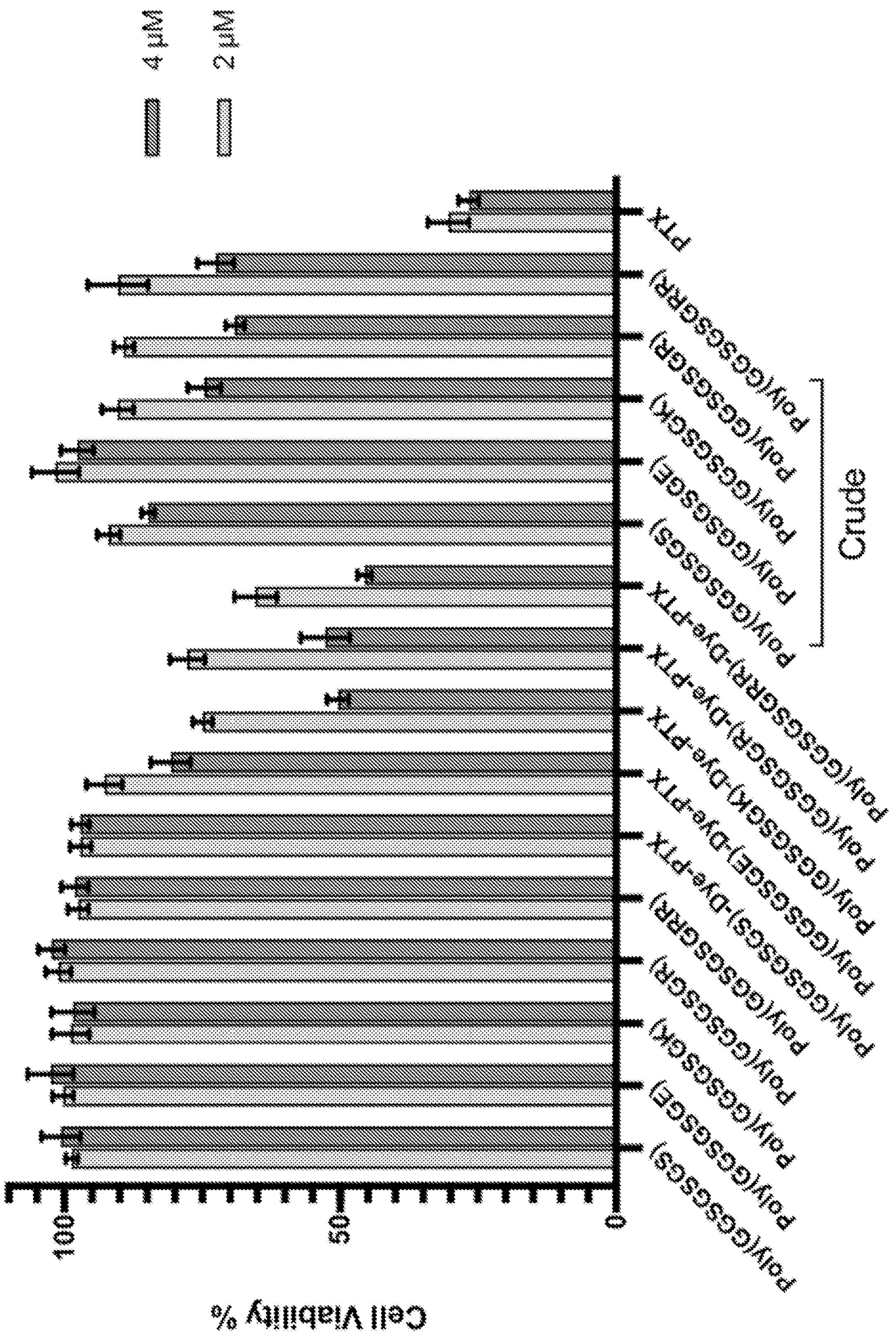
FIG. 29. Cytotoxicity of purified polymer-drug conjugates, polymers without drugs, and crude polymers. Cell viability was measured relative to vehicle control. Cells were incubated for 72 hrs after treatment with the polymers.
Figure 30:
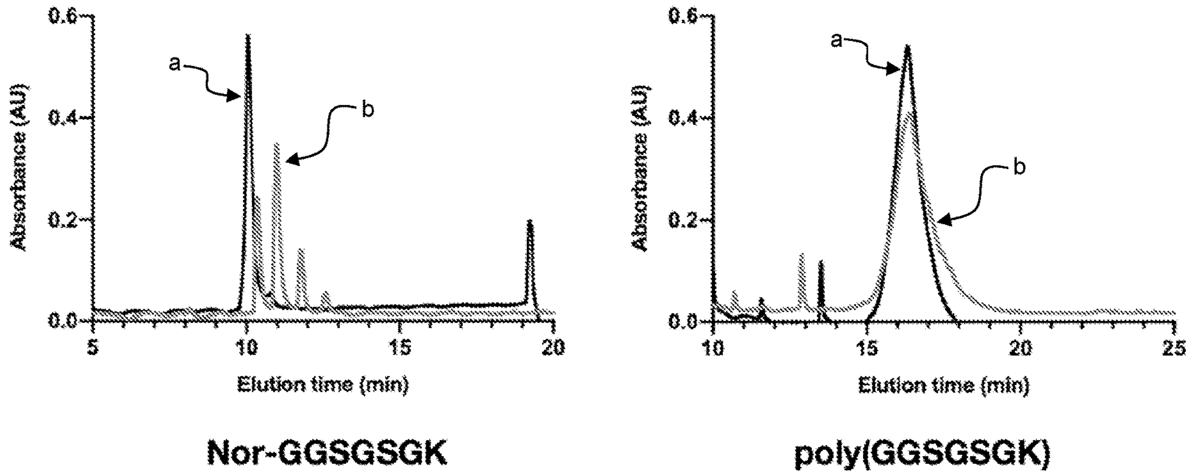
FIG. 30. RP-HPLC assay of the proteolytic cleavage of monomer Nor-GGSGSGK and polymer Poly(GGSGSGK). The traces in black (labeled "a") are the materials without pronase treatment and the red traces (labeled "b") were the same materials after pronase treatment for 3 hrs.
Figure 31:
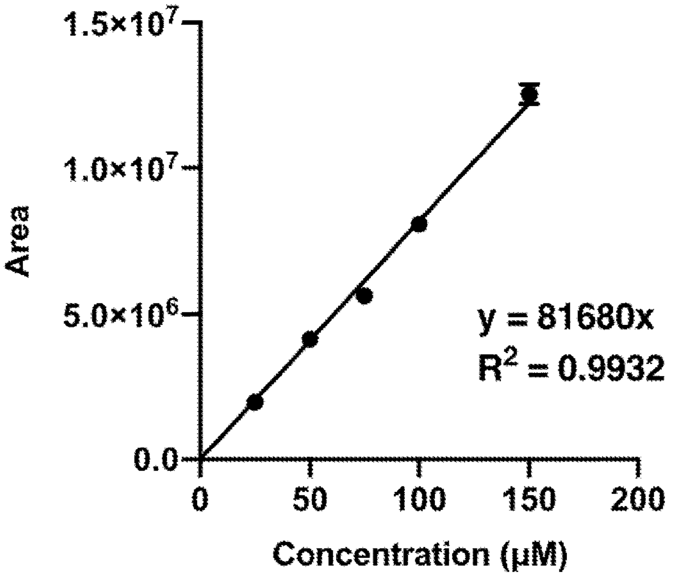
FIG. 31. Standard curves, correlating peak area on RP-HPLC chromatograms with concentration on a 50 μL injection, for the determination of the concentration of intact peptide monomer remaining after proteolytic cleavage.
Figure 32A:
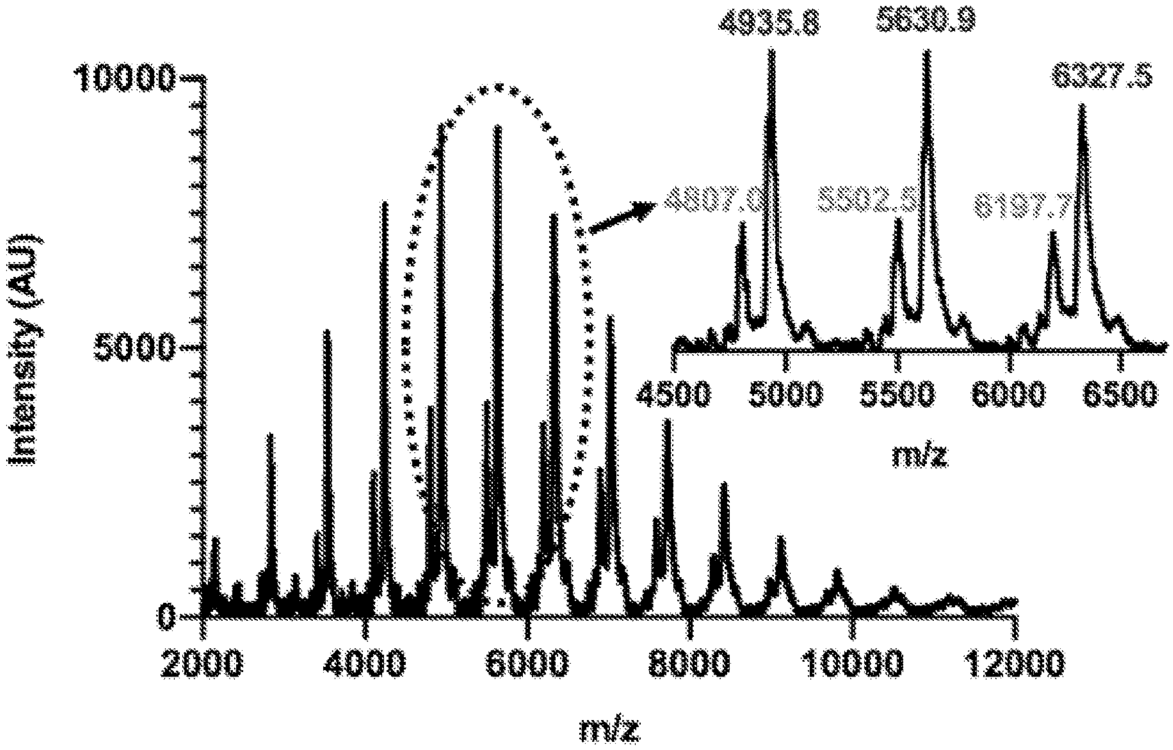
FIGS. 32A-32D. MALDI-TOF-MS spectra of polymer Poly(GGSGSGK) after pronase treatment. Numbers in blue were the mass of intact polymers; Numbers in green were the mass of polymers that lost one lysine (−128.1); Numbers in purple were the mass of polymers that lost two lysine; Numbers in red were the mass of polymers that lost three lysine.
Figure 32B:
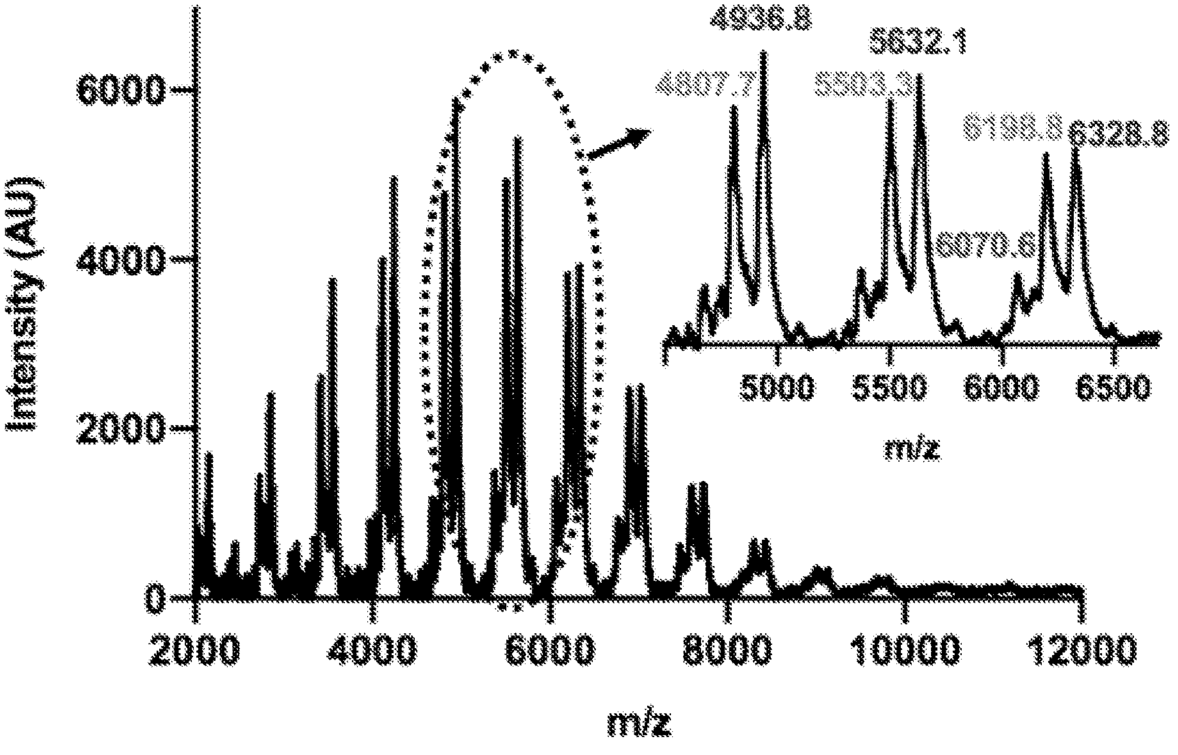
Figure 32C:
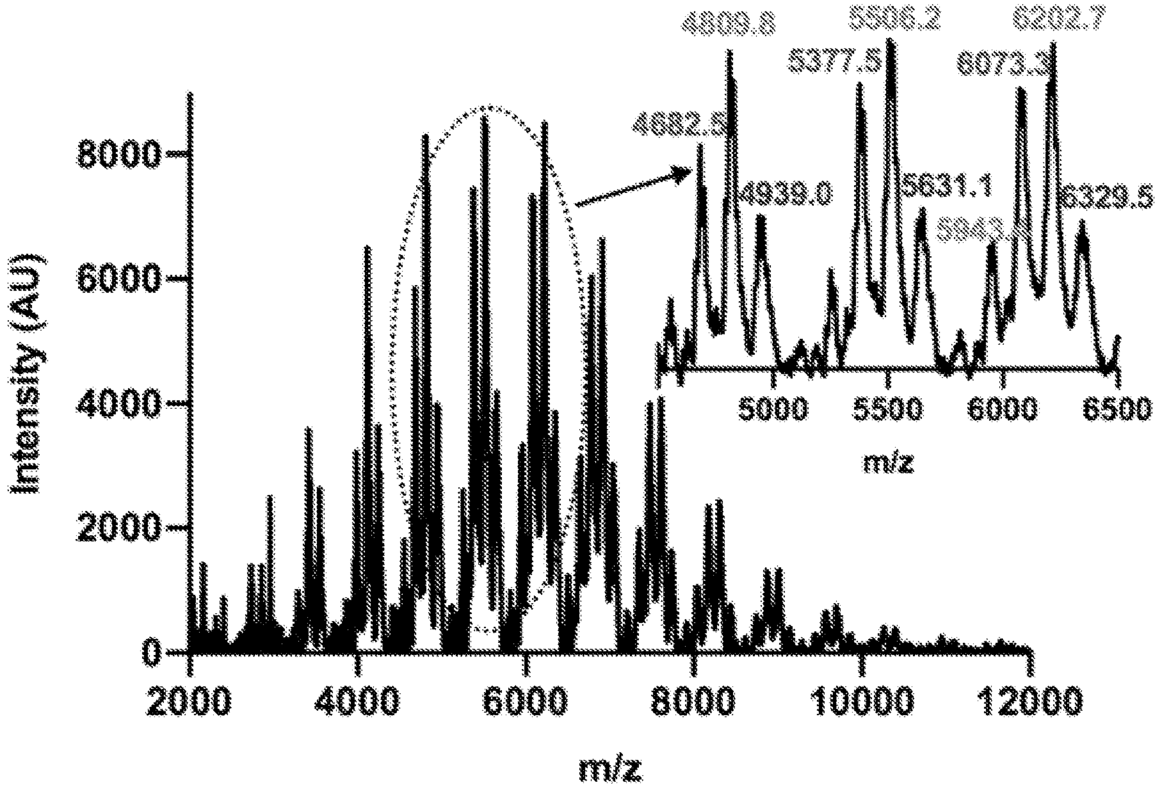
Figure 32D:
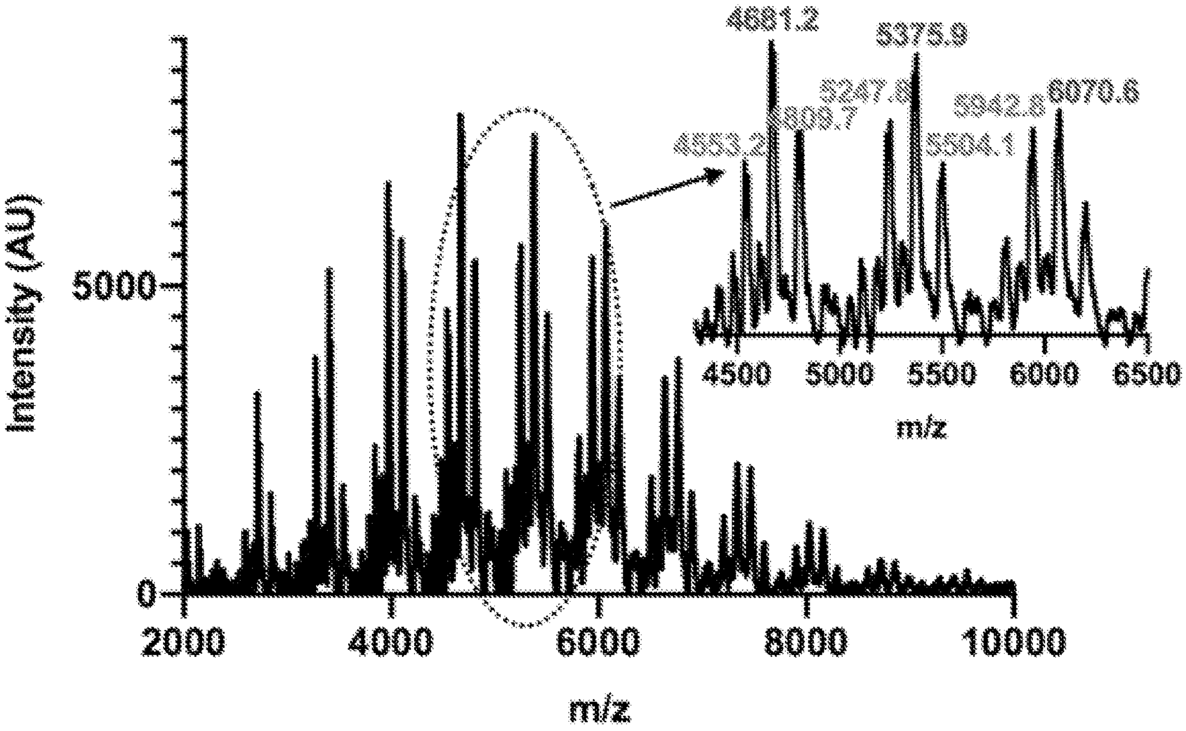
Figure 33:
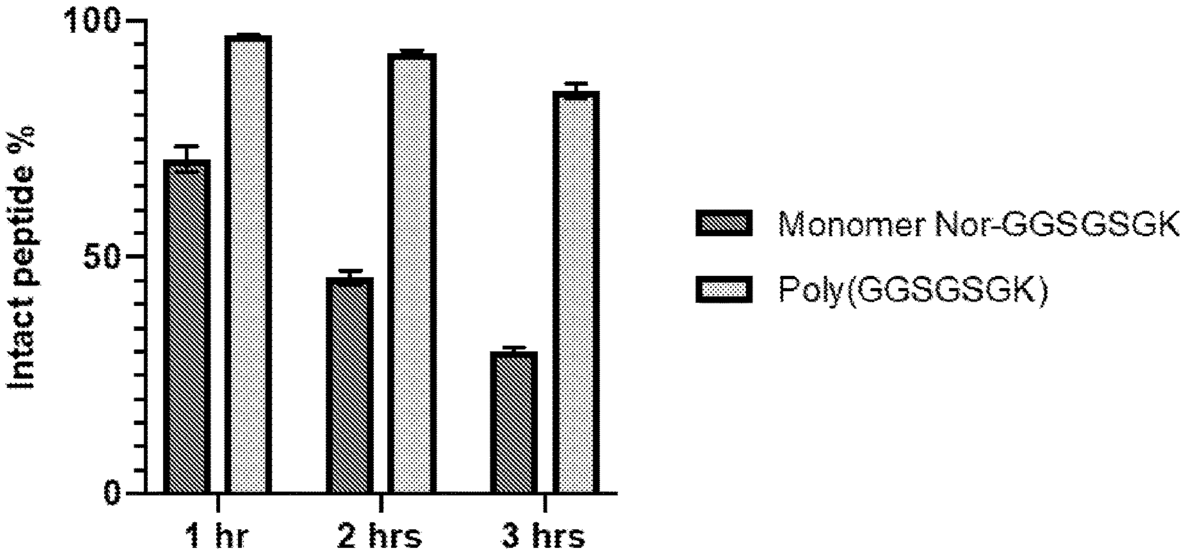
FIG. 33. Comparison of intact peptide percentage of Monomer Nor-GGSGSGK and polymer Poly(GGSGSGK) after pronase treatment.
Figure 34:
FIG. 34. Exemplary chain termination agents that may be used in a method of making the polymer, according to certain embodiments disclosed herein.
Figure 34:
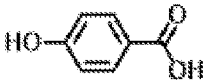
Figure 34:
Figure 34:
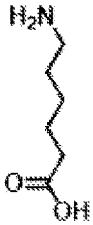
Figure 34:
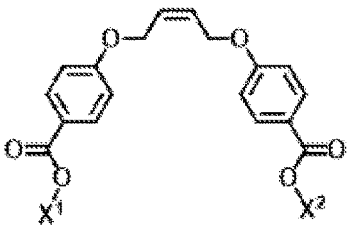
Figure 34:
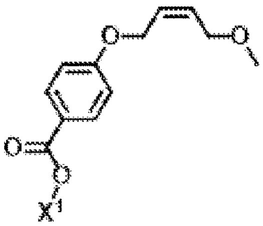
Figure 34:
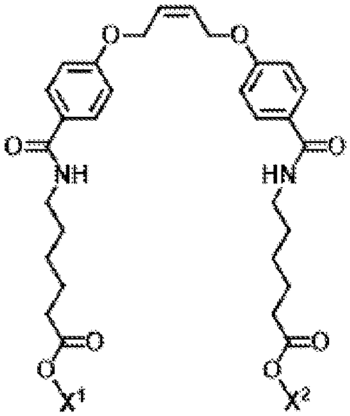
Figure 34:
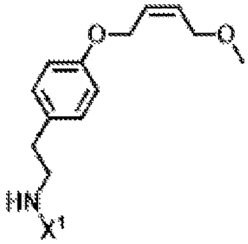
Figure 34:
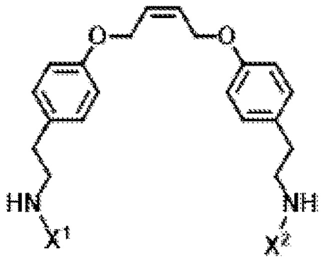
Figure 34:
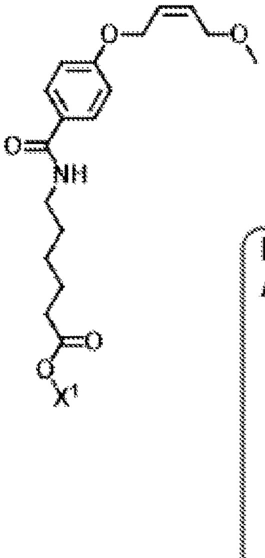
Figure 34:
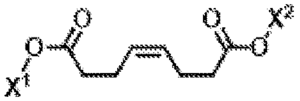
Figure 34:
Figure 34:
Figure 35A:
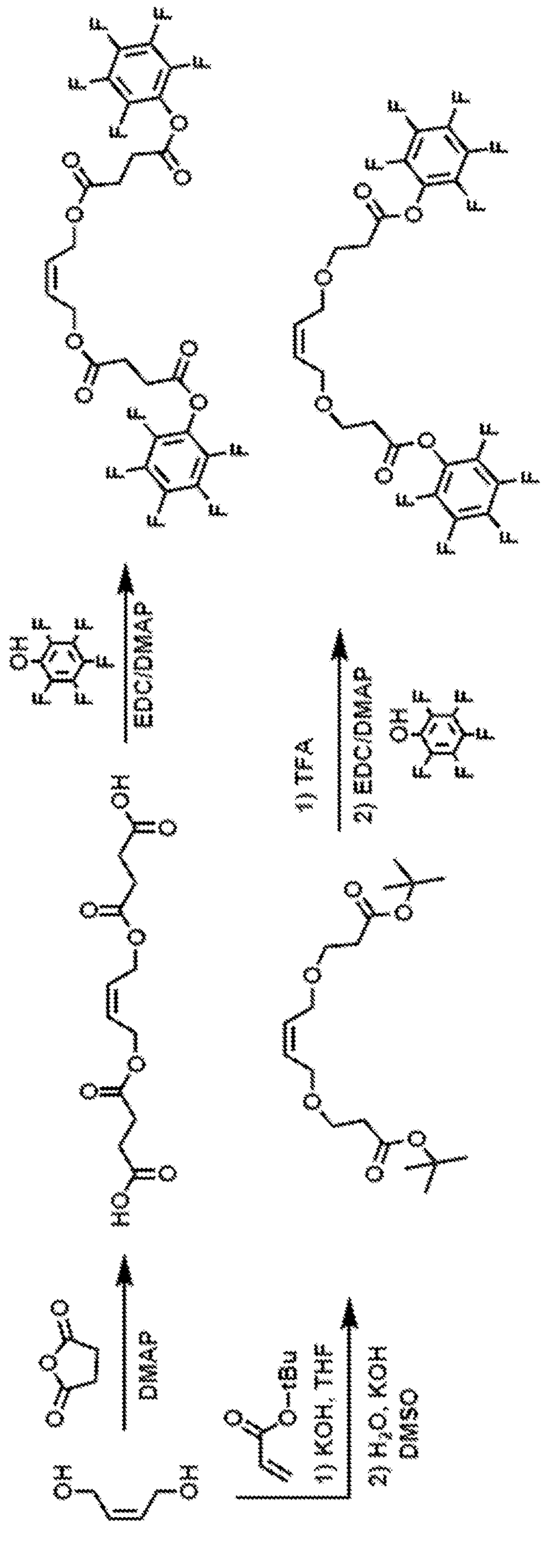
FIG. 35A-35B. Exemplary chain termination agents and aspects of making chain termination agents that may be used in a method of making the polymer, according to certain embodiments disclosed herein.
Figure 35B:
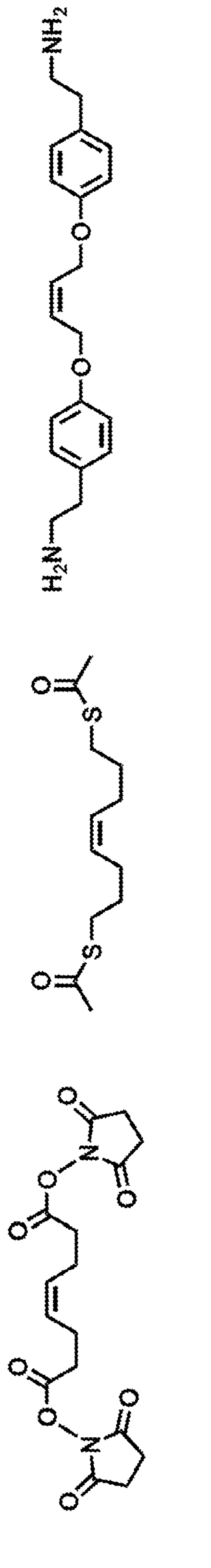

To evaluate the in vitro bioactivity of peptide brush polymer-drug conjugates carrying different charges, we performed a flow cytometry assay to quantify cellular uptake efficiency (FIGS. 10A-10B and 26). Polymers bearing positive charges enter A549 lung carcinoma cells significantly more efficiently than polymers bearing neutral or negative charges. Moreover, confocal microscopy confirmed that positively charged poly(GGSGSGRR)-Dye-PTX exhibited significantly improved cell uptake than neutral analogue poly(GGSGSGS)-Dye-PTX (FIG. 10B). This is in good agreement with flow cytometry assay. The cytotoxicity of polymer-drug conjugates was assessed in this same cell line. All peptide brush polymers without paclitaxel exhibited no toxicity, showing near 100% cell viability after incubation for 3 days, indicative of excellent cytocompatibility of peptide brush polymers (FIG. 8). In the case of purified polymer-drug conjugates, cytotoxicity of positively charged polymer-drug conjugates was markedly higher than their neutral and negatively charged analogues, which is in good agreement with the cell-uptake results from flow cytometry (FIGS. 10A-10B and 26). It is worth noting that purified polymer-drug conjugates showed higher cytotoxicity than that of their corresponding crude products, regardless of the nature of charges (FIGS. 27-29). This can be attributed to the higher drug loading of pure polymer-drug conjugates than crude product, which contains some polymer species that lack drug.

The stability of drug delivery systems serves as a basis for enhancing half-life of therapeutic cargos during the course of delivery to targeted areas. To evaluate the stability of peptide brush polymers, positively charged poly (GGSGSGK) and its single peptide analogue GGSGSGK were treated with pronase, a robust proteolytic enzyme isolated from the extracellular fluid of *Streptomyces griseus*. RP-HPLC and MALDI-TOF mass spectroscopy were used to quantify the cleavage of peptides (FIGS. 30-33). As expected, the peptide underwent rapid degradation in the presence of pronase, resulting in approximately 75% peptide cleavage after 3 hours. In comparison, the peptide brush polymer remained intact under the same conditions, revealing the enhanced stability of peptide side chains against aggressive digestion conditions.

In summary of the embodiments discussed above, we have developed a new approach to generate well-defined drug-terminated peptide brush polymers via ROMP. This was enabled by employing a paclitaxel-modified chain terminating agent which could subsequently act as a tag to enable facile separations by reverse phase HPLC. We note that at least 50% of polymer chain ends were conjugated with the drug. This less than stoichiometric yield is likely due to the livingness of ROMP under the investigated conditions. In this study, a simple and non-functional core amino acid sequence GGSGSG was used as a proof-of-concept peptide building block from which charge could be varied. We contemplate that this approach allows for the incorporation of a wide variety of functional peptides, including tumor-targeting and therapeutic peptides, enabling synergistic therapy with the terminal drug. In addition, we demonstrated that HPLC could be used to efficiently purify terminally-labeled polymers away from mixtures and unmodified polymers, yielding the appropriate control polymers and increasing the efficiency of the drug carrier with respect to paclitaxel.

REFERENCES CORRESPONDING TO EXAMPLE 1

1. A. Kakkar, G. Traverso, 0. C. Farokhzad, R. Weissleder and R. Langer, *Nat. Rev*. Chem., 2017, 1, 0063.
2. C. Alvarez-Lorenzo and A. Concheiro, *Chem. Commun.,* 2014, 50, 7743-7765.
3. C. F. Song, T. T. Lin, Q. Zhang, S. Thayumanavan and L. Ren, *J. Control Release,* 2019, 293, 1-9.
4. L. Yang, H. Sun, Y. Liu, W. J. Hou, Y. Yang, R. Cai, C. Cui, P. H. Zhang, X. S. Pan, X. W. Li, L. Li, B. S. Sumerlin and W. H. Tan, *Angew. Chem. Int. Ed.,* 2018, 57, 17048-17052.
5. C. E. Callmann, C. V. Barback, M. P. Thompson, D. J. Hall, R. F. Mattrey and N. C. Gianneschi, *Adv. Mater.,* 2015, 27, 4611-4615.
6. K. Dutta, D. Hu, B. Zhao, A. E. Ribbe, J. M. Zhuang and S. Thayumanavan, *J. Am. Chem. Soc.,* 2017, 139, 5676-5679.
7. X. Y. Tan, B. B. Li, X. G. Lu, F. Jia, C. Santori, P. Menon, H. Li, B. H. Zhang, J. J. Zhao and K. Zhang, *J. Am. Chem. Soc.,* 2015, 137, 6112-6115.
8. Y. Q. Dai, H. Sun, S. Pal, Y. L. Zhang, S. Park, C. P. Kabb, W. D. Wei and B. S. Sumerlin, *Chem. Sci,* 2017, 8, 1815-1821.
9. H. Sun, C. P. Kabb, Y. Q. Dai, M. R. Hill, I. Ghiviriga, A. P. Bapat and B. S. Sumerlin, *Nat. Chem.,* 2017, 9, 817-823.
10. S. Senapati, A. K. Mahanta, S. Kumar and P. Maiti, Signal Transduct. Tar., 2018, 3, 7.
11. B. Louage, L. Nuhn, M. D. P. Risseeuw, N. Vanparijs, R. De Coen, I. Karalic, S. Van Calenbergh and B. G. De Geest, *Angew. Chem. Int. Ed.,* 2016, 55, 11791-11796.
12. B. Louage, M. J. van Steenbergen, L. Nuhn, M. D. P. Risseeuw, I. Karalic, J. Winne, S. Van Calenbergh, W. E. Hennik and B. G. De Geest, *ACS Macro Lett.,* 2017, 6, 272-276.
13. G. Moad, *Polym. Chem.,* 2017, 8, 177-219.

14. D. Vinciguerra, M. Jacobs, S. Denis, J. Mougin, Y. Guillaneuf, G. Lazzari, C. Zhu, S. Mura, P. Couvreur and J. Nicolas, *J. Control Release,* 2019, 295, 223-236.
15. Y. Y. Bao, E. Guegain, J. Mougin and J. Nicolas, *Polym. Chem.,* 2018, 9, 687-698.
16. F. H. Wang, M. Porter, A. Konstantopoulos, P. C. Zhang and H. G. Cui, *J. Control Release,* 2017, 267, 100-118.
17. W. Ma, H. Su, A. G. Cheetham, W. F. Zhang, Y. Z. Wang, Q. C. Kan and H. G. Cui, *J. Control Release,* 2017, 263, 102-111.
18. L. Adamiak, M. A. Touve, C. L. M. LeGuyader and N. C. Gianneschi, *ACS Nano,* 2017, 11, 9877-9888.
19. A. P. Blum, J. K. Kammeyer and N. C. Gianneschi, *Chem. Sci.,* 2016, 7, 989-994.
20. A. P. Blum, J. K. Kammeyer, J. Yin, D. T. Crystal, A. M. Rush, M. K. Gilson and N. C. Gianneschi, *J. Am. Chem. Soc.,* 2014, 136, 15422-15437.
21. A. Blum, D. Nelles, F. Hidalgo, M. Touve, D. Sim, A. A. Madrigal, G. Yeo and N. C. Gianneschi, *Angew. Chem. Int. Ed.,* 2019, DOI: 10.1002/anie.201904894.
22. H. Sun, W. Choi, N. Zang, C. Battistella, M. P. Thompson, W. Cao, X. Zhou, C. Forman and N. Gianneschi, *Angew. Chem. Int. Ed.,* 2019, DOI: 10.1002/anie.201908634.
23. D. Owensiii and N. Peppas, *Int. J. Pharm.,* 2006, 307, 93-102.
24. M. T. Proetto, J. Sanning, M. Peterlechner, M. Thunemann, L. Stegemann, S. Sadegh, A. Devor, N. C. Gianneschi and C. A. Strassert, *Chem. Commun.,* 2019, 55, 501-504.
25. S. O. Poelma, S. S. Oh, S. Helmy, A. S. Knight, G. L. Burnett, H. T. Soh, C. J. Hawker and J. R. de Alaniz, *Chem. Commun.,* 2016, 52, 10525-10528.
26. R. B. Greenwald, Carl W. Gilbert, Annapurna Pendri, Charles D. Conover, Jing Xia, and Anthony Martinez, *J. med. chem.,* 1996, 39, 424-431.
27. S. Behzadi, V. Serpooshan, W. Tao, M. A. Hamaly, M. Y. Alkawareek, E. C. Dreaden, D. Brown, A. M. Alkilany, O. C. Farokhzad and M. Mahmoudi, *Chem. Soc. Rev.,* 2017, 46, 4218-4244.
28. Y. Z. Min, J. M. Caster, M. J. Eblan and A. Z. Wang, *Chem. Rev.,* 2015, 115, 11147-11190.
29. S. Billiet, K. De Bruycker, F. Driessen, H. Goossens, V. Van Speybroeck, J. Winne and F. Du Prez, *Nat. Chem.,* 2014, 6, 815-821.

Supplementary Information to Example 1

Included in this section are certain embodiments of polymers and methods disclosed herein.

1. General Methods: All reagents were purchased from commercial sources and used without further purification. A549 lung carcinoma cells were obtained from subcultures of cells from ATCC. Sealed ampules of DMF-$d_7$ (Sigma-Aldrich) were degassed before use. Norbornenyl-glycine was prepared as described[1]. Modified 2$^{nd}$ Generation Grubbs Ruthenium initiator $(IMesH_2)(C_5H_5N)_2(Cl)_2Ru{=}CHPh$ was prepared as described[2]. Polymerizations were performed in a glove box. Peptide monomers were synthesized on a Biotage Alstra peptide synthesizer. Analytical RP-HPLC analysis was performed on a Waters Symmetry column (150×4.60 mm) using a Waters 1525 Binary HPLC pump equipped with Waters 2998 Photodiode Array Detector. Peptide monomers were purified on a Semi-Prep RP-HPLC using a Waters SunFire column (250×19 mm). The solvent system for both HPLC instruments consists of 0.1% TFA in water (buffer A) and 0.1% TFA in acetonitrile (buffer B). $^1$H and $^{13}$C NMR spectra were recorded on a Bruker 400 MHz NMR spectrometer. Chemical shifts were reported in ppm relative to the residual solvent peak or TMS peak. ESI-MS spectra were performed on a LCQ-Advantage mass spectrometer. MALDI-TOF-MS spectra were performed on a Bruker Ultraflextreme mass spectrometer. MALDI-TOF-MS spectra of polymers were performed using a matrix solution of 2,5-dihydroxybenzoic acid in 1:3 water:acetonitrile with 0.1% TFA (30 mg/ml), and polymer solutions in water (1 mg/ml). The solutions were mixed in a 10:1 ratio (matrix:polymer). DLS measurements were performed on a Wyatt DynaPro NanoStar. Absorbance at 570 nm was measured in 96 well plates using a TECAN Spark 10M microplate reader. Flow cytometry measurements were performed using a BD Accuri C6 Plus. Confocal images were taken on a Nikon TI-E+A1 microscope (Nikon, Japan).

2. Experimental:

2.1. Synthesis of PTX-Containing Chain Transfer Agent:

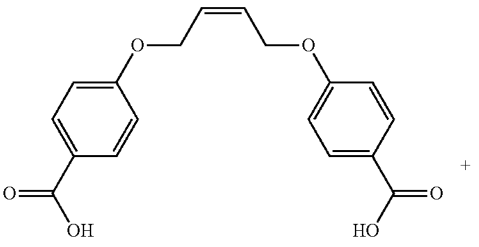

(1)

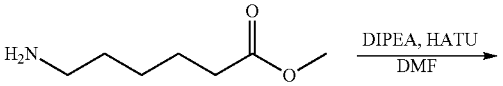

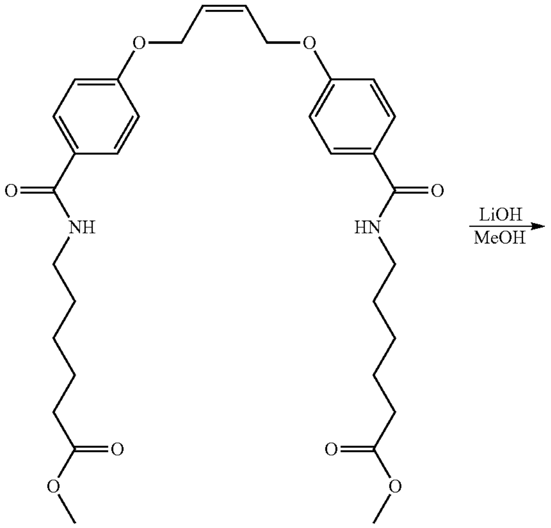

(2)

-continued

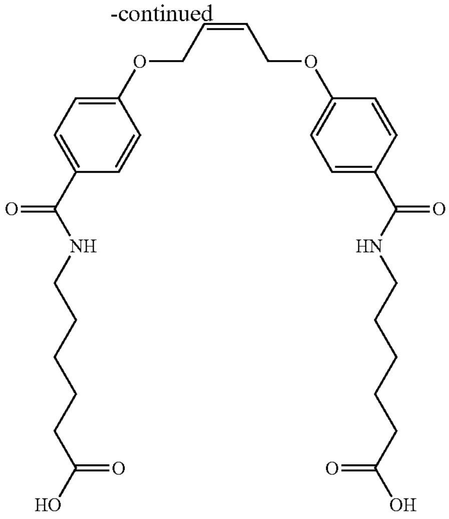

(3)

(I). Synthesis of dimethyl 6,6'-((4,4'-(but-2-ene-1,4-diylbis(oxy))bis(benzoyl))bis(azanediyl))(Z)-dihexanoate (2) (Z)-4,4'-(but-2-ene-1,4-diylbis(oxy))dibenzoic acid (1) was prepared as previously described.[3] To a solution of (1) (182.4 mg, 1.0 equiv.) in 10 mL DMF, HATU (472 mg, 2.2 equiv.) and DIPEA (450 μL, 4.6 equiv.) were added. The mixture was stirred at room temperature for 30 minutes. To the mixture 6-Aminocaproic acid methyl ester hydrochloride (237 mg, 2.3 equiv.) and DIPEA (240 μL, 2.5 equiv.) were added. The reaction was stirred for another 48 hours and then concentrated to dryness. The residue was resuspended in $CH_2Cl_2$ and washed by water (×1) and HCl (aq) (1M) (×3). The organic layer was collected and dried by $Na_2SO_4$, filtered and concentrated. The obtained solid was then purified by flash chromatography (4:1 Ethyl Acetate: Petroleum Ether) to give the product as a white solid. $^1H$ NMR (400 MHz, $CDCl_3$): δ (ppm) 1.39 (m, 4H, 2×$CH_2$), 1.63 (m, 8H, 4×$CH_2$), 2.31 (t, 4H, 2×$CH_2$), 3.41 (t, 4H, 2×$CH_2$), 3.65 (s, 6H, 2×$CH_3$), 4.70 (d, 4H, 2×$CH_2$), 5.92 (t, 2H, 2×CH), 6.88 (d, 4H, 4×Ar), 7.73 (d, 4H, 4×Ar). $^{13}C$ NMR (101 MHz, $CDCl_3$): 24.45, 26.41, 29.29, 33.85, 39.59, 51.50, 64.35, 114.39, 127.45, 128.37, 128.77, 160.74, 167.03, 174.09. ESI-MS (+): m/z 605.28 $[M+Na]^+$.

(II). Synthesis of (Z)-6,6'-((4,4'-(but-2-ene-1,4-diylbis(oxy))bis(benzoyl))bis(azanediyl))dihexanoic acid (3): To a container charged with (2) (100.6 mg, 1 equiv.) was added 4:1 MeOH:$H_2O$ (100 mL) containing LiOH (85.4 mg, 20.6 equiv.). The mixture was stirred at 35° C. for 6 h and then MeOH was removed by rotary evaporation until a white precipitate formed. The mixture was diluted by water and acidified with HCl (conc.). The resulting white solid was collected by vacuum filtration, washed with water and dried under vacuum. $^1H$ NMR (400 MHz, MeOD): δ (ppm) 1.42 (m, 4H, 2×$CH_2$), 1.64 (m, 8H, 4×$CH_2$), 2.31 (t, 4H, 2×$CH_2$), 3.36 (m, 4H, 2×$CH_2$), 4.78 (d, 4H, 2×$CH_2$), 5.92 (t, 2H, 2×CH), 6.99 (d, 4H, 4×Ar), 7.78 (d, 4H, 4×Ar). $^{13}C$ NMR (101 MHz, MeOD): 25.79, 27.60, 30.26, 34.85, 40.79, 65.49, 115.46, 128.24, 129.52, 130.10, 162.58, 169.82, 177.55. ESI-MS (−): m/z 553.16 $[M-H]^-$.

(III). Synthesis of PTX-containing chain transfer agent (4):

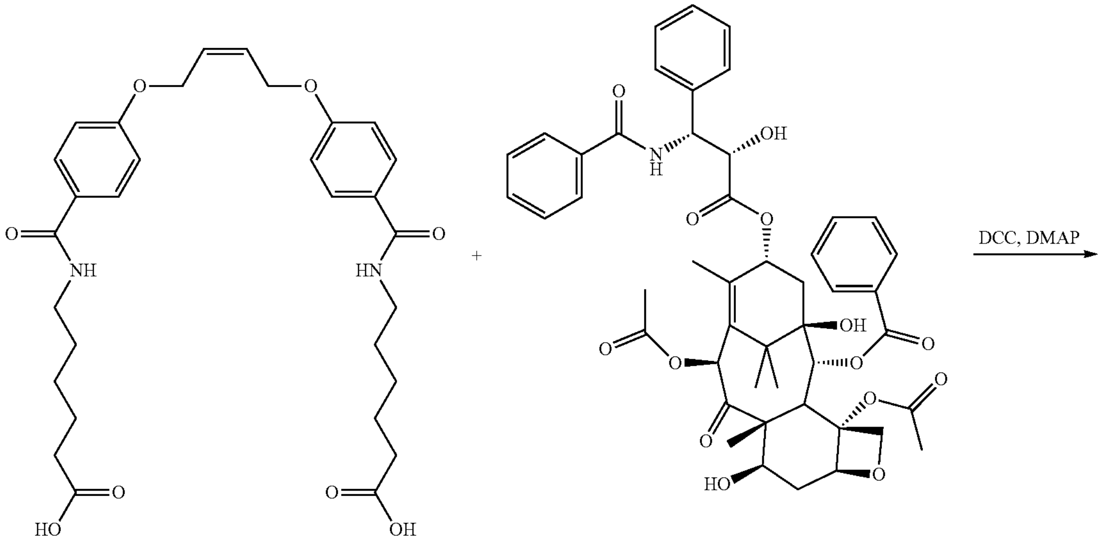

(3)

-continued

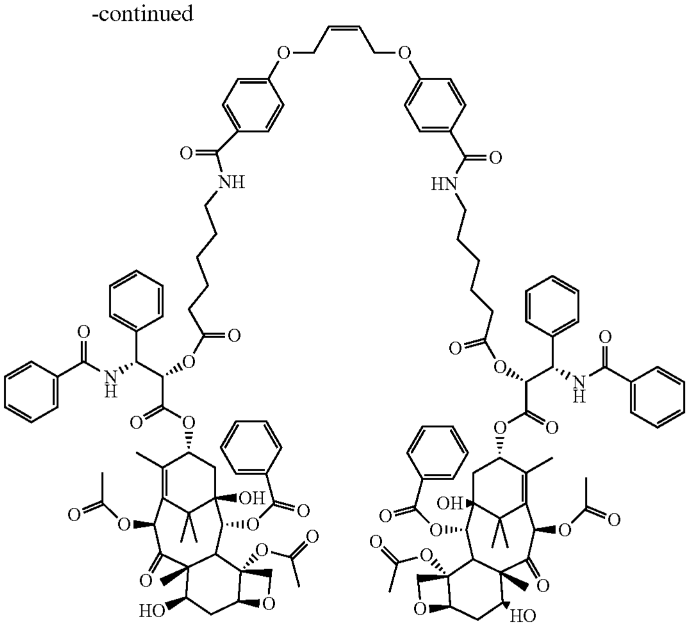

(4)

To a solution of (3) (60.1 mg, 1 equiv.), paclitaxel (260.2 mg, 3 equiv.) and DMAP (2.65 mg, 0.2 equiv.) in 4:1 DCM:DMF (10 mL) in a 0° C. ice bath was added DCC (53.8 mg, 2.4 equiv.) slowly. The reaction was stirred for 30 minutes and then the ice bath was removed and the reaction was stirred for another 8 h. The mixture was filtered and washed with water (×1) and HCl (aq) (1M) (×2), then dried ($Na_2SO_4$), filtered and concentrated to dryness. The white crude material was purified by flash chromatography (3:1 Ethyl Acetate:Petroleum Ether to 100% Ethyl Acetate). $^1$H NMR (500 MHz, $CDCl_3$): δ (ppm) 1.12 (s, 6H, 2×$CH_3$), 1.19 (s, 6H, 2×$CH_3$), 1.37 (m, 4H, 2×$CH_2$), 1.56-1.67 (m, 14H, 4×$CH_2$, 2×$CH_3$), 1.78 (s, 2H, 2×OH), 1.87 (m, 2H, $CH_2$), 1.92 (s, 6H, 2×$CH_3$), 2.07-2.12 (dd, 2H, $CH_2$), 2.21 (s, 6H, 2×$CH_3$), 2.29-2.34 (dd, 2H, $CH_2$), 2.42 (m, 10H, 2×$CH_3$, 2×$CH_2$), 2.54 (m, 4H, $CH_2$, 2×OH), 3.29-3.41 (m, 4H, 2×$CH_2$), 3.80 (d, 2H, 2×CH), 4.18-4.31 (dd, 4H, 2×$CH_2$), 4.44 (t, 2H, 2×CH), 4.69 (d, 4H, 2×$CH_2$), 4.96 (d, 2H, 2×CH), 5.50 (d, 2H, 2×CH), 5.67 (d, 2H, 2×CH), 5.91 (t, 2H, 2×CH), 5.94-5.97 (dd, 2H, 2×CH), 6.16-6.21 (m, 4H, 4×CH), 6.29 (s, 2H, 2×NH), 6.89 (d, 4H, 4×Ar), 7.15 (t, 2H, 2×NH), 7.32 (m, 2H, 2×Ar), 7.36 (t, 4H, 4×Ar), 7.40 (d, 8H, 8×Ar), 7.46 (t, 2H, 2×Ar), 7.51 (t, 4H, 4×Ar), 7.61 (t, 2H, 2×Ar), 7.67 (d, 4H, 4×Ar), 7.74 (d, 4H, 4×Ar), 8.12 (d, 4H, 4×Ar). $^{13}$C NMR (101 MHz, $CDCl_3$): 9.73, 14.92, 21.15, 22.19, 22.77, 24.37, 26.11, 26.85, 29.23, 29.80, 33.70, 35.68, 39.69, 43.27, 45.73, 53.18, 58.56, 64.45, 71.88, 72.17, 74.16, 75.21, 75.72, 76.53, 79.09, 81.13, 84.56, 114.56, 126.89, 127.26, 127.40, 128.26, 128.62, 128.74, 128.81, 128.85, 129.14, 129.38, 130.30, 132.04, 132.89, 133.77, 133.82, 137.08, 142.78, 160.92, 167.02, 167.22, 167.45, 168.46, 169.93, 171.29, 172.83, 203.92. MALDI-TOF-MS (+): m/z 2249.08 $[M+Na]^+$.

2.2. Synthesis of Dye Monomer:

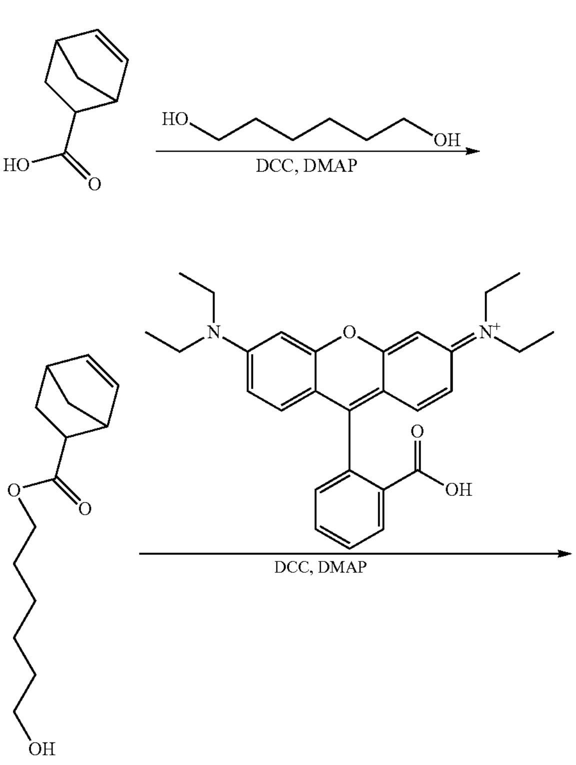

(5)

-continued

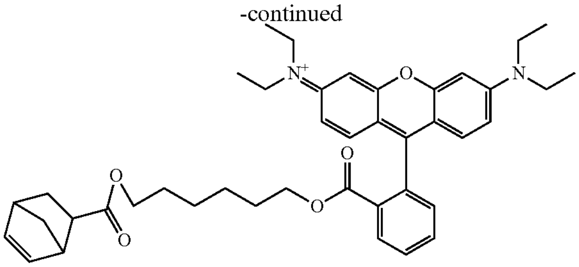

(6)

(I) Synthesis of 6-hydroxyhexyl bicyclo[2.2.1]hept-5-ene-2-carboxylate (5): To a solution of 5-Norbornene-2-carboxylic acid (102.1 mg, 1 equiv.), hexane-1,6-diol (360.3 mg, 4.1 equiv.) and DMAP (9.0 mg, 0.1 equiv.) in 1 mL DCM, was slowly added a solution of DCC (198.2 mg, 1.3 equiv.) in 1 mL DCM at 0° C. in an ice bath. The reaction was stirred for 30 minutes and then ice bath was removed and the reaction left to stir for another 6 h. The mixture was filtered, washed with HCl (aq) (1M) (×3), then dried ($Na_2SO_4$), filtered and concentrated. The crude material was further purified by flash column (4:1 Petroleum Ether:Ethyl Acetate). $^1H$ NMR (400 MHz, $CDCl_3$): δ (ppm) 1.34-1.42 (m, 5H, $2\times CH_2$, $CH_2$), 1.52 (dd, 1H, $CH_2$), 1.58 (m, 2H, $1\times CH_2$), 1.66 (m, 2H, $1\times CH_2$), 1.89-1.94 (m, 2H, $1\times CH_2$), 2.20-2.24 (m, 1H, 1×CH), 2.92 (s, 1H, 1×CH), 3.03 (s, 1H, 1×CH), 3.63 (t, 2H, $1\times CH_2$), 4.09 (t, 2H, $1\times CH_2$), 6.10-6.15 (m, 2H, 2×CH). $^{13}C$ NMR (101 MHz, $CDCl_3$): 25.47, 25.82, 28.75, 30.39, 32.65, 41.70, 43.29, 46.42, 46.68, 62.75, 64.49, 135.82, 138.09, 176.46. ESI-MS (+): m/z 261.06 $[M+Na]^+$.

(II) Synthesis of dye monomer (6): To a solution of (5) (50.2 mg, 1 equiv.), rhodamine B (121.6 mg, 1.2 equiv.) and DMAP (2.6 mg, 0.1 equiv.) in 1 mL of DCM, was added slowly a solution of DCC (56.8 mg, 1.3 equiv.) in 0.5 mL of DCM at 0° C. in an ice bath. The reaction was stirred for 30 minutes and then ice bath was removed, and the reaction left to stir for another 6 hrs. The mixture was filtered and further purified by flash chromatography (40:1 $CH_2Cl_2$:MeOH to 20:1 $CH_2Cl_2$:MeOH) and Semi-Prep RP-HPLC (65-90% buffer B). $^1H$ NMR (400 MHz, $CDCl_3$): δ (ppm) 1.19-1.33 (m, 17H, $2\times CH_2$, $4\times CH_3$, $CH_2$), 1.44-1.57 (m, 6H, $2\times CH_2$, CH, CH), 1.88 (m, 1H, $CH_2$), 2.18 (m, 1H, 1×CH), 2.90 (s, 1H, 1×CH), 2.99 (s, 1H, 1×CH), 3.60 (q, 8H, $4\times CH_2$), 4.02 (s, 4H, $2\times CH_2$), 6.10 (d, 2H, 2×CH), 6.81 (s, 4H, Ar), 7.06 (d, 2H, Ar), 7.30 (d, 1H, Ar), 7.72-7.81 (m, 2H, Ar), 8.28 (d, 1H, Ar). $^{13}C$ NMR (101 MHz, $CDCl_3$): 12.32, 25.26, 28.03, 28.30, 30.13, 41.42, 42.99, 45.83, 46.14, 46.42, 63.99, 65.37, 96.20, 113.37, 113.81, 117.26, 129.90, 130.04, 130.20, 131.09, 132.80, 133.25, 135.49, 137.88, 155.36, 157.61, 158.91, 159.68, 160.06, 164.95, 176.11. ESI-MS (+): m/z 663.29 $[M+H]^+$.

2.3. Synthesis of Peptide Monomers:

Peptide monomers were synthesized via standard FMOC-based solid phase peptide synthesis using Rink Amide MBHA resin. FMOC was deprotected using a solution of 20% piperidine in DMF. Amino acid couplings were carried out using HBTU and DIPEA (resin/amino acid/HBTU/DIPEA 1:3:2.95:6) for 45 mins. Norbornenyl-glycine (1.2 equiv.) coupling was carried out using HATU (1.15 equiv.) and DIPEA (2.4 equiv.) for 6 hrs. The final peptide monomers were cleaved from the resin using a mixture of TFA/H2O/TIPS (95:2.5:2.5) for 2 hrs and precipitated from cold ether. The crude products were further purified by semi-prep HPLC using UV-Vis detector at 214 nm.

2.4. Synthesis of Polymers:

To stirred solutions of peptide monomers (10 equiv., 0.03 mmol/L) in DMF-$d_7$ (0.5 mL) were added modified $2^{rd}$ Generation Grubbs initiator (1 equiv.) in a small volume of DMF-$d_7$. The polymerizations were stirred for 4 to 5 h, after which a solution of the dye monomer (0.2 equiv.) in a small volume DMF-$d_7$ was added to the reactions and left to stir for 1 hour. To each reaction PTX-containing chain transfer agent (4) in a small volume of dry DMF (2 equiv.) was added. After 12 h, ethyl vinyl ether was added to ensure full termination. The polymers were precipitated into a cold 1:2 dichloromethane:ether solution (×3) and then purified by RP-HPLC with the UV-Vis detector monitoring at 214 nm. Each peak obtained from HPLC was characterized by MALDI-TOF-MS.

2.5. In Vitro Analyses:

2.5.1. Cell Culture:

A549 lung carcinoma cells were cultured in Ham's F-12k medium, supplemented with 10% fetal bovine serum and 1% antibiotics, and maintained at 37° C. in 5% $CO_2$.

2.5.2. Cellular Uptake Studies:

By flow cytometry: Cells were plated at a density of 100,000 cells per well in a 24-well plate 16 hrs before treatment. Polymeric materials at 10× the desired concentration (with respect to polymer) were diluted with PBS, added to the appropriate wells, and the plates incubated for 4 hrs at 37° C. The media was then removed and the cells washed twice with PBS. Cells that were incubated with polymers bearing positive charge (poly(GGSGSGK)-Dye-PTX/poly(GGSGSGR)-Dye-PTX/poly(GGSGSGRR)-Dye-PTX) were then incubated with heparin (0.5 mg/$mL^{-1}$ in PBS) for five minutes (×3) and rinsed twice with PBS to remove any un-internalized polymer adhered to the cell surface. The cells were subsequently dissociated from the culture plate by treatment with trypsin for 5 minutes, followed by media addition and PBS. The cells were transferred to centrifuge tubes and centrifuged at 1000 rpm to form a cell pellet. The supernatant was discarded, cells resuspended in PBS, and centrifuged again. The final obtained cell pellets were resuspended in a small volume of PBS containing 1% FBS and analyzed by flow cytometry (10,000 gated events on three separate cultures per condition).

By confocal microscopy: Cells were plated at a density of 50,000 cells in glass bottom plates and incubated for 18 hrs before treatment. 4 μM Poly(GGSGSGRR)-Dye-PTX and poly(GGSGSGS)-Dye-PTX were added to each plate, followed by incubation for 4 hrs. After that, the media was removed and the cells were washed twice with PBS. Cells treated with poly(GGSGSGRR)-Dye-PTX were incubated with heparin (0.5 mg/mL-1 in PBS) for five minutes (×3) and rinsed twice with PBS. Diluted hoechest 33342 staining solution for live cells was then add to the wells for 10 minutes. The cells were gently washed with PBS for three times and 4% paraformaldehyde was added to fix the cells. After 10 minutes, the fixation solution was removed and cells washed three times with PBS.

2.5.3. Cytotoxicity Assays:

The cytotoxicity of all polymers was assessed using the MTT metabolic assay. A549 cells were plated at a density of 2,000 cells/well in a 96-well plate 18 hrs prior to treatment. Materials at 10× the desired concentration (with respect to polymer) were diluted with PBS, added to the appropriate wells, and the plates incubated for 4 hrs at 37° C. Following incubation, the materials were removed, cells were washed twice with PBS, supplemented with 100 μL Ham's F-12K media, and incubated for an additional 48 or 72 hrs.

2.5.4 Proteolytic Degradation Assays:

Monomer Nor-GGSGSGK and polymer Poly (GGSGSGK) (50 μM, with respect to peptide concentration) were treated with pronase (0.35 U/mL) in DPBS at 37° C. After treatment, the enzyme was heat denatured at 65° C. for 15 min.

REFERENCES CORRESPONDING TO SUPPLEMENTARY INFORMATION FOR EXAMPLE 1

1. R. M. Conrad and R. H. Grubbs, Angew. *Chem. Int. Ed.,* 2009, 48, 8328-8330.
2. M. S. Sanford, J. A. Love and R. H. Grubbs, *Organometallics,* 2001, 20, 5314-5318.
3. M. P. Thompson, L. M. Randolph, C. R. James, A. N. Davalos, M. E. Hahn and N. C. Gianneschi, *Polym. Chem.,* 2014, 5, 1954-1964.

STATEMENTS REGARDING INCORPORATION BY REFERENCE AND VARIATIONS

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups are disclosed separately. When a Markush group or other grouping is used herein, all individual members of the group and all combinations and subcombinations possible of the group are intended to be individually included in the disclosure. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Whenever a range is given in the specification, for example, a temperature range, a time range, or a composition or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The term "and/or" is used herein, in the description and in the claims, to refer to a single element alone or any combination of elements from the list in which the term and/or appears. In other words, a listing of two or more elements having the term "and/or" is intended to cover embodiments having any of the individual elements alone or having any combination of the listed elements. For example, the phrase "element A and/or element B" is intended to cover embodiments having element A alone, having element B alone, or having both elements A and B taken together. For example, the phrase "element A, element B, and/or element C" is intended to cover embodiments having element A alone, having element B alone, having element C alone, having elements A and B taken together, having elements A and C taken together, having elements B and C taken together, or having elements A, B, and C taken together.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A polymer comprising:

a plurality of repeating units, each repeating unit comprising a polymer backbone group directly or indirectly covalently linked to one or two side chain moieties, the polymer is of formula FX1:

$$Q^1\text{-}[M(Z)_u]_n\text{-}Q^2 \quad \text{(FX1);}$$

wherein:

n is an integer selected from a range of 2 to 1000;

u is 1 or 2;

each M is independently the polymer backbone group of one of the repeating units and each M is independently a ROMP-polymerized monomer;

each Z is independently one of the one or two side chain moieties and each Z independently comprises a peptide moiety or a non-peptide therapeutic moiety;

each Z is independently directly or indirectly covalently attached to an M;

each M is covalently attached to at least one other M and each M is independently directly or indirectly covalently attached to one or two of Z, such that 100% of the ROMP-polymerized monomers (M) are each individually attached to one or two side chain moieties (Z);

$Q^1$ is a first polymer-terminating group;

$Q^2$ is a second polymer-terminating group;

the polymer comprises a plurality of peptide moieties;

at least one Z of the polymer comprises a non-peptide therapeutic moiety, $Q^1$ comprises a non-peptide therapeutic moiety, and/or $Q^2$ comprises a non-peptide therapeutic moiety;

wherein the polymer comprises at least two peptide moieties; and wherein the at least two peptide moieties include at least two unique peptide moieties.

2. The polymer of claim 1, wherein n and a fraction ("P") of all side chain moieties in the polymer that are side chain moieties comprising a peptide moiety are selected to provide for cellular uptake.

3. The polymer of claim 2, wherein cellular uptake of the polymer is provided by a combination of parameters n, P, and peptide moiety charge.

4. The polymer of claim 1, wherein $Q^1$, $Q^2$, or a combination thereof, comprises a non-peptide therapeutic moiety.

5. The polymer of claim 1, wherein at least one of the plurality of peptide moieties is a non-cell-penetrating peptide or a therapeutic peptide.

6. The polymer of claim 1, wherein at least one of the plurality of peptide moieties comprises a sequence having 80% or greater sequence homology of GGSGSGS (SEQ ID NO:1), GGSGSGE (SEQ ID NO:2), GGSGSGK (SEQ ID NO:3), GGSGSGR (SEQ ID NO:4), GGSGSGRR (SEQ ID NO:5), or a combination thereof.

7. The polymer of claim 1, wherein at least one of the plurality of peptide moieties has a positive charge.

8. The polymer of claim 1, wherein the polymer has a net positive charge.

9. The polymer of claim 1, wherein at least one of the plurality of peptide moieties is a positively charged peptide moiety, and wherein a cell uptake efficiency of the polymer is higher due to the presence of the at least one positively charged peptide moiety, compared to a cell uptake efficiency of an equivalent polymer free of a positively charged group.

10. The polymer of claim 1, wherein each of a number of peptide moieties corresponding to at least a fraction of the plurality of peptide moieties is a hydrophilic peptide such that the polymer is hydrophilic.

11. The polymer of claim 1, wherein each M is independently a ROMP-polymerized substituted or unsubstituted norbornene or a ROMP-polymerized substituted or unsubstituted oxanorbornene monomer.

12. The polymer of claim 1, wherein the polymer is of formula FX2a or FX2b:

(FX2a)

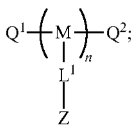

or (FX2b)

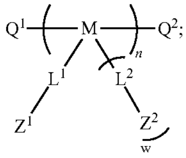

wherein:

each of $L^1$ and $L^2$ is independently a covalent linking group;

each of Z, $Z^1$, and $Z^2$ is independently one of the one or two side chain moieties;

n is an integer selected from a range of 2 to 1000; and w is 1 or 0.

13. The polymer of claim 12, wherein each of $L^1$ and $L^2$ is independently selected from a single bond, an oxygen, and one or more substituted or unsubstituted groups having an alkyl group, an alkenylene group, an arylene group, an alkoxy group, an acyl group, a carboxyl group, an aliphatic group, an amide group, an aryl group, an amine group, an ether group, a ketone group, an ester group, a triazole group, a diazole group, a pyrazole group, or combinations thereof.

14. The polymer of claim 1, wherein each M covalently attached to one or two side chain moieties is of formula FX3a, FX3b, FX3c, FX3d, FX3e, FX3f, FX3g, or FX3h:

(FX3a)

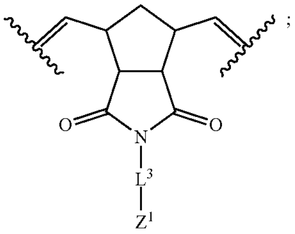

(FX3b)

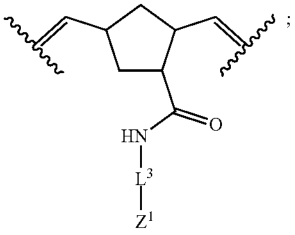

(FX3c)

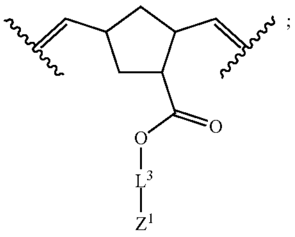

-continued (FX3d)

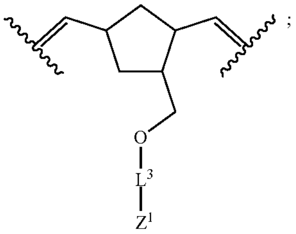

(FX3e)

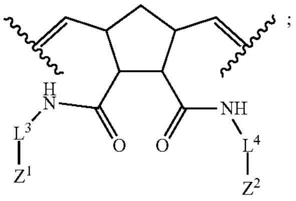

(FX3f)

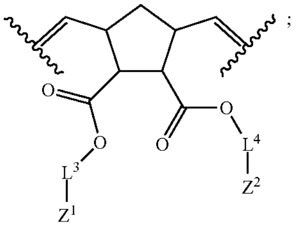

(FX3g)

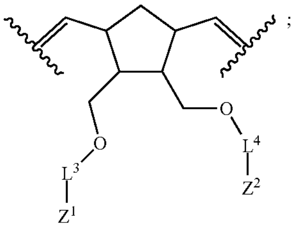

or (FX3h)

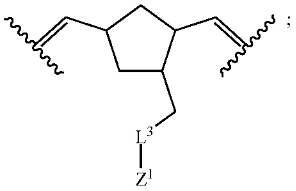

wherein each of $L^3$ and $L^4$ is optionally present, and is independently a covalent linking group; and wherein each of $Z^1$ and $Z^2$ is independently one of the one or two side chain moieties.

15. The polymer of claim 14, wherein each of $L^3$ and $L^4$ is independently selected from a single bond, an oxygen, and one or more substituted or unsubstituted groups having an alkyl group, an alkenylene group, an arylene group, an alkoxy group, an acyl group, a carboxyl group, an aliphatic group, an amide group, an aryl group, an amine group, an ether group, a ketone group, an ester group, a triazole group, a diazole group, a pyrazole group, or combinations thereof.

16. The polymer of claim 1, wherein $Q^1$ and/or $Q^2$ is of formula FX4a or FX4b:

(FX4a)

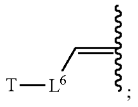

(FX4b)

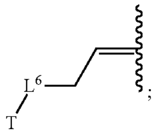

wherein:

T is a non-peptide therapeutic moiety; and $L^6$ is a covalent linking group selected from a single bond, an oxygen, and one or more substituted or unsubstituted groups having an alkyl group, an alkenylene group, an arylene group, an alkoxy group, an acyl group, a carboxyl group, an aliphatic group, an amide group, an aryl group, an amine group, an ether group, a ketone group, an ester group, a triazole group, a diazole group, a pyrazole group, or combinations thereof.

17. The polymer of claim 16, wherein $L^6$ is of formula FX5a, FX5b, FX5c, FX5d, FX5e, FX5f, FX5g, or any combination thereof:

(FX5a)

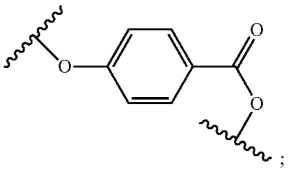

(FX5b)

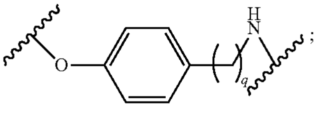

(FX5c)

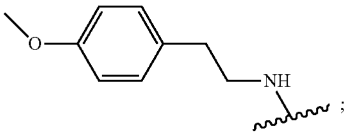

(FX5d)

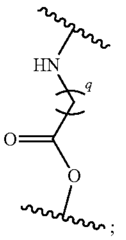

-continued

FX5e

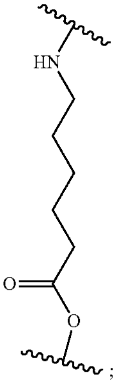

(FX5f)

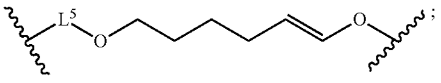

or (FX5g)

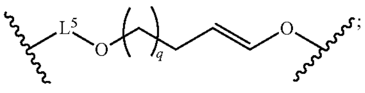

wherein:

q is an integer selected from a range of 1 to 10; and $L^5$ is a covalent linking group.

18. The polymer of claim 1, wherein $Q^1$ and/or $Q^2$ is of formula FX6a, FX6b, FX6c, or FX6d:

(FX6a)

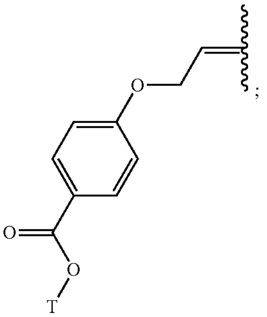

-continued (FX6b)

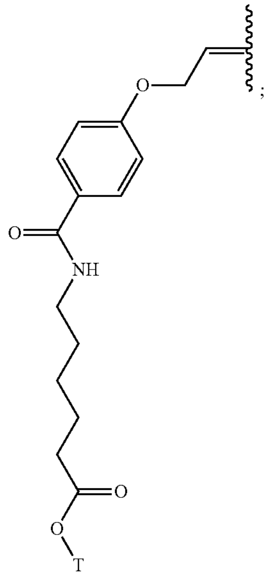

FX6c

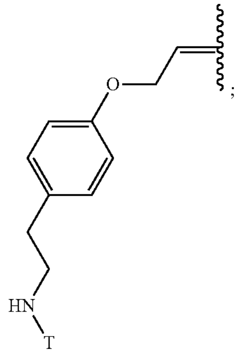

or

FX6d

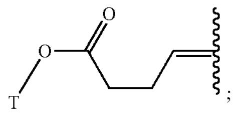

wherein T is a non-peptide therapeutic moiety.

19. The polymer of claim 1, wherein the non-peptide therapeutic moiety is a therapeutic agent and is not a diagnostic agent.

20. The polymer of claim 1, wherein the non-peptide therapeutic moiety is a cell growth or proliferation inhibitory agent, an anti-inflammatory agent, an anti-tumor or anti-cancer agent, an anti-apoptotic agent, anti-diabetic agent, anti-obesity agent, anti-infective agent, anti-bacterial agent, anti-viral agent, an agent for promoting cell growth and differentiation, an agent for preventing pain, an agent for preventing or treating neural degeneration, an agent for promoting neurogenesis; an immunosuppressant agent, an immunostimulant agent, an MMP-inhibitor agent, a corticosteroid, an anti-angiogenic agent, a pro-angiogenic agent, an NSAID, paclitaxel, or a combination thereof.

21. The polymer of claim 1, wherein each non-peptide therapeutic moiety is released from the polymer when the polymer is exposed to an acidic solution.

22. The polymer of claim 1, wherein the polymer has a polydispersity index of less than 1.5.

23. A liquid composition comprising an aqueous plurality of polymers, each polymer is according to claim 1, wherein the liquid composition is a therapeutic formulation having a therapeutically effective concentration of the aqueous plurality of polymers, wherein the therapeutic formulation is free of polymers that do not include the non-peptide therapeutic moiety.

24. The liquid composition of claim 23, wherein each polymer of the aqueous plurality of polymers is individually solvated by water.

25. A method of treating or managing a condition in a subject comprising:

administering to a subject an effective amount of a polymer comprising:

a plurality of repeating units, each repeating unit comprising a polymer backbone group directly or indirectly covalently linked to one or two side chain moieties, the polymer is of formula FX1:

$$Q^1\text{-}[M(Z)_u]_n\text{-}Q^2 \qquad \text{(FX1);}$$

wheren:

n is an integer selected from a range of 2 to 1000;

u is 1 or 2;

each M is independently the polymer backbone group of one of the repeating units and each M is independently a ROMP-polymerized monomer;

each Z is independently one of the one or two side chain moieties (Z) and each Z independently comprises a peptide moiety or a non-peptide therapeutic moiety; wherein the polymer comprises a plurality of peptide moieties;

each Z is independently directly or indirectly covalently attached to an M;

each M is covalently attached to at least one other M and each M is independently directly or indirectly covalently attached to one or two of Z, such that 100% of the ROMP-polymerized monomers are each individually attached to one or two side chain moieties;

$Q^1$ is a first polymer-terminating group;

$Q^2$ is a second polymer-terminating group;

at least one Z of the polymer comprises a non-peptide therapeutic moiety, $Q^1$ comprises a non-peptide therapeutic moiety, and/or $Q^2$ comprises a non-peptide therapeutic moiety;

wherein the polymer comprises at least two peptide moieties; and wherein the at least two peptide moieties include at least two unique peptide moieties.

26. The method of claim 25, wherein the condition is myocardial ischemia, acute myocardial infarction, heart failure, rheumatoid arthritis, articular cartilage damage, acute and/or chronic epidermal wound, liver failure, nerve damage, acute brain injury, spinal disk injury, or a combination thereof.

27. A method of treating or managing a condition in a subject comprising:

administering to the subject an effective amount of a liquid composition having water and a plurality of aqueous polymers; wherein each of the aqueous polymers independently comprises:

a plurality of repeating units, each repeating unit comprising a polymer backbone group directly or indirectly covalently linked to one or two side chain moieties, the polymer is of formula FX1:

$$Q^1\text{-}[M(Z)_u]_n\text{-}Q^2 \qquad \text{(FX1);}$$

wherein:

n is an integer selected from a range of 2 to 1000;

u is 1 or 2;

each M is independently the polymer backbone group of one of the repeating units and each M is independently a ROMP-polymerized monomer;

each Z is independently one of the one or two side chain moieties (Z) and each Z independently comprises a peptide moiety or a non-peptide therapeutic moiety; wherein the polymer comprises a plurality of peptide moieties;

each Z is independently directly or indirectly covalently attached to an M;

each M is covalently attached to at least one other M and each M is independently directly or indirectly covalently attached to one or two of Z, such that 100% of the ROMP-polymerized monomers are each individually attached to one or two side chain moieties;

$Q^1$ is a first polymer-terminating group;

$Q^2$ is a second polymer-terminating group;

at least one Z of the polymer comprises a non-peptide therapeutic moiety, $Q^1$ comprises a non-peptide therapeutic moiety, and/or $Q^2$ comprises a non-peptide therapeutic moiety;

wherein the polymer comprises at least two peptide moieties; and wherein the at least two peptide moieties include at least two unique peptide moieties.

28. A method for synthesizing a polymer, the method comprising steps of:

ROMP-polymerizing of a plurality of monomers, each monomer being directly or indirectly covalently attached to at least one side chain moiety; and terminating ROMP-polymerization with a chain termination agent, wherein the chain termination agent comprises a non-peptide therapeutic moiety;

wherein a synthesized polymer comprises:

a plurality of repeating units, each repeating unit comprising a polymer backbone group directly or indirectly covalently linked to one or two side chain moieties, the polymer is of formula FX1:

$$Q^1\text{-}[M(Z)_u]_n\text{-}Q^2 \quad \text{(FX1);}$$

where:

n is an integer selected from a range of 2 to 1000;

u is 1 or 2;

each M is independently the polymer backbone group of one of the repeating units and each M is independently a ROMP-polymerized monomer;

each Z is independently one of the one or two side chain moieties and each Z independently comprises a peptide moiety or a non-peptide therapeutic moiety; wherein the polymer comprises a plurality of peptide moieties;

each Z is independently directly or indirectly covalently attached to an M;

each M is covalently attached to at least one other M and each M is independently directly or indirectly covalently attached to one or two of Z, such that 100% of the ROMP-polymerized monomers are each individually attached to one or two side chain moieties;

$Q^1$ is a first polymer-terminating group;

$Q^2$ is a second polymer-terminating group; and $Q^1$ comprises a non-peptide therapeutic moiety and/or $Q^2$ comprises a non-peptide therapeutic moiety;

wherein the polymer comprises at least two peptide moieties; and wherein the at least two peptide moieties include at least two unique peptide moieties.

29. The method of claim 28, wherein the chain termination agent is of formula FX7a or FX7b:

(FX7a)

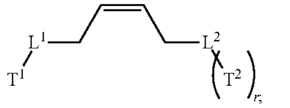

or (FX7b)

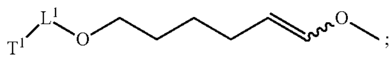

;

wherein:

r is 0 or 1;

if r is 1, each of $L^1$ and $L^2$ is independently a covalent linker group selected from a single bond, oxygen, $C_2$-$C_{10}$ alkenylene, $C_3$-$C_{10}$ arylene, and one or more substituted or unsubstituted groups having an alkyl group, an alkenylene group, an arylene group, an alkoxy group, an acyl group, a carboxyl group, an aliphatic group, an amide group, an aryl group, an amine group, an ether group, a ketone group, an ester group, a triazole group, a diazole group, a pyrazole group, or combinations thereof;

if r is 0, each of $L^2$ is selected from a $C_1$-$C_{10}$ alkyl, $C_1$-$C_{10}$ alkoxy, $C_1$-$C_{10}$ acyl, or combinations thereof, and each of $T^1$ and $T^2$ is independently a non-peptide therapeutic moiety.

30. The method of claim 29, wherein the chain termination agent is of formula FX7c, FX7d, FX7e, FX7f, FX7g, FX7h, FX7i, or FX7j:

(FX7c)

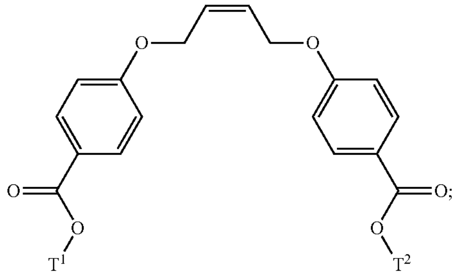

(FX7d)

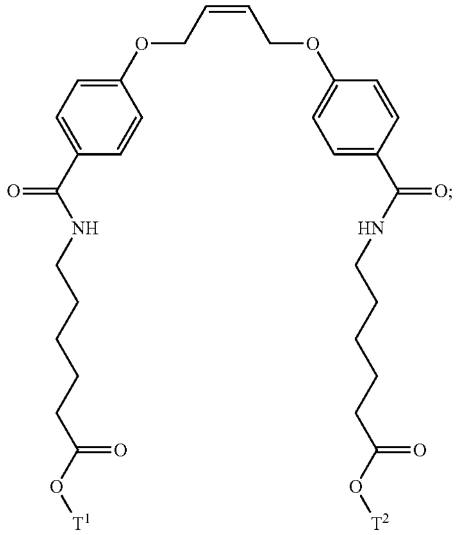

-continued
(FX7e)
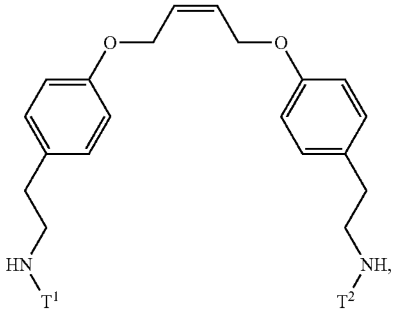
(FX7f)
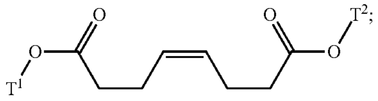
(FX7g)
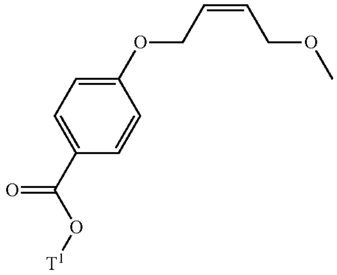
;
-continued
(FX7h)
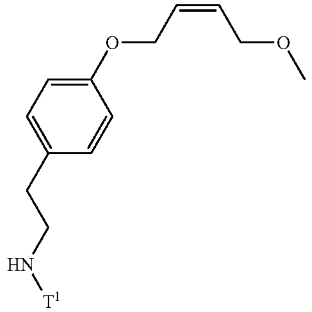
;
(FX7i)
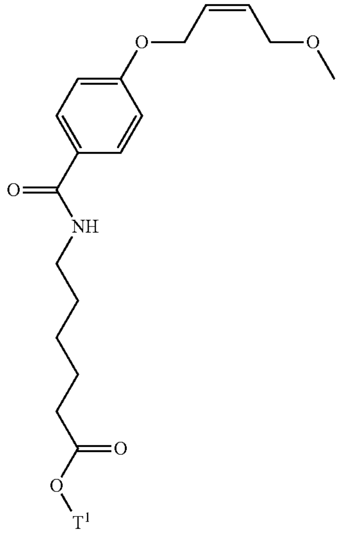
; or
(FX7j)
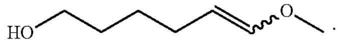
.
* * * * *